US008680270B2

(12) United States Patent
Schotzinger et al.

(10) Patent No.: US 8,680,270 B2
(45) Date of Patent: Mar. 25, 2014

(54) METALLO-OXIDOREDUCTASE INHIBITORS USING METAL BINDING MOIETIES IN COMBINATION WITH TARGETING MOIETIES

(75) Inventors: Robert J. Schotzinger, Raleigh, NC (US); William J. Hoekstra, Chapel Hill, NC (US)

(73) Assignee: Viamet Pharmaceuticals, Inc., Morrisville, NC (US)

( * ) Notice: Subject to any disclaimer, the term of this patent is extended or adjusted under 35 U.S.C. 154(b) by 778 days.

(21) Appl. No.: 12/515,676

(22) PCT Filed: Nov. 21, 2007

(86) PCT No.: PCT/US2007/085385
§ 371 (c)(1),
(2), (4) Date: Aug. 23, 2010

(87) PCT Pub. No.: WO2008/064311
PCT Pub. Date: May 29, 2008

(65) Prior Publication Data
US 2010/0305078 A1   Dec. 2, 2010

Related U.S. Application Data

(60) Provisional application No. 60/866,693, filed on Nov. 21, 2006, provisional application No. 60/941,218, filed on May 31, 2007.

(51) Int. Cl.
*C07D 403/10* (2006.01)
*A61K 31/506* (2006.01)
*A61K 31/41* (2006.01)
*A61P 31/04* (2006.01)

(52) U.S. Cl.
USPC ........... 544/243; 544/334; 514/256; 548/252; 548/254

(58) Field of Classification Search
USPC ............ 544/243, 334; 514/256; 548/252, 254
See application file for complete search history.

(56) References Cited

U.S. PATENT DOCUMENTS

| 3,717,655 | A |   | 2/1973 | Godefroi el al. |
| 4,327,104 | A |   | 4/1982 | Timmler et al. |
| 5,278,175 | A |   | 1/1994 | Ray et al. |
| 5,773,443 | A | * | 6/1998 | Ray et al. ............. 514/256 |

FOREIGN PATENT DOCUMENTS

| EP | 0 548 553 A1 | 6/1993 |
| WO | WO 03/072143 A1 | 9/2003 |

OTHER PUBLICATIONS

Wolff Manfred E. "Burger's Medicinal Chemistry, 5ed, Part 1" John Wiley & Sons, 1995, pp. 975-977.*
Banker, G.S. et al, "Modern Pharmaceutices, 3ed.", Marcel Dekker, New York. 1996, pp. 451 and 596.*
Freshney et al.,Culture of Animal Cells, A Manual of Basic Technique, Alan R. Liss, Inc., 1983, New York, p. 4.*
Dermer et al., Bio/Technology, 1994, 12:320.*
Turner et al., Current Pharmaceutical Design. 2, 209-224, 1996.*
Sugar et al., Diagno Microbiol. Infect. Dis. 21" 129-133, 1995.*
Ji, H., "A Three-Dimensional Model of Lanosterol 14α-Demethylase of *Candida albicans* and Its Interaction with Azole Antifungals," *J. Med. Chem.*, 2000, pp. 2493-2505, vol. 43.

* cited by examiner

*Primary Examiner* — Venkataraman Balasubramanian
(74) *Attorney, Agent, or Firm* — Alston & Bird LLP

(57) ABSTRACT

The presently disclosed subject matter is directed to metallo-oxidoreductase inhibitors having metal binding moities linked to a targeting moiety through a linking group or a direct bond, methods for screening for metallo-oxidoreductase inhibitors, and methods of treating an oxidoreductase related disorder by administering a metallo-oxidoreductase inhibitor to a subject in need of treatment thereof.

4 Claims, 69 Drawing Sheets

Carbonyl

X — N-Carbonyl-imidazolin-2-thione

Y — Acetoacetamide

Z — α-Carbonyl-methylphosphonic acid

AA — N-Carbonyl-N'-Hydroxyguanidine

AB — Glycolamide

AC — N-Carbonyl-glycinamide

AD — O-Acyl-oxyacetic acid

AE — N-Cyanomethyl carboxamide

AF — N-Acyl-piperazine

AG — N-Acyl-piperazin-3-one

Carbonyl

AH — N-Acyl-thiomorpholine

AI — N-Acyl-morpholine

*Fig. 3*
Miscellaneous
A 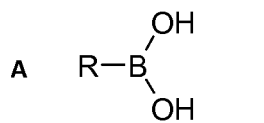 Boronic Acid
B 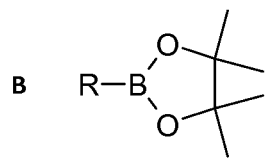 Pinacol boronic ester
Sulfur
C  Thiol
D 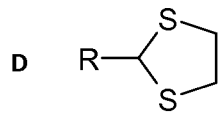 1,3-Dithiolane
E 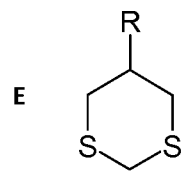 5-Dithiane
F 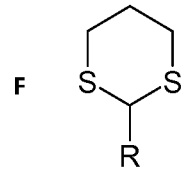 2-Dithiane
G 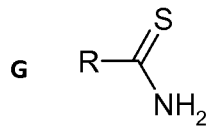 Thioamide
Nitrogen
H 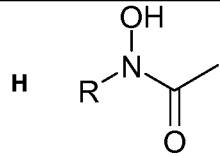 N-Acetyl-N-hydroxylamine
I 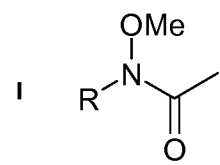 N-Acetyl-N-methoxylamine
J 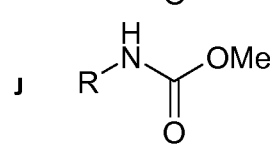 O-Methyl-carbamate

Fig. 3
Miscellaneous
K 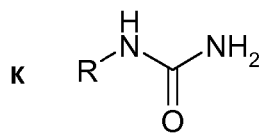 Urea
L 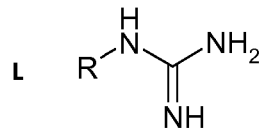 Guanidine
M 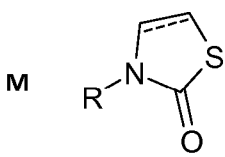 2-Oxo-thiazol(idine)
N 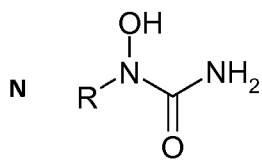 N-Hydroxy urea
O 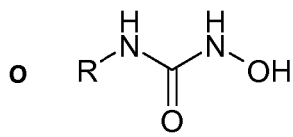 N-Hydroxy-urea
P 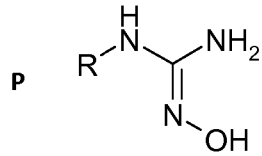 Hydroxy-guanidine
Q 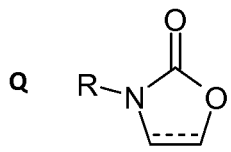 2-Oxo-oxazol(idine)
R 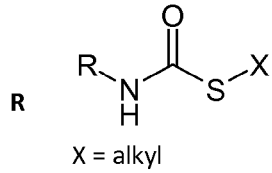 S-Alkyl thiocarbamate
X = alkyl
S 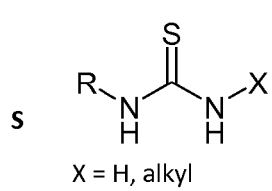 N-Substituted-thiourea
X = H, alkyl
Phosphorus Miscellaneous

5-Membered Aromatic Rings with 1 Heteroatom

A     Pyrrole

B     Furan

C     Thiophene

Fig. 5
5-Membered Aromatic Rings with 2 Heteroatoms
A  1-N-imidazole
B  Substituted 1-N-Imidazole
C  Imidazole
D  Oxazole
E  Thiazole
F  1-N-Pyrazole
G  Pyrazole
H  Isoxazole
I  Isothiazole

5-Membered Aromatic Rings with 3 Heteroatoms

A  1-N-(1,2,4-Triazole)

B  Substituted 1-N-(1,2,4-triazole)

C  1,2,4-Triazole

D  Substituted 4-N-(1,2,4-Triazole)

E  1,2,4-Oxadiazole

F  1,2,4-Thiadiazole

G  1,3,4-Oxadiazole

H  1,3,4-Thiadiazole

I  N-Substituted-1-N-(1,2,3-triazole)

J  1,2,3-Triazole

K  1,2,3-Oxadiazole

L  1,2,3-Thiadiazole

M  1,2,5-Oxadiazole

Fig. 6
5-Membered Aromatic Rings with 3 Heteroatoms
N 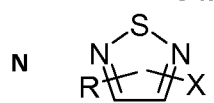 1,2,5-Thiadiazole
O 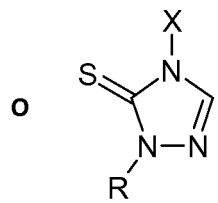 Substituted 1-N-(1,2,4-Triazol-5-thione)

5-Membered Aromatic Rings with 4 or 5 Heteroatoms

5-Membered Rings with 1 Heteroatom (Non-Aromatic)

A  Pyrrolidinone
B  3-Hydroxy pyrrolidinone
C  Succinimide
D  Maleimide
E  N-Hydroxy pyrrolidinone
F  Butyrolactone
G  3-Hydroxy butyrolactone
H  Thiobutyrolactone
I  3-Hydroxy thiobutyrolactone 5-Membered Rings with 2 Heteroatoms (non-aromatic)

A  Pyrazolone
B  Isothiazolin-3-one
C  Isothiazolin-5-one
D  Isoxazolin-3-one
E  Isoxazolin-5-one
F  2-Imidazolin-2-one
G  Hydantoin
H  2-Thiazolidone
I  Thiazolidinedione
J  2-Oxazolidone
K  Oxazolidine-2,4-dione 6-Membered Aromatic Rings with 0 Heteroatoms Ortho-disubstituted benzene 6-Membered Aromatic Rings with 1 Heteroatoms A                                                                          Pyridine

6-Membered Aromatic Rings with 2 Heteroatoms

A  Pyridazine

B  Pyrimidine

C  Pyrazine

6-Membered Aromatic Rings with 3 Heteroatoms

A  1,2,4-Triazine

B  1,3,5-Triazine

C  1,2,3,4-Tetrazine

6-Membered Rings with 1 Heteroatom (non-aromatic)

A — N-Substituted-dihydropyridinone

B — N-Hydroxy-2-pyridone

C — 3-Hydroxy-2-pyridone

D — 3-Hydroxy-4-pyridone

E — 3-Hydroxy-4-pyanone

6-Membered Rings with 2 Heteroatom (non-aromatic)

6-Membered Rings with 2 Heteroatom (non-aromatic)

J     2,5-Dioxopiperazine

K     Thiomorpholine

L     Morpholine

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Lanosterol Demethylase Inhibitors

Fig. 160
Lanosterol Demethylase Inhibitors
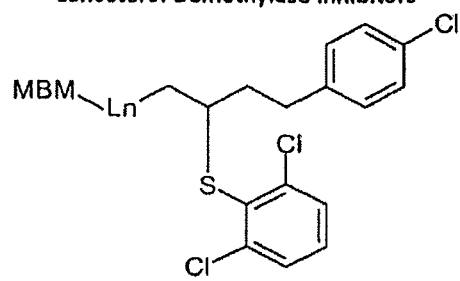
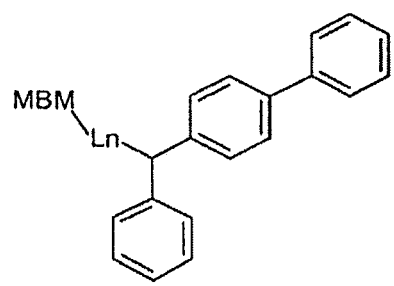
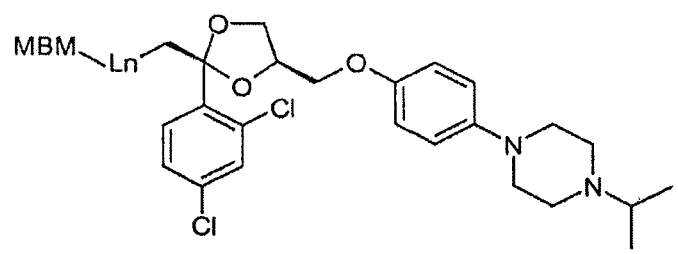
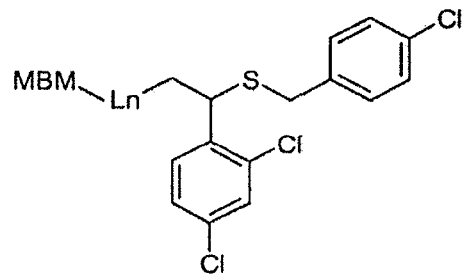

Lanosterol Demethylase Inhibitors

Lanosterol Demethylase Inhibitors

Lanosterol Demethylase Inhibitors

Lanosterol Demethylase Inhibitors

5-Lipoxygenase Inhibitors

Fig. 17B
5-Lipoxygenase Inhibitors
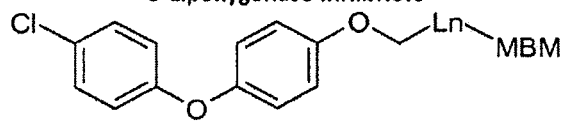
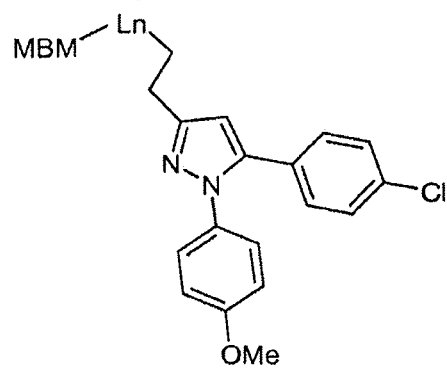
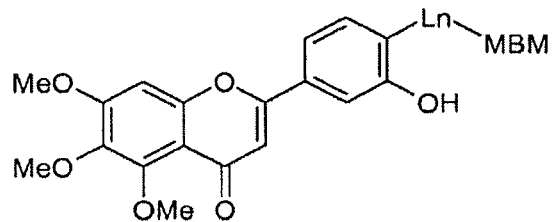
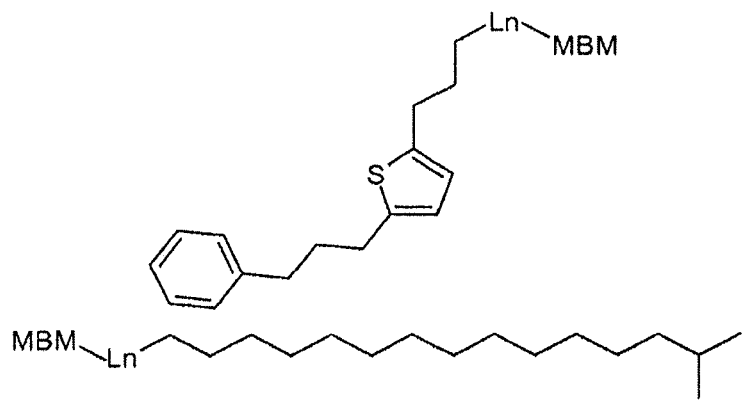
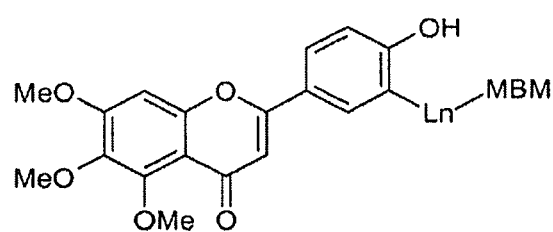

5-Lipoxygenase Inhibitors

Aromatase Inhibitors

Aromatase Inhibitors

Cyclooxygenase Inhibitors

Cyclooxygenase Inhibitors

Cyclooxygenase Inhibitors

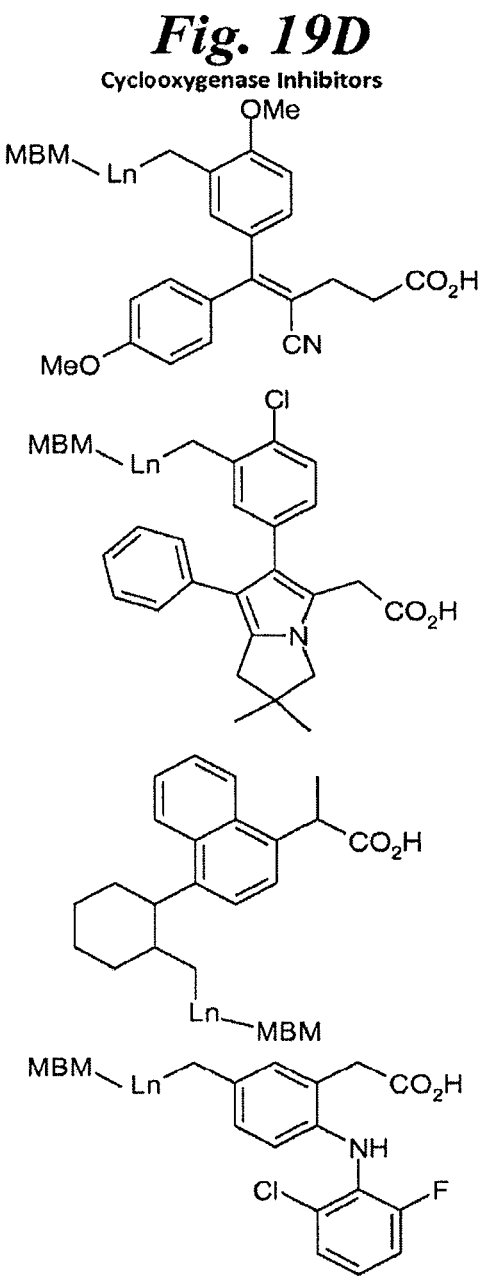

Cyclooxygenase Inhibitors

Heme Oxygenase Inhibitors

Heme Oxygenase Inhibitors

Fig. 21
Xanthine Oxidase Inhibitors
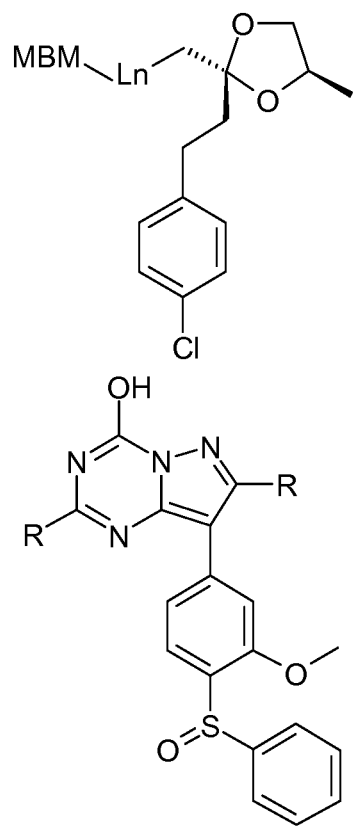
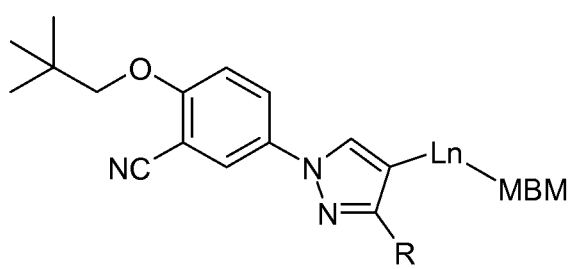
At least one of the
R= -Ln-MBM
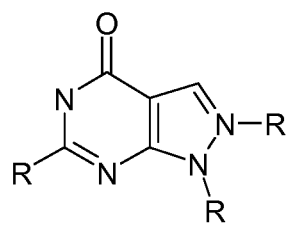
At least one of the
R= -Ln-MBM 17a-Hydroxylase Inhibitors 17a-Hydroxylase Inhibitors

Fig. 23A
Aldosterone Synthase Inhibitors
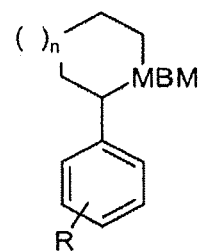
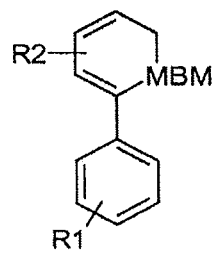
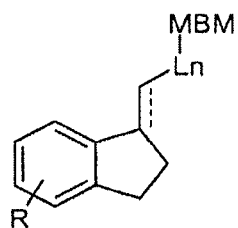
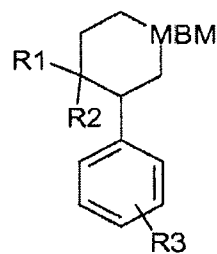
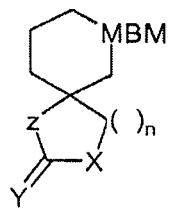

Fig. 23B
Aldosterone Synthase Inhibitors
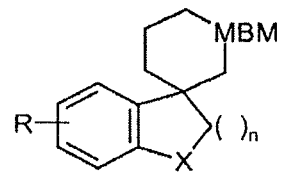
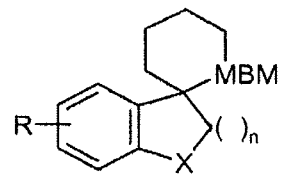
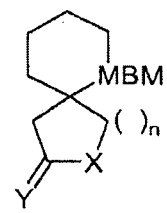
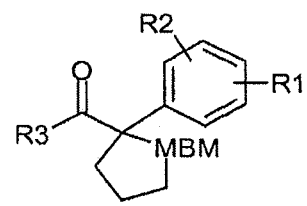
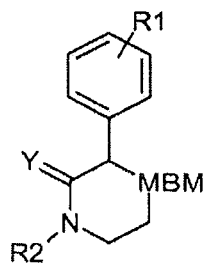
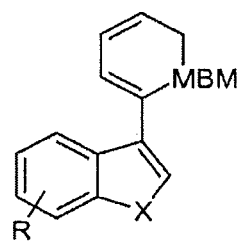

Aldosterone Synthase Inhibitors

Retinoic Acid Hydroxylase (CYP26) Inhibitors

Retinoic Acid Hydroxylase (CYP26) Inhibitors

Alcohol Dehydrogenase Inhibitors

Deoxy-Xylulose Phosphate Reductoisomerase Inhibitors

Indoleamine 2,3-Dioxygenase Inhibitors

Nitric Oxide Synthase Inhibitors

Vascular Adhesion Protein-1 Inhibitors

METALLO-OXIDOREDUCTASE INHIBITORS USING METAL BINDING MOIETIES IN COMBINATION WITH TARGETING MOIETIES

TECHNICAL FIELD

The presently disclosed subject matter is directed to metallo-oxidoreductase inhibitors having metal binding moieties linked to a targeting moiety through a linking group or a direct bond, methods for screening for metallo-oxidoreductase inhibitors, and methods of treating an oxidoreductase related disorder.

BACKGROUND

An oxidoreductase is an enzyme that catalyzes the transfer of electrons from one molecule (the oxidant, also called the hydrogen donor or electron donor) to another (the reductant, also called the hydrogen acceptor or electron acceptor). Oxidoreductases are classified as EC 1 in the EC number classification of enzymes. Oxidoreductases can be further classified into 22 subclasses. Many oxidoreductase enzymes are metalloenzymes that contain one or more metal ions. Some exemplary enzymes in this group are 1-deoxy-d-xylulose-5-phosphate reductoisomerase, 5-lipoxygenase, 17-alpha hydroxylase, alcohol dehydrogenase, aldosterone synthase, aromatase, cyclooxygenase, heme oxygenase, indoleamine 2,3-dioxygenase, lanosterol demethylase, nitric oxide synthase, retinoic acid hydroxylase, vascular adhesion protein-1, and xanthine oxidase.

Despite the importance of the metal ions to metallo-oxidoreductases activity, the current evaluation and development of metallo-oxidoreductases inhibitors typically ignores the activity of the metal ions in the design of the inhibitors. For example, a survey of decades of research on xanthine oxidase (XO) inhibitors reveals many of the studies were randomly performed, that it was difficult to rationalize a division of the different type of inhibitors, and none of the research focused on inhibitors that would interact with the metal ions of XO. See Borges et al., *Current Medicinal Chemistry*, 9:195-217 (2002), herein expressly incorporated by reference.

As described in more detail herein, certain candidate metallo-oxidoreductase inhibitors are known in the art. While some of these candidates have shown promise, there is a need for novel selective inhibitors of oxidoreductase enzymes, such as 5-lipoxygenase, 17-alpha hydroxylase, alcohol dehydrogenase, aldosterone synthase, aromatase, cyclooxygenase, heme oxygenase, indoleamine 2,3-dioxygenase, lanosterol demethylase, nitric oxide synthase, retinoic acid hydroxylase, vascular adhesion protein-1, and xanthine oxidase. The presently disclosed subject matter addresses, in whole or in part, these and other needs in the art.

SUMMARY

The presently disclosed subject matter is directed to a two-prong approach to inhibiting metallo-oxidoreductases. As metallo-oxidoreductases are metalloenzymes, the presently disclosed subject matter is directed to the combination of a metal binding moiety (MBM) in conjunction with a targeting moiety (TM), optionally linked through a linker. Thus, the presently disclosed subject matter results in more efficacious inhibitors by combining the affinity and specificity of two different but proximal sites of the metalloprotein.

In this way, both additive and synergistic binding effects, including both binding affinity and binding specificity, can be utilized. As will be appreciated by those in the art, the binding affinity and binding specificity can work in a variety of ways. Some metal binding moieties, such as the hydroxamates, bind tightly to zinc ions, for example. However, these inhibitors tend to be not very specific, and can exhibit toxic effects from binding zinc in a variety of metalloproteins. The presently disclosed subject matter provides for enhanced specificity of tight metal binding moieties by using specificity to the region of the metalloprotein in proximity to the metal binding site to allow for better targeting and a reduction in toxicity due to non-specific binding. Similarly, the addition of two moieties with low affinity and/or low specificity can result in an inhibitor with high affinity and/or high specificity. Thus, any combination of "good" and "poor" metal binding moieties can be linked to either "good" or "poor" targeting moieties to result in "good" inhibitors.

In one embodiment, the presently disclosed subject matter provides metallo-oxidoreductase inhibitors comprising a metal binding moiety and a targeting moiety, optionally with linkers. In some embodiments, the metallo-oxidoreductase inhibitor includes a 5-lipoxygenase inhibitor, a 17-alpha hydroxylase inhibitor, an alcohol dehydrogenase inhibitor, an aldosterone synthase inhibitor, an aromatase inhibitor, a cyclooxygenase inhibitor, a heme oxygenase inhibitor, an indoleamine 2,3-dioxygenase inhibitor, a lanosterol demethylase inhibitor, a nitric oxide synthase inhibitor, a retinoic acid hydroxylase inhibitor, a vascular adhesion protein-1 inhibitor, and a xanthine oxidase inhibitor.

The presently disclosed subject matter also includes pharmaceutical compositions comprising a pharmaceutical carrier and one or more of the presently disclosed metallo oxidoreductase inhibitors, or a prodrug or salt thereof.

In some embodiments, the metal binding moiety is selected from the group consisting of a sulfonyl moiety, a carbonyl moiety, a boronic acid or boronic ester moiety, a sulfur-containing moiety, a nitrogen-containing moiety, a phosphorous-containing moiety, a 5-membered heteroaromatic ring having one heteroatom, a 5-membered aromatic ring having two heteroatoms, a 5-membered heteroaromatic ring having three heteroatoms, a 5-membered heteroaromatic ring having four heteroatoms, a 5-membered heteroaromatic ring having five heteroatoms, a 5-membered saturated or partially unsaturated heteroalkyl ring having one heteroatom, a 5-membered saturated or partially unsaturated heteroalkyl ring having two heteroatoms, a six-membered aromatic ring, a 6-membered heteroaromatic ring having one heteroatom, a 6-membered aromatic ring having two heteroatoms, a 6-membered heteroaromatic ring having three heteroatoms, a 6-membered heteroaromatic ring having four heteroatoms, a 6-membered unsaturated or partially saturated heteroalkyl ring having one heteroatom, and a 6-membered unsaturated or partially saturated heteroalkyl ring having two heteroatoms, with the proviso that certain combinations of metal binding moieties, targeting moieties, and optional linkers are excluded from the presently disclosed subject matter.

In an additional aspect, the presently disclosed subject matter provides a method for screening for inhibitors of metallo-oxidoreductases, the method including (a) providing a candidate inhibitor comprising: (i) a targeting moiety; (ii) a metal binding moiety; and (iii) an optional linker; (b) contacting the inhibitor candidate with a metallo-oxidoreductase; and (c) determining the activity of the metallo-oxidoreductase. In some embodiments of the screening method, the targeting moiety comprises a lanosterol or a lanosterol derivative.

In some embodiments, the presently disclosed subject matter provides a method of treating a metallo-oxidoreductase related disorder comprising administering a composition of any of the presently disclosed metallo-oxidoreductase or a prodrug or salt thereof to a patient in need thereof, wherein the disorder is selected from disorders associated with 5-lipoxygenase, 17-alpha hydroxylase, alcohol dehydrogenase, aldosterone synthase, aromatase, cyclooxygenase, heme oxygenase, indoleamine 2,3-dioxygenase, lanosterol demethylase, nitric oxide synthase, retinoic acid hydroxylase, vascular adhesion protein-1, and xanthine oxidase.

In an additional aspect, the presently disclosed subject matter provides a method of inhibiting a metallo-oxidoreductase, the method including contacting a metallo-oxidoreductase with a presently disclosed inhibitor, wherein the metallo-oxidoreductase is selected from the group consisting of 5-lipoxygenase, 17-alpha hydroxylase, alcohol dehydrogenase, aldosterone synthase, aromatase, cyclooxygenase, heme oxygenase, indoleamine 2,3-dioxygenase, lanosterol demethylase, nitric oxide synthase, retinoic acid hydroxylase, vascular adhesion protein-1, and xanthine oxidase.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Having thus described the presently disclosed subject matter in general terms, reference will now be made to the accompanying Drawings, which are not necessarily drawn to scale, and wherein:

FIGS. 1-15B depict representative metal binding moieties and derivatives thereof including attachment points to the presently disclosed targeting moieties. In each of FIGS. 1-15B, R represents the attachment of the targeting moiety, with an optional linker as described herein. X represents optional individually selected substitution groups, as outlined herein. Z is a heteroatom selected from the group of oxygen, nitrogen, e.g., NH or N-alkyl, and sulfur. As will be appreciated by those in the art, in some cases, the X groups are hydrogen and are generally not depicted. In addition, when non-hydrogen X substitution groups are used, in general, only one X group is preferred. In some cases, and for all the structures herein, as outlined below, two adjacent X groups can be joined to form cyclic structures (including 1 or more cyclic and/or heterocyclic structures, including cyclic aromatic) structures.

Figure 1:
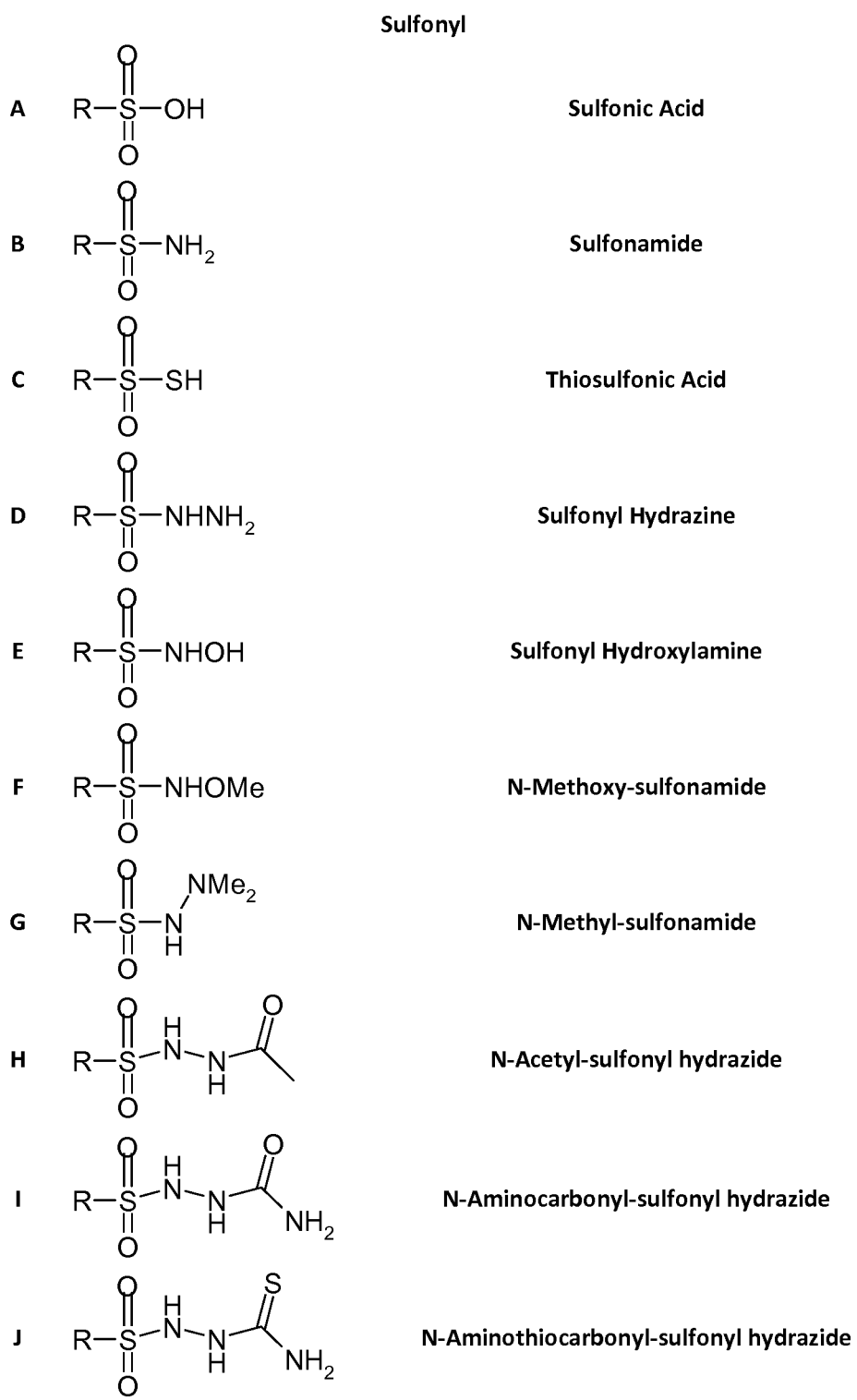
Figure 1:
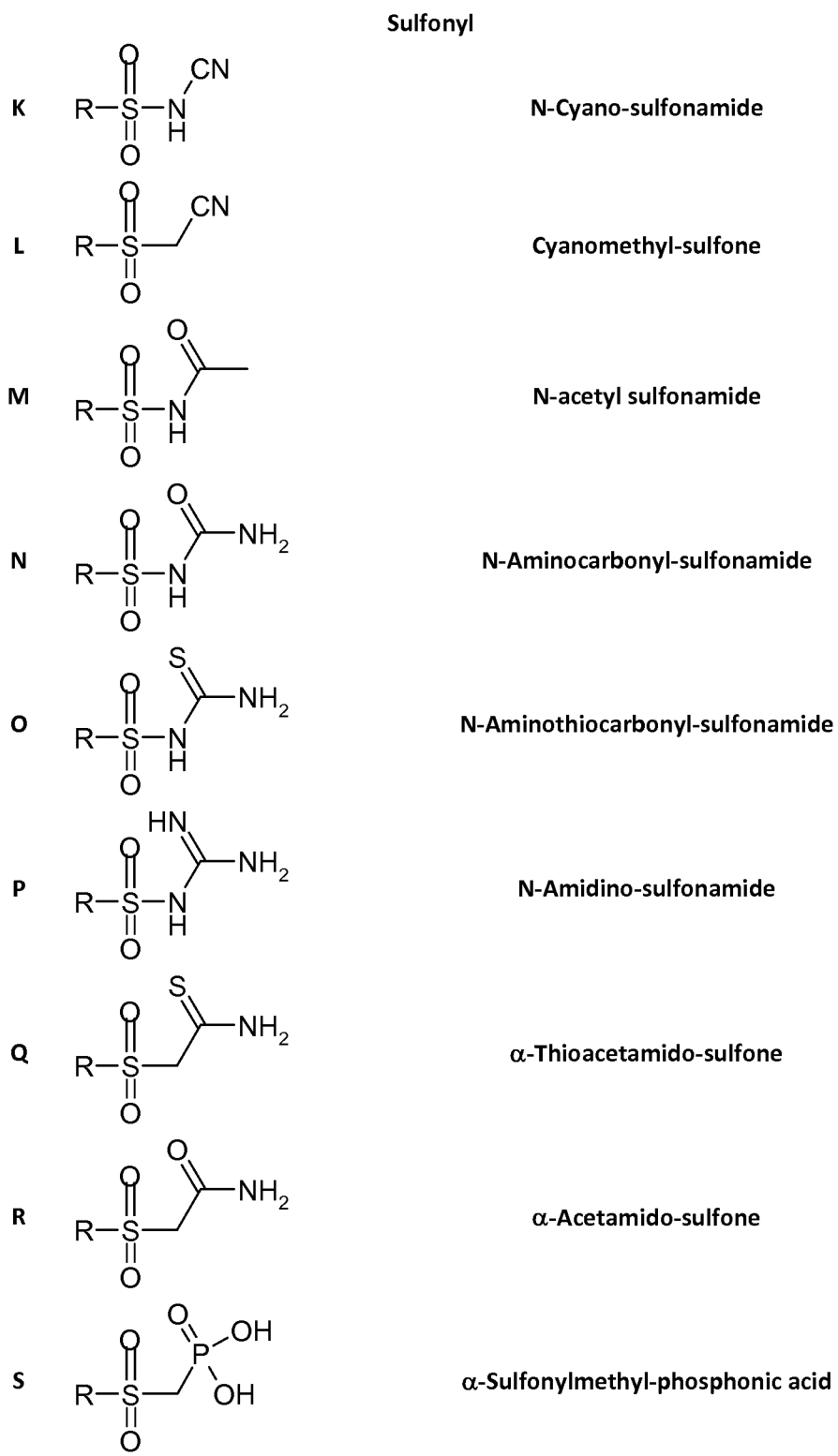
Figure 1:
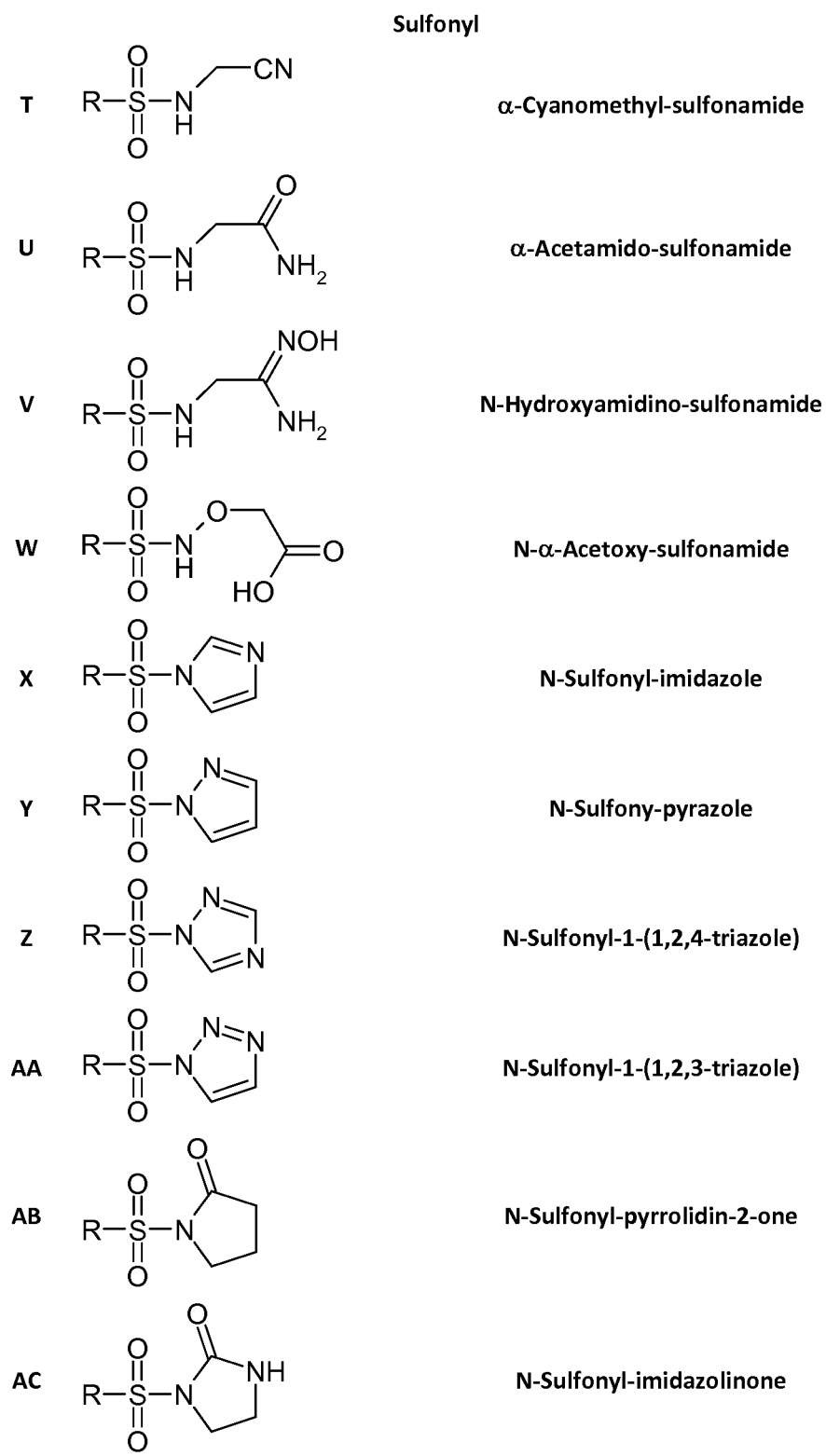
Figure 1:
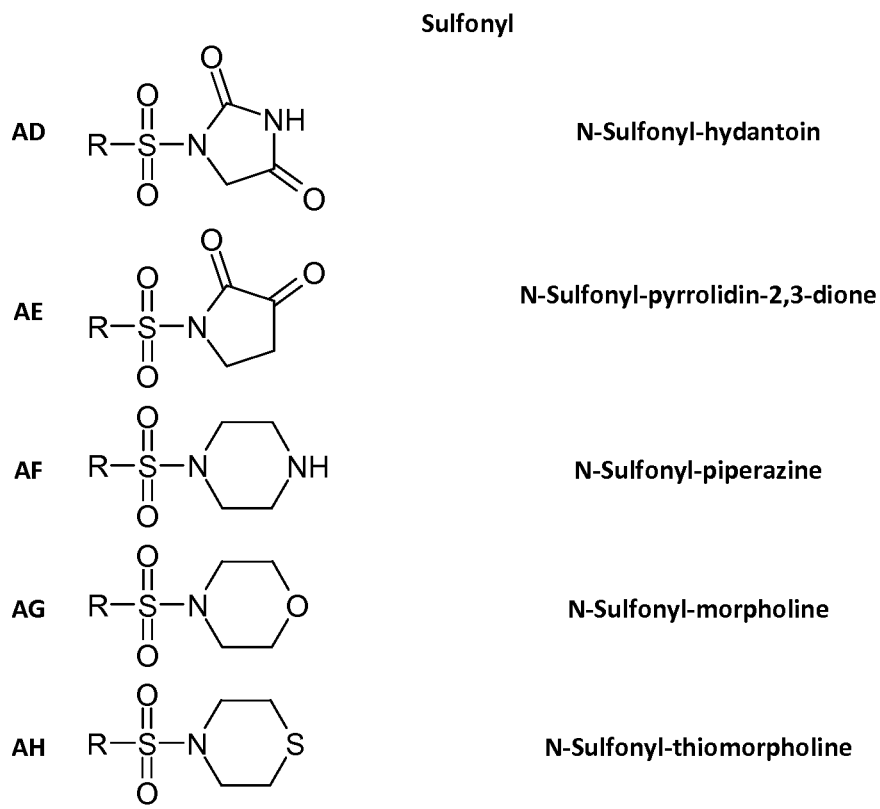
Figure 2:
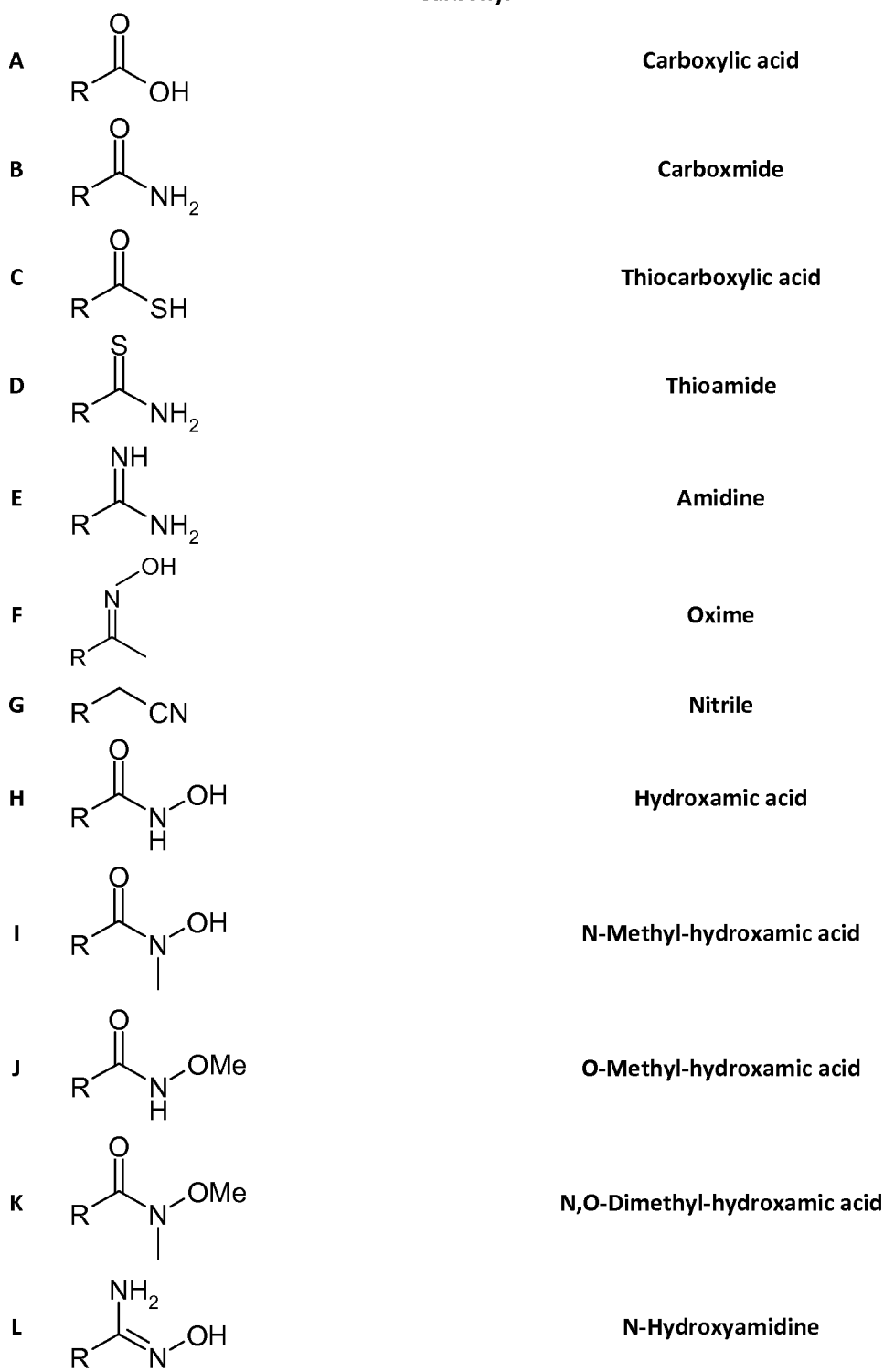
Figure 2:
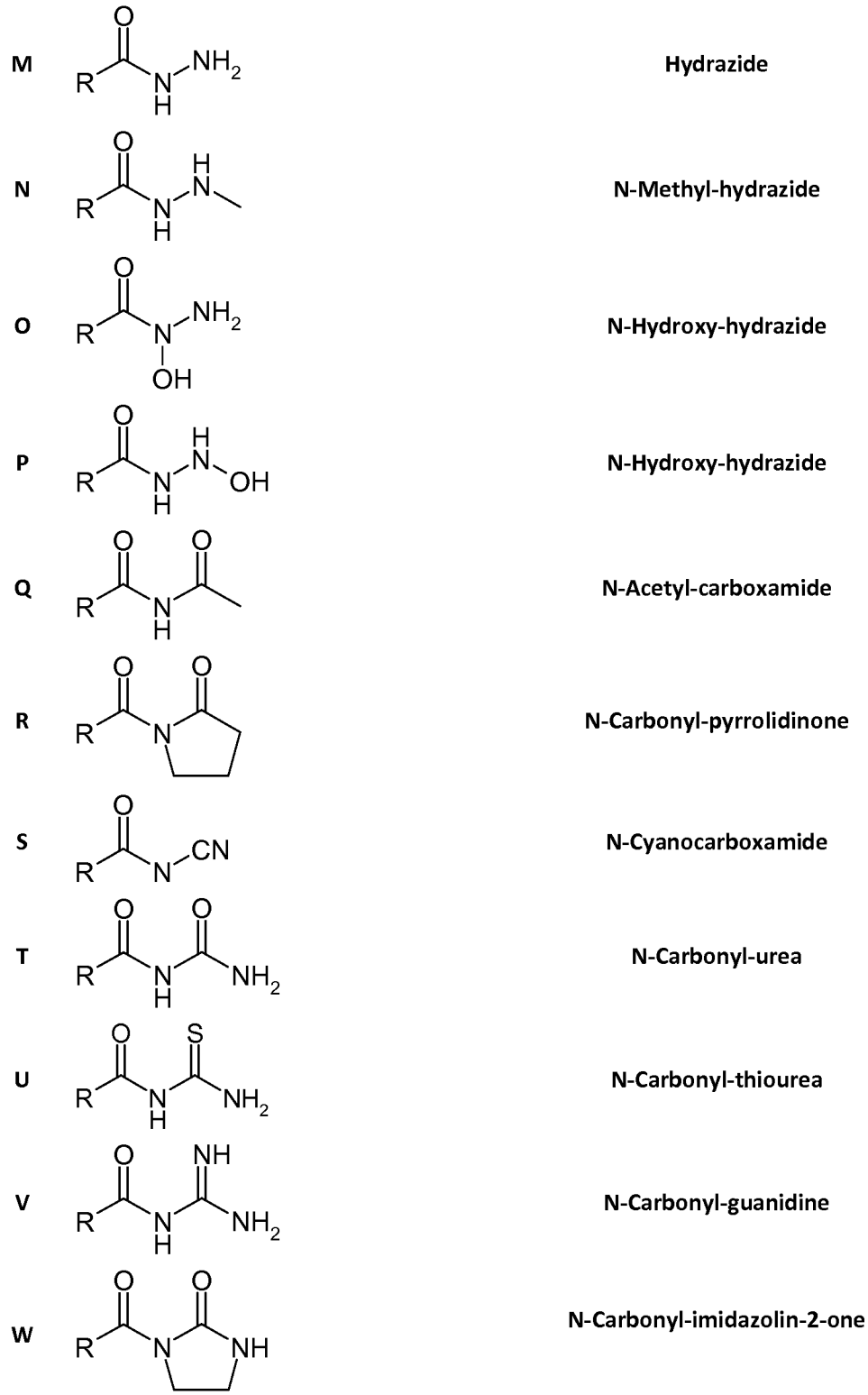
Figure 2:
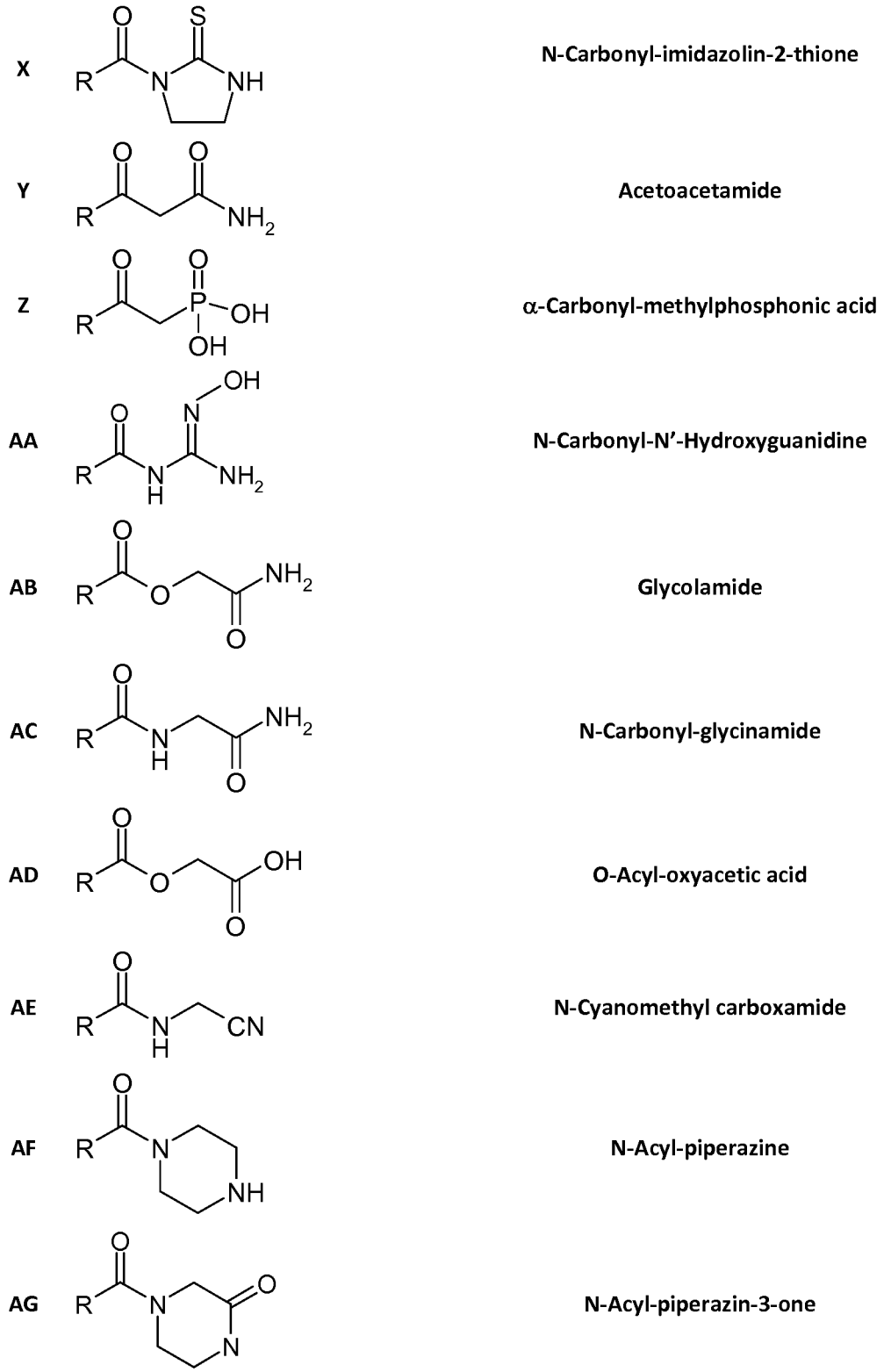
Figure 2:
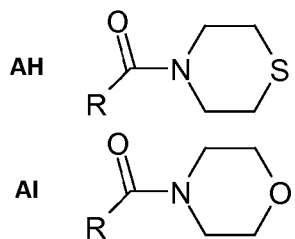
Figure 3:
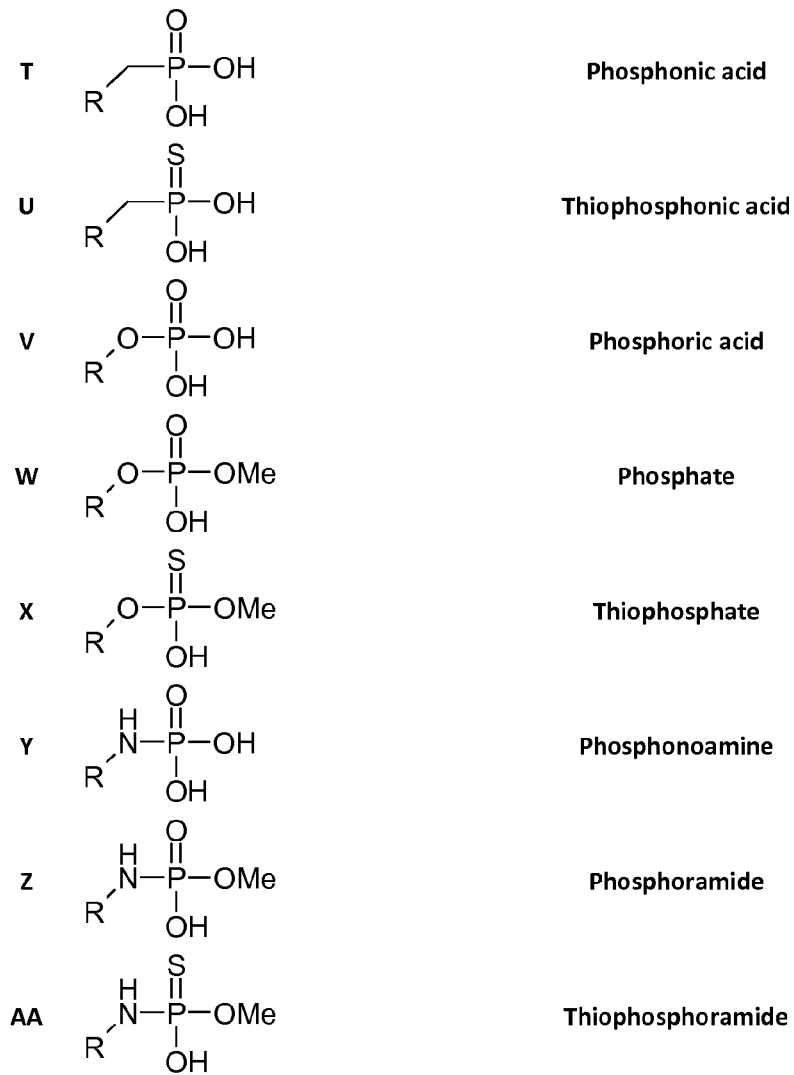
Figure 4:
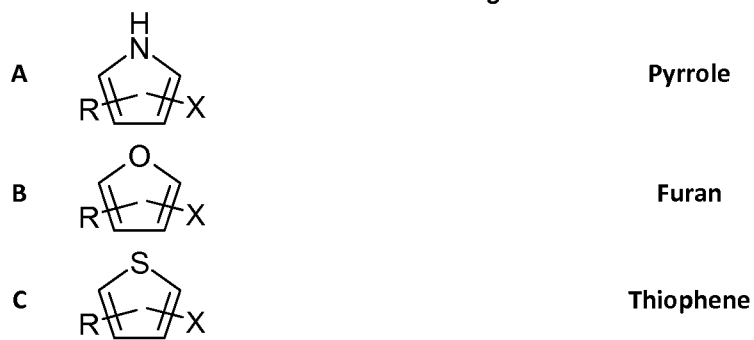
Figure 6:
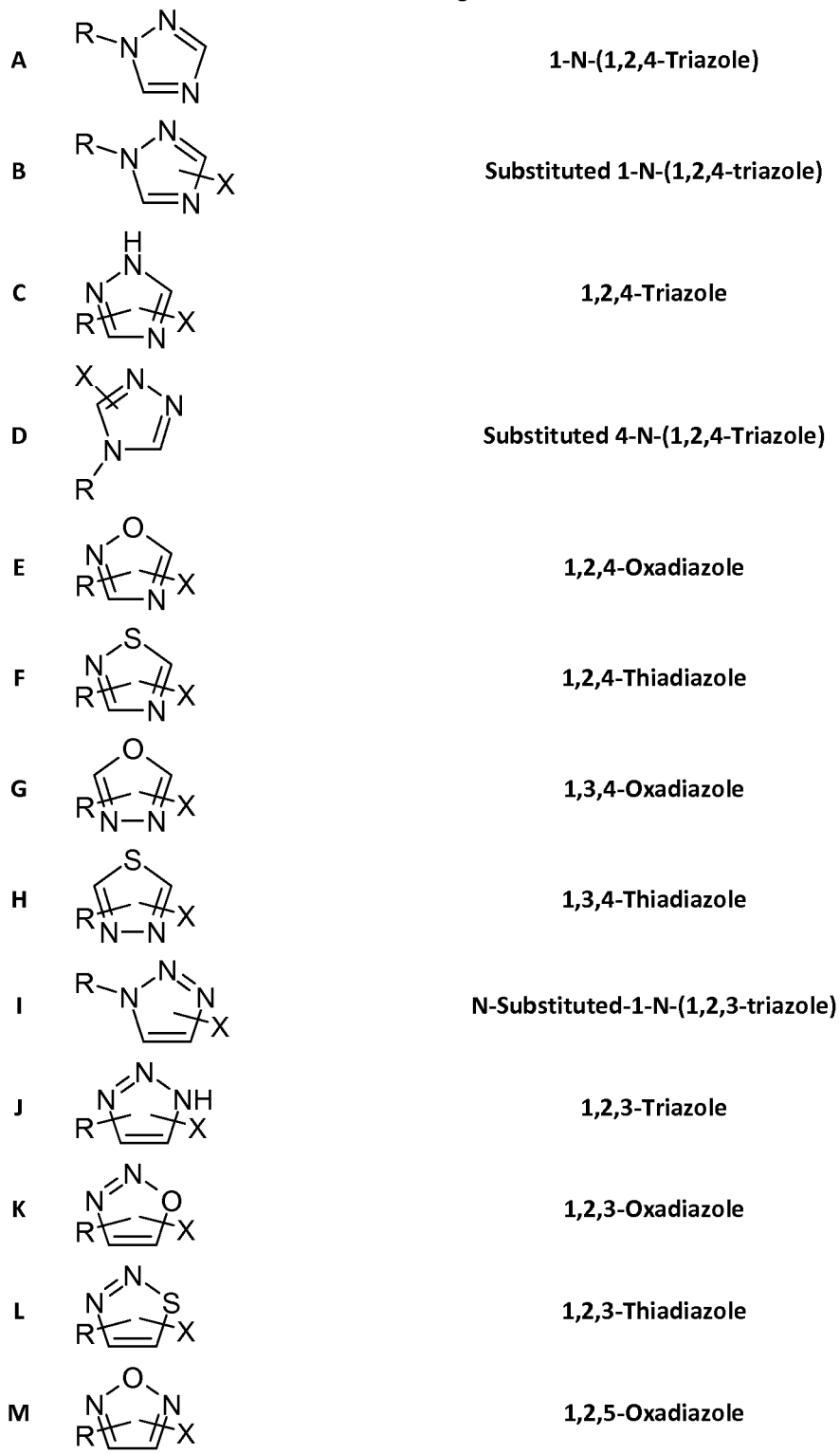
Figure 7:
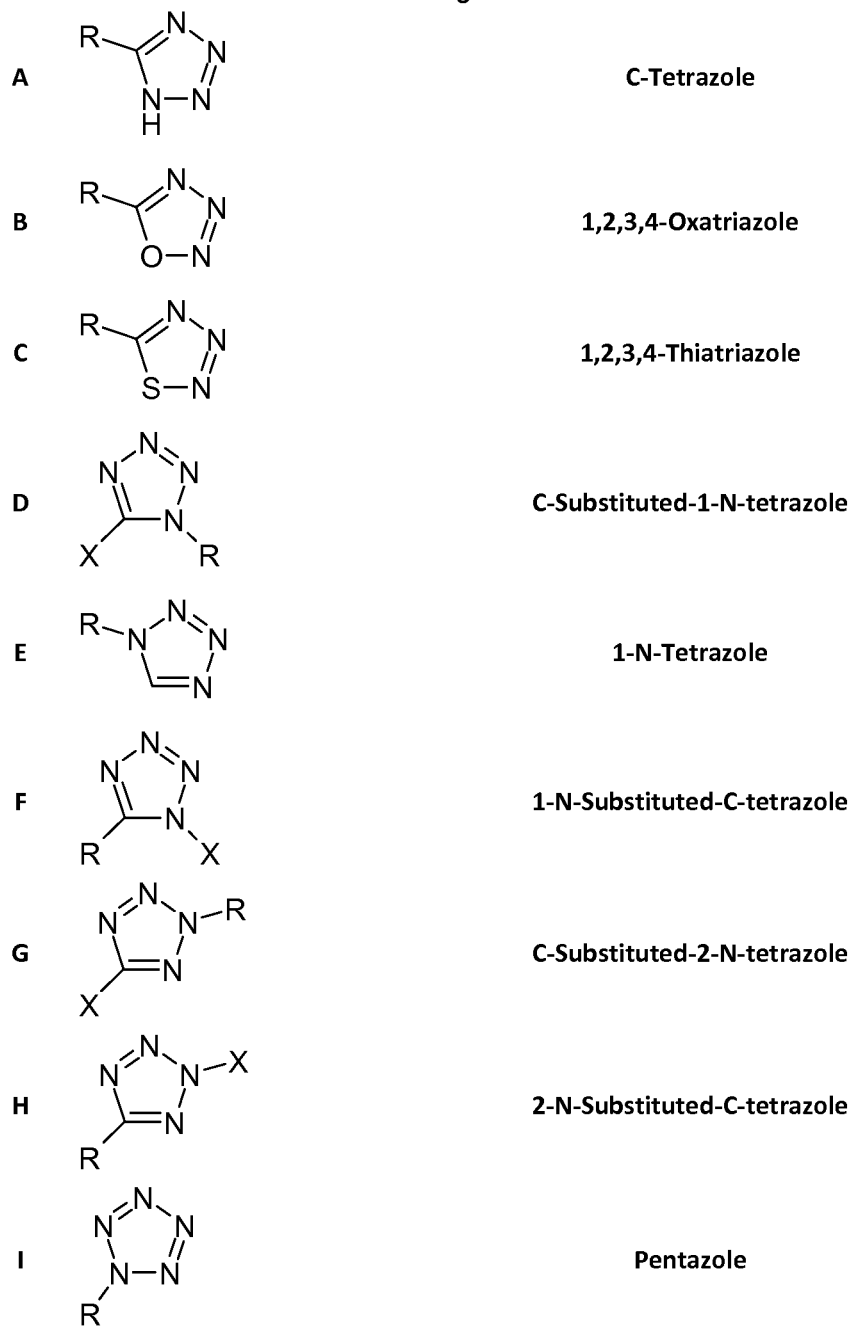
Figure 8:
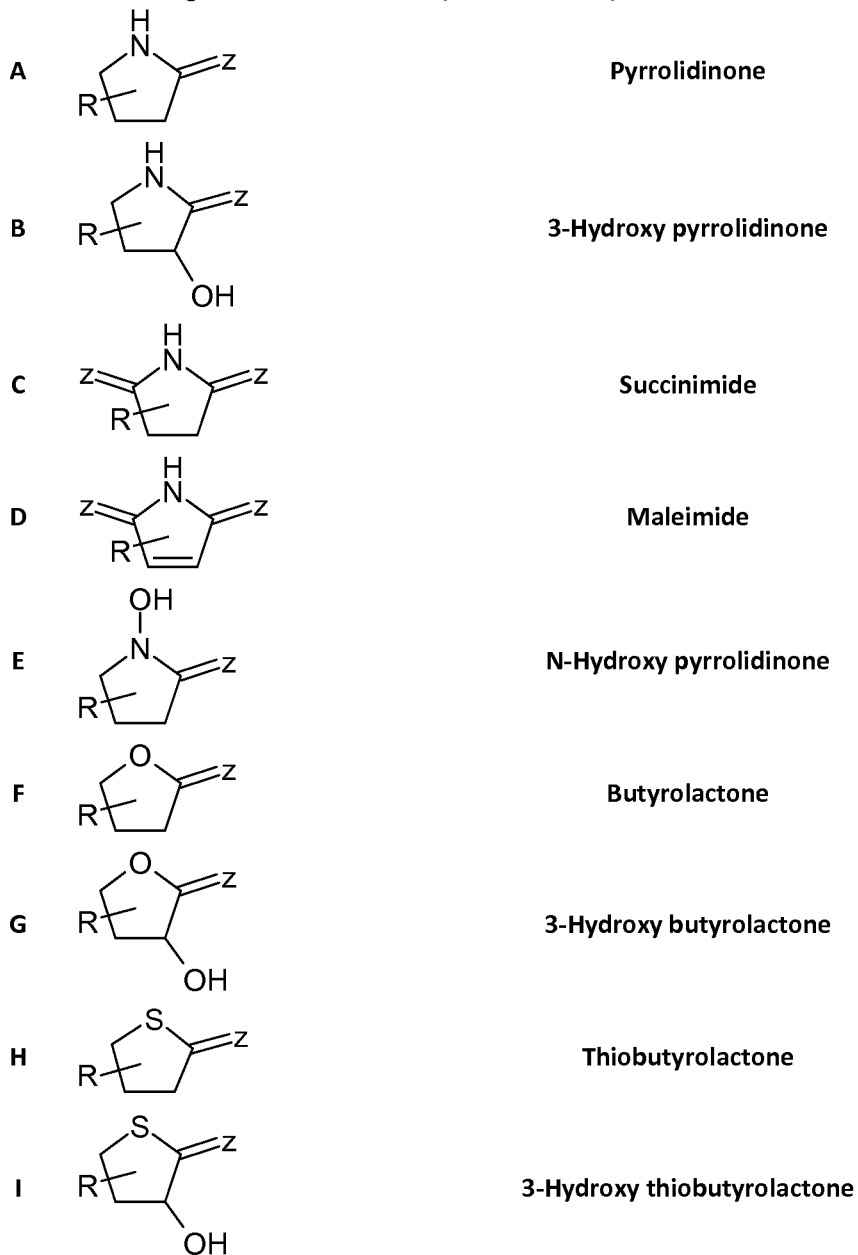
Figure 9:
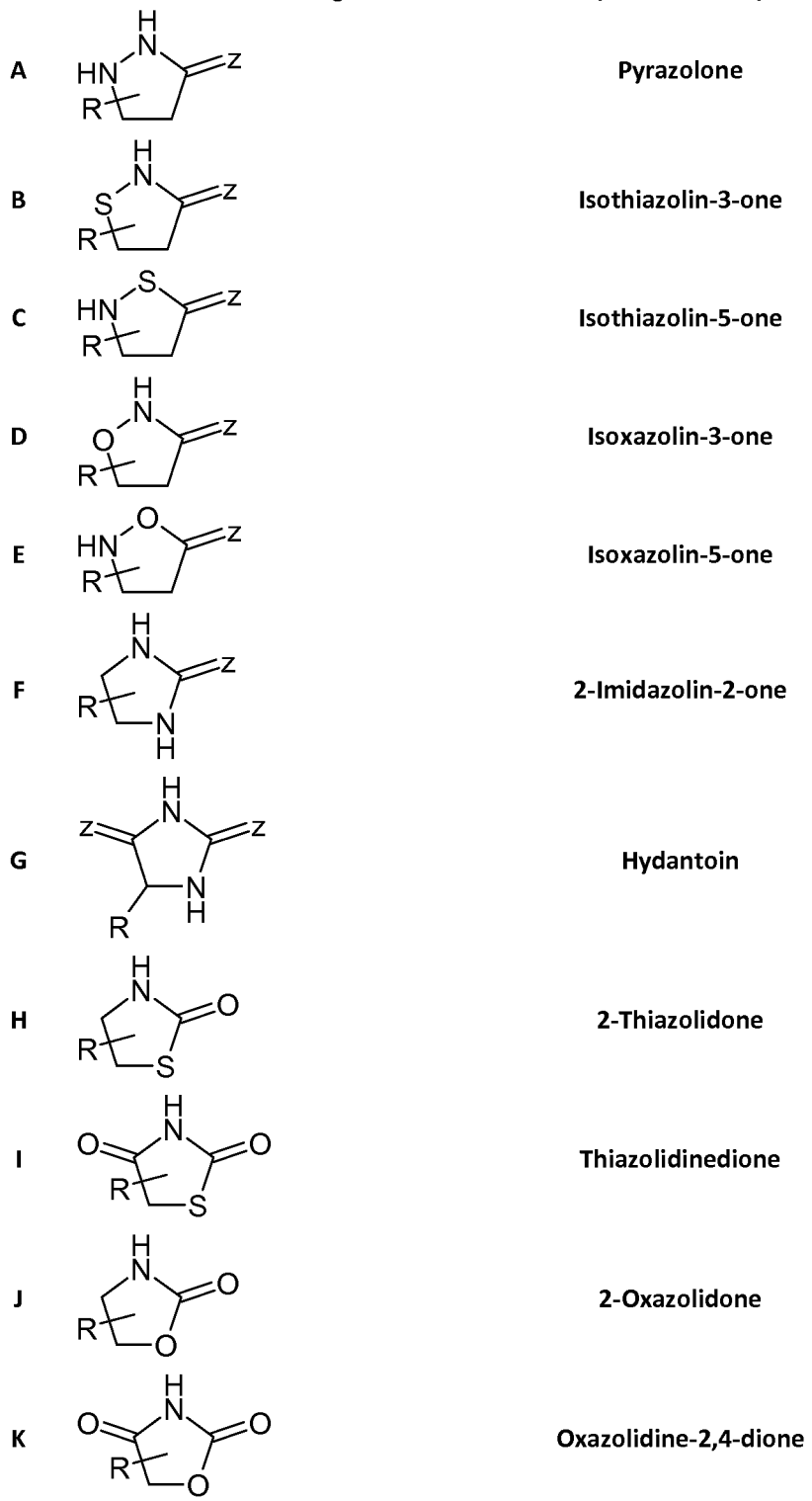
Figure 10:
Figure 11:
Figure 12:
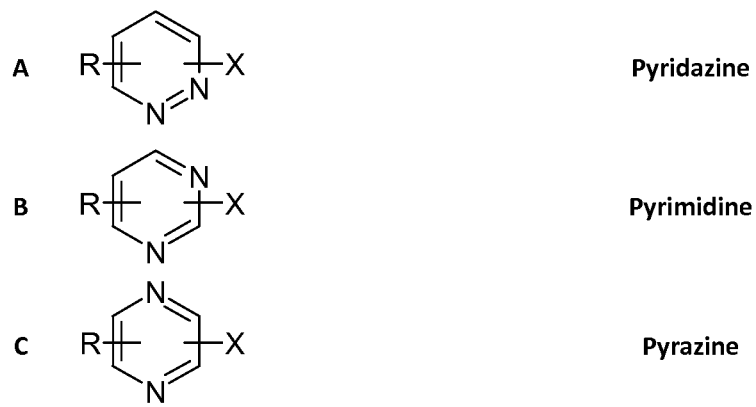
Figure 13:
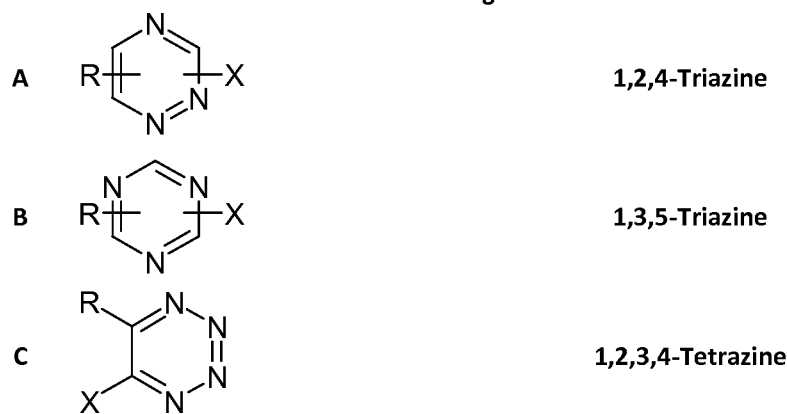
Figure 14:
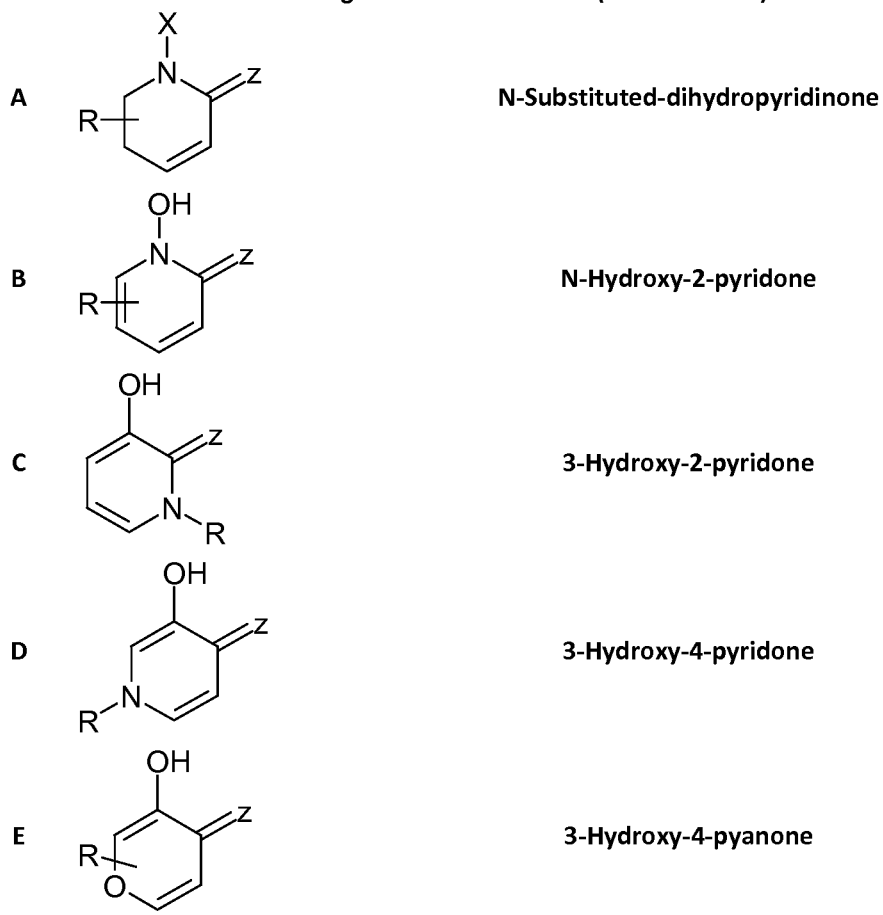

For all classes of metal binding moieties recited herein, the presently disclosed subject matter can include or exclude any member of the class individually; for example, the depiction of the sulfonyl-based metal binding moieties in FIG. 1 can, in some embodiments, exclude any member; e.g., "sulfonyl-based metal binding moieties except sulfonamide." Each member can be specifically and independently included or excluded.

FIGS. 1A-1AH depict sulfonyl-based metal binding moieties.

FIGS. 2A-2AI depict carbonyl-based metal binding moieties.

FIGS. 3A-3AA depict various metal binding moieties of the presently disclosed subject matter. FIGS. 3A-B depict boronic acid-based metal binding moieties. FIGS. 3C-E depict sulfur-based metal binding moieties. FIGS. 3F-3S depict nitrogen-based metal binding moieties. FIGS. 3T to 3AA depict phosphorus-based metal binding moieties.

FIGS. 4A-C depict metal binding moieties based on 5-membered aromatic heterocycles having one heteroatom, wherein R and X are as described herein.

FIGS. 5A-5I depict metal binding moieties based on 5-membered aromatic heterocycles having two heteroatoms, wherein R and X are as described herein.

FIGS. 6A-6O depict metal binding moieties based on 5-membered aromatic heterocycles having three heteroatoms, wherein R and X are as described herein.

FIGS. 7A-7I depict metal binding moieties based on 5-membered aromatic heterocycles having four or five heteroatoms, wherein R and X are as described herein.

FIGS. 8A-8I depict metal-binding moieties based on 5-membered non-aromatic rings having one heteroatom, wherein R and X are as described herein.

FIGS. 9A-9K depict metal-binding moieties based on 5-membered non-aromatic rings having two heteroatoms, wherein R and X are as described herein.

FIG. 10A depicts metal binding moieties based on 6-membered aromatic heterocycles having no heteroatoms, wherein R and X are as described herein.

FIG. 11A depicts metal binding moieties based on 6-membered aromatic heterocycles having one heteroatom, wherein R and X are as described herein.

FIGS. 12A-12C depict metal binding moieties based on 6-membered aromatic heterocycles having two heteroatoms, wherein R and X are as described herein.

FIGS. 13A-13C depict metal binding moieties based on 6-membered aromatic heterocycles having three or four heteroatoms, wherein R and X are as described herein.

FIGS. 14A-14E depict metal binding moieties based on 6-membered non-aromatic rings having one heteroatom, wherein R and X are as described herein.

Figure 15A:
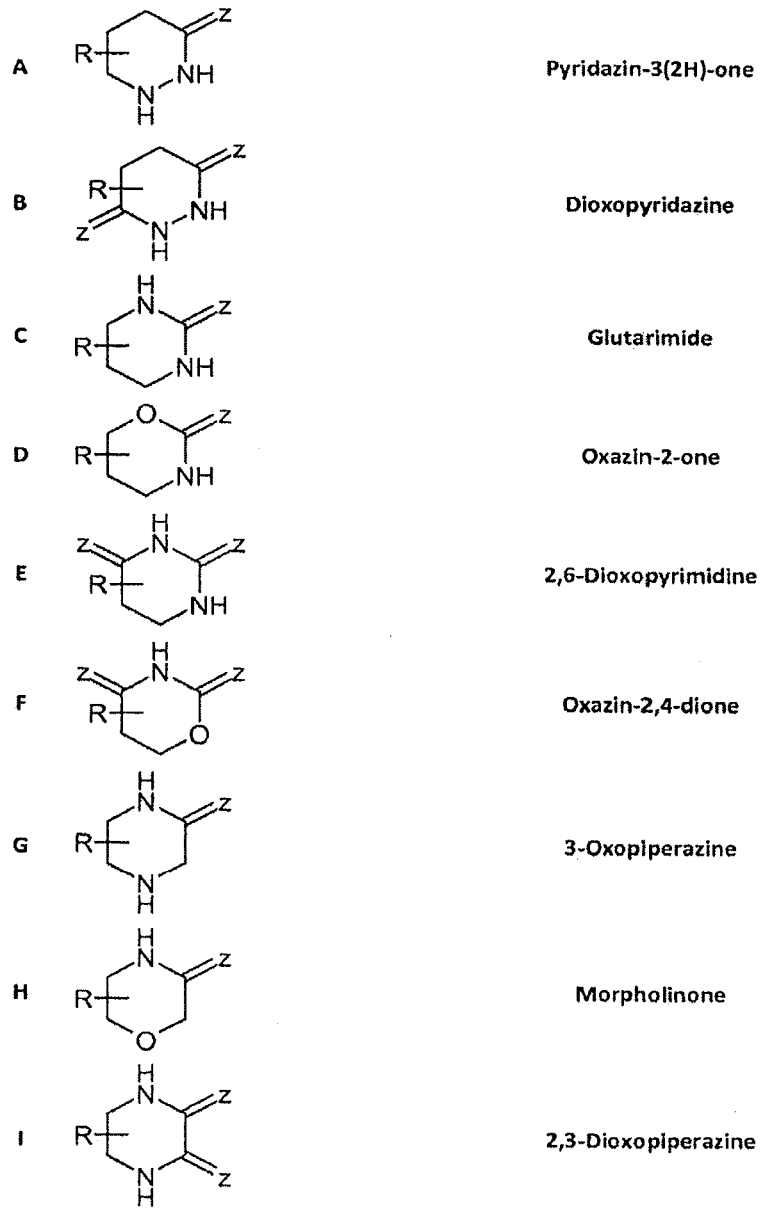
Figure 15B:
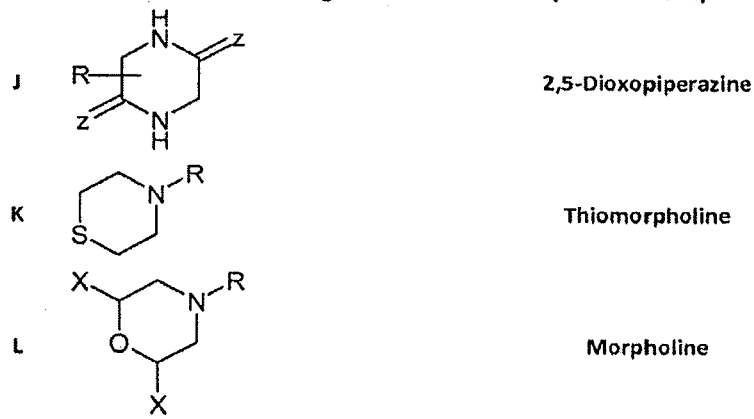

FIGS. 15A-15-L depict metal binding moieties based on 6-membered non-aromatic rings having two heteroatoms, wherein R and X are as described herein.

Figure 16A:
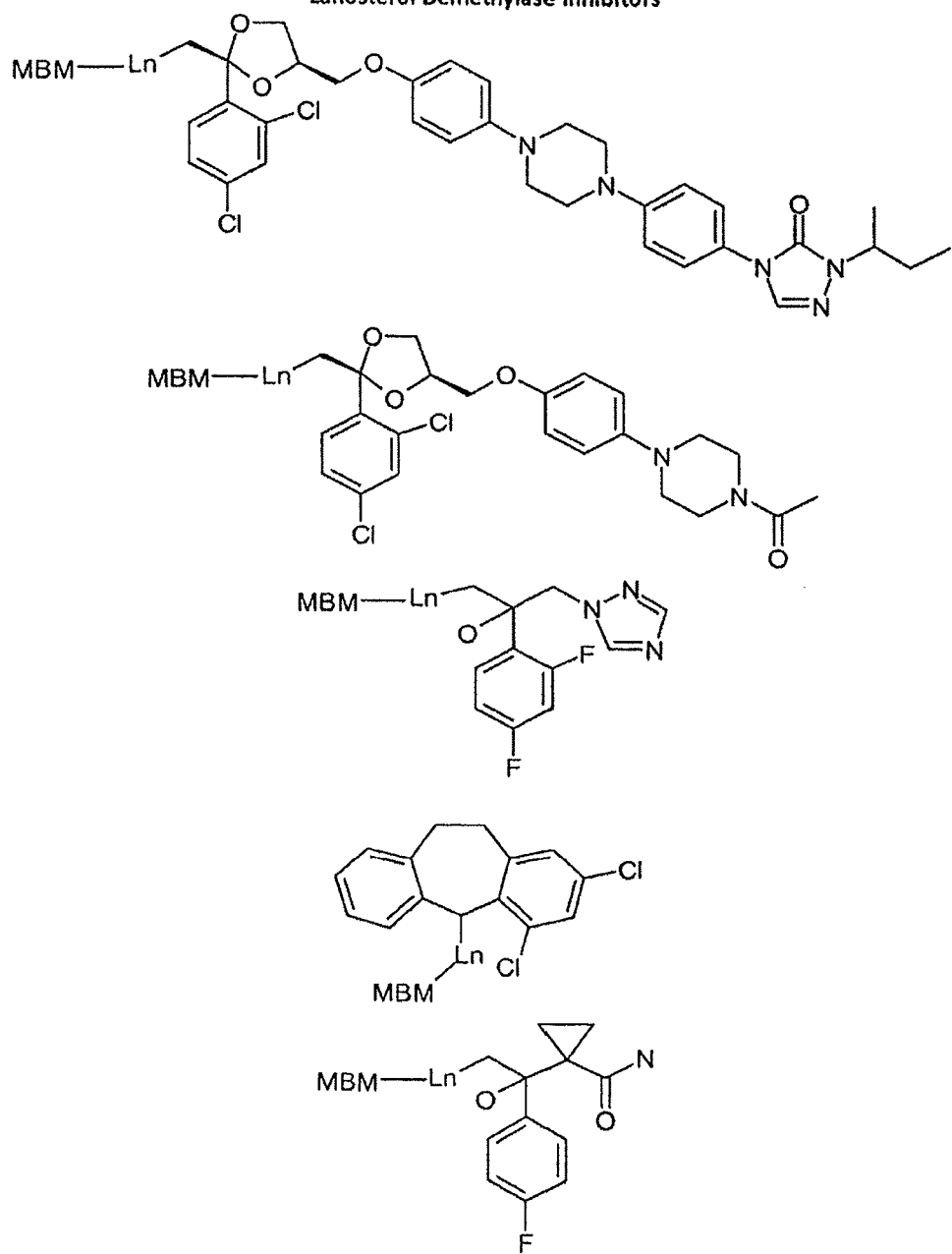
Figure 16B:
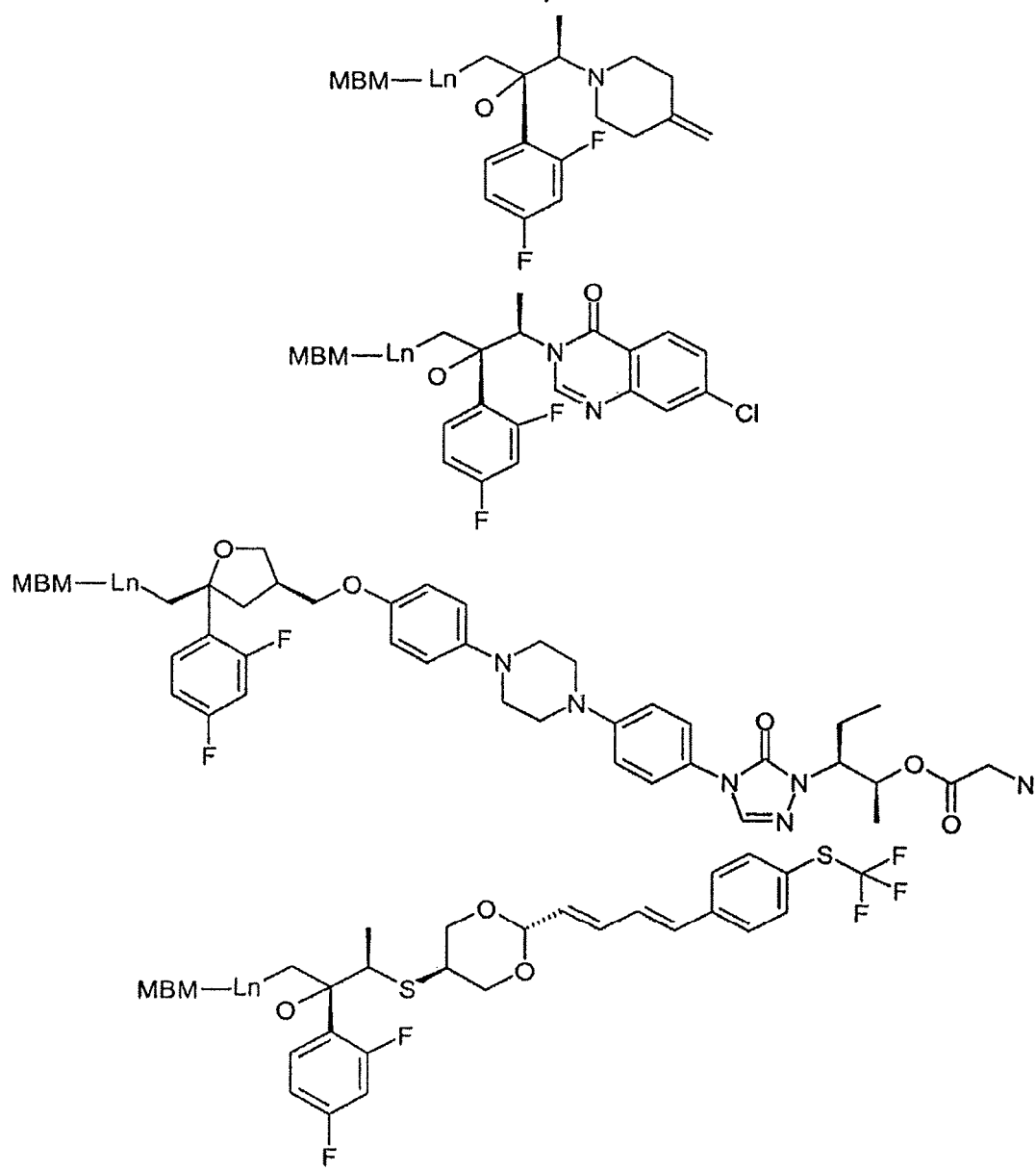
Figure 16C:
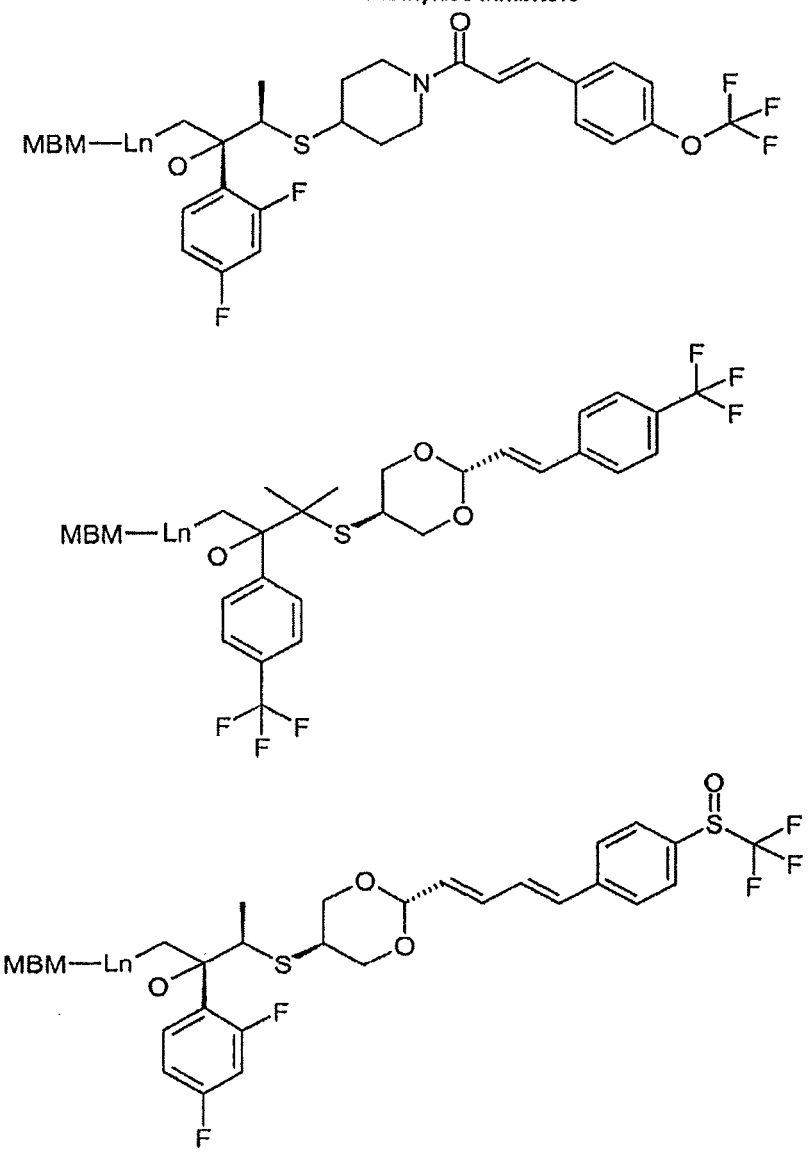
Figure 16D:
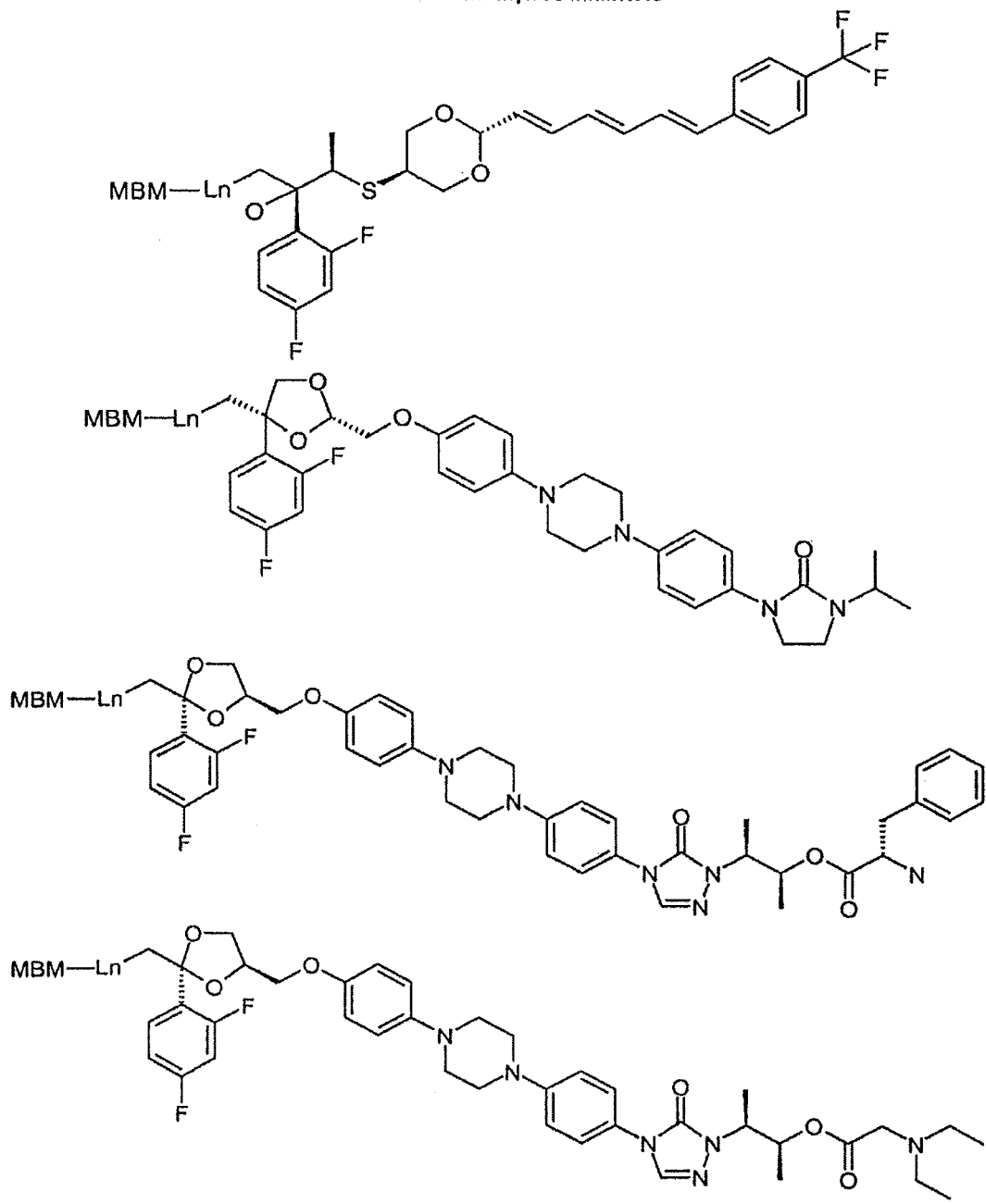
Figure 16E:
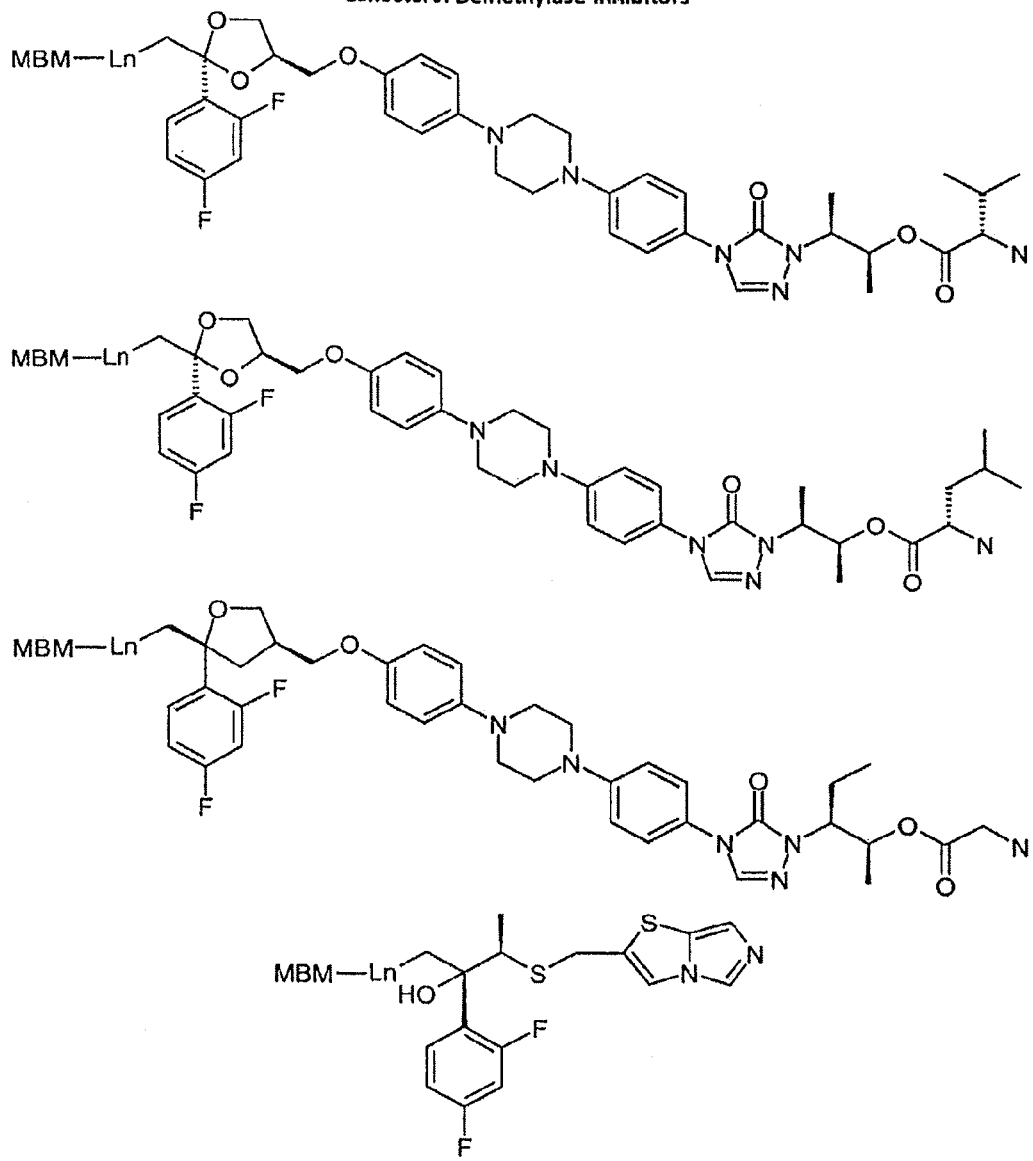
Figure 16F:
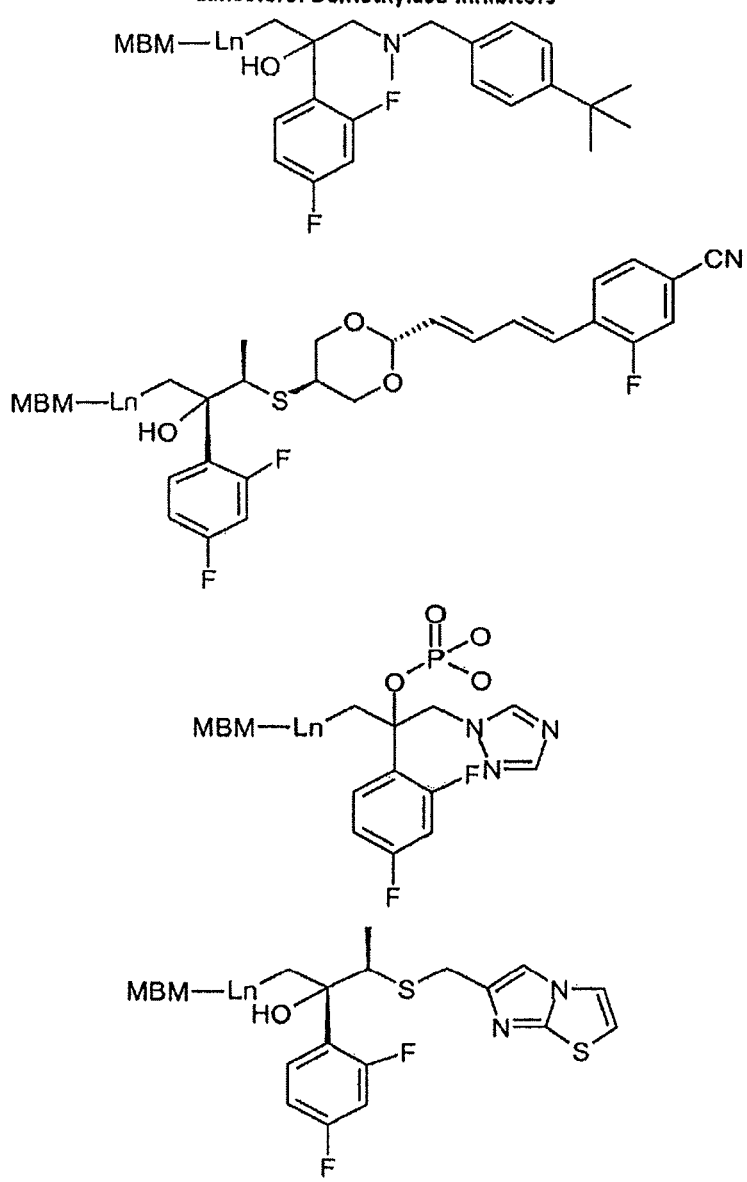
Figure 16G:
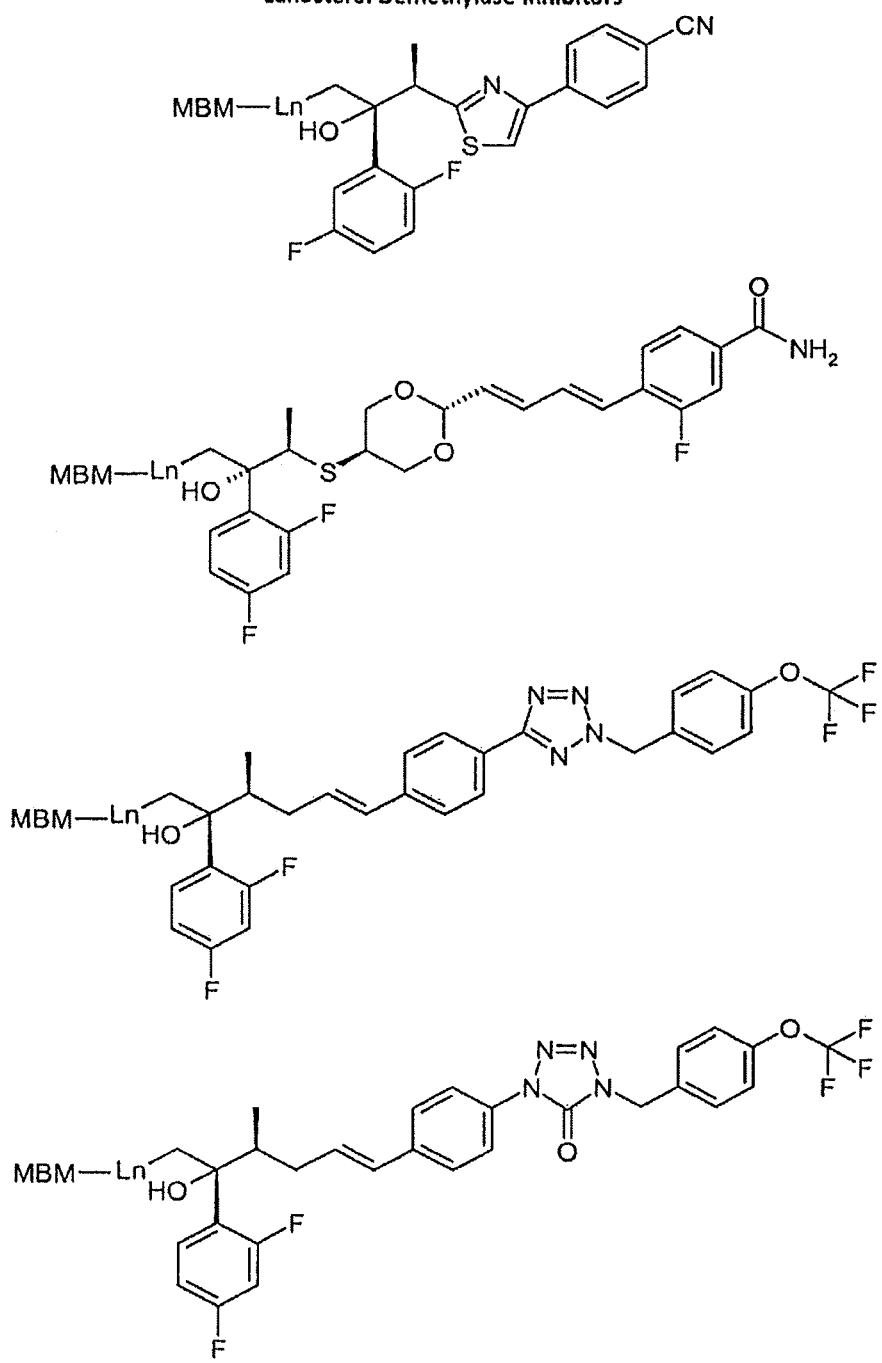
Figure 16H:
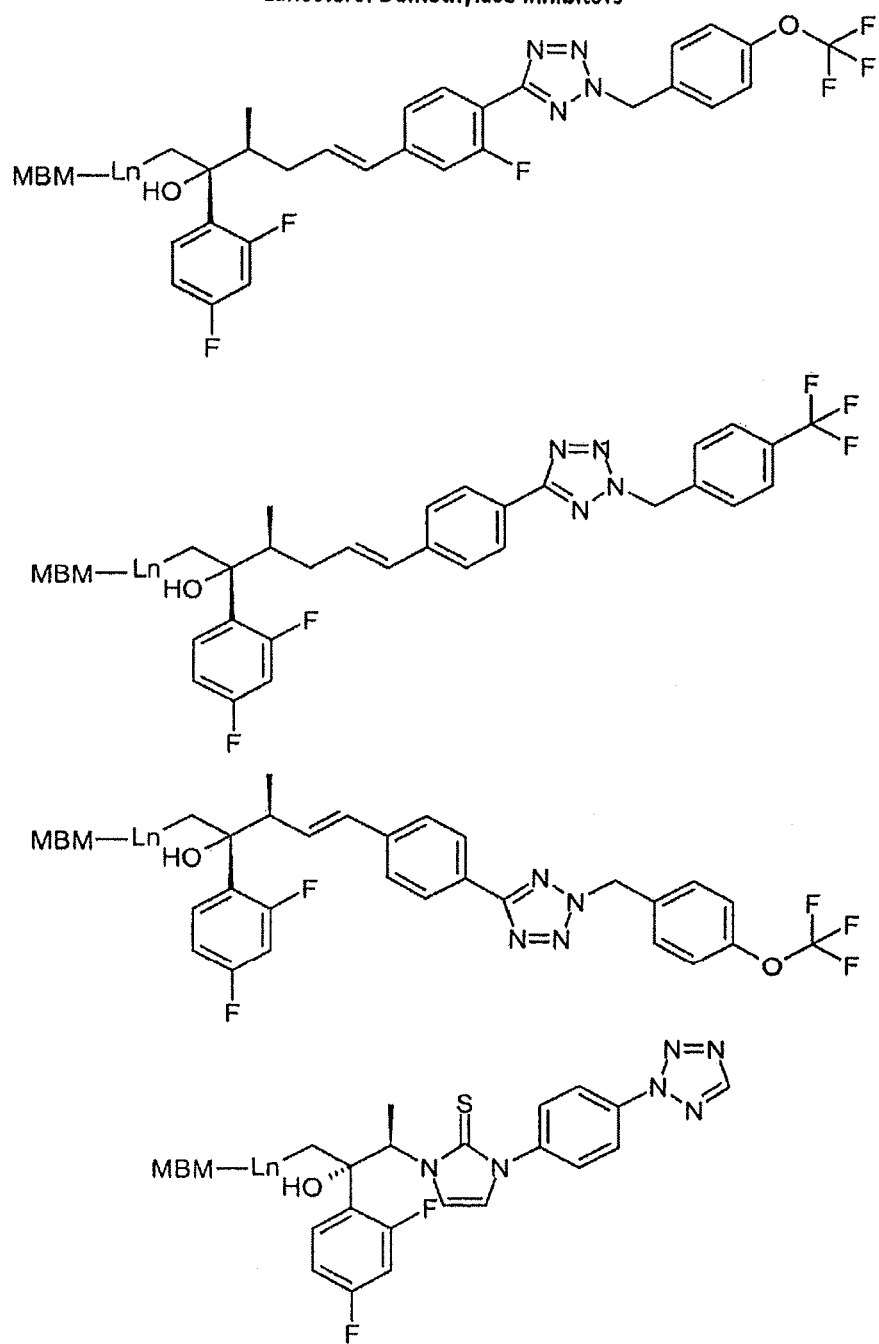
Figure 16I:
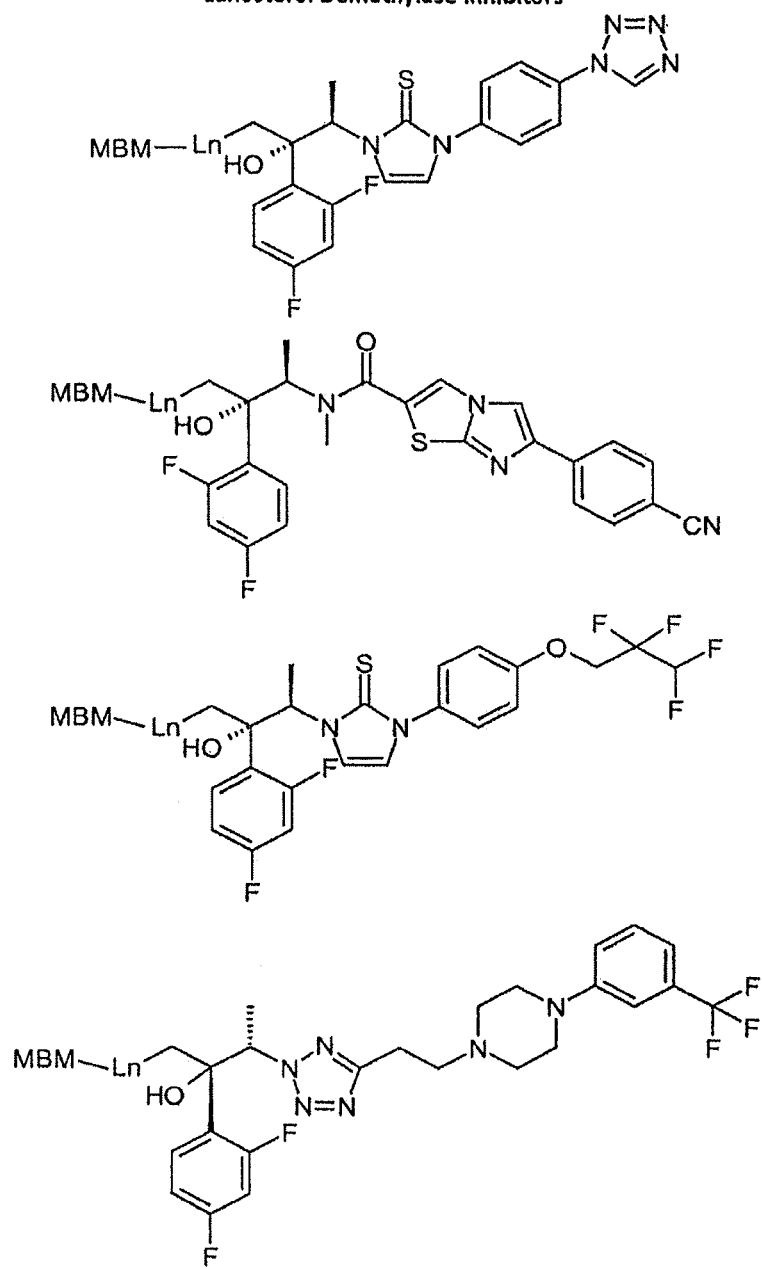
Figure 16J:
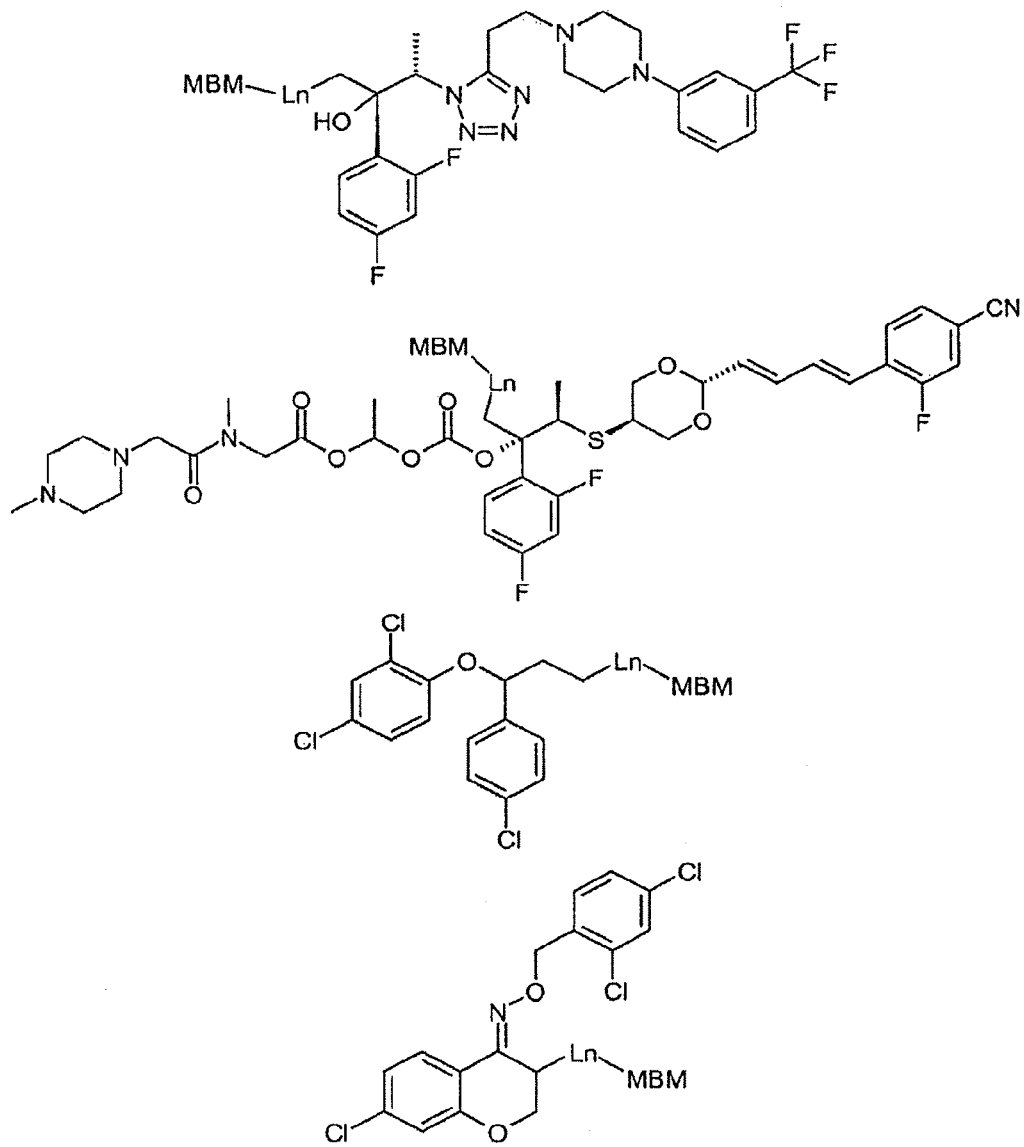
Figure 16K:
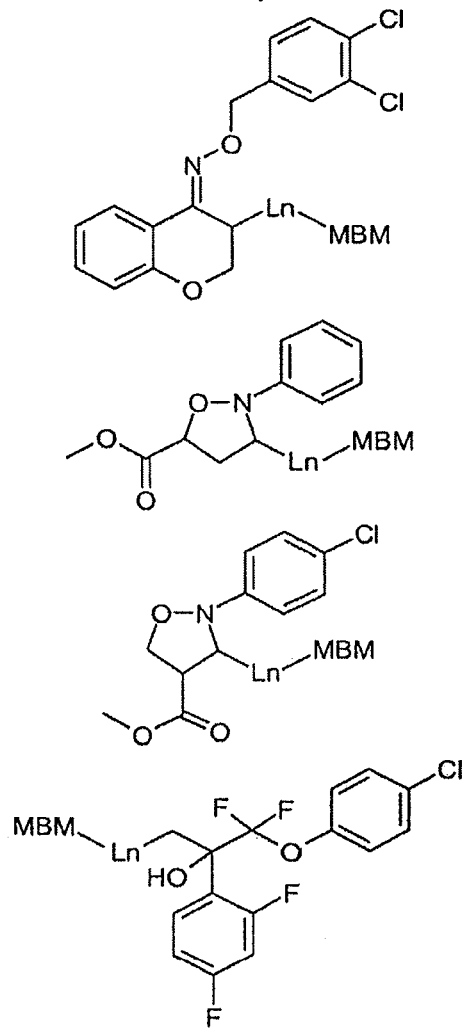
Figure 16L:
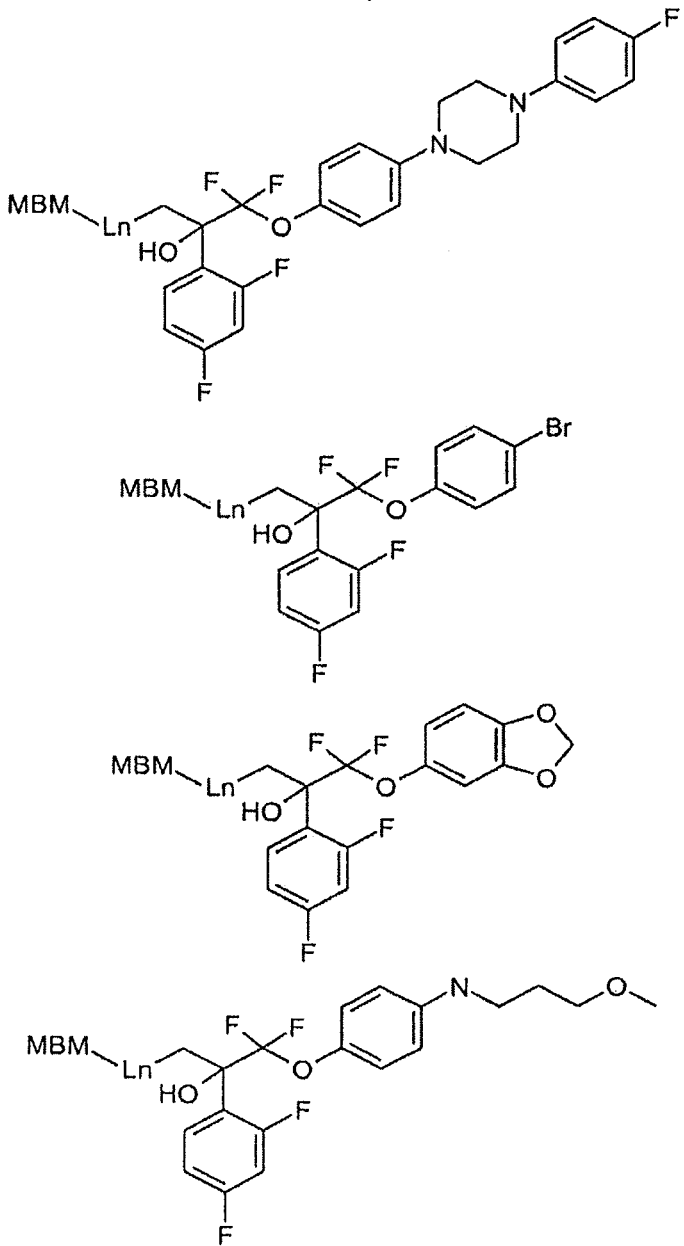
Figure 16M:
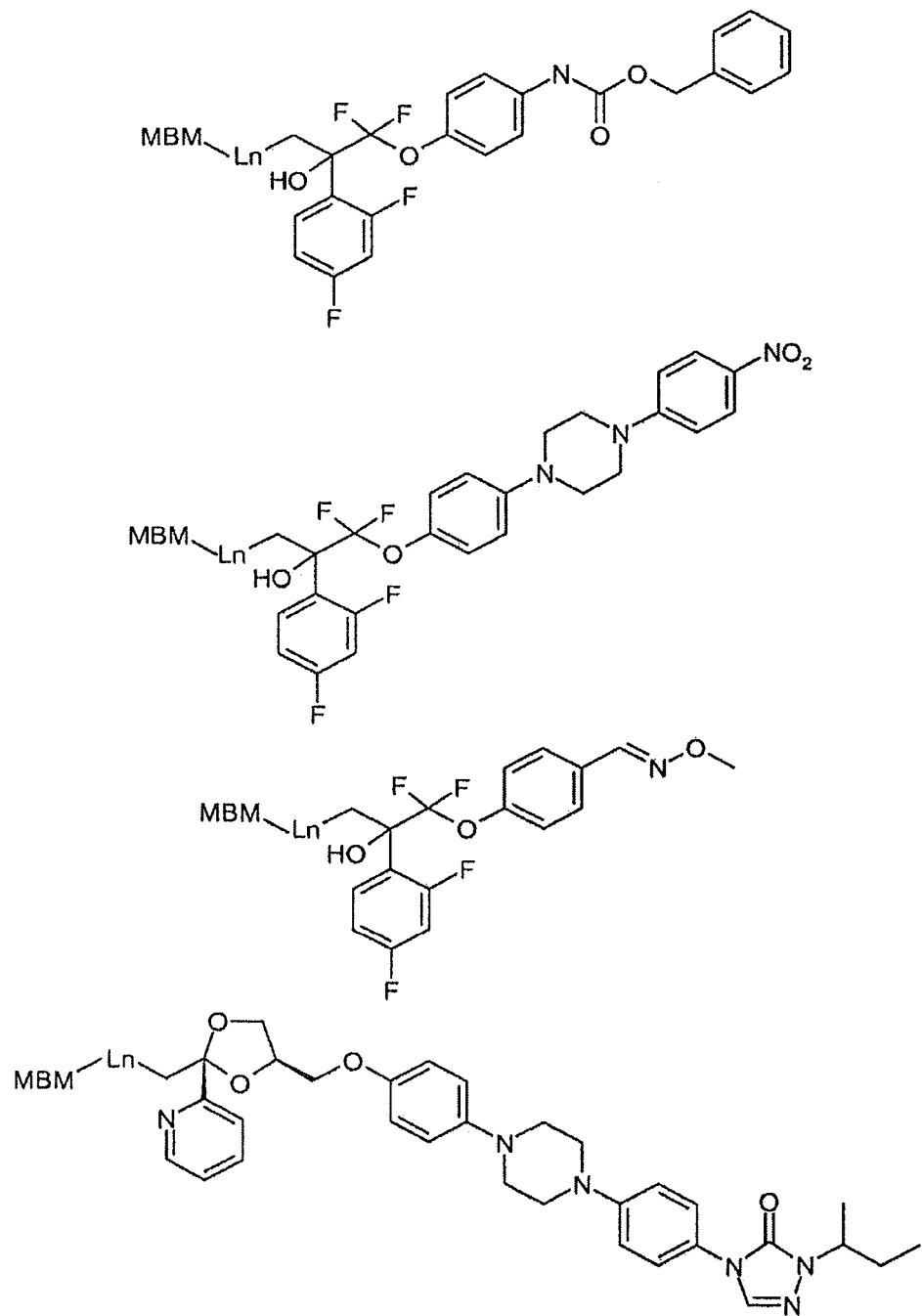
Figure 16N:
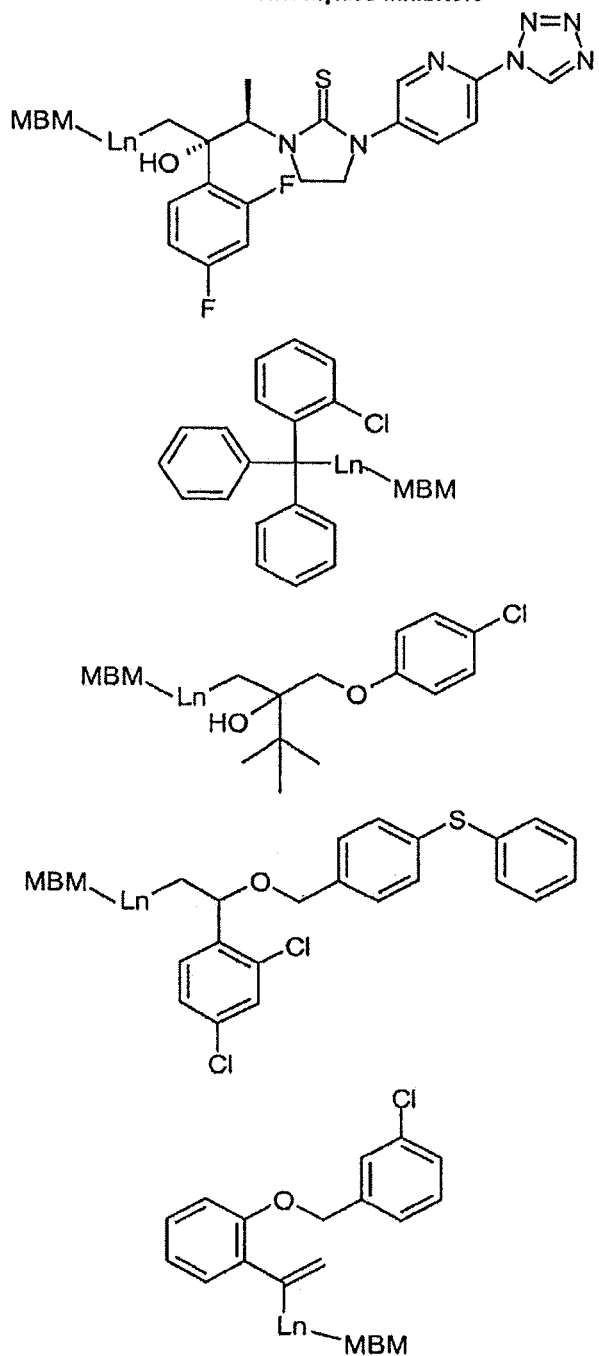
Figure 16P:
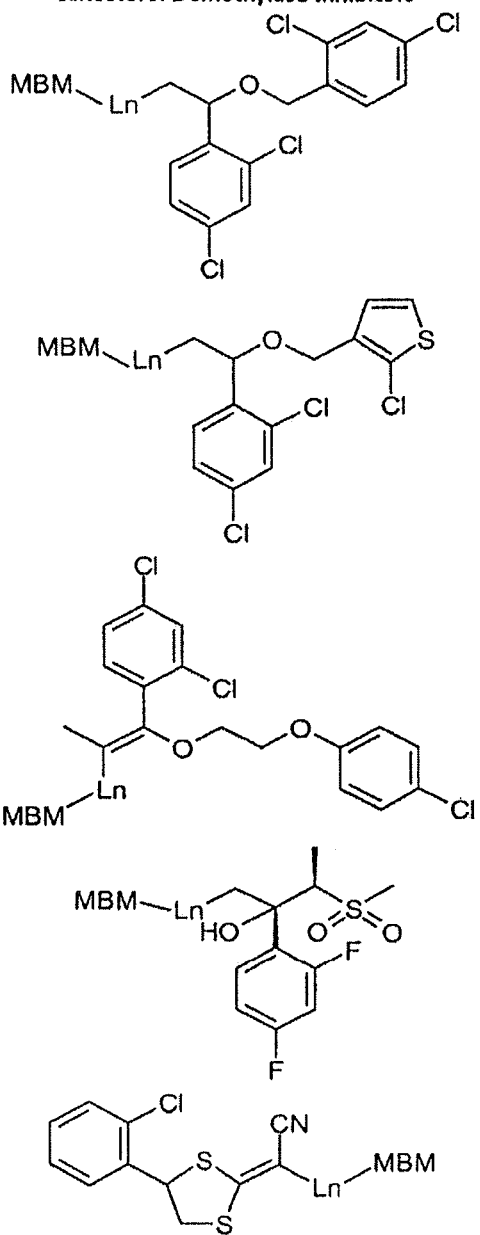
Figure 16Q:
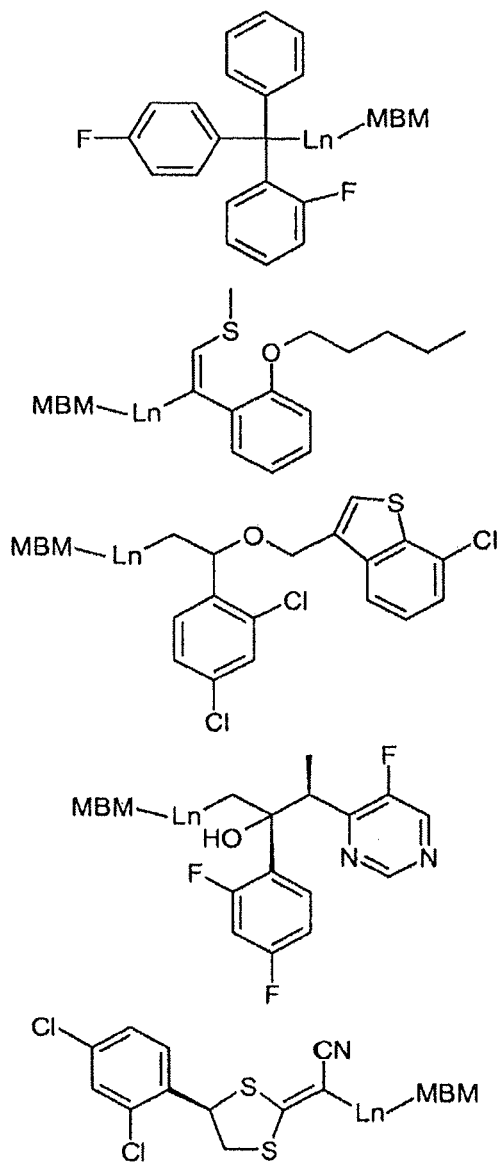
Figure 16R:
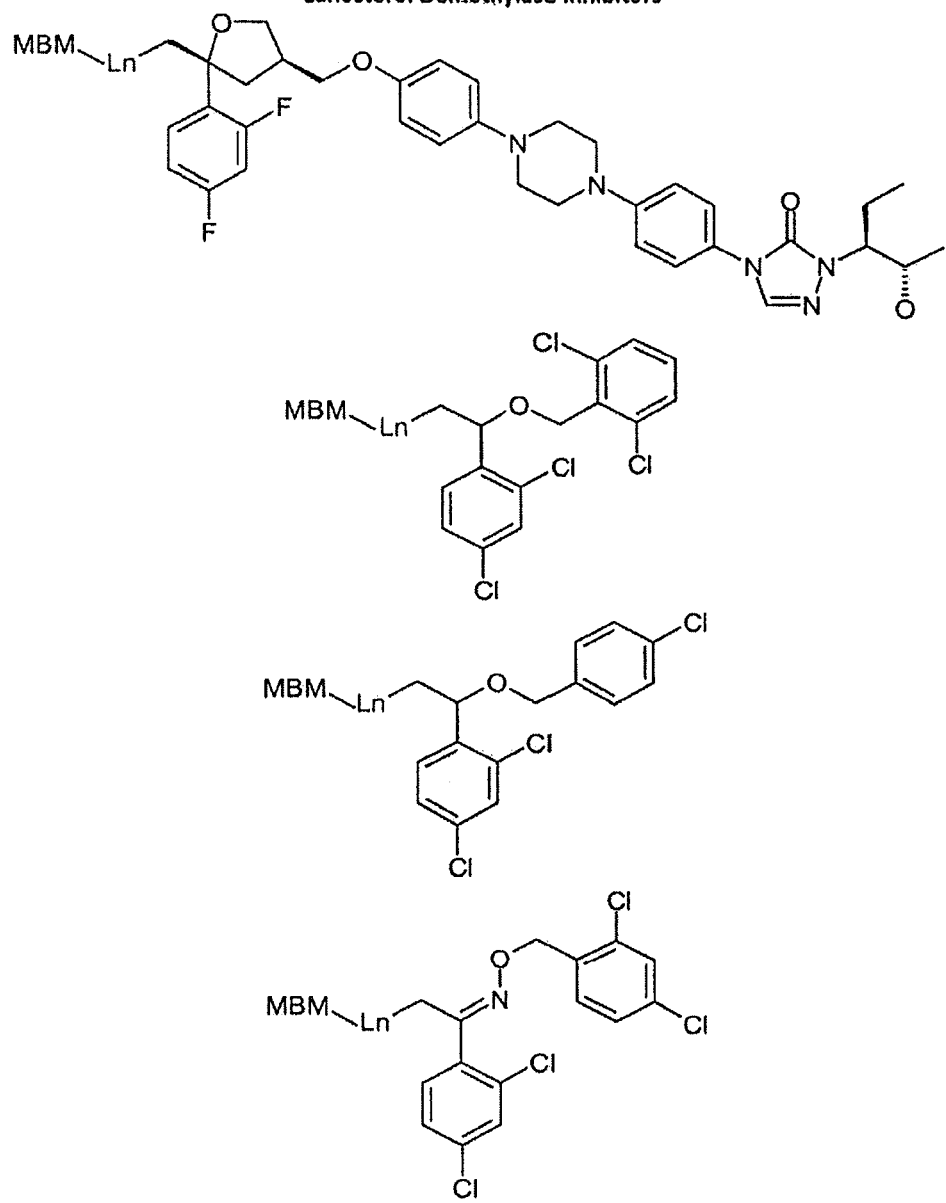
Figure 16S:
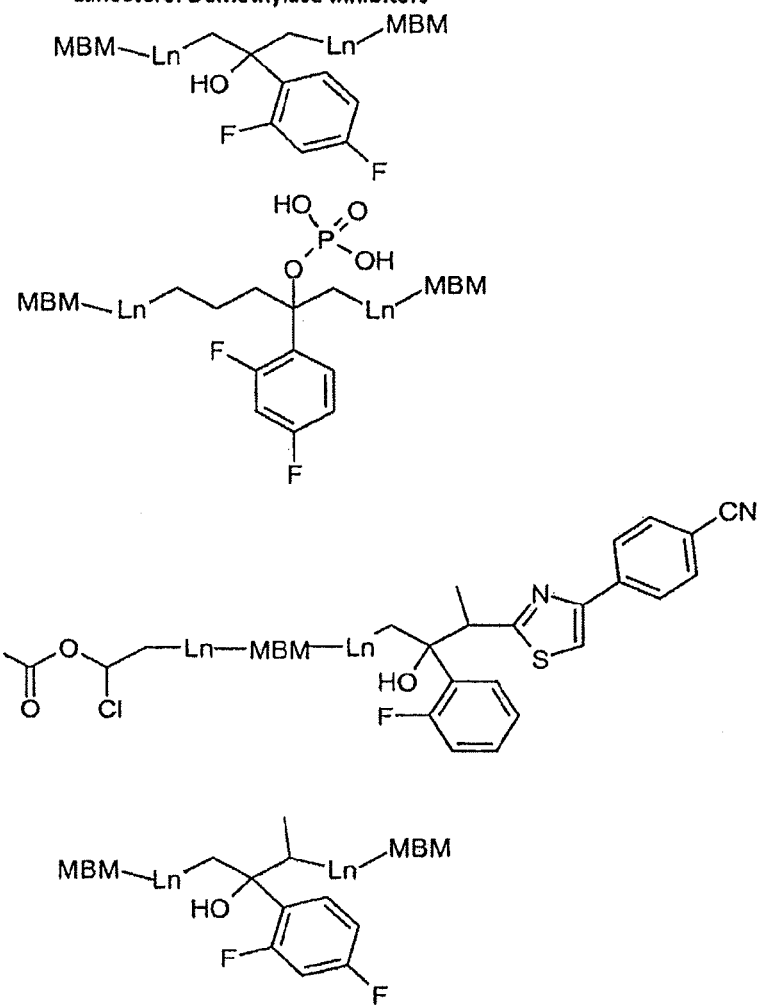

FIG. 16A-16S depicts structures useful as targeting moieties for lanosterol demethylase.

Figure 17A:
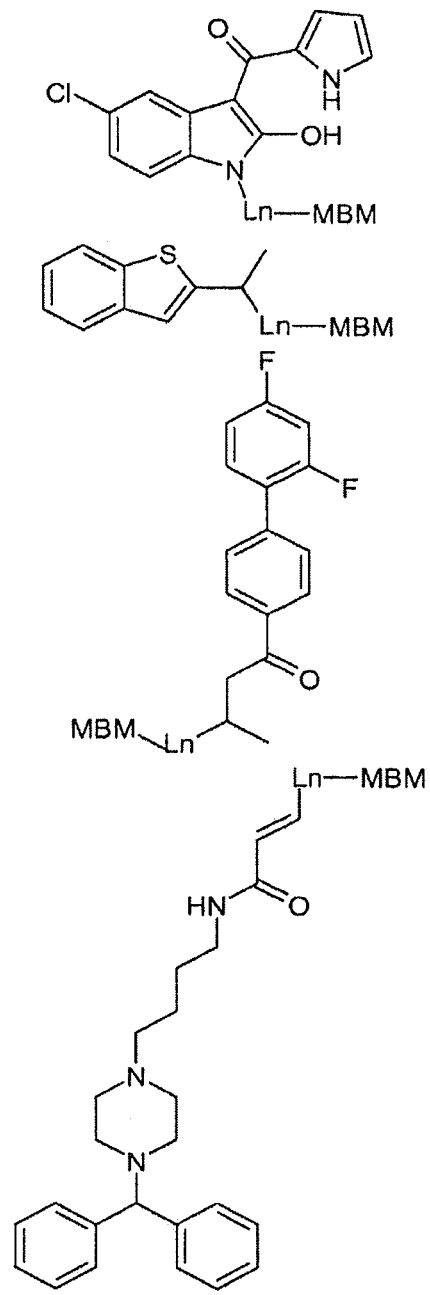
Figure 17C:
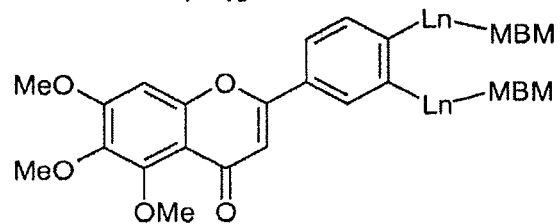

FIG. 17A-17C depicts structures useful as targeting moieties for 5-lipoxygenase.

Figure 18A:
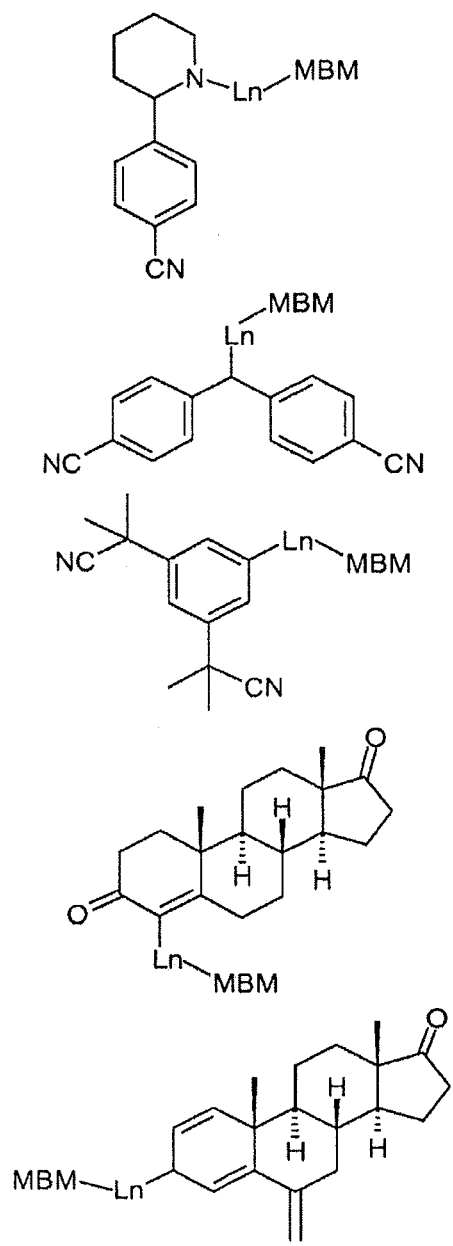
Figure 18:
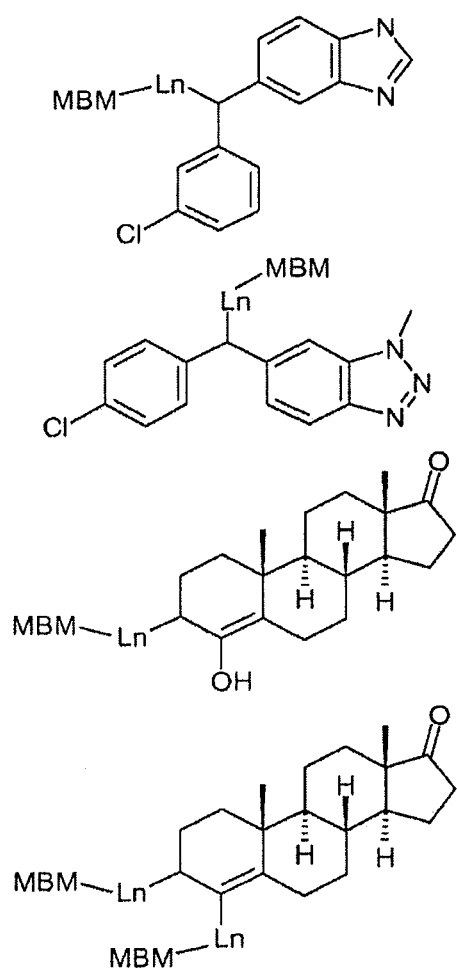
Figure 19A:
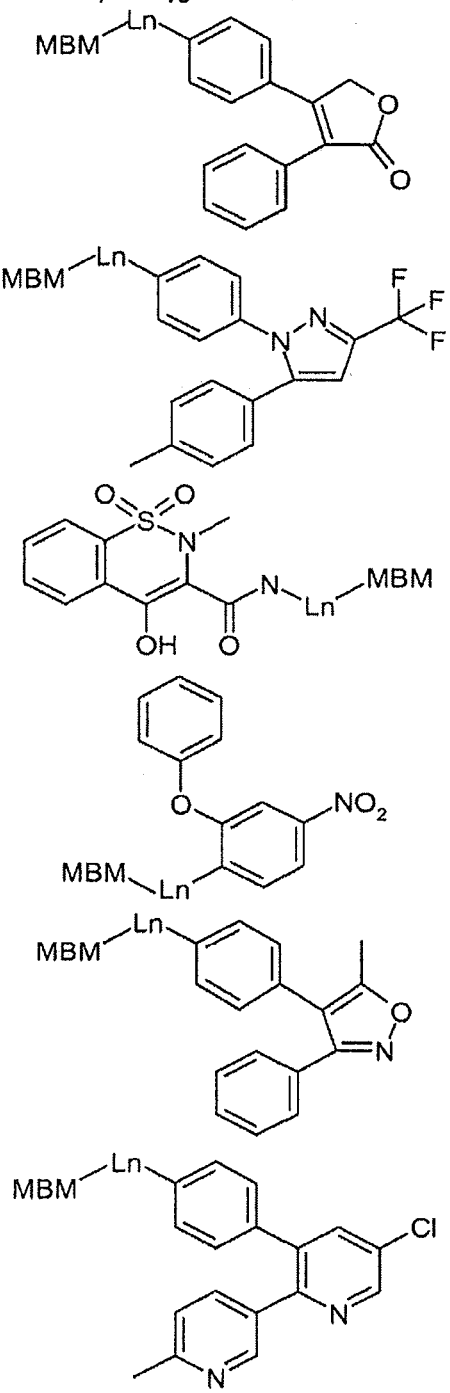
Figure 19B:
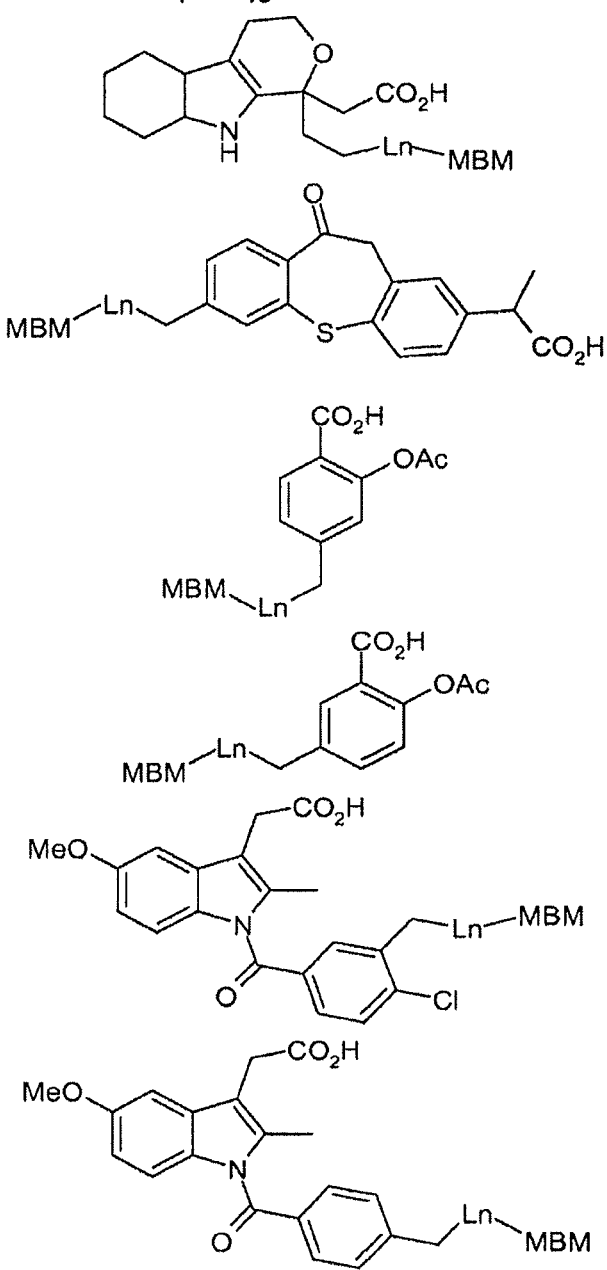
Figure 19C:
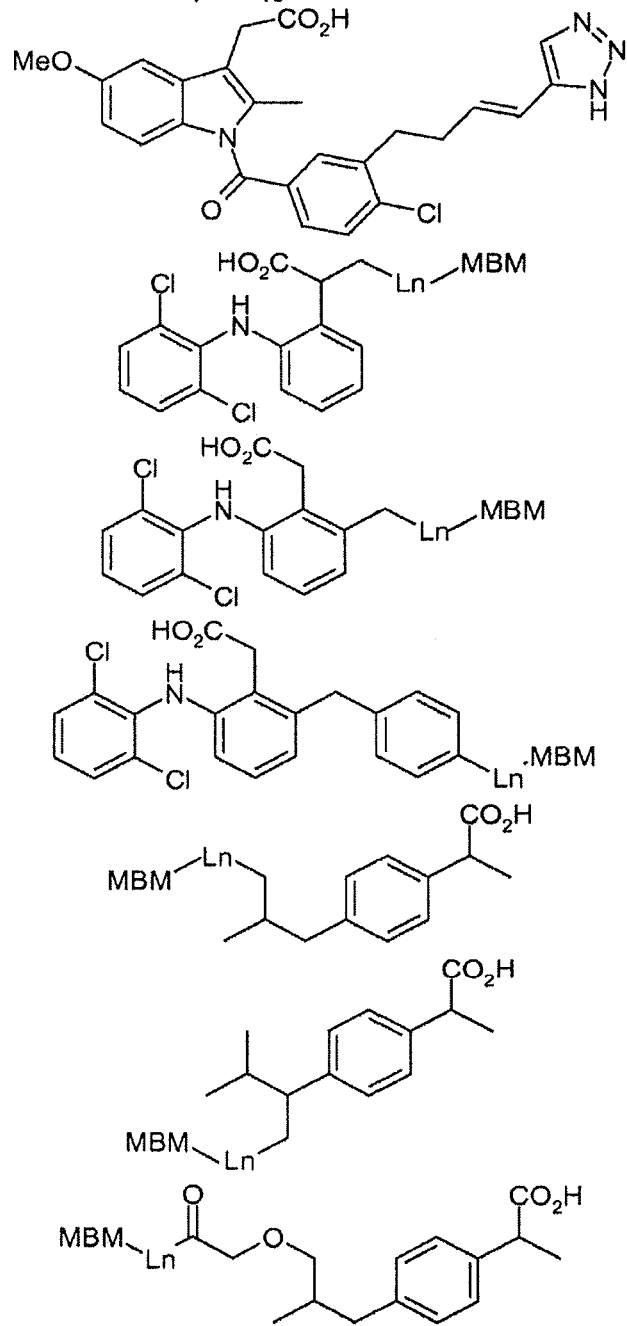
Figure 19E:
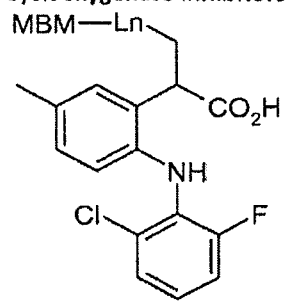

FIG. 18A-18B depicts structures useful as targeting moieties for aromatase.

FIG. 19A-19E depicts structures useful as targeting moieties for cyclooxygenase.

Figure 20A:
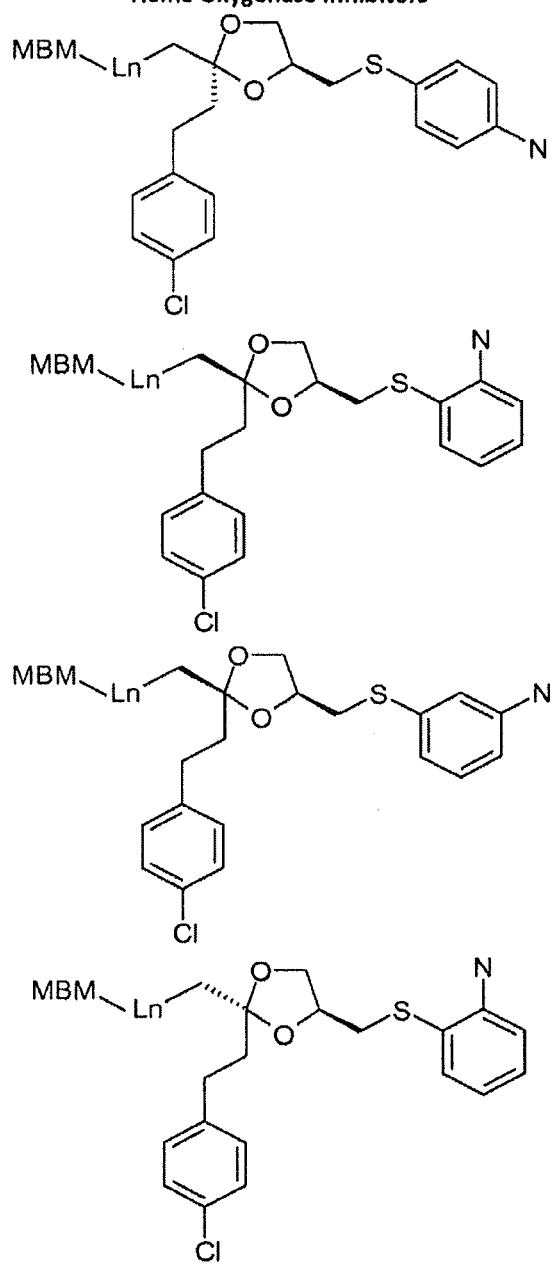
Figure 20B:
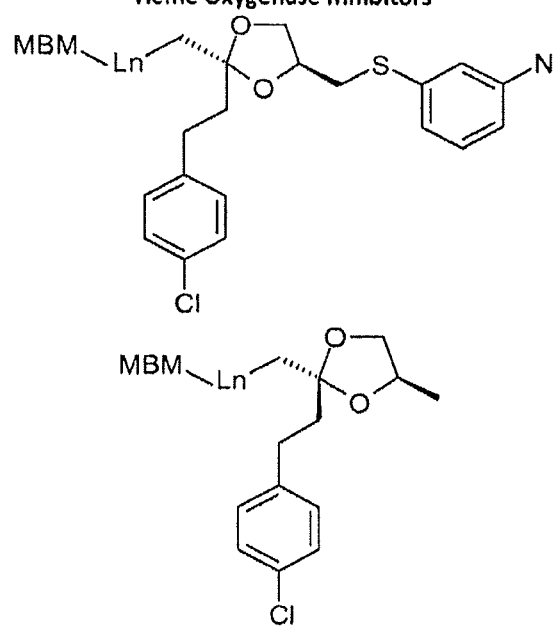

FIG. 20A-20B depicts structures useful as targeting moieties for heme oxygenase.

FIG. 21 depicts structures useful as targeting moieties for and xanthine oxidase.

Figure 22A:
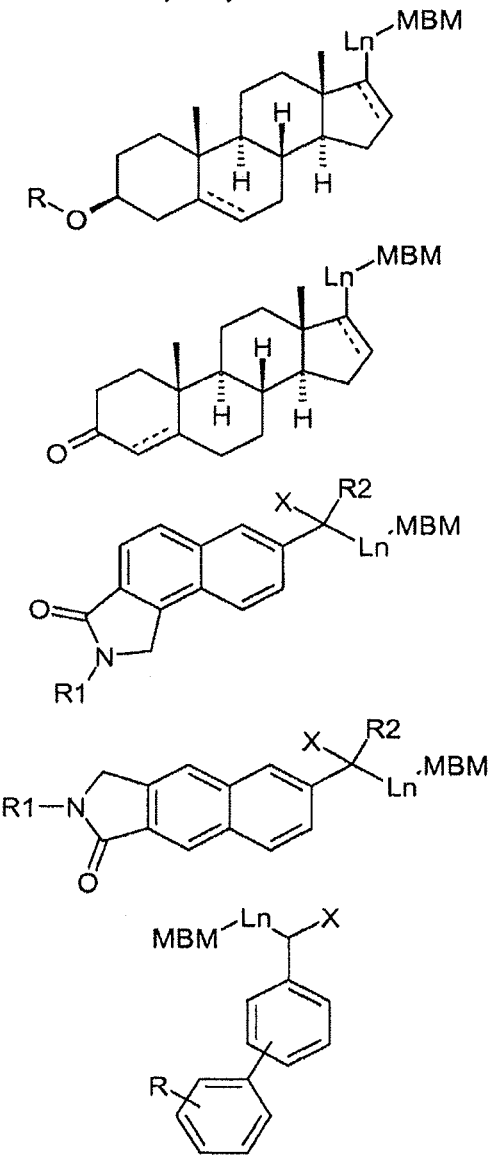
Figure 22:
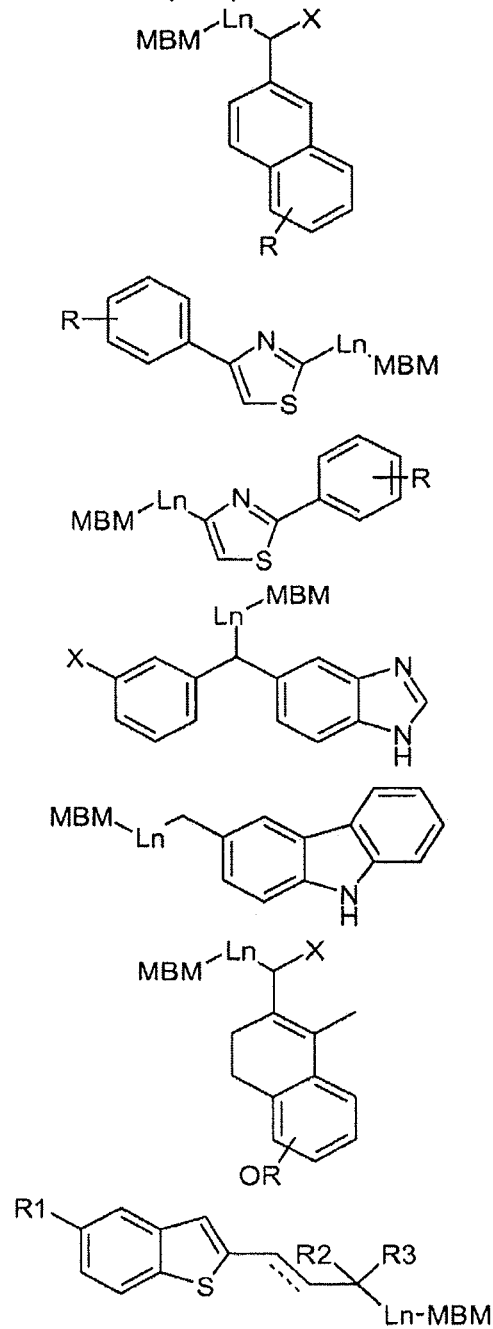

FIG. 22A-22B depicts structures useful as targeting moieties for 17-a hydroxylase.

Figure 23C:
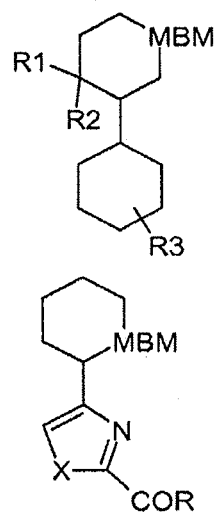

FIG. 23A-23C depicts structures useful as targeting moieties for aldosterone synthase.

Figure 24A:
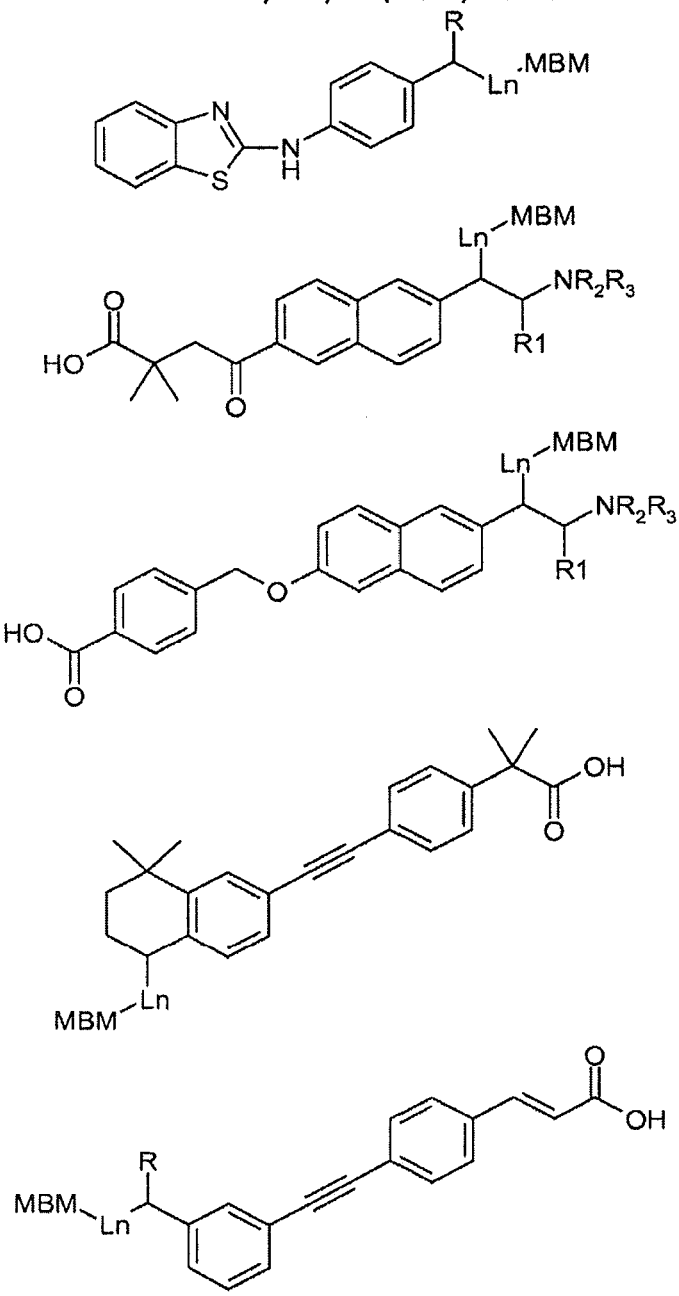
Figure 24B:
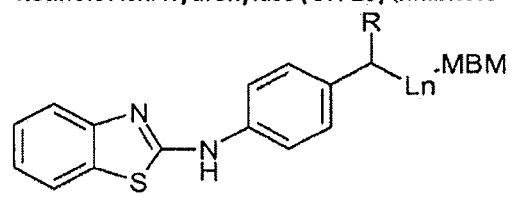

FIG. 24A-24B depicts structures useful as targeting moieties for retinoic acid hydroxylase (CYP26).

Figure 25:
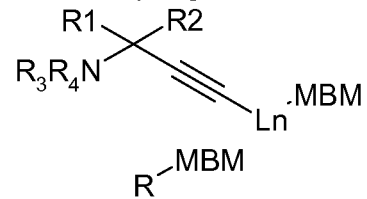

FIG. 25 depicts structures useful as targeting moieties for alcohol dehydrogenase.

Figure 26:
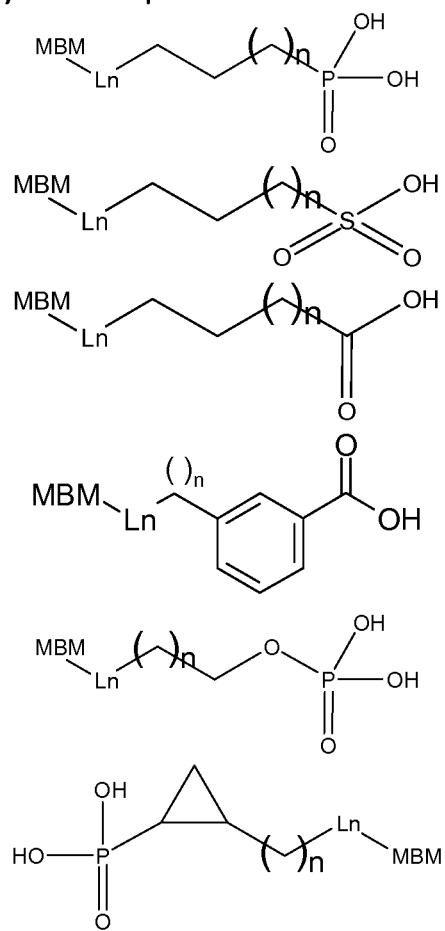

FIG. 26 depicts structures useful as targeting moieties for deoxy-xylulose phosphate reductoisomerase.

Figure 27:
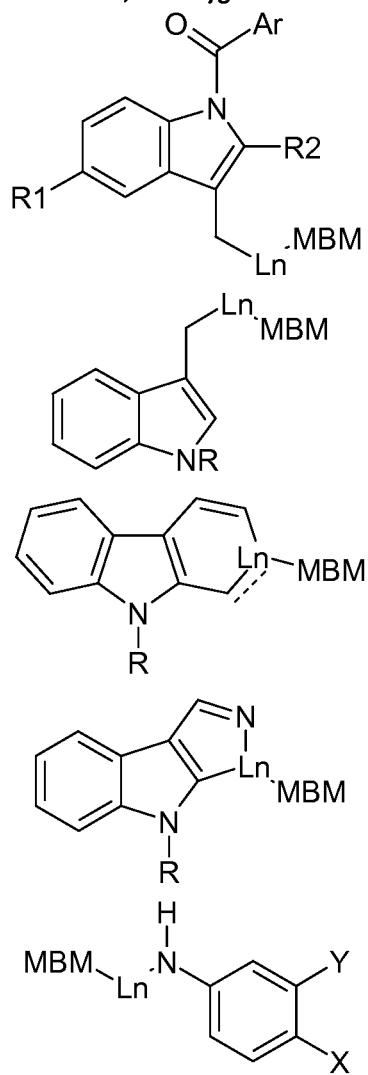

FIG. 27 depicts structures useful as targeting moieties for indoleamine 2,3-dioxygenase.

Figure 28:
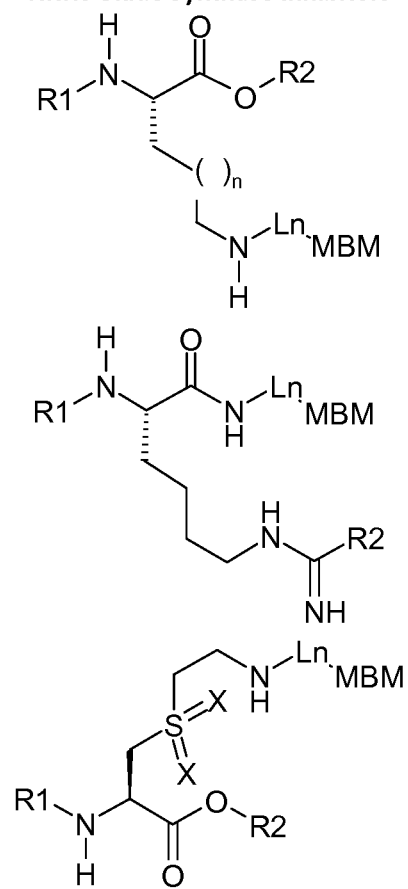

FIG. 28 depicts structures useful as targeting moieties for nitric oxide synthase.

Figure 29:
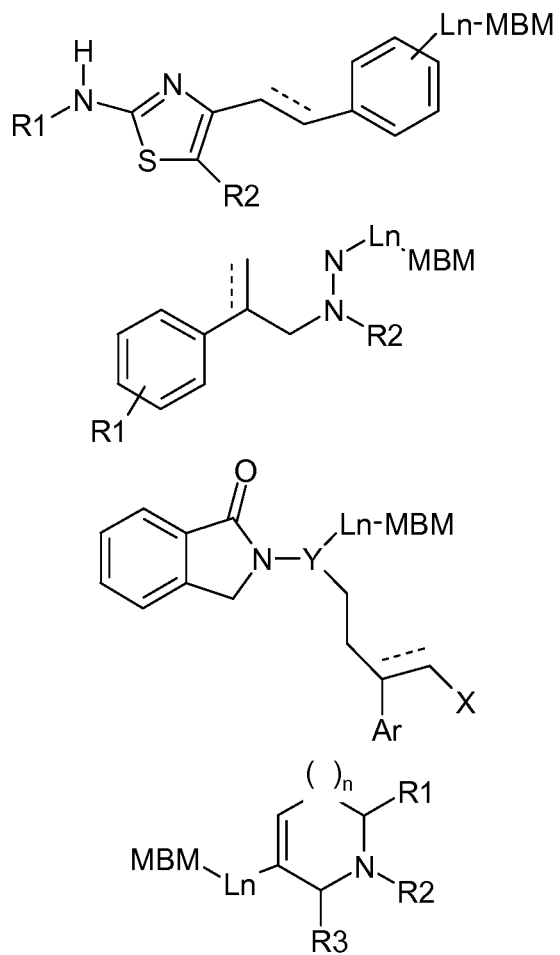

FIG. 29 depicts structures useful as targeting moieties for vascular adhesion protein-1.

DETAILED DESCRIPTION

The presently disclosed subject matter now will be described more fully hereinafter with reference to the accompanying Drawings, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

I. Inhibitors of Metallo-Oxidoreductases

The presently disclosed subject matter provides inhibitors of metallo-oxidoreductase comprising one or more metal binding moieties, a targeting moiety, and optionally a linker.

By "inhibitor" herein is meant a molecule that is capable of inhibiting a metallo-oxidoreductase. By "inhibit" herein is meant to decrease the activity of the metallo-oxidoreductase, as compared to the activity of the metallo-oxidoreductase in the absence of the inhibitor. In some embodiments, the term "inhibit" represents at least a 5% to 25% decrease in the activity; in some embodiments, a 50% to 75% decrease in the activity; and, in some embodiments, a 95% to 100% decrease in the activity, e.g., a 95%, 96%, 97%, 98%, 99%, or 100% decrease of the activity. The activity of each metallo-oxidoreductase can vary, and is described in more detail herein. An assay for measuring individual activity is described below.

A. Metal Binding Moieties

By "metal binding moiety (MBM)" herein is meant a moiety that is capable of binding to one or more metal ions through one or more coordination atoms of the MBM, resulting in a coordinate/covalent attachment of the metal to the coordination atom(s). In general, this binding is accomplished through at least one pair of unpaired electrons. As is appreciated by those in the art, the nature of the coordination bond can have covalent characteristics, but is generally referred to as a "coordinate" or "coordinate/covalent" bond.

In some embodiments, the metal binding moieties provides a single coordination atom for binding to the metal ion of a metallo-oxidoreductase, such as the heme iron ion of the lanosterol demethylase molecule. In other embodiments, two or more coordination atoms are provided by the metal binding moieties. When two or more coordination atoms are provided by the metal binding moieties, the metal binding moieties can be referred to as a "chelator" or a "ligand". The number of coordination sites is an intrinsic characteristic of the metal being bound: those molecules that use two different atoms to form two bonds to a metal are said to be bidentate. The terms tridentate, tetradentate, pentadentate, and the like then refer to metal binding moieties that use three, four or five atoms, and the like, to form the same number of bonds, respectively.

In general, the nature of the coordination atom depends on the metal to be bound. In general, useful heteroatoms for use as coordination atoms include nitrogen, oxygen and sulfur.

As will be appreciated by those in the art, a wide variety of suitable metal binding moieties can be used. The metal binding moieties can be macrocyclic or non-macrocyclic in structure. "Macrocyclic" in this context includes at least 12 atoms in a cyclic structure, frequently containing heteroatoms, binding of a metal in the interior of the cycle and generally planar.

In many embodiments, the metal binding moieties are not macrocyclic, but can contain cyclic structures.

Generally, in some embodiments, the metal binding moiety is selected from the group consisting of a sulfonyl moiety, a carbonyl moiety, a boronic acid or boronic ester moiety, a sulfur-containing moiety, a nitrogen-containing moiety, a phosphorous-containing moiety, a 5-membered heteroaromatic ring having one heteroatom, a 5-membered aromatic ring having two heteroatoms, a 5-membered heteroaromatic ring having three heteroatoms, a 5-membered heteroaromatic ring having four or five heteroatoms, a 5-membered saturated or partially unsaturated heteroalkyl ring having one heteroatom, a 5-membered saturated or partially unsaturated heteroalkyl ring having two heteroatoms, a six-membered aromatic ring, a 6-membered heteroaromatic ring having one heteroatom, a 6-membered aromatic ring having two heteroatoms, a 6-membered heteroaromatic ring having three or four heteroatoms, a 6-membered unsaturated or partially saturated heteroalkyl ring having one heteroatom, and a 6-membered unsaturated or partially saturated heteroalkyl ring having two heteroatoms; wherein, in some embodiments, the metal binding moiety is not a metal binding moiety selected from the group consisting of:

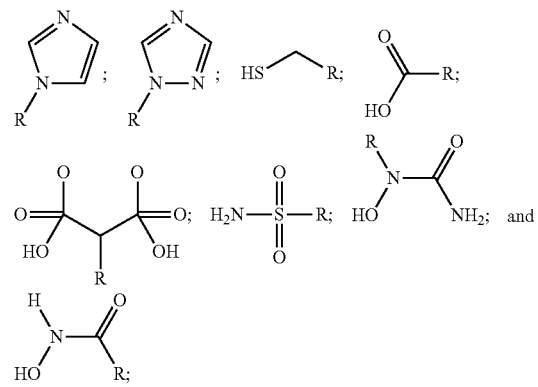

wherein: R is an attachment site through which the metal binding moiety can be attached to the targeting moiety, optionally through a linker, $L_n$.

One class of suitable metal binding moieties includes five-membered ring structures having at least one heteroatom and can be aromatic or non-aromatic. Subclasses of this class include, but are not limited to, five membered rings having one heteroatom (51HA), including five-membered aromatic rings having one heteroatom (5A1HA) and five-membered non-aromatic rings having one heteroatom (5NA1HA); five-membered rings having two heteroatoms (again, either aromatic or not: 5A2HA and 5NA2HA); five-membered rings having three heteroatoms (either aromatic or not, 5A3HA and 5NA3HA) and five-membered aromatic rings having four or five heteroatoms (5A4HA, 5A5HA). As outlined above, each class or subclass can include or exclude any member of the class or subclass individually. Additionally, each heteroatom can be included or excluded independently and individually as well; for example, the five membered aromatic rings having one heteroatom can exclude nitrogen as the heteroatom.

Another class of suitable metal binding moieties includes six-membered ring structures having none or at least one heteroatom that can be aromatic or non-aromatic. Subclasses of this class include, but are not limited to, six-membered aromatic rings having no heteroatoms (6A), six-membered rings having one heteroatom (61HA), including six-membered aromatic rings having one heteroatom (6A1HA) and six-membered non-aromatic rings having one heteroatom (6NA1HA); six membered rings having two heteroatoms (again, either aromatic or not: 6A2HA and 6NA2HA); six-membered rings having three or four heteroatoms (either aromatic or not, 6A3HA and 6NA3HA or 6A4HA and 6NA4HA). As outlined above, each class or subclass can include or exclude any member of the class or subclass individually. Additionally, as for the five-membered ring structures, each heteroatom can be included or excluded independently, as well.

It should be noted that in embodiments where adjacent substitution groups form a cyclic structure, the actual metal binding moiety can be based on a 5- or 6-membered ring, and can include additional ring structures.

FIGS. 1A-1AH depict representative sulfonyl-based metal binding moieties including, but not limited to, sulfonic acid, sulfonamide, thiosulfonic acid, sulfonyl hydrazine, sulfonyl hydroxylamine, N-methoxy-sulfonamide, N-methyl-sulfonamide, N-acetyl-sulfonyl hydrazide, N-aminocarbonyl-sulfonyl hydrazide, N-aminothiocarbonyl-sulfonyl hydrazide, N-cyano-sulfonamide, cyanomethyl-sulfone, N-acetyl sulfonamide, N-aminocarbonyl-sulfonamide, N-aminothiocarbonyl-sulfonamide, N-amidino-sulfonamide, α-thioacetamido-sulfone. α-acetamido-sulfone, α-sulfonylmethyl-phosphonic acid, α-cyanomethyl-sulfonamide, α-acetamido-sulfonamide, N-hydroxyamidino-sulfonamide, N-α-acetoxy-sulfonamide, N-sulfonyl-imidazole, N-sulfonyl-pyrazole, N-sulfonyl-1-(1,2,4-triazole), N-sulfonyl-1-(1,2,3-triazole), N-sulfonyl-pyrrolidin-2-one, N-sulfonyl-imidazolinone, N-sulfonyl-hydantoin, N-sulfonyl-pyrrolidin-2,3-dione, N-sulfonyl-piperazine, N-sulfonyl-morpholine, and N-sulfonyl-thiomorpholine.

In some embodiments, the sulfonyl moiety has the following general formula

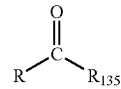

wherein: R is an attachment site through which the metal binding moiety can be attached to a targeting moiety, optionally through a linker, $L_n$, wherein n can be 0 or 1; and $R_{134}$ is selected from the group consisting of —OH, —SH, —NHNH$_2$, —NHOH, —NHOCH$_3$, —NHN(CH$_3$)$_2$, —NHNHC(=O)CH$_3$, —NHNHC(=O)NH$_2$, —NHNHC(=S)NH$_2$, —NHC≡N, —CH$_2$C≡N, —NHC(=O)CH$_3$, —NHC(=O)NH$_2$, —NHC(=S)NH$_2$, —NHC(=NH)NH$_2$, —CH$_2$C(=S)NH$_2$, —CH$_2$C(=O)NH$_2$, —CH$_2$P(=O)(OH)$_2$, —NHCH$_2$C≡N, —NHCH$_2$C(=O)—NH$_2$, —NHCH$_2$C(=NOH)—NH$_2$, —NHOCH$_2$C(=O)OH,

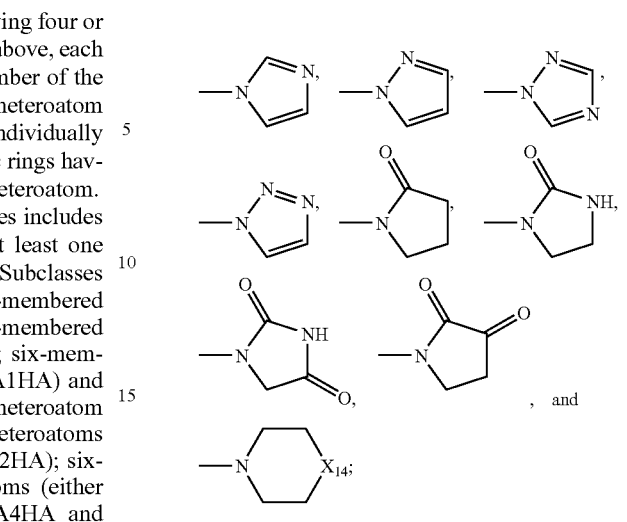

wherein $X_{14}$ is NH, O, or S.

FIGS. 2A-2AI depict representative carbonyl-based metal binding moieties including, but not limited to, carboxylic acid, carboxmide, thiocarboxylic acid, thioamide, amidine, oxime, nitrile, hydroxamic acid, N-methyl-hydroxamic acid, O-methyl-hydroxamic acid, N,O-dimethyl-hydroxamic acid, N-hydroxyamidine, hydrazide, N-methyl-hydrazide, N-hydroxy-hydrazide, N-hydroxy-hydrazide, N-acetyl-carboxamide, N-carbonyl-pyrrolidinone, N-cyanocarboxamide, N-carbonyl-urea, N-carbonyl-thiourea, N-carbonyl-guanidine, N-carbonyl-imidazolin-2-one, N-carbonyl-imidazolin-2-thione, acetoacetamide, α-carbonyl-methylphosphonic acid, N-carbonyl-N'-hydroxyguanidine, glycolamide, N-carbonyl-glycinamide, O-acyl-oxyacetic acid, N-cyanomethyl carboxamide, N-acyl-piperazine, N-acyl-piperazin-3-one, N-acyl-thiomorpholine, and N-acyl-morpholine.

In some embodiments, the carbonyl moiety has the following general formula:

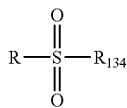

wherein: R is an attachment site through which the metal binding moiety can be attached to a targeting moiety, optionally through a linker, $L_n$, wherein n can be 0 or 1; and $R_{24}$ is selected from the group consisting of —NH$_2$, —SH, —NHNH$_2$, —N(OH)NH$_2$, —NHOH, —NCH$_3$OH, —NHOCH$_3$, —NCH$_3$OCH$_3$, —NHNHCH$_3$, —NHNHOH, —NHNHC(=O)CH$_3$, —NHNHC(=O)NH$_2$, —NHNHC(=S)NH$_2$, —NHC≡N, —NHC(=NH)NH$_2$, —CH$_2$C(=O)NH$_2$, —CH$_2$P(=O)(OH)$_2$, —NHCH$_2$C≡N, —NHCH$_2$C(=O)—NH$_2$, —NHC(=NOH)—NH$_2$, —OCH$_2$C(=O)—NH$_2$, —OCH$_2$C(=O)—OH,

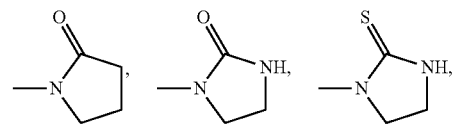

-continued

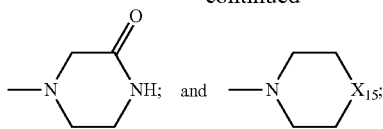

wherein X$_{15}$ is NH, S, or O; or R$_{135}$ is selected from the group consisting of:

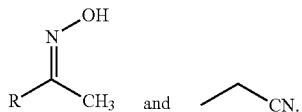

FIGS. 3A and 3B depict representative boron-based metal binding moieties including, but not limited to, boronic acid and pinacol boronic ester.

In some embodiments, the boronic acid or boronic ester moiety is selected from the group consisting of:

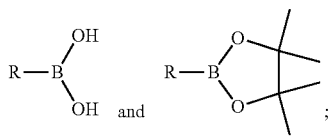

wherein: R is an attachment site through which the metal binding moiety can be attached to a targeting moiety, optionally through a linker, L$_n$, wherein n can be 0 or 1.

FIGS. 3C-3G depict representative sulfur-based metal binding moieties including, but not limited to, thiol, 1,3-dithiolane, 5-dithiane, 2-dithiane, and thioamide. In some embodiments, the sulfur-containing moiety is selected from the group consisting of: R—SH, R—C(=S)—NH$_2$,

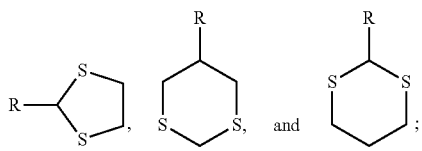

wherein: R is an attachment site through which the metal binding moiety can be attached to a targeting moiety, optionally through a linker, L$_n$, wherein n can be 0 or 1.

FIGS. 3H-3S depict representative nitrogen-based metal binding moieties including, but not limited to, N-acetyl-N-hydroxylamine, N-acetyl-N-methoxylamine, O-methyl-carbamate, urea, guanidine, 2-oxo-thiazol(idine), N-hydroxy urea, N-hydroxy-urea, hydroxy-guanidine, 2-oxo-oxazol (idine), S-alkyl thiocarbamate, and N-substituted-thiourea. In some embodiments, the nitrogen-containing moiety has the following formula:

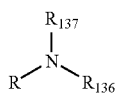

wherein: R is an attachment site through which the metal binding moiety can be attached to a targeting moiety, optionally through a linker, L$_n$, wherein n can be 0 or 1; and R$_{136}$ is selected from the group consisting of: —C(=O)—CH$_3$, —C(=O)—OCH$_3$, —C(=O)—NH$_2$, —C(=NH)—NH$_2$, —C(=O)—NHOH, —C(=NOH)—NH$_2$, —C(=O)—S—R$_{138}$, wherein R$_{138}$ is H or alkyl, —C(=S)—NH—R$_{139}$, wherein R$_{139}$ is H or alkyl, and; R$_{137}$ is selected from the group consisting of: —H, —OH, and —OCH$_3$; provided that when R$_{137}$ is OH, R$_{136}$ is not —C(=O)—NH$_2$ or —C(=O)—CH$_3$; or R$_{137}$ and R$_{136}$ together combine to form:

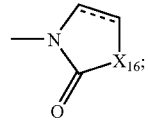

wherein: X$_{16}$ is S or O; and a dashed line indicates that a bond can be present or absent.

FIGS. 3T-3AA depict representative phosphorous-based metal binding moieties including, but not limited to, phosphonic acid, thiophosphonic acid, phosphoric acid, phosphate, thiophosphate, phosphonoamine, phosphoramide, and thiophosphoramide. In some embodiments, the phosphorous-containing moiety has the following formula:

R—R$_{140}$—P(=X$_{17}$)(OH)(R$_{141}$)

wherein: R is an attachment site through which the metal binding moiety can be attached to a targeting moiety, optionally through a linker, L$_n$, wherein n can be 0 or 1; and X$_{17}$ is O or S; R$_{140}$ is selected from the group consisting of —CH$_2$—, —O—, and —NH—; and R$_{141}$ is selected from the group consisting of —OH and —OCH$_3$.

FIGS. 4A-4C depict representative 5-membered aromatic rings having one heteroatom including, but not limited to, pyrrole, furan, and thiophene. In some embodiments, the 5-membered heteroaromatic ring having one heteroatom has the following formula:

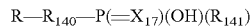

wherein: X$_{18}$ is selected from the group consisting of NH, O, and S; R is an attachment site through which the metal binding moiety can be attached to a targeting moiety, optionally through a linker, L$_n$, wherein n can be 0 or 1; and R$_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol.

In some embodiments, the heteroatom in the 5-membered aromatic ring having one heteroatom is not oxygen.

In some embodiments, the heteroatom in the 5-membered aromatic ring having one heteroatom is not nitrogen.

In some embodiments, the heteroatom in the 5-membered aromatic ring having one heteroatom is not sulfur.

FIGS. 5A-5I depict representative 5-membered aromatic rings having two heteroatoms including, but not limited to, 1-N-imidazole, substituted 1-N-imidazole, imidazole, oxazole, thiazole, 1-N-pyrazole, pyrazole, isoxazole, and isothiazole.

In some embodiments, the 5-membered aromatic ring having two heteroatoms is selected from the group consisting of:

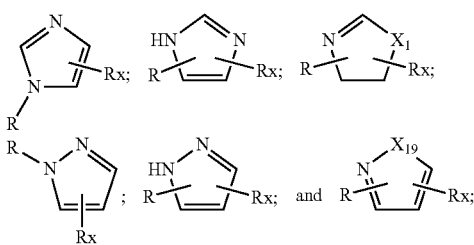

wherein: $X_{19}$ is O or S; and R is an attachment site through which the metal binding moiety can be attached to a targeting moiety, optionally through a linker, $L_n$, wherein n can be 0 or 1; and $R_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol; under the proviso that the metal binding moiety is not:

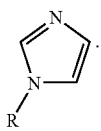

In some embodiments, one of the heteroatoms in the 5-membered aromatic ring having two heteroatoms is not oxygen.

In some embodiments, neither heteroatom in the 5-membered aromatic ring having two heteroatoms is oxygen.

In some embodiments, one of the heteroatoms in the 5-membered aromatic ring having two heteroatoms is not nitrogen.

In some embodiments, neither heteroatom in the 5-membered aromatic ring having two heteroatoms is nitrogen.

In some embodiments, one of the heteroatoms in the 5-membered aromatic ring having two heteroatoms is not sulfur.

In some embodiments, neither heteroatom in the 5-membered aromatic rings having two heteroatoms is sulfur.

FIGS. 6A-6O depict representative 5-membered aromatic rings having three heteroatoms including, but not limited to, 1-N-(1,2,4-triazole), substituted 1-N-(1,2,4-triazole), 1,2,4-triazole, substituted 4-N-(1,2,4-triazole), 1,2,4-oxadiazole, 1,2,4-thiadiazole, 1,3,4-oxadiazole, 1,3,4-thiadiazole, N-substituted-1-N-(1,2,3-triazole), 1,2,3-triazole, 1,2,3-oxadiazole, 1,2,3-thiadiazole, 1,2,5-oxadiazole, 1,2,5-thiadiazole, and substituted 1-N-(1,2,4-triazol-5-thione).

In some embodiments, the 5-membered heteroaromatic ring having three heteroatoms is selected from the group consisting of:

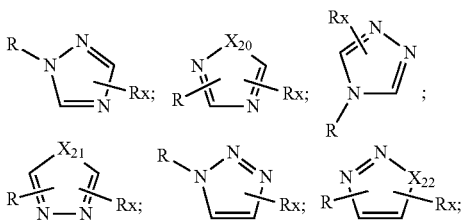

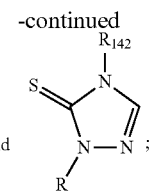

wherein: $X_{20}$ and $X_{22}$ are each independently selected from the group consisting of NH, O, and S; $X_{21}$ and $X_{23}$ are each independently O or S; R is an attachment site through which the metal binding moiety can be attached to a targeting moiety, optionally through a linker, $L_n$, wherein n can be 0 or 1; and $R_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol; and $R_{142}$ is H or alkyl; under the proviso that the metal binding moiety is not:

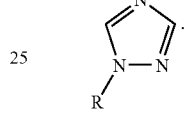

In some embodiments, one of the heteroatoms in the 5-membered aromatic ring having three heteroatoms is not oxygen.

In some embodiments, two of the heteroatoms in the 5-membered aromatic ring having three heteroatoms are not oxygen.

In some embodiments, none of the heteroatoms in the 5-membered aromatic ring having three heteroatoms is oxygen.

In some embodiments, one of the heteroatoms in the 5-membered aromatic ring having three heteroatoms is not nitrogen.

In some embodiments, two of the heteroatoms in the 5-membered aromatic ring having three heteroatoms are not nitrogen.

In some embodiments, none of the heteroatoms in the 5-membered aromatic ring having three heteroatoms is nitrogen.

In some embodiments, one of the heteroatoms in the 5-membered aromatic ring having three heteroatoms is not sulfur.

In some embodiments, two of the heteroatoms in the 5-membered aromatic ring having three heteroatoms are not sulfur.

In some embodiments, none of the heteroatoms in the 5-membered aromatic ring having three heteroatoms is not sulfur.

FIGS. 7A-7I depict representative 5-membered aromatic rings having four or five heteroatoms including, but not limited to, C-tetrazole, 1,2,3,4-oxatriazole, 1,2,3,4-thiatriazole, C-substituted-1-N-tetrazole, 1-N-tetrazole, 1-N-substituted-C-tetrazole, C-substituted-2-N-tetrazole, 2-N-substituted-C-tetrazole, and pentazole.

In some embodiments, the 5-membered heteroaromatic ring having four or five heteroatoms is selected from the group consisting of:

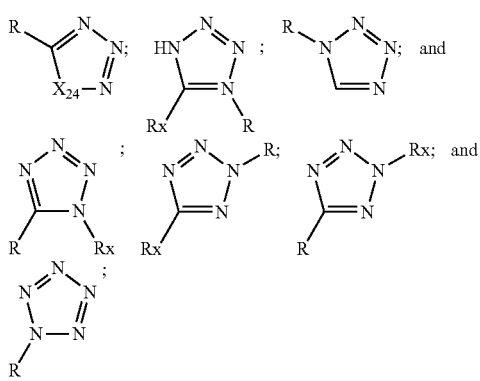

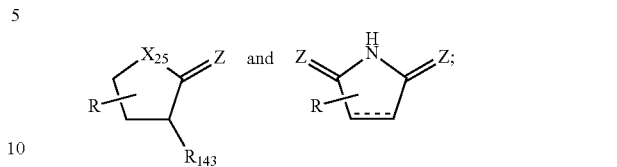

wherein: $X_{24}$ is selected from the group consisting of NH, O, and S; R is an attachment site through which the metal binding moiety can be attached to a targeting moiety, optionally through a linker, $L_n$, wherein n can be 0 or 1; and $R_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol.

In some embodiments, one of the heteroatoms in the 5-membered aromatic ring having four or five heteroatoms is not oxygen.

In some embodiments, two of the heteroatoms in the 5-membered aromatic ring having four or five heteroatoms are not oxygen.

In some embodiments, three of the heteroatoms in the 5-membered aromatic ring having four or five heteroatoms are not oxygen.

In some embodiments, none of the heteroatoms in the 5-membered aromatic ring having four or five heteroatoms is oxygen.

In some embodiments, one of the heteroatoms in the 5-membered aromatic ring having four or five heteroatoms is not nitrogen.

In some embodiments, two of the heteroatoms in the 5-membered aromatic ring having four or five heteroatoms are not nitrogen.

In some embodiments, three of the heteroatoms in the 5-membered aromatic ring having four or five heteroatoms are not nitrogen.

In some embodiments, none of the heteroatoms in the 5-membered aromatic ring having four or five heteroatoms is nitrogen.

In some embodiments, one of the heteroatoms in the 5-membered aromatic ring having four or five heteroatoms is not sulfur.

In some embodiments, two of the heteroatoms in the 5-membered aromatic ring having four or five heteroatoms are not sulfur.

In some embodiments, three of the heteroatoms in the 5-membered aromatic ring having four or five heteroatoms are not sulfur.

In some embodiments, none of the heteroatoms in the 5-membered aromatic ring having four or five heteroatoms is sulfur.

FIGS. 8A-8I depict representative 5-membered non-aromatic rings having one heteroatom including, but not limited to, pyrrolidinone, 3-hydroxy pyrrolidinone, succinimide, maleimide, N-hydroxy pyrrolidinone, butyrolactone, 3-hydroxy butyrolactone, thiobutyrolactone, and 3-hydroxy thiobutyrolactone.

In some embodiments, the 5-membered saturated or partially unsaturated heteroalkyl ring having one heteroatom is selected from the group consisting of:

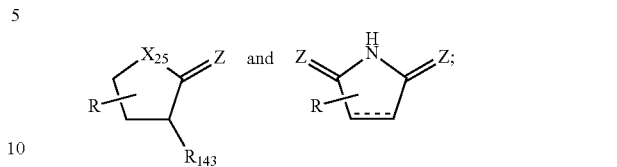

wherein: $X_{25}$ is selected from the group consisting of NH, NOH, O, and S; and each Z is independently selected from the group consisting of O, S, and $NR_{143}$, wherein $R_{143}$ is H or alkyl; R is an attachment site through which the metal binding moiety can be attached to a targeting moiety, optionally through a linker, $L_n$, wherein n can be 0 or 1; and $R_{143}$ is selected from the group consisting of H and OH; and wherein a dashed line indicates that a bond can be present or absent.

In some embodiments, the heteroatom in the 5-membered non-aromatic ring having one heteroatom is not oxygen.

In some embodiments, the heteroatom in the 5-membered non-aromatic ring having one heteroatom is not nitrogen.

In some embodiments, the heteroatom in the 5-membered non-aromatic ring having one heteroatom is not sulfur.

FIGS. 9A-9K depict representative 5-membered non-aromatic rings having two heteroatoms including, but not limited to, pyrazolone, isothiazolin-3-one, isothiazolin-5-one, isoxazolin-3-one, isoxazolin-5-one, 2-imidazolin-2-one, hydantoin, 2-thiazolidone, thiazolidinedione, 2-oxazolidone, and oxazolidine-2,4-dione.

In some embodiments, the 5-membered saturated or partially unsaturated heteroalkyl ring having two heteroatoms is selected from the group consisting of:

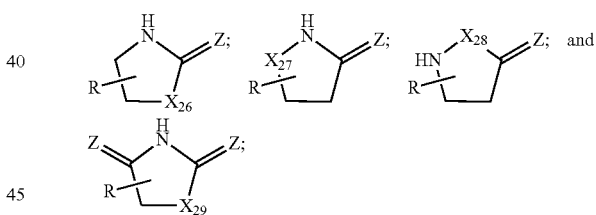

wherein: R is an attachment site through which the metal binding moiety can be attached to a targeting moiety, optionally through a linker, $L_n$, wherein n can be 0 or 1; $X_{26}$, $X_{27}$, and $X_{29}$ are each independently selected from the group consisting of NH, O, and S; $X_2$ is O or S; and each Z is independently selected from the group consisting of O, S, and $NR_{144}$, wherein $R_{144}$ is H or alkyl.

In some embodiments, one of the heteroatoms in the 5-membered non-aromatic ring having two heteroatoms is not oxygen.

In some embodiments, neither heteroatom in the 5-membered non-aromatic ring having two heteroatoms is oxygen.

In some embodiments, one of the heteroatoms in the 5-membered non-aromatic ring having two heteroatoms is not nitrogen.

In some embodiments, neither heteroatom in the 5-membered non-aromatic ring having two heteroatoms is nitrogen.

In some embodiments, one of the heteroatoms in the 5-membered non-aromatic ring having two heteroatoms is not sulfur.

In some embodiments, neither heteroatom in the 5-membered non-aromatic ring having two heteroatoms is sulfur.

FIG. 10A depicts representative 6-membered aromatic rings having no heteroatoms including, but not limited to, ortho-disubstituted benzene.

In some embodiments, the six-membered aromatic ring has the following formula:

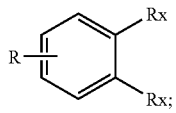

wherein: R is an attachment site through which the metal binding moiety can be attached to a targeting moiety, optionally through a linker, $L_n$, wherein n can be 0 or 1; and each $R_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol.

FIG. 11A depicts representative 6-membered aromatic rings having one heteroatom including, but not limited to, pyridine.

In some embodiments, the 6-membered heteroaromatic ring having one heteroatom has the following formula:

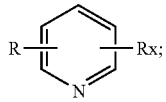

wherein: R is an attachment site through which the metal binding moiety can be attached to a targeting moiety, optionally through a linker, $L_n$, wherein n can be 0 or 1; and $R_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol.

FIGS. 12A-12C depict representative 6-membered aromatic rings having two heteroatoms including, but not limited to, pyridazine, pyrimidine, and pyrazine.

In some embodiments, the 6-membered aromatic ring having two heteroatoms is selected from the group consisting of:

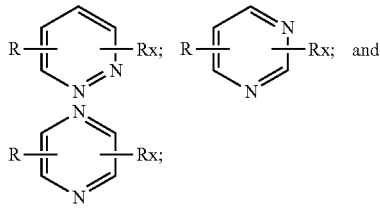

wherein: R is an attachment site through which the metal binding moiety can be attached to a targeting moiety, optionally through a linker, $L_n$, wherein n can be 0 or 1; and $R_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol.

FIGS. 13A-13C depict representative 6-membered aromatic rings having three or four heteroatoms including, but not limited to, 1,2,4-triazine, 1,3,5-triazine, and 1,2,3,4-tetrazine.

In some embodiments, the 6-membered heteroaromatic ring having three or four heteroatoms is selected from the group consisting of:

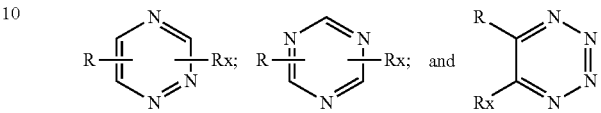

wherein: R is an attachment site through which the metal binding moiety can be attached to a targeting moiety, optionally through a linker, $L_n$, wherein n can be 0 or 1; and $R_x$ is selected from the group consisting of hydrogen, alkyl, alcohol, aromatic, amino, amido, carbonyl, carboxyl, cyano, nitro, ethers, esters, aldehydes, sulfonyl, a silicon moiety, halogen, a sulfur-containing moiety, a phosphorus containing moiety, and an ethylene glycol.

FIGS. 14A-14E depict representative 6-membered non-aromatic rings having one heteroatom including, but not limited to, N-substituted-dihydropyridinone, N-hydroxy-2-pyridone, 3-hydroxy-2-pyridone, 3-hydroxy-4-pyridone, and 3-hydroxy-4-pyanone.

In some embodiments, the 6-membered unsaturated or partially saturated heteroalkyl ring having one heteroatom is selected from the group consisting of:

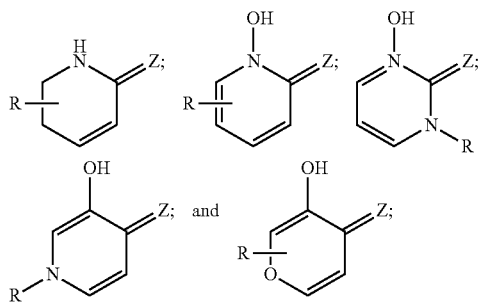

wherein: R is an attachment site through which the metal binding moiety can be attached to a targeting moiety, optionally through a linker, $L_n$, wherein n can be 0 or 1; and Z is selected from the group consisting of O, S, and $NR_{145}$, wherein $R_{145}$ is H or alkyl.

In some embodiments, the heteroatom in the 6-membered non-aromatic ring having one heteroatom is not oxygen.

In some embodiments, the heteroatom in the 6-membered non-aromatic ring having one heteroatom is not nitrogen.

In some embodiments, the heteroatom in the 6-membered non-aromatic ring having one heteroatom is not sulfur.

FIGS. 15A-15L depict representative 6-membered non-aromatic rings having two heteroatoms including, but not limited to, pyridazin-3(2H)-one, dioxopyridazine, glutarimide, oxazin-2-one, 2,6-dioxopyrimidine, oxazin-2,4-dione, 3-oxopiperazine, morpholinone, 2,3-dioxopiperazine, 2,5-dioxopiperazine, thiomorpholine, and morpholine.

In some embodiments, the 6-membered unsaturated or partially saturated heteroalkyl ring having two heteroatoms is selected from the group consisting of:

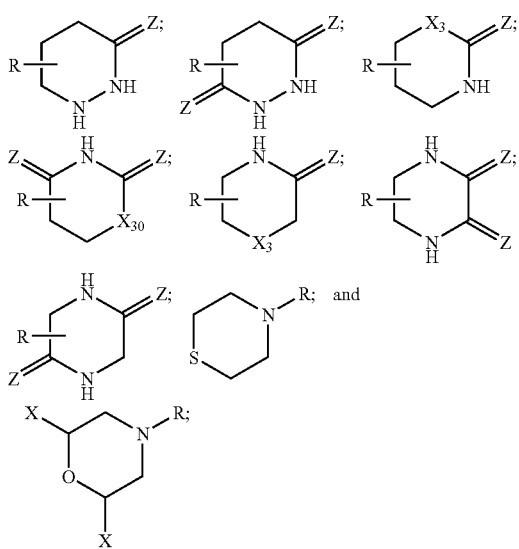

wherein: R is an attachment site through which the metal binding moiety can be attached to a targeting moiety, optionally through a linker, $L_n$, wherein n can be 0 or 1; $X_{30}$ is selected from the group consisting of $NR_{146}$, wherein $R_{146}$ is H or alkyl; and each Z is independently selected from the group consisting of O, S, and $NR_{147}$, wherein $R_{147}$ is H or alkyl.

In some embodiments, one of the heteroatoms in the 6-membered non-aromatic ring having two heteroatoms is not oxygen.

In some embodiments, neither heteroatom in the 6-membered non-aromatic ring having two heteroatoms is oxygen.

In some embodiments, one of the heteroatoms in the 6-membered non-aromatic ring having two heteroatoms is not nitrogen.

In some embodiments, neither heteroatom in the 6-membered non-aromatic ring having two heteroatoms is nitrogen.

In some embodiments, one of the heteroatoms in the 6-membered non-aromatic ring having two heteroatoms is not sulfur.

In some embodiments, neither heteroatom in the 6-membered non-aromatic ring having two heteroatoms is sulfur.

As shown in the Figures, the metal binding moieties have an attachment site, generally depicted as "R", which is used to attach the targeting moiety, described below, optionally using a linker, wherein the linker can be present or absent.

As depicted in the Figures, in addition to the attachment site, many of the metal binding moieties can be optionally derivatized, for example as depicted using an "X" substitution group, which also can be referred to as an "$R_x$" group as depicted in the appended claims. In some cases these X groups, or $R_x$ groups, can provide additional coordination atoms. Suitable substitution groups are known in the art and include, but are not limited to, hydrogen, linkers (which can be depicted herein as "L" or "$L_n$", with n being 0 or 1) alkyl, alcohol, aromatic, amino, amido, carbonyl, carboxyl, cyano, nitro, ethers, esters, aldehydes, sulfonyl, silicon moieties, halogens, sulfur containing moieties, phosphorus containing moieties, and ethylene glycols. In the structures depicted herein, X is hydrogen when the position is unsubstituted. It should be noted that some positions can allow two substitution groups, X and X', in which case the X and X' groups can be either the same or different. Generally, in some embodiments, only a single non-hydrogen X group is attached at any particular position; that is, preferably at least one of the X groups at each position is not hydrogen. Thus, if X is an alkyl or aryl group, there is generally an additional hydrogen attached to the carbon, although not necessarily depicted herein. In addition, X groups on adjacent carbons can be joined to form ring structures (including heterocycles, aryl and heteroaryls), which can be further derivatized as outlined herein.

By "alkyl group" or grammatical equivalents herein is meant a straight or branched chain alkyl group, with straight chain alkyl groups being preferred. If branched, it can be branched at one or more positions, and unless specified, at any position. "Alkyl" in this context includes alkenyl and alkynyl, and any combination of single, double and triple bonds. The alkyl group can range from about 1 to about 30 carbon atoms ($C_1$-$C_{30}$), with a preferred embodiment utilizing from about 1 to about 20 carbon atoms ($C_1$-$C_{20}$), with about $C_1$ through about $C_{12}$ to about $C_{15}$ being preferred, and $C_1$ to $C_5$ being particularly preferred, although in some embodiments the alkyl group can be much larger. Also included within the definition of an alkyl group are cycloalkyl groups such as $C_5$ and $C_6$ rings, and heterocyclic rings with nitrogen, oxygen, sulfur or phosphorus, as well as cycloalkyl and heterocycloalkyl groups with unsaturated bonds. Alkyl also includes heteroalkyl, with heteroatoms of sulfur, oxygen, nitrogen, and silicone being preferred. Alkyl includes substituted alkyl groups. By "substituted alkyl group" herein is meant an alkyl group as defined herein further comprising one or more substitution moieties "X", as defined herein.

By "amino groups" or grammatical equivalents herein is meant —$NH_2$, —NHX and —$NX_2$ groups, with X being as defined herein.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SX), and sulfides (—XSX—). By "phosphorus containing moieties" herein is meant compounds containing phosphorus, including, but not limited to, phosphines and phosphates. By "silicon containing moieties" herein is meant compounds containing silicon.

By "ether" herein is meant an —O—X group. Preferred ethers include alkoxy groups, with —O—$(CH_2)_2CH_3$ and —O—$(CH_2)_4CH_3$ being preferred.

By "ester" herein is meant a —COOX group, including carboxyl groups. By "carboxyl" herein is meant a —COOH group.

By "halogen" herein is meant bromine, iodine, chlorine, or fluorine. Preferred substituted alkyls are partially or fully halogenated alkyls such as $CF_3$, and the like.

By "aldehyde" herein is meant —XCOH groups.

By "alcohol" herein is meant —OH groups, and alkyl alcohols —XOH.

By "amido" herein is meant —XCONH— or XCONX— groups.

By "ethylene glycol" or "(poly)ethylene glycol" herein is meant a —$(O—CH_2—CH_2)_n$— group, although each carbon atom of the ethylene group also can be singly or doubly substituted, i.e. —$(O—CX_2—CX_2)_n$—, with X as described above. Ethylene glycol derivatives with other heteroatoms in place of oxygen (i.e., —$(N—CH_2—CH_2)_n$— or —$(S—CH_2—CH_2)_n$—, or with substitution groups) are also useful.

By "aryl group" or grammatical equivalents herein is meant an aromatic monocyclic or polycyclic hydrocarbon moiety generally containing 5 to 14 carbon atoms (although larger polycyclic rings structures can be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heteroaryl. "Heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heteroaryl includes for example pyrrolyl, pyridyl, thienyl, or furanyl (single ring, single heteroatom); oxazolyl, isoxazolyl, oxadiazolyl, or imidazolyl (single ring, multiple heteroatoms); benzoxazolyl, benzothiazolyl, or benzimidazolyl, (multi-ring, multiple heteroatoms); quinolyl, benzofuranyl or indolyl (multi-ring, single heteroatom). "Aryl" includes substituted aryl and substituted heteroaryl groups as well, with one or more X groups as defined herein.

X substituents can be used to modify the solubility of the candidate inhibitors, or alter the electronic environment of the metal binding moiety. For example, additional selected ring substituents are utilized to alter the solubility of the resulting candidate inhibitor in either aqueous or organic solvents. Typically, the substitution of alkyl, alkoxy, perfluoroalkyl, CN, amino, alkylamino, dialkylamino, 1-(acyloxy)alkyl ester of carboxy, aryl or heteroaryl onto the metal binding moiety results in an candidate inhibitor that is more soluble in non-polar solvents. Alternatively, substitution is by a "water solubilizing group", i.e., a sulfonic acid, salt of sulfonic acid, salt of amine, carboxy, carboxyalkyl, carboxyalkoxy, carboxyalkylamino, or carboxyalkylthio or other substituent that results in a candidate inhibitor that is more soluble in aqueous solution. Similarly, careful selection of the identity of linker and targeting moiety is also used to modify the solubility of the final candidate inhibitor with those candidate inhibitors containing charged or ionizable groups usually enhancing water solubility.

Alternatively, a ring substituent is used as a reactive site to further modify candidate inhibitors to attach the candidate inhibitors to a carrier or substrate as is more fully outlined below.

A number of suitable metal binding moieties are depicted in FIGS. 1-15B. It should be noted, that in some combinations of metal binding moieties, targeting moieties, and optional linkers, the metal binding moiety is not a metal binding moiety selected from the group consisting of:

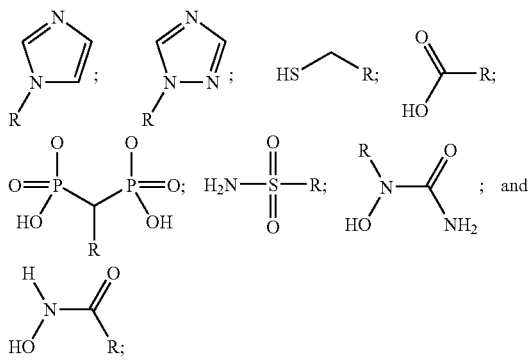

wherein: R is an attachment site through which the metal binding moiety can be attached to the targeting moiety, optionally through linker, $L_n$.

B. Targeting Moieties

In addition to the metal binding moieties, the presently disclosed inhibitors comprise targeting moieties. By "targeting moiety" herein is meant a functional group that serves to target or direct the inhibitor to a particular location or association. Thus, for example, a targeting moiety can be used to bring the metal binding moiety to the vicinity of a metal ion that is essential to the function of metallo-oxidoreductases enzymes such as lanosterol demethylase. That is, the targeting moiety has binding affinity and/or binding specificity for the lanosterol demethylase, preferably in proximity of the metal binding site, such that the metal binding moieties can bind the metal ion. As described below, optional linkers are used to provide proper spacing. All inhibitors listed in the sections bellow find use as targeting moieties; in some case, moieties of the inhibitor or targeting moiety are removed to be replaced with metal binding moieties and optional linkers.

1. 1-deoxy-d-xylulose-5-phosphate reductoisomerase 1-deoxy-d-xylulose-5-phosphate reductoisomerase, also known as DXPRI or DXR, is a manganese-containing oxidoreductase metalloenzyme found throughout the bacterial kingdom. Isopentenyl diphosphate is the precursor of various isoprenoids that are essential to all living organisms. It is produced by the mevalonate pathway in humans but by an alternate route in plants, protozoa, and many bacteria. DXR catalyzes the second step of this non-mevalonate pathway, which involves an NADPH-dependent rearrangement and reduction of 1-deoxy-D-xylulose 5-phosphate to form 2-C-methyl-D-erythritol 4-phosphate. DXR has been a target for the development of anti-infective agents. Henriksson et al., *J. Biol. Chem.* 2007 Jul. 6; 282(27):19905-16.

Fosmidomycin has reached clinical trials for the treatment of malaria. Fosmidomycin inhibits the synthesis of isoprenoid via inhibition of DXR in *Plasmodium falciparum*, and suppresses the growth of multidrug-resistant strains in vitro. Fosmidomycin has been shown to possess activity against *Plasmodium falciparum* in vitro and in the mouse model. In an open-label, uncontrolled trial, the efficacy and safety of fosmidomycin, in an oral dose of 1,200 mg every 8 h for 7 days, were evaluated in the treatment of acute uncomplicated *Plasmodium falciparum* malaria in 20 adult subjects in Gabon and Thailand. All subjects were clinically and parasitologically cured on day 7 (primary end point). Parasite and fever clearance were rapid, with means of 44 and 41 h, respectively. On day 28, seven out of nine subjects (78%) were cured in Gabon and two out of nine subjects (22%) were cured in Thailand. The drug was well tolerated, although mild gastrointestinal side effects were recorded for five subjects. Analysis of hematological and biochemical parameters showed no clinically significant changes throughout the study. Lell et al., *Antimicrob. Agents Chemother.* 2003 February; 47(2):735-8. In another clinical trial, fosmidomycin was administered for 5, 4, or 3 days (1.2 g every 8 h), in nine, eight, and ten evaluable patients, respectively. All treatment regimens were well tolerated. Cure rates by day 14 were 89% (eight of nine), 88% (seven of eight), and 60% (six of ten), for treatment durations of 5, 4, and 3 days, respectively. Missinou et al., *Lancet* 2002 Dec. 14; 360(9349): 1941-2.

Analogs of the antibiotic fosmidomycin, an inhibitor of the methylerythritol phosphate pathway to isoprenoids, were synthesized and evaluated against the recombinant *Synechocystis* sp. PCC6803 1-deoxy-d-xylulose 5-phosphate reductoisomerase. Fosfoxacin, the phosphate analog of fosmidomycin, and its acetyl congener were found to be more potent inhibitors of DXR than fosmidomycin. Woo et al., *Bioorg Med Chem.* 2006 Apr. 1; 14(7):2375-85. A series of fosmidomycin analogues featuring restricted conformational mobility has been synthesized and evaluated as inhibitors of 1-deoxy-D-xylulose 5-phosphate reductoisomerase and as growth inhibitors of *P. falciparum*. An enantiomerically pure trans-cyclopropyl N-acetyl analogue showed comparable inhibitory activity as fosmidomycin toward *E. coli* DXR and proved equally active when tested in vitro for *P. falciparum* growth inhibition. Conversely, an alpha-phenyl cis-cyclopropyl analogue showed virtually no inhibition of the enzyme. Devreux et al., *J Med Chem.* 2006 Apr. 20; 49(8):2656-60. A series of pyridine-2-one and quinolin-2-one derivatives have been demonstrated to have potent activity against bacterial DXR (see WO 2003103668). A series of novel 3'-amido-3'-deoxy-N(6)-(1-naphthylmethyl)adenosines was synthesized and was tested for anti-malarial activity versus the Dd2 strain of *Plasmodium falciparum*. Further, this series and 62 adenosine derivatives were analyzed regarding 1-deoxy-d-xylulose 5-phosphate reductoisomerase inhibition. Biological evaluations revealed that the investigated 3',N(6)-disubstituted adenosine derivatives displayed moderate but significant activity against the *P. falciparum* parasite in the low-micromolar range. Herforth et al., *Bioorg Med Chem.* 2004 Feb. 15; 12(4):755-62.

FIG. 26 depicts a number of inhibitors of DXR, which are suitable for use as targeting moieties in the presently disclosed subject matter. FIG. 26 shows the structure of these known inhibitors along with possible sites of attachment of the linkers and metal binding moieties ("R"), as well as possible derivatives.

In some embodiments, the metallo-oxidoreductase inhibitor is a DXR inhibitor comprising a targeting moiety, a metal binding moiety, and optionally a linker, and wherein the inhibitor has a formula selected from the group consisting of:

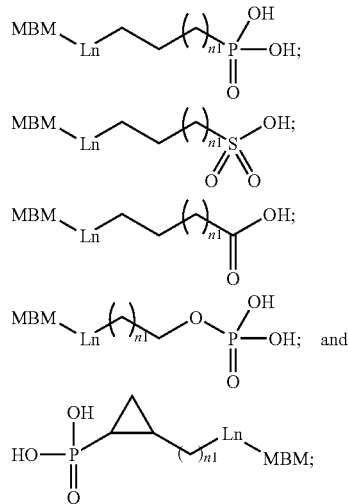

wherein n1 is an integer from 1 to 2; and

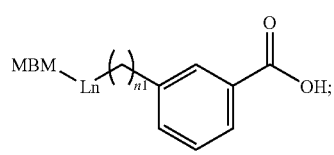

wherein n1 an integer from 1 to 2; and wherein:
MBM is a metal binding moiety;
$L_n$ is a linker, wherein n is an integer from 0 to 1;
under the proviso that the metal binding moiety is not a metal binding moiety selected from the group consisting of:

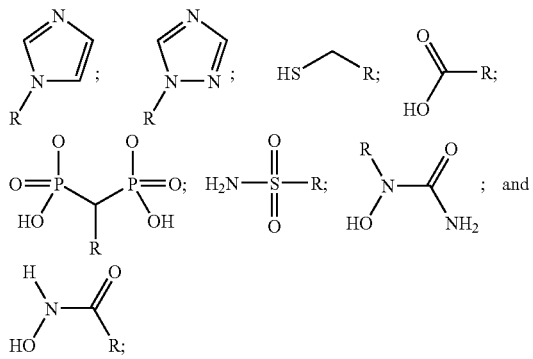

wherein: R is an attachment site through which the metal binding moiety can be attached to the targeting moiety, optionally through linker, $L_n$.

In some embodiments, the deoxy-xylulose phosphate reductoisomerase inhibitor is selected from the group of deoxy-xylulose phosphate reductoisomerase inhibitors presented in FIG. 26.

In addition to these targeting moieties, other known targeting moieties, identified by the screens outlined below or shown to bind to DXR can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

DXR activity can be measured by established methods. See Shigi et al., *J. Antimicrob. Chemother.*, 1989, 24: 131; Woo et al., *Bioorg. Med. Chem.*, 2006 Apr. 1; 14(7): 2375-85; Devreux et al., *J Med Chem.* 2006 Apr. 20; 49(8): 2656-60.

2. 5-Lipoxygenase (5-LO)

5-Lipoxygenase (5-LO) (EC 1.13.11.34, also known as leukotriene-$A_4$ synthase, $D^5$-lipoxygenase; 5D-lipoxygenase, arachidonic 5-lipoxygenase, arachidonic acid 5-lipoxygenase, C-5-lipoxygenase, LTA synthase, or leukotriene $A_4$ synthase) is a nonheme, iron-containing enzyme that catalyzes oxygenation of polyunsaturated fatty acids. 5-Lipoxygenase (5-LO) catalyzes the first step in the conversion of arachidonic acid (AA) into leukotrienes (LTs) that are mediators of inflammatory and allergic reactions. Recently, the 5-LO pathway has also been associated with atherosclerosis and osteoporosis. It also has been shown that cellular 5-LO activity is regulated in a complex manner that can involve different signaling pathways. 5-LO can be activated by an increase in intracellular $Ca^{2+}$ concentration, diacylglycerols, phosphorylation by MAPKAP kinase-2 and ERK. Werz and Steinhilber, *Biochem. Pharmacol.*, 70:327-33 (2005).

Both plant and mammalian LOs have been shown to undergo functionally important, $Ca^{2+}$-regulated binding to membranes, followed by production of lipid-derived bioactive mediators. Mammalian 5-lipoxygenase (5-LO) is of exceptional importance because it converts arachidonic acid (AA) to 5-hydroperoxyeicosatetraenoic acid (5-HPETE) and then to leukotriene $A_4$, a key intermediate in biosynthesis of all leukotrienes that act as potent mediators of allergy, inflammation, apoptosis, and tumorigenesis. Leukotriene production in stimulated myeloid cells is preceded by a $Ca^{2+}$-mediated binding of 5-LO to nuclear membranes. A $Ca^{2+}$-independent, phosphorylation-mediated 5-LO translocation to the nuclear membrane and activation has also been documented. See Pande et al., *Biophys J.*, 88:4084-4094 (2005), and references cited therein, all expressly incorporated by reference. For review on 5-lipoxygenase, see Radmark, *Am. J. Respir. Crit. Care Med.*, 161:S11-S15 (2000).

Compounds which inhibit 5-lipoxygenase have been described. U.S. Pat. No. 6,376,528 describes compounds that inhibit of 5-LO. U.S. Pat. No. 5,234,950 describes tetrahydrofuran derivatives. U.S. Pat. No. 5,098,932 describes cyclic ether derivatives. U.S. Pat. No. 5,354,865 describes tetrahydropyrans. U.S. Pat. Nos. 4,873,259, 5,220,059 and 5,288, 751 describe hydroxyureas as lipoxygenase inhibitors. Acetylene derivatives have been described as having 5-LO inhibitor activity in WO92/0162. Each of which is incorporated herein by reference, particularly for the description and structures depicted therein.

5-lipoxygenase inhibitors also include masoprocol (nordihydroguaiaretic acid), tenidap [5-chloro-2,3-dihydro-3-(hydroxy-2-thienylmethylene)-2-oxo-1H-indole-1-carboxamide], zileuton, flobufen, lonapalene, tagorizine, Abbott A-121798, Abbott A-76745, Abbott A-78773, Abbott A-79175, Abbott ABT 761, Dainippon AL-3264, Bayer Bay-x-1005, Biofor BF-389, bunaprolast, Cytomed CMI-392, Takeda CV-6504, enazadrem phosphate, Leo Denmark ETH-615, flezelastine hydrochloride, Merck Frosst L 663536, Merckle ML-3000, 3M Pharmaceuticals R-840, rilopirox, Schering Plough SCH 40120, tepoxalin, linazolast (TMK-688), Zeneca ZD-2138, Bristol-Myers Squibb BU-4601A, carbazomycin C, lagunamycin, Wellcome BW-70C, Ciba-Geigy CGS-26529, Warner-Lambert CI 1004, Warner-Lambert PD-136005, Warner-Lambert PD-145246, Elsai E 3040, Fujirebio F-1322, Fujisawa FR 110302, Merck Frosst L 699333, Merck Frosst L 739010, Lilly LY-269415, Lilly LY 178002, Hoechst Roussel P 8892, SmithKline Beecham SB-202235, American Home Products WAY-121520, American Home Products WAY-125007, Zeneca ZD 7717, Zeneca ZM-216800, Zeneca ZM 230487, 1,2-dihydro-n-(2-thiazolyl)-1-oxopynolo(3,2,1-kl)phenothiazine-1-carboxamide, Abbott A-65260, Abbott A-69412, Abbott-63162, American Home Products AHR-5333, Bayer Bay-q-1531, Boehringer Ingelheim BI-L-357, Boehringer Ingelheim BI-L-93BS, Boehringer Ingelheim BIL 226XX, Bristol-Myers Squibb BMY-30094, carbazomycin B, Wellcome BW-B218C, Chauvin CBS-1114, Ciba-Geigy CGS-21595, Ciba-Geigy CGS-22745, Ciba-Geigy CGS-23885, Ciba-Geigy CGS 24891, Ciba-Geigy CGS-8515, Chiesi CHF-1909, Warner-Lambert CI-986, Warner-Lambert CI 987, cirsiliol, docebenone, Eisai E 5110, Eisai E-6080, enofelast, epocarbazolin-A, eprovafen, evandamine, Fisons FPL 62064, Zeneca ICI-211965, Kyowa Hakko KF-8940, Merck & Co L-651392, Merck & Co L-651896, Merck & Co L-652343, Merck & Co L-656224, Merck & Co L-670630, Merck & Co L-674636, Lilly LY-233569, Merck & Co MK-591, nitrosoxacin-A, Ono ONO-5349, Ono ONO-LP-219, Ono ONO-LP-269, Warner-Lambert PD-127443, Purdue Frederick PF-5901, Rhone-Poulenc Rorer Rev-5367, Rhone-Poulenc Rorer RG-5901-A, Rhone-Poulenc Rorer RG-6866, Roussel-Uclaf RU-46057, Searle SC-41661A, Searle SC-45662, Sandoz SDZ-210-610, SmithKline Beecham SK&F-104351, SmithKline Beecham SK&F-104493, SmithKline Beecham SK&F-105809, Synthelabo SL-81-0433, Teijin TEI-8005, Terumo TMK-777, Terumo TMK-781, Terumo TMK-789, Terumo TMK-919, Terumo TMK-992, Teikoku Hormone TZI-41127, American Home Products WAY-120739, American Home Products WY 47288, American Home Products Wy-48252, American Home Products Wy-50295, and Yoshitomi Y-19432. See U.S. Pat. No. 6,376,528, which is incorporated herein by reference in its entirety.

Ginkgetin, a biflavone from *Ginkgo biloba* leaves, has been reported to have a dual cyclooxygenase-2/5-lipoxygenase inhibitory activity. Son et al., *Biological & Pharmaceutical Bulletin*, 28:2181-84 (2005), herein incorporated by reference.

FIG. 17A-17C depicts a number of inhibitors of 5-lipoxygenase, which are suitable for use as targeting moieties in the presently disclosed subject matter. FIG. 17 shows the structure of these known inhibitors along with possible sites of attachment of the linkers and metal binding moieties ("R"), as well as possible derivatives.

In some embodiments, the metallo-oxidoreductase inhibitor is a 5-lipoxygenase inhibitor comprising a targeting moiety, a metal binding moiety, and optionally a linker, and wherein the inhibitor has a formula selected from the group consisting of:

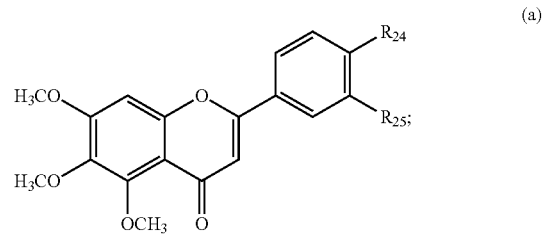

(a)

wherein $R_{24}$ and $R_{25}$ are each independently selected from the group consisting of —OH and $L_n$-MBM, wherein $L_n$ is a linking group, n is an integer from 0 to 1, and MBM is a metal binding moiety, provided that at least one of $R_{25}$ and $R_{25}$ is $L_n$-MBM;

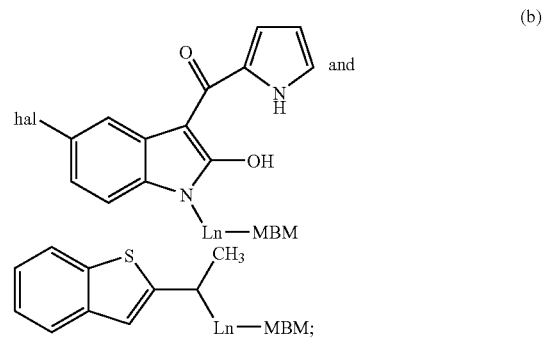

(b)

-continued

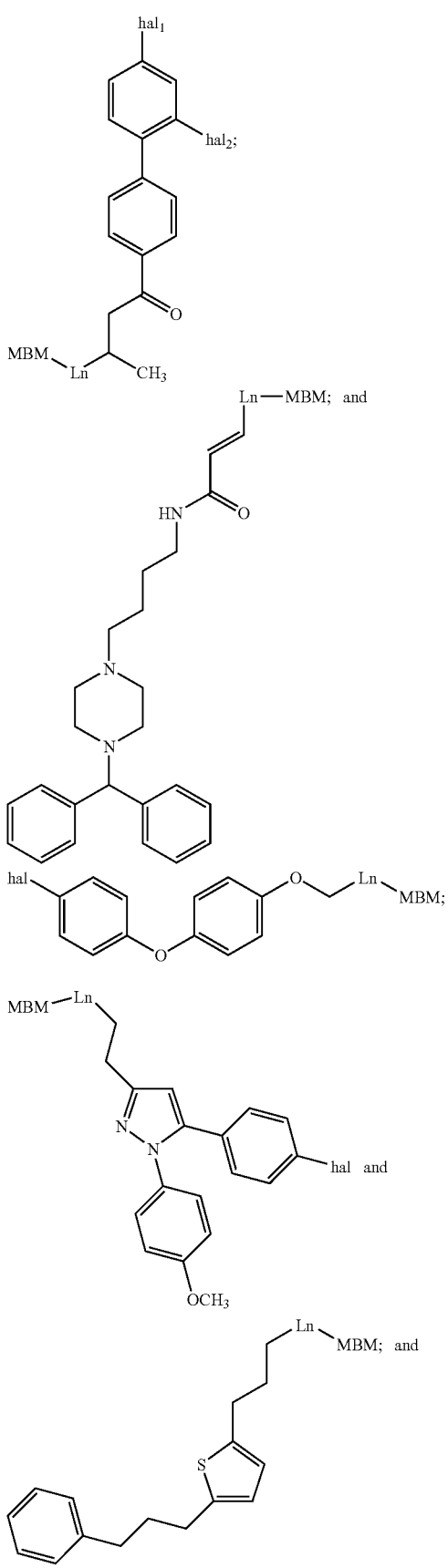

-continued (c)

(e)

MBM—Ln—(CH2 chain)—CH(CH3)CH3;

wherein:
MBM is a metal binding moiety;
$L_n$ is a linker, wherein n is an integer from 0 to 1;
under the proviso that the metal binding moiety is not a metal binding moiety selected from the group consisting of:

wherein: R is an attachment site through which the metal binding moiety can be attached to the targeting moiety, optionally through linker, $L_n$.

In some embodiments, the 5-lipoxygenase inhibitor is selected from the group of 5-lipoxygenase inhibitors presented in FIG. 17A-17C.

In addition to these targeting moieties, other known targeting moieties, identified by the screens outlined below or shown to bind to 5-lipoxygenase can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

5-lipoxygenase activity can be measured using established methods. See e.g., Rouzer et al., *Proc Natl Acad Sci.*, 83:857-861 (1986); Riendeau et al., *Biochem. J.*, 263:565-572 (1989); and Pande et al., *Biophys J.*, 88:4084-4094 (2005), herein incorporated by reference.

3. 17-Alpha Hydroxylase 17-alpha hydroxylase (AH) is a heme-containing member of the cytochrome P450 family and is also known as CYP17. AH catalyzes two mixed-function oxidase reactions utilizing cytochrome P450 oxidoreductase and the microsomal electron transfer system. The two reactions catalyzed by P450c17 are the 17-hydroxylation of the C21 steroids, pregnenolone ($\Delta^5$ steroid) or progesterone ($\Delta^4$ steroid), followed by the cleavage of the C17-20 bond to produce the C19 steroids, dehydroepiandrosterone (DHEA) or androstenedione, respectively. Each reaction requires one molecule of NADPH and one molecule of molecular $O_2$. In this two-step reaction, 17-hydroxypregnenolone or 17-hydroxyprogesterone is formed as an intermediate. Due to the pivotal importance of AH in the synthesis of androgens, AH has been a target for androgen-related diseases such as prostate cancer. Payne and Hales, *Endocrine Reviews*, 25 (6): 947-970.

The in vivo antitumoral effects of liarozole against androgen-dependent and independent Dunning rat prostatic tumors has been examined Liarozole, at a dose of 120 mg/100 gm food, equivalent to 100 mg/kg per day, inhibited the growth of the slow growing, well-differentiated, androgen-dependent Dunning-H tumor (median tumor volume decrease of 60%). At the same dose it also significantly reduced the growth of the androgen-independent, moderately differentiated PIF-1 (–60%) and androgen-independent, anaplastic AT-6 tumors (–73%). Dijkman et al., *J. Urol.*, 1994 January; 151(1):217-22. See also U.S. Pat. No. 4,859,684, which is incorporated herein by reference in its entirety.

A series of 1- and 4-(2-naphthylmethyl)-1H-imidazoles (3 and 4) were synthesized and evaluated as C(17,20)-lyase inhibitors. Several 6-methoxynaphthyl derivatives showed potent C(17,20)-lyase inhibition, suppression of testosterone biosynthesis in rats and reduction in the weight of prostate and seminal vesicles in rats, Matsunaga et al., *Bioorg Med Chem.*, 2004 Aug. 15; 12(16):4313-36. See also U.S. Pat. Nos. 6,573,289 and 7,084,149, each of which is incorporated herein by reference in its entirety.

A series of novel delta 16-17-azolyl steroids was synthesized via the nucleophilic vinylic "addition-elimination" substitution reaction of 3 beta-acetoxy-17-chloro-16-formylandrosta-5,16-diene (2) and azolyl nucleophiles. Several of the novel delta 16-17-azolyl steroids were potent inhibitors of human and rat testicular P450(17) alpha. Njar et al., *J. Med. Chem.*, 1998 Mar. 12; 41(6):902-12. See also U.S. Pat. No. 5,994,335, which is incorporated herein by reference in its entirety.

The in vivo effects of 17-(3-pyridyl)androsta-5,16-dien-3 beta-ol (CB7598) and 17-(3-pyridyl)androsta-5,16-dien-3-one (CB7627), novel potent steroidal inhibitors of AH, on WHT mice were compared with those of castration and two clinically active compounds, ketoconazole and flutamide. Flutamide and surgical castration caused significant reductions in the weights of the ventral prostate and seminal vesicles. CB7598, in its 3 beta-O-acetate form (CB7630), and CB7627 caused significant reductions in the weights of the ventral prostate, seminal vesicles, kidneys and testes when administered once daily for 2 weeks. Barrie et al., *J. Steroid Biochem Mol Biol.*, 1994 September; 50(5-6):267-73. See also U.S. Pat. No. 5,604,213, which is incorporated herein by reference in its entirety.

A series of novel nonsteroidal C(17,20)-lyase inhibitors were synthesized using de novo design based on its substrate, 17 alpha-hydroxypregnenolone, and several compounds exhibited potent C(17,20)-lyase inhibition. However, in vivo activities were found to be short-lasting, and in order to improve the duration of action, a series of benzothiophene derivatives were evaluated. Several compounds were identified to have powerful in vivo efficacy with extended duration of action. The key structural determinants for the in vivo efficacy were demonstrated to be the 5-fluoro group on the benzothiophene ring and the 4-imidazolyl moiety. Matsunaga et al., *Bioorg Med Chem.*, 2004 May 1; 12(9):2251-73.

FIG. 22A-22B depicts a number of inhibitors of AH, which are suitable for use as targeting moieties in the presently disclosed subject matter. FIG. 22A-22B shows the structure of these known inhibitors along with possible sites of attachment of the linkers and metal binding moieties ("R"), as well as possible derivatives.

In some embodiments, the metallo-oxidoreductase inhibitor is a 17a-hydroxylase inhibitor comprising a targeting moiety, a metal binding moiety, and optionally a linker, and wherein the inhibitor has a formula selected from the group consisting of:

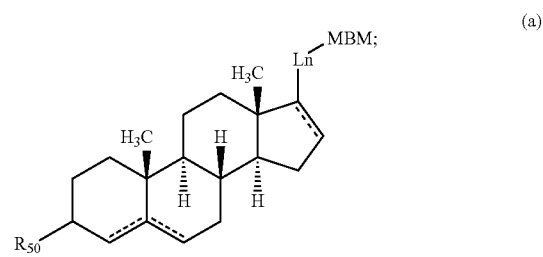

(a)

wherein:

$R_{50}$ is selected from the group consisting of (=O) and —$OR_{51}$, wherein $R_{51}$ is alkyl;

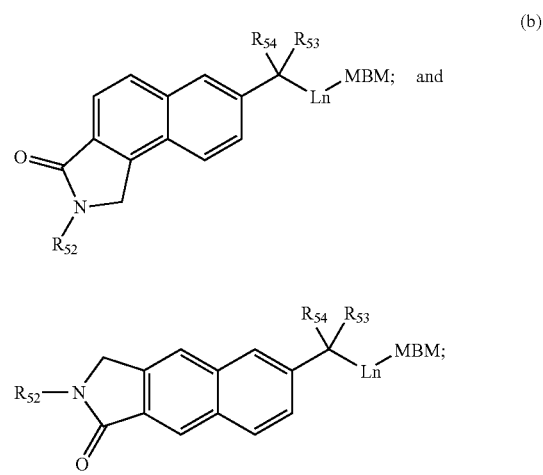

(b)

and wherein:

$R_{52}$ and each $R_{53}$ are independently H and alkyl;

$R_{54}$ is H or OH;

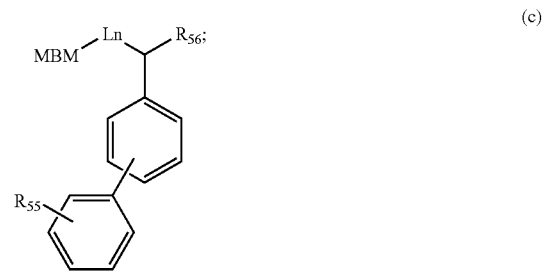

(c)

wherein:

MBM can be fused to cyclic hydrocarbon;

$R_{55}$=H, halogen, alkyl, $CONHR_{57}$, wherein $R_{57}$ is alkyl; and $R_{56}$ is H or OH;

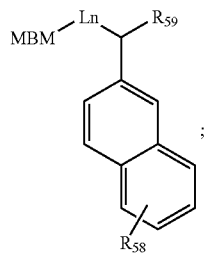
(d)

wherein:

MBM can be fused to cyclic hydrocarbon;

$R_{58}$=H, halogen, alkyl, $CONHR_{60}$, wherein $R_{60}$ is alkyl; and $R_{59}$ is H or OH;

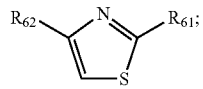

wherein:

$R_{61}$ and $R_{62}$ are each independently -Ln-MBM or unsubstituted phenyl or phenyl substituted with halogen, alkyl, or alkoxyl;

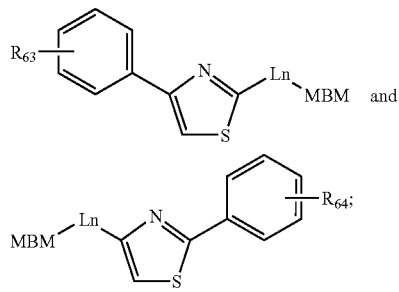

wherein $R_{63}$ and $R_{64}$ are each independently selected from the group consisting of H, halogen, alkyl, and alkoxy;

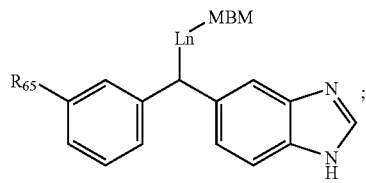
(f)

wherein $R_{65}$ is H or halogen;

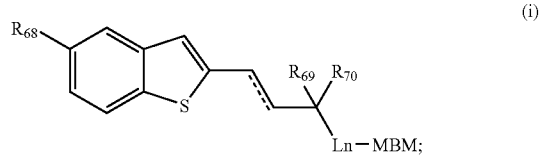
(g)

(h)

wherein:
$R_{66}$ is H or alkyl; and
$R_{67}$ is H or OH;

(i)

wherein:
$R_{68}$ is H or halogen;
$R_{69}$ and $R_{70}$ are H or alkyl;
wherein:
MBM is a metal binding moiety;
$L_n$ is a linker, wherein n is an integer from 0 to 1;
under the proviso that the metal binding moiety is not a metal binding moiety selected from the group consisting of:

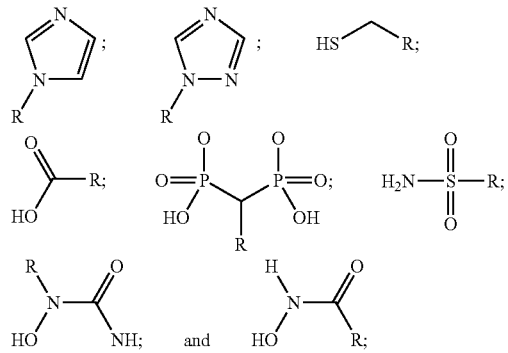

wherein: R is an attachment site through which the metal binding moiety can be attached to the targeting moiety, optionally through linker, $L_n$.

In some embodiments, the 17a-hydroxylase inhibitor is selected from the group of 17a-hydroxylase inhibitors presented in FIG. 22A-22B.

In addition to these targeting moieties, other known targeting moieties, identified by the screens outlined below or shown to bind to AH can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

AH activity can be measured using established methods. See Duc et al., *J. Steroid Biochem Mol Biol.*, 2003 April; 84(5):537-42; Matsunaga et al., *Bioorg. Med. Chem.* 2004 May 1; 12(9):2251-73; Njar et al., *J. Med. Chem.*, 1998 Mar. 12; 41(6):902-12.

4. Alcohol Dehydrogenases (ADH)

Alcohol Dehydrogenases (ADH, EC 1.1.1.1, also known as aldehyde reductase, alcohol dehydrogenase (NAD), aliphatic alcohol dehydrogenase, ethanol dehydrogenase, NAD-dependent alcohol dehydrogenase, NAD-specific aromatic alcohol dehydrogenase, NADH-alcohol dehydrogenase, NADH-aldehyde dehydrogenase, primary alcohol dehydrogenase, or yeast alcohol dehydrogenase) catalyzes the initial steps in the metabolism of ethylene glycol and methanol to their toxic metabolites. Ethylene glycol is first metabolized to glycoaldehyde which then undergoes further oxidation to glycolate, glyoxylate, and oxalate. It is glycolate and oxalate that are primarily responsible for the metabolic acidosis and renal damage that are seen in ethylene glycol poisoning. Methanol is first metabolized to formaldehyde and then undergoes subsequent oxidation via formaldehyde dehydrogenase to become formic acid, which is primarily responsible for the metabolic acidosis and visual disturbances that are associated with methanol poisoning.

Alcohol dehydrogenases (ADH) are a group of dehydrogenase enzymes that occur in many organisms and facilitate the conversion between alcohols and aldehydes or ketones. The reaction requires coenzyme $NAD^+$ as a hydrogen acceptor and has a broad specificity for alcohol substrates. In humans and many other animals, they serve to break down alcohols which could otherwise be toxic; in yeast and many bacteria they catalyze the opposite reaction as part of fermentation. ADH has been the target for the development of agents to treat methanol and ethylene glycol poisoning. Edenberg, *Prog Nucleic Acid Res Mol Biol.* 2000; 64:295-341.

Human alcohol dehydrogenases isoenzymes are dimeric, zinc-dependent oxidoreductases with subunit molecular masses of 40 kDa. The ADH system is the major pathway for the metabolism of beverage ethanol as well as biological important alcohols or aldehydes like retinol, 3β-hydroxysteroids, ω-hydroxy fatty acids, and 4-hydroxynonenal. Seven ADH genes (ADH1-ADH7) have been identified in humans. The ADH1-ADH5 genes encode the α, β, γ, π, and χ subunits, respectively, and the ADH7 gene encodes the σ subunit. Polymorphism occurs at both the ADH2 (β1, β2, β3) and ADH3 (γ1, γ2) loci, such that nine distinct human ADH subunits have been identified. The human ADH isoenzymes have been assigned to five distinct classes based on their amino acid sequences, electrophoretic and enzymatic properties, and their sensitivity to inhibition by pyrazole and its four-substituted derivatives. The dimeric human αα, ββ, and γγ isoenzymes and their polymorphic variants comprise the class I forms, and are the most sensitive to inhibition by 4-methylpyrazole. In contrast, the ππ, χχ, σσ, and ADH6 isoenzymes comprise the class II, III, IV, and V forms, respectively, and are less sensitive to 4-methylpyrazole inhibition. Xie and Hurley, *Protein Science*, 8:2639-2644 (1999). The $NAD^+$-binding domain consists of a central beta-sheet of six strands flanked by alpha helices. $NAD^+$ binds to the C-terminus of the beta-sheet. The catalytic domain also has an alpha/beta structure. The inter-domain interface forms a cleft which contains the active catalytic site. The interface is formed by two helices, one from each domain crossing over each other. Each dimer contains two zinc ions $Zn^{2+}$, with the one at the catalytic site being mandatory for catalysis. The alcohol substrate binds inside the cleft where the $Zn^{2+}$ cation is, and the nicotinamide ring of the NAD finds its way pointing into the cleft. The dimer forms with the two NAD-binding domains packing together such that their two central beta sheets combine to form a 12-stranded beta sheet. The catalytic domains are situated at opposite ends.

ADH inhibitors include auramine O, allicin, 1,5-anilinonaphthalenesulfonic acid, 1,7-anilinonaphthalenesulfonic acid, 1,8-anilinonaphthalenesulfonic acid, berberine, canavanine, 2,2'-diprypyl, imidazole, m-methylbenzamide, 4-methylpyrazole, pyrazole, 4-pentylpyrazole, O-phenanthroline, alrestatin, anthranic acid, O-carboxybenzaldehyde, 2,3-dimethylsuccinic acid, ethacrynic acid, isonicotinic acid, phenacemide, quercetin, quercitrin, sorbinil, tetramethyleneglutaric acid, valproic acid, propranolol, 2,2,2-trichloroethanol, 4,5-diaminopyrazole and its derivatives and 2-ethyl-5-methyl-2H-3,4-diaminopyrazole. See U.S. Patent Application Publication 20030138390, which is incorporated herein by reference in its entirety.

Fomepizole (4-methylpyrazole) is a competitive inhibitor of ADH. Pyrazole and its 4-substituted derivatives competitively inhibit the binding of alcohol substrates through the formation of a tight enzyme.$NAD^+$.inhibitor complex, in which pyrazole nitrogens interact with both zinc and $NAD^+$. Xie et al., *J. Biol. Chem.*, 272:18558-18563 (1997), herein incorporated by reference.

CNAD (5-beta-D-ribofuranosylnicotinamide adenine dinucleotide) is an isomeric and isomeric analogue of NAD, in which the nicotinamide ring is linked to the sugar via a C-glycosyl (C5-C1') bond. CNAD acts as a general dehydrogenase inhibitor but shows unusual specificity and affinity for liver alcohol dehydrogenase. Goldstein et al., *J. Med. Chem.*, 37:392-9 (1994), herein incorporated by reference.

Other inhibitors include dimethyl sulfoxide, Perlman and Wolff, *Science*, 160:317-9 (1968); and p-methylbenzyl hydroperoxide, Skursky et al., *Biochem Int.*, 26:899-904 (1992), herein incorporated by reference.

FIG. 25 depicts a number of inhibitors of ADH, which are suitable for use as targeting moieties in the presently disclosed subject matter. FIG. 25 shows the structure of these known inhibitors along with possible sites of attachment of the linkers and metal binding moieties ("R"), as well as possible derivatives.

In some embodiments, the metallo-oxidoreductase inhibitor is an alcohol dehydrogenase inhibitor comprising a targeting moiety, a metal binding moiety, and optionally a linker, and wherein the inhibitor has a formula selected from the group consisting of:

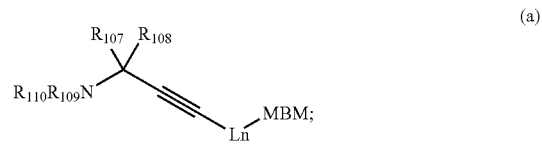

(a)

wherein $R_{107}$, $R_{108}$, $R_{109}$, and $R_{110}$ are each independently H or alkyl; and

(b)

wherein $R_{111}$ is alkyl;
wherein:
MBM is a metal binding moiety;
$L_n$ is a linker, wherein n is an integer from 0 to 1;
under the proviso that the metal binding moiety is not a metal binding moiety selected from the group consisting of:

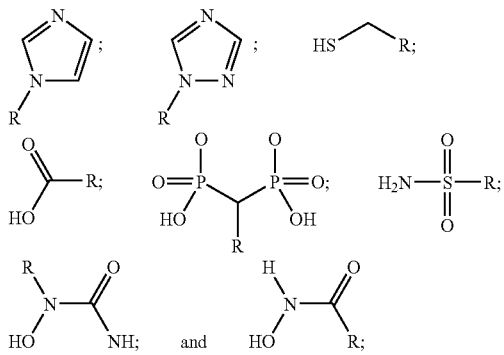

wherein: R is an attachment site through which the metal binding moiety can be attached to the targeting moiety, optionally through linker, $L_n$.

In some embodiments, the alcohol dehydrogenase inhibitor is selected from the group of alcohol dehydrogenase inhibitors presented in FIG. 25.

In addition to these targeting moieties, other known targeting moieties, identified by the screens outlined below or shown to bind to alcohol dehydrogenases can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

Alcohol dehydrogenase activity can be measured using established methods. See e.g., Vallee and Hoch, *Proc Natl Acad Sci USA*, 41:327-38 (1955); Kato et al., *Clin. Chem.*, 30:1817-20 (1984), herein incorporated by reference.

5. Aldosterone Synthase

Aldosterone synthase (AS) is a heme-containing member of the cytochrome P450 family and is also known as CYP11B2. Aldosterone synthesis from 11-deoxycorticosterone is catalyzed by AS and occurs in three sequential reactions, each utilizing one molecule of NADPH and one molecule of oxygen and the mitochondrial electron transfer system. The three sequential reactions are: the 11β-hydroxylation of 11-deoxycorticosterone, the hydroxylation of carbon 18, followed by oxidation of the carbon 18 hydroxyl group to yield the carbon 18 aldehyde group resulting in the formation of aldosterone. Because of the known relationship between aldosterone and electrolyte and fluid retention, AS has been a target for the development of agents to treat hypertension and congestive heart failure. Payne and Hales, *Endocrine Reviews*, 25(6):947-970.

A series of imidazo[1,5a]pyridine derivatives have demonstrated the ability to inhibit the cytochrome P450 enzyme aldosterone synthase that are potentially useful for the treatment of hypokalemia, hypertension, congestive heart failure, renal failure, restenosis, atherosclerosis, obesity, and other aldosterone-related conditions. See U.S. Pat. No. 7,223,866 and U.S. Patent Application Publication No. 2006/058,342, each of which is incorporated herein by reference in its entirety.

A series of heteroaryl-substituted naphthalenes and quinolines (1-31) have been demonstrated to be highly active and selective inhibitors of AS. A 6-ethoxy derivative was found to be the most selective AS inhibitor (IC50=12 nM; K(i) value=8 nM; CYP11B1 IC50=5419 nM; selectivity factor=451), showing no inhibition of human CYP3A4 (50 nM) and CYP2D6 (20 nM). Voets et al., *J. Med. Chem.* 2005 Oct. 20; 48(21):6632-42.

A series of heteroaryl-substituted dihydronaphthalenes and indenes (1-16) were shown to be potent and selective inhibitors of human AS. The most active inhibitor was the 6-methoxydihydronaphthalene derivative (IC(50)=2 nM), showing a K(i) value of 1.3 nM and a competitive type of inhibition. Voets et al., *J. Med. Chem.* 2006 Apr. 6; 49(7): 2222-31.

A broad range of bis-heterocyclic imidazolyl and heterocyclic spiro-compounds compounds have been demonstrated to be potent inhibitors of AS. See WO2005118541, WO 2006005726, WO 2006 128851, WO 2006128852, WO2006128853 and WO 2007065942, each of which is incorporated herein by reference in its entirety.

A series of condensed imidazolo derivatives has been demonstrated to be potent inhibitors of AS. See U.S. Patent Application Publication No. 2007/049616, which is incorporated herein by reference in its entirety.

FIG. 23A-23C depicts a number of inhibitors of AS, which are suitable for use as targeting moieties in the presently disclosed subject matter. FIG. 23A-23C shows the structure of these known inhibitors along with possible sites of attachment of the linkers and metal binding moieties ("R"), as well as possible derivatives.

In some embodiments, the metallo-oxidoreductase inhibitor is an aldosterone synthase inhibitor comprising a targeting moiety, a metal binding moiety, and optionally a linker, and wherein the inhibitor has a formula selected from the group consisting of:

(a)

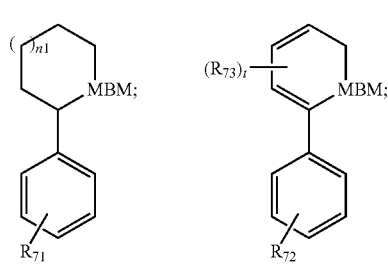

wherein:
n1 is an integer from 0 to 2;
t is an integer from 0 to 2;
$R_{71}$ is selected from the group consisting of H, cyano, halogen, alkyl, and aryl;
$R_{72}$ is selected from the group consisting of H, cyano, halogen, alkyl, and aryl;
$R_{73}$ is selected from the group consisting of alkyl, cycloalkyl, aryl, heteroaryl, alkoxy, and $CF_3$;

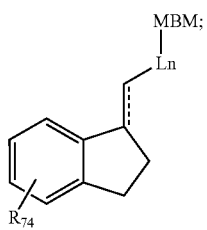

(b)

wherein:
R$_{74}$ is selected from the group consisting of cyano, halogen, and alkyl; and a dashed line indicates that a bond can be present or absent;

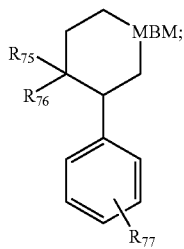

(c)

wherein:
R$_{75}$ and R$_{76}$ are each independently H or alkyl; and
R$_{77}$ is selected from the group consisting of H, cyano, halogen, and alkyl.

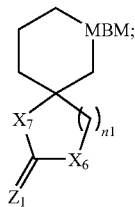

(d)

wherein:
n1 is an integer from 0 to 1;
X$_6$ is O or NR, wherein R is selected from the group consisting of H, alkyl, acyl, and aryl;
Z$_1$ is selected from the group consisting of O, NR, and —CH$_2$—; and
X$_7$ is O or —CH$_2$—;

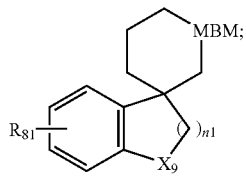

(e)

wherein:
n1 is an integer from 0 to 1;
R$_{79}$ is selected from the group consisting of cyano, halogen, and alkyl;
X$_8$ is O or NR$_{80}$, wherein R$_{80}$ is selected from the group consisting of H, alkyl, acyl, and aryl;

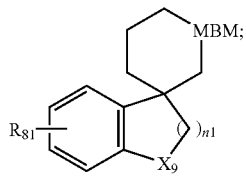

(f)

n1 is an integer from 0 to 1;
R$_{81}$ is selected from the group consisting of cyano, halogen, and alkyl;
X$_9$ is O or NR$_{82}$, wherein R$_{82}$ is selected from the group consisting of H, alkyl, acyl, and aryl;

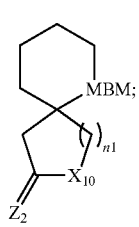

(g)

n1 is an integer from 0 to 1;
X$_{10}$ is O or NR$_{83}$, wherein R$_{83}$ is selected from the group consisting of H, alkyl, acyl, and aryl; and
Z$_2$ is selected from the group consisting of O, NR$_{84}$, —CH$_2$—, wherein R$_{84}$ is selected from the group consisting of H, alkyl, acyl, and aryl;

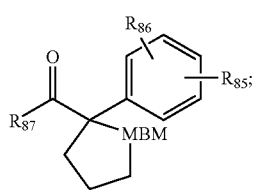

(h)

wherein:
R$_{85}$ and R$_{86}$ are each independently H, halogen, cyano, alkyl, and alkoxyl;
R$_{87}$ is selected from the group consisting of OR$_{88}$, NR$_{89}$R$_{90}$, wherein R$_{88}$, R$_{89}$, and R$_{90}$ are each independently selected from the group consisting of H, alkyl, and aryl;

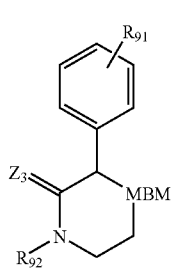

(i)

wherein:

$R_{91}$ and $R_{92}$ are each independently selected from the group consisting of H, halogen, cyano alkyl, alkoxyl, and aryl; and $Z_3$ is O or —$CH_2$—;

(j)

[Structure with MBM attached to indole-like ring system containing $X_{11}$ and $R_{93}$]

wherein:

$X_{11}$ is selected from the group consisting of O, S, and NH; and $R_{93}$ is selected from the group consisting of H, cyano, halogen, alkyl, and aryl;

(k)

[Structure with MBM, $R_{94}$, $R_{95}$ on a cyclohexane, attached to phenyl with $R_{96}$]

wherein:

$R_{94}$ and $R_{95}$ are each independently H or alkyl;

$R_{96}$ is selected from the group consisting of H, cyano, halogen, alkyl; or $R_{96}$ is part of a fused aromatic ring structure; and (l)

[Structure with MBM on cyclohexane attached to azole ring with $X_{12}$ and $COR_{97}$]

wherein:

$X_{12}$ is O or S; and $R_{97}$ is alkyl;

wherein:

MBM is a metal binding moiety;

$L_n$ is a linker, wherein n is an integer from 0 to 1;

under the proviso that the metal binding moiety is not a metal binding moiety selected from the group consisting of:

[Structures: imidazole-R; triazole-R; HS—CH$_2$—R; HOOC—R; bisphosphonate; H$_2$N—SO$_2$—R; hydroxyurea-type; and hydroxamic acid HO—NH—CO—R]

wherein: R is an attachment site through which the metal binding moiety can be attached to the targeting moiety, optionally through linker, $L_n$.

In some embodiments, the aldosterone inhibitor is selected from the group of aldosterone inhibitors presented in FIG. 23A-23C.

In addition to these targeting moieties, other known targeting moieties, identified by the screens outlined below or shown to bind to AS can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

AS activity can be measured using established methods. See Ehmer et al., *J. Steroid Biochem. Mol. Biol.* 2002 81:173-179; Voets et al., *J. Med. Chem.* 2006 Apr. 6; 49(7):2222-31; Ulmschneider et al., *J. Med. Chem.* 2005, 48(5): 1563.

6. Aromatase

Aromatase (CYP19) belongs to EC 1.14.14.1., a group of heme-thiolate proteins (P-450), acting on a wide range of substrates including many xenobiotics, steroids, fatty acids, vitamins and prostaglandins; reactions catalysed include hydroxylation, epoxidation, N-oxidation, sulfooxidation, N-, S- and O-dealkylations, desulfation, deamination, and reduction of azo, nitro and N-oxide groups.

Aromatase is a cytochrome P-450 enzyme complex responsible for the conversion of the 4-en-3-one androgens, androst-4-ene-3,17-dione (AD) and testosterone, into estrogens, estrone and estradiol. Aromatization of the androgens is thought to proceed through three sequential oxygenations at the C-19 position, respectively. In the third step, the angular methyl group at C-19 and 1b,2b-hydrogens are eliminated to result in the aromatization of the A-ring of the androgen molecule to form estrogen. In human, aromatase is the product of the CYP19 gene, which is expressed in many tissues including the granulosa and luteal cells of the ovary, bone, brain, placenta, testis, and adipose tissue. Kovacic et al., *Molecular Endocrinology*, 18: 252-259 (2004). Aromatase plays a critical role in breast cancer development by converting androgen to estrogen which plays an important role in breast cancer development. Approximately 60% of premenopausal and 75% of postmenopausal patients have estrogen-dependent carcinomas. Kinoshita and Chen, *Cancer Research*, 63:3546-55 (2003) Inhibitors of aromatase are valuable as therapeutic agents in the treatment of the advance breast cancer. Numazawa et al., *Chem. Pharm. Bull.*, 50(5): 703-05 (2002).

CYP19 is the key cytochrome P450 responsible for the conversion of C19 androgens (e.g., testosterone) to C18 estrogenic steroids. Estrogen is essential for establishing and maintaining pregnancy and expression of secondary sexual characteristics Inhibitors of CYP19 have been developed to treat estrogen-dependent breast cancer, especially in post-menopausal patients. CYP19 inhibitors (e.g., environmental toxins) also can play a major role in "endocrine disruptor" toxicity.

Aromatase like other mammalian members of the P450 hemeproteins superfamily, is a membrane-bound protein and has resisted structure-function analysis by means of X-ray crystallographic methods. As such, a three-dimensional (3-D) model of aromatase has been constructed base on "core structure" identified from the structures of the soluble, bacterial P450s. The modeling suggest that the imidazole ring of vorozole, a known inhibitor, points toward the heme, allowing one of the nitrogens to covalently bind to the heme irons. Graham-Lorence et al., *Protein Science*, 4:1065-1080 (1995). More recently, a 3-D structure of human aromatase (CYP19) was modeled on the basis of the crystal structure of rabbit CYP2C5, the first solved X-ray structure of an eukaryotic cytochrome P450 and was evaluated by docking S-fadrozole and the steroidal competitive inhibitor (19R)-10-thiiranylestr-4-ene-3,17-dione, into the enzyme active site. Loge et al., *Journal of Enzyme Inhibition and Medicinal Chemistry*, 20:581-585 (2005).

Pharmacologically, aromatase inhibitors can be divided into two classes: the so-called non-steroidal inhibitors that are either phenobarbitones (such as aminoglutethimide) or imidazole/triazole derivatives (fadrozole, letrozole, and anastrozole), or the steroidal compounds (formestane, exemestane) that are derivatives of androstenedione. These compounds differ in their effect on the aromatase enzyme. The non-steroidal compounds bind to the p450 domain of the aromatase protein, whereas the steroidal compounds bind to the substrate pocket. While the non-steroidal compounds bind reversibly, the steroidal compounds bind irreversibly, and have therefore been coined as "aromatase inactivators." Another major difference is that the main metabolite of exemestane, 17-hydro-exemestane, has androgenic activity. In line with this, exemestane suppresses the sex hormone-binding globulin in a dose-dependent manner in vivo. Oral, but not parenteral, administration of formestane has a similar effect. The third-generation aromatase inhibitors anastrozole, letrozole, and exemestane have been evaluated in prospective, randomized trials as adjuvant treatment of early-stage breast cancer. These trials evaluated different ways to incorporate aromatase inhibitors in the adjuvant setting: (1) as monotherapy (anastrozole), (2) as combination therapy with tamoxifen (anastrozole), (3) as sequential therapy with 2-3 years of tamoxifen followed by 2-3 years of the aromatase inhibitor (anastrozole and exemestane), and 4) as sequential therapy with 5 years of tamoxifen followed either by the aromatase inhibitor or placebo (letrozole). Joensuu et al., *Acta Oncol.*, 44:23-31(2005).

4β,19-dihydroxy-5-ene steroid is one of the most powerful competitive inhibitor of aromatase among the steroidal compounds, and its structurally related analog 4-ene-6β,19-diol, is a weak aromatase inhibitor. Numazawa et al., *Chem. Pharm. Bull.*, 50:703-05 (2002), herein incorporated by reference.

Other known inhibitors include 19-Methylandrostenedione, Numazawa et al., *Biol. Pharm. Bull.,* 29:1242-1245 (2006); 2- and 4-halogeno (F, Cl, and Br) estrones and their estradiol analogs as well as 6beta-methyl and phenyl estrones, Numazawa et al., *Steroids,* 71:371-9 (2006); 4-hydroxyandrostenedione, Dowsett and Coombes, *Breast Cancer Res. Tret.,* 30:81-87 (1994); Vorozole, Wouters et al., *Breast Cancer Res. Tret.,* 30:89-94 (1994); a dimer of 2-(4-pyridylmethy)-1-indanone, Gupta, et al., *Arch. Pharm. (Weinheim),* 337:398-401 (2004); 17 alpha-methyl testosterone, Mor et al., *J. Steroid Biochem. Mol. Biol.,* 79:239-46 (2001); 5-[(aryl)(1H-imidazol-1-yl)methyl]-1H-indoles, Leze et al., *Bioorg Med. Chem. Lett.,* 16:1134-7 (2006); 1-[(benzofuran-2-yl)(phenylmethyl)pyridine, -imidazole, and -triazole, Saberi et al., *J. Med. Chem.,* 49:1016-22 (2006); and ICI 182,780, Long et al., *J. Steroid Biochem. Mol. Biol.,* 67:293-304 (1998), all of these are incorporated herein by reference, particularly for the description and structures depicted therein.

FIG. 18A-18B depicts a number of inhibitors of aromatase, which are suitable for use as targeting moieties in the presently disclosed subject matter. FIG. 18A-18B shows the structure of these known inhibitors along with possible sites of attachment of the linkers and metal binding moieties ("R"), as well as possible derivatives.

In some embodiments, the metallo-oxidoreductase inhibitor is an aromatase inhibitor comprising a targeting moiety, a metal binding moiety, and optionally a linker, and wherein the inhibitor has a formula selected from the group consisting of:

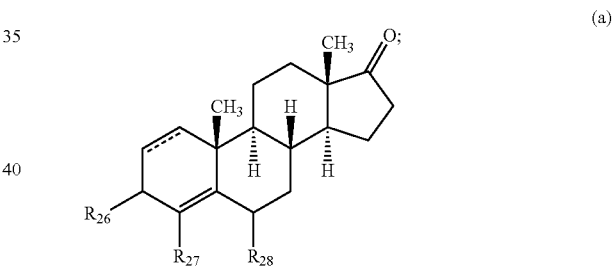

(a)

wherein:

$R_{26}$ and $R_{27}$ are each independently selected from the group consisting of —OH, =O, and $L_n$-MBM, and combinations thereof, wherein $L_n$ is a linking group, wherein n is an integer from 0 to 1, and MBM is a metal binding moiety, provided that at least one of $R_{26}$ and $R_{27}$ is $L_n$-MBM;

$R_{28}$ is H or =O; and a dashed line indicates that a bond is present or absent;

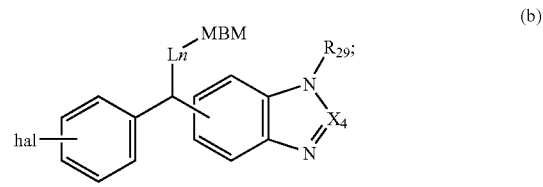

(b)

wherein:
$R_{29}$ is alkyl; and
$X_4$ is CH or N;

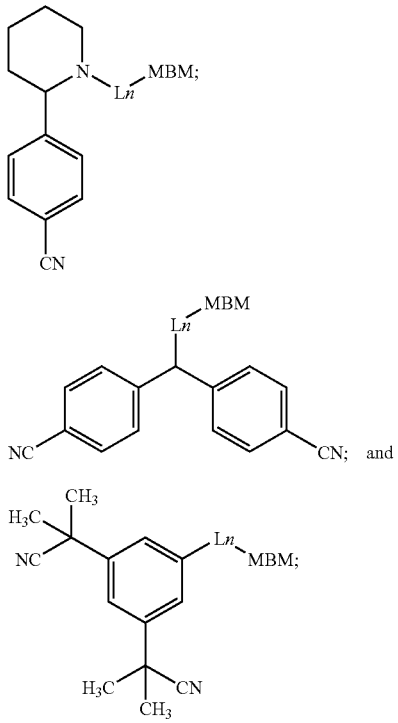

wherein:
MBM is a metal binding moiety;
$L_n$ is a linker, wherein n is an integer from 0 to 1;
under the proviso that the metal binding moiety is not a metal binding moiety selected from the group consisting of:

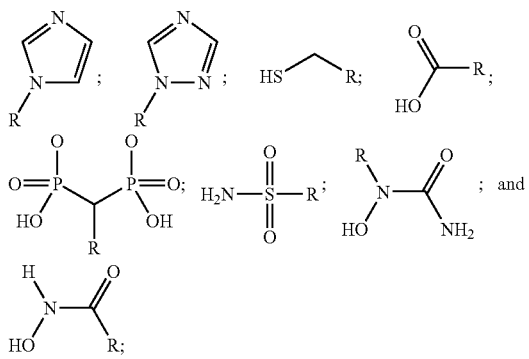

wherein: R is an attachment site through which the metal binding moiety can be attached to the targeting moiety, optionally through linker, $L_n$.

In some embodiments, the aromatase inhibitor is selected from the group of aromatase inhibitors presented in FIG. 18A-18B.

In addition to these targeting moieties, other known targeting moieties, identified by the screens outlined below or shown to bind to aromatase can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

Aromatase activity can be measured using established methods. See e.g., Lephart and Simpson, *Methods Enzymol.*, 206:477-483 (1991); Willingham et al., *Gen. Comp. Endocrinol*, 119:202-207 (2000); Kragie et al., *Endocr. Res.*, 28: 129 (2002); and Stresser et al., *Anal. Biochem.*, 284: 427 (2000), herein all incorporated by reference.

7. Cyclooxygenases (COX)

Cyclooxygenases (COX, EC 1.14.99.1, also known as prostaglandin synthase, prostaglandin G/H synthase, (PG)H synthase, PG synthetase, prostaglandin synthetase, fatty acid cyclooxygenase, or prostaglandin endoperoxide synthetase) acts both as a dioxygenase and as a peroxidase. Prostaglandin endoperoxide H synthase (PGHS) is a heme-containing, bi-functional enzyme that catalyzes the incorporation of two molecules of $O_2$ into arachidonic acid to yield the hydroperoxy endoperoxide, prostaglandin $G_2$ ($PGG_2$). $PGG_2$ diffuses from the cyclooxygenase active site and binds at the peroxidase active site where it is reduced to the hydroxy endoperoxide, $PGH_2$, the precursor to prostaglandins, thromboxane, and prostacyclin. The conversion of arachidonic acid (AA) to prostaglandin (PG) $H_2$, the immediate precursor to prostaglandins, thromboxanes, and prostacyclin. In mammalian tissues, there are two isoforms of PGHS designated PGHS-1 (or cyclooxygenase-1 (COX-1)) and PGHS-2 (or COX-2). COX-1 is generally considered the homeostatic form of the enzyme as it is constitutively expressed in a number of tissues, whereas COX-2 is sensitive to induction in many tissues by a broad range of physiological and pathological stimuli. Inhibition of COX enzymes by non-steroidal anti-inflammatory drugs (NSAIDs) accounts for their anti-inflammatory and analgesic activities, as well as their gastrointestinal toxicity. Development of selective COX-2 inhibitors has reduced the gastrointestinal liability. COX-1 and COX-2 have very similar structures characterized by a membrane-binding domain comprised of amphipathic helices forming the entrance to a long hydrophobic channel. This channel leads deep inside the protein, and at its upper end comprises the cyclooxygenase active site. The cyclooxygenase active site is separated from the opening near the membrane-binding domain by a constriction made up of the residues Arg-120, Tyr-355, and Glu-524. Arachidonic acid, when bound productively for turnover, is positioned with its carboxylic acid ion-paired to Arg-120, its 13-pro-S-hydrogen adjacent to the catalytically important Tyr-385, and its ω-end projecting into a channel that abuts Gly-533. Crystal structures of COX enzymes with carboxylic acid-containing NSAIDs show that the inhibitors are positioned in a similar fashion with their carboxylates coordinated to Arg-120 and their aromatic functionality projecting into the cyclooxygenase active site toward Tyr-385. Diarylheterocycle inhibitors of COX-2 bind in the cyclooxygenase active site above Arg-120 and insert their sulfonamide or sulfone groups into a side pocket bordered by Val-523. Rowlinson et al., *J. Biol. Chem.*, 278: 45763-45769 (2003); and Harman et al., *J. Biol. Chem.*, Vol. 279, Issue 41, 42929-42935, Oct. 8, 2004, herein all incorporated by reference.

Cyclooxygenases (COXs) catalyze the conversion of arachidonic acid into prostaglandin $H_2$ ($PGH_2$). Arachidonic acid, produced by the breakdown of membrane phospholipids, is metabolized by COX into $PGH_2$ in a two-step reaction that also produces free radical superoxide. There are three isoforms of COX. COX-1 is present in most cells and is involved in normal cellular physiology, such as gastric secretion and platelet function. COX-2 is expressed constitutively in some organs, such as brain, but is markedly upregulated by a wide variety of stimuli, most notably inflammatory mediators. COX-3, a splice variant of COX-1, is highly sensitive to inhibition by acetaminophen and is most abundant in heart and brain. COX-2 is the rate-limiting enzyme for prostanoid synthesis and has been implicated in the basic mechanisms of several brain diseases, including stroke, multiple sclerosis and neurodegenerative diseases. The approval by the Food and Drug Administration (FDA) of highly selective COX-2 inhibitors for the treatment of pain and rheumatoid arthritis (RA) raised the possibility that these agents could also be used in the treatment of neurological diseases including stroke. However, the occurrence of serious cardiovascular complications in patients receiving COX-2 inhibitors has led to the recent withdrawal from the market of a popular COX-2 inhibitor and has called for a re-evaluation of the therapeutic potential of these drugs. Iadecola et al., *Stroke*, 36:182-85 (2005).

COX-2 appears to be the target for the anti-inflammatory effects of NSAIDs and COX-1 for their side effects. Many studies since the early 1990s have shown that the broad range of classical NSAIDs inhibit both COX-1 and COX-2 although with a general tendency toward COX-1 selectivity. This appears to be associated with gastrointestinal toxicity: the more COX-1-selective drugs appear to have the tendency to cause more gastrointestinal damage. This has provided the rationale for the development of selective inhibitors of COX-2. The first two compounds to enter the market place following deliberate development as COX-2-selective agents were rofecoxib (Vioxx™) and celecoxib (Celebrex™); these joined some exisfing NSAIDs, most notably etodolac (Lodine™), meloxicam (Mobic™, Mobicox™), and nimesulide (Aulin™, Mesulid™, Nimed™, and others), that display some level of COX-2 selectivity. Recently the number of therapeutically available COX-2-selective agents has been increased by the addition of valdecoxib (Bextra™) and etoricoxib (Arcoxia™), lumiracoxib (Prexige™). Warner and Mitchell, The FASEB Journal, 18:790-804 (2004), herein incorporated by reference.

U.S. Pat. No. 6,376,528 describes compounds that inhibit of COX-2. Compounds which selectively inhibit COX-2 have been described. U.S. Pat. No. 5,380,738 describes oxazoles which selectively inhibit cyclooxygenase-2. U.S. Pat. No. 5,344,991 describes cyclopentenes which selectively inhibit cyclooxygenase-2. U.S. Pat. No. 5,393,790 describes spiro compounds which selectively inhibit cyclooxygenase-2. WO document WO94/15932 describes thiophene and furan derivatives which selectively inhibit cyclooxygenase-2. WO94/27980 describes oxazoles which selectively inhibit cyclooxygenase-2. WO95/00501 describes compounds which selectively inhibit cyclooxygenase-2. WO94/13635 describes compounds which selectively inhibit cyclooxygenase-2. WO94/20480 describes compounds which selectively inhibit cyclooxygenase-2. WO94/26731 describes compounds which selectively inhibit cyclooxygenase-2. WO documents WO95/15316 describes pyrazolyl sulfonamide derivatives which selectively inhibit cyclooxygenase-2, all of these patents and patent application publications are incorporated herein by reference, particularly for the description and structures depicted therein.

Known selective COX-2 inhibitors have been described in numerous patents that been summarized in U.S. Pat. No. 6,649,629, all of which are incorporated herein by reference, particularly for the description and structures depicted therein.

In addition, aryl substituted compounds that are COX-2 selective inhibitors have been described in U.S. Pat. No. 6,825,185. Also has been described are members of the chromene class of compounds. U.S. Patent Application Publication No. 20050101597; 1H-indole derivatives, U.S. Pat. No. 6,599,929; 4'-methanesulfonyl-biphenyl derivative, U.S. Pat. No. 6,583,321; 3,4-dihydro-1H-naphthalene derivative, U.S. Pat. No. 6,768,019; diaryl 1,2,4-triazole derivative U.S. Patent Application Publication No. 20060009495; 5-chloro-3-(4-methanesulfonylphenyl)-6'-methyl-[2,3']bipyridinyl, U.S. Pat. No. 6,858,631; bipyridinyl derivatives, U.S. Pat. No. 6,946,558; etodolac, Shigemura et al., *Urology*, 66:1239-44 (2005); numesulide; Czembriek et al., *Oncol. Rep.*, 14:1523-6 (2005); valdecoxib, all of these patents and patent application publications are incorporated herein by reference, particularly for the description and structures depicted therein.

Ginkgetin, a biflavone from *Ginkgo biloba* leaves, has been reported to have a dual cyclooxygenase-2/5-lipoxygenase inhibitory activity. Son et al., *Biological & Pharmaceutical Bulletin*, 28:2181-84 (2005), herein incorporated by reference.

For a general review of cyclooxygenase and inhibitors, see Warner and Mitchell, *The FASEB Journal*, 18:790-804 (2004), herein incorporated by reference.

FIG. 19A-19E depicts a number of inhibitors of COX, which are suitable for use as targeting moieties in the presently disclosed subject matter. FIG. 19A-19E shows the structure of these known inhibitors along with possible sites of attachment of the linkers and metal binding moieties ("R"), as well as possible derivatives.

In some embodiments, the metallo-oxidoreductase inhibitor is a cyclooxygenase inhibitor comprising a targeting moiety, a metal binding moiety, and optionally a linker, and wherein the inhibitor has a formula selected from the group consisting of:

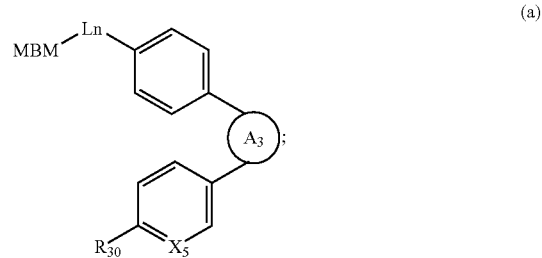
(a)

wherein:

$R_{30}$ is alkyl;

$X_5$ is CH or N; and $A_3$ is selected from the group consisting of:

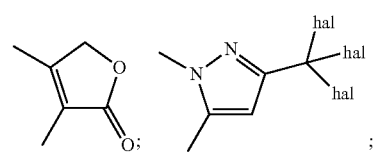

-continued

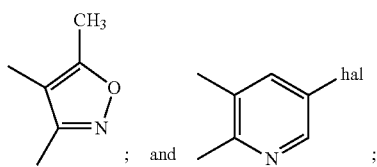
; and

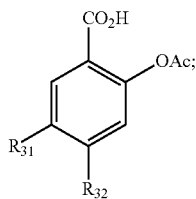
;

(b)

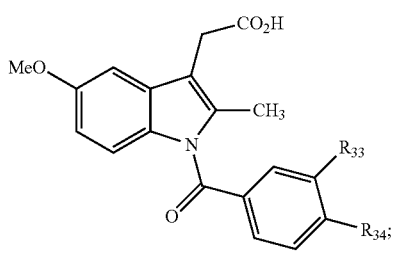

wherein:

R$_{31}$ and R$_{32}$ are H or —CH$_2$-L$_n$-MBM, provided at least one of R$_{31}$ and R$_{32}$ is —CH$_2$-L$_n$-MBM;

(c)

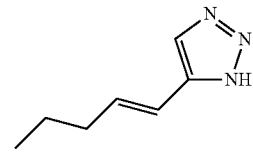

wherein R$_{33}$ and R$_{34}$ are selected from the group consisting of hal, —CH$_2$-L$_n$-MBM, and

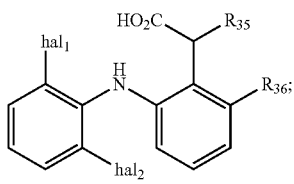

provided at least one of R$_{33}$ and R$_{34}$ is —CH$_2$-L$_n$-MBM;

(d)

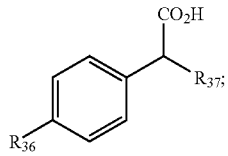

wherein R$_{35}$ and R$_{36}$ are selected from the group consisting of H, —CH$_2$-(phenyl)$_m$-L$_n$-MBM, wherein m and n are integers from 0 to 1; and provided at least one of R$_{36}$ and R$_{36}$ is —CH$_2$-(phenyl)$_m$-L$_n$-MBM;

(e)

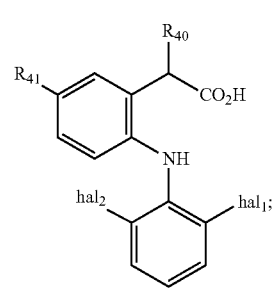

wherein:

R$_{37}$ is alkyl; and

R$_{38}$ is —(CH$_2$)$_y$—CH—(R$_{39}$)—CH$_2$—(O—CH$_2$—C(=O))$_z$-L$_n$-MBM;

wherein:

n, y, and z are each independently an integer from 0 to 1;

R$_{39}$ is straight-chain or branched alkyl; and (f)

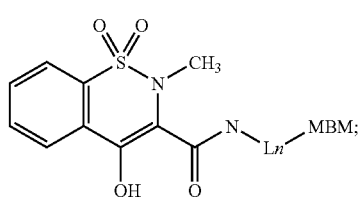

wherein:

R$_{40}$ is H or —CH$_2$-L$_n$-MBM;

R$_{41}$ is CH$_3$ or —CH$_2$-L$_n$-MBM, provided that at least one of R$_{40}$ and R$_{41}$ is —CH$_2$-L$_n$-MBM;

(g)

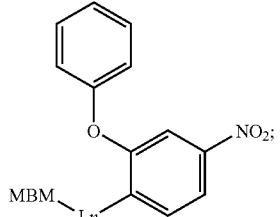

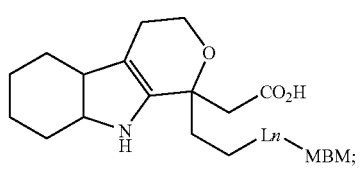

-continued

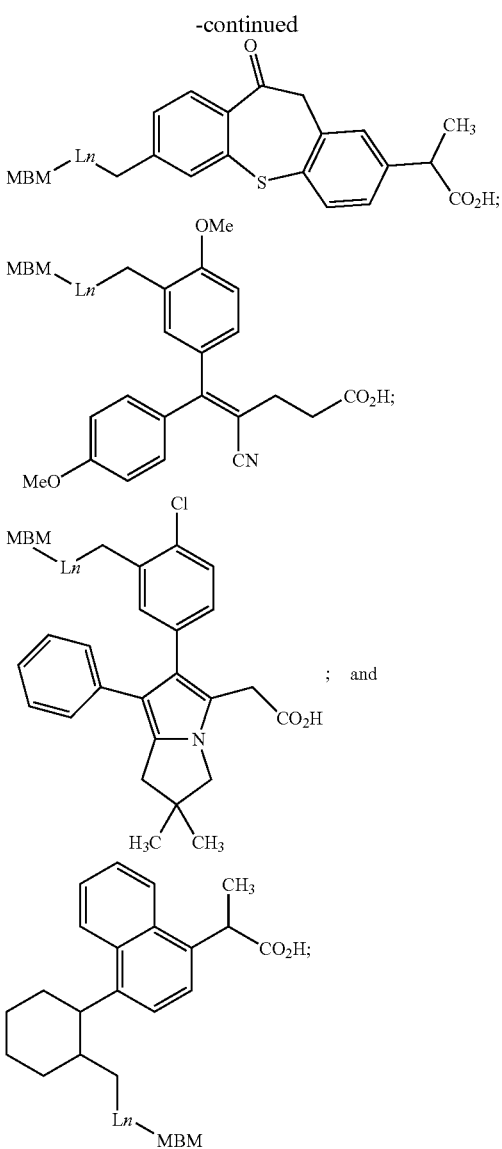

wherein:

MBM is a metal binding moiety;

$L_n$ is a linker, wherein n is an integer from 0 to 1;

under the proviso that the metal binding moiety is not a metal binding moiety selected from the group consisting of:

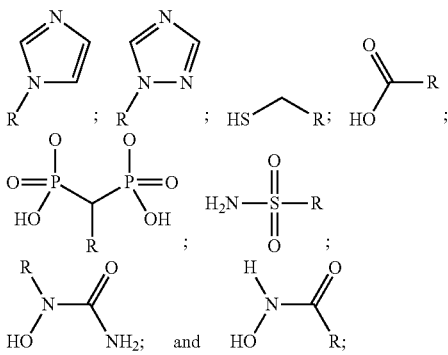

wherein: R is an attachment site through which the metal binding moiety can be attached to the targeting moiety, optionally through linker, $L_n$.

In some embodiments, the cyclooxygenase inhibitor is selected from the group of cyclooxygenase inhibitors presented in FIG. 19.

In addition to these targeting moieties, other known targeting moieties, identified by the screens outlined below or shown to bind to cyclooxygenase can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

Cyclooxygenase activity can be measured using established methods. See e.g., Kulmacz and Lands, *Prostaglandins*, 25:531-540 (1983). Rowlinson et al., *J. Biol. Chem.*, 278: 45763-45769 (2003), Xie et al., *Proc. Nat. Acad. Sci. USA*, 88, 2692-2696 (1991); and Forghani et al., *Anal. Biochem.*, 264:216-221 (1998), herein all incorporated by reference.

8. Heme Oxygenase (HO)

Heme oxygenase (decyclizing) (EC 1, 14.99.3) is also known as ORP33 proteins, haem oxygenase, heme oxidase, or haem oxidase. In mammals, carbon monoxide (CO) is formed mainly via the action of heme oxygenase (HO) on its substrate, heme. Under normal physiological conditions, some 85% of the CO produced by humans derives from heme, while the remainder arises through processes that do not involve heme, such as lipid peroxidation. While the majority of heme oxidation takes place in the liver and spleen during the housekeeping degradation of heme, the formation of CO from heme occurs in significant quantities in other structures such as blood vessels, kidneys and the brain. Cellular heme derived from ubiquitously disposed heme proteins such as cytochromes, peroxidases, respiratory burst oxidases, pyrrolases, catalase, nitric oxide synthases, hemoglobin, and myoglobin is degraded by the heme oxygenase enzyme system. The heme oxygenase enzyme opens the heme ring, resulting in the liberation of equimolar quantities of biliverdin, iron, and carbon monoxide. Agarwal and Nick, *J. Am. Soc. Nephrol.*, 11:965-973 (2000).

Heme oxygenases (HO) consist of constitutive and inducible isozymes (HO-1, HO-2). They catalyze the rate-limiting step in the metabolic conversion of heme to the bile pigments (i.e., biliverdin and bilirubin) and thus constitute a major intracellular source of iron and carbon monoxide (CO). Endogenously produced CO has been shown to possess intriguing signaling properties affecting numerous critical cellular functions including but not limited to inflammation, cellular proliferation, and apoptotic cell death. Ryter et al., *Physiol Rev.*, 86:583-650 (2006). The fact that HO-1 is strongly induced by its substrate, heme, and by oxidant stress, in conjunction with the robust ability of HO-1 to guard against oxidative insult, suggests a countervailing system to oxidative stress injury. HO-1 is a regulator of endothelial cell integrity and oxidative stress. Upregulation of HO-1 by pharmacological agents, including cobalt protoporphyrin (CoPP), has been shown to increase superoxide dismutase and to decrease reactive oxygen species (ROS) and NAD (P) H oxidase activity in vitro and in vivo. It has also been demonstrated that overexpression of the HO-1 gene in human, rabbit and rat endothelial cells not only renders the cells resistant to agents that elicit oxidative stress but also enhances cell growth and angiogenesis via HO-1-derived CO. Upregulation of HO-1 has also been shown to prevent endothelial cell death and sloughing in diabetic rats. Di Noia et al., *J. Biol. Chem.*, 281:15687-15693 (2006).

HO activity is attributable to two isozymes, HO-1 (molecular weight B32kDa, a stress protein induced by a number of stimuli including heat shock, heavy metals, heme, and reactive oxygen species) and HO-2 (molecular weight B36.5 kDa and constitutive). Tissues such as spleen, which are rich in reticuloendothelial cells, are thought to contain maximally upregulated levels of HO-1 under physiological conditions, while the hippocampus and vascular endothelial cells possess its counterpart HO-2. Kinobe et al., *British Journal of Pharmacology*, 147:307-315 (2006), herein incorporated by references. The crystal structure of HO-1 has been solved that reveals a novel helical fold with the heme sandwiched between two helices. The proximal helix provides a heme iron ligand, His 25. Conserved glycines in the distal helix near the oxygen binding site allow close contact between the helix backbone and heme in addition to providing flexibility for substrate binding and product release. Regioselective oxygenation of the alpha-meso heme carbon is due primarily to steric influence of the distal helix. Shuller et al., *Nat. Struct. Biol.* 1999 September; 6(9):860-7.

Heme plays an important role in many biologically relevant molecules, where it functions in the active site of enzymes or as a regulatory prosthetic group. Examples of the former are cytochromes P450 (CYPs) and nitric oxide synthase (NOS), and an example of the latter are soluble guanylyl cyclase (sGC). It was concluded that metalloporphyrin inhibitors of HO can be selective, and useful, when used at the appropriate concentrations. For example, chromium mesoporphyrin IX (CrMP) was one of the more useful drugs in broken cell preparations where a 10 mM concentration inhibited HO by 90%, with little or no effect on sGC or NOS. Kinobe et al., *British Journal of Pharmacology*, 147:307-315 (2006).

Inhibition of HO activity has also been demonstrated for other metalloporphyrins, for example, zinc protoporphyrin IX (ZnPP), tin protoporphyrin IX (SnPP), zinc deuteroporphyrin IX 2,4-bis-ethylene glycol (ZnBG), and zinc N-methylprotoporphyrin IX (ZnMePP). Appleton et al., *Drug Metabolism and Disposition*, 27:1214-1219 (1999), herein incorporated by reference.

Also found to be HO inhibitors are iron deuteroporphyrin 2,4 disulfonic, and iron deuteroporphyrin 2,4 bis glycol. Mitrione et al, *Am. J. Med. Sci.*, 296:180-6 (1988), herein incorporated by reference.

Azalanstat, an imidazole-dioxolane compound designed for the inhibition of mammalian lanosterol 14a-demethylase, have been used as lead compound to develop imidazole-dioxolane compounds as inhibitors of the enzyme activity of HO-1 and HO-2, which have high selectivity for HO-1 compared to HO-2. Kinobe et al., *British Journal of Pharmacology*, 147:307-315 (2006), herein incorporated by reference.

FIG. 20A-20B depicts a number of inhibitors of heme oxygenase, which are suitable for use as targeting moieties in the presently disclosed subject matter. FIG. 20A-20B shows the structure of these known inhibitors along with possible sites of attachment of the linkers and metal binding moieties ("R"), as well as possible derivatives.

In some embodiments, the metallo-oxidoreductase inhibitor is a heme oxygenase inhibitor comprising a targeting moiety, a metal binding moiety, and optionally a linker, and wherein the inhibitor has a formula selected from the group consisting of:

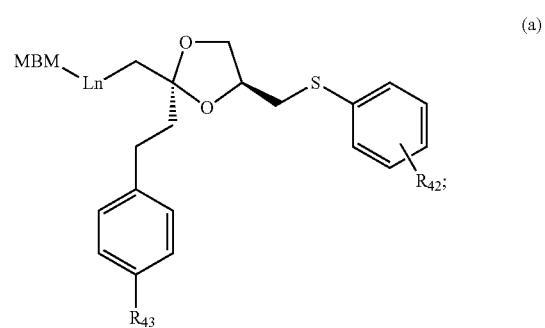

(a)

wherein:
R$_{42}$ is H or —NH$_2$; and
R$_{43}$ is H or halogen; and

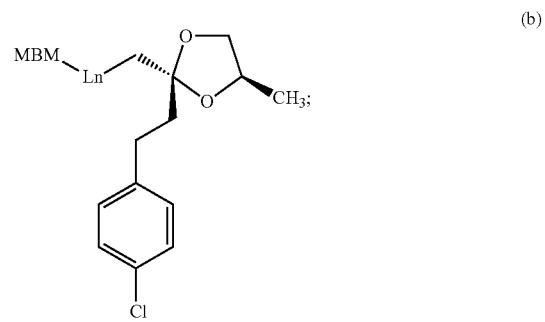

(b)

wherein:
MBM is a metal binding moiety;
L$_n$ is a linker, wherein n is an integer from 0 to 1;
under the proviso that the metal binding moiety is not a metal binding moiety selected from the group consisting of:

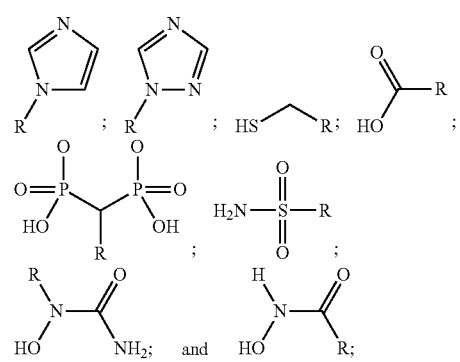

wherein: R is an attachment site through which the metal binding moiety can be attached to the targeting moiety, optionally through linker, L$_n$.

In some embodiments, the heme oxygenase inhibitor is selected from the group of heme oxygenase inhibitors presented in FIG. 20A-20B.

In addition to these targeting moieties, other known targeting moieties, identified by the screens outlined below or shown to bind to heme oxygenase can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

Heme oxygenase activity can be measured using established methods. See e.g., Lutton, et al., *Proc. Natl. Acad. Sci. USA,* 94: 1432-1436 (1997); Appleton et al., *Drug Metabolism and Disposition,* 27:1214-1219 (1999); U.S. Pat. No. 5,888,982; Ryter et al., *Free Radic. Biol. Med.,* 24:959-71 (1998); Lee and Chau, *Nature Medicine,* 8:240-246 (2002); and Kinobe et al., *British Journal of Pharmacology,* 147:307-315 (2006), each of which is incorporated herein by reference in its entirety.

9. Indoleamine 2,3-Dioxygenase

Indoleamine 2,3-dioxygenase (IDO) is a heme-containing metalloenzyme which catalyzes the initial rate-limiting step in tryptophan catabolism, which leads to the biosynthesis of nicotinamide adenine dinucleotide. By depleting tryptophan from local microenvironments, IDO can block activation of T lymphocytes, which are particularly sensitive to loss of this essential amino acid. Notably, IDO is needed to prevent T cell-mediated rejection of allogenic concepti. IDO is overexpressed in many cancers, where it has been implicated in immune escape. IDO is also an established target for the development of agents to treat inflammatory diseases such as osteoarthritis. Muller et al., *Nature Medicine* 11, 312-319 (2005).

Acemetacin, an inhibitor of IDO, is marketed for the treatment of osteoarthritis. A recent report demonstrates that acemetacin is equally effective to celecoxib in this regard. Leeb et al., *67th Ann. Sci. Meet. Am. Coll. Rheumatol.* (October 23-28, Orlando) 2003, Abst 70. See also WO 2004094409.

A series on novel indole derivatives have been demonstrated to be inhibitors of IDO. See WO 2004094409.

A series of substituted naphthalene and anthracene diones have been demonstrated to be potent and selective inhibitors of IDO. See WO2006005185.

A series of carbxoamidine derivatives have been demenostrated to be inhibitors of IDO. See WO 2006122150.

A series of N-hydroxyamidinoheterocycles have been described as modulators of indoleamine 2,3-dioxygenase. See WO 2007075598.

A series of N-hydroxyguanidines have been described as modulators of indoleamine 2,3-dioxygenase. See U.S. Patent Application No. 2007203140, which is incorporated herein by reference in its entirety.

Annulin A and Annulin B are IDO inhibitors isolated from the northeastern pacific marine hydroid *Garveia annulata.* Pereira et al., *J. Nat. Prod.* 2006, 69(10): 1496.

FIG. 27 depicts a number of inhibitors of IDO, which are suitable for use as targeting moieties in the presently disclosed subject matter. FIG. 27 shows the structure of these known inhibitors along with possible sites of attachment of the linkers and metal binding moieties ("R"), as well as possible derivatives.

In some embodiments, the metallo-oxidoreductase inhibitor is an indoleamine 2,3-dioxygenase inhibitor comprising a targeting moiety, a metal binding moiety, and optionally a linker, and wherein the inhibitor has a formula selected from the group consisting of:

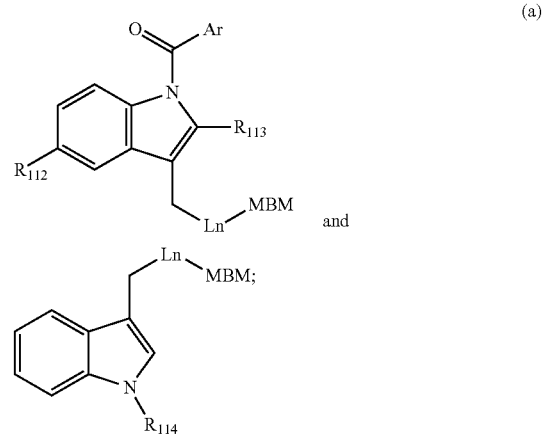

wherein:

$R_{114}$ is selected from the group consisting of H, alkyl, CO-alkyl, and CO-aryl;

$R_{112}$ and $R_{113}$ are each selected from the group consisting of H, alkyl, halogen, and alkoxy; and Ar is a substituted phenyl or heteroaryl;

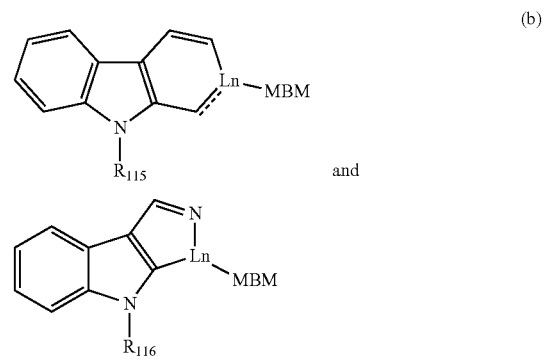

wherein $R_{115}$ and $R_{116}$ are each independently selected from the group consisting of H, alkyl, CO-alkyl, and CO-aryl; and

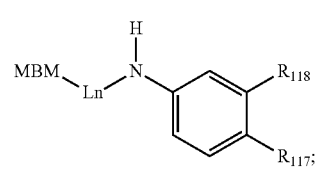

wherein:

MBM is a metal binding moiety;

$L_n$ is a linker, wherein n is an integer from 0 to 1;

$R_{117}$ and $R_{118}$ are independently selected from the group consisting of H, alkyl, —C(=O)-alkyl, and —C(=O)-aryl;

under the proviso that the metal binding moiety is not a metal binding moiety selected from the group consisting of:

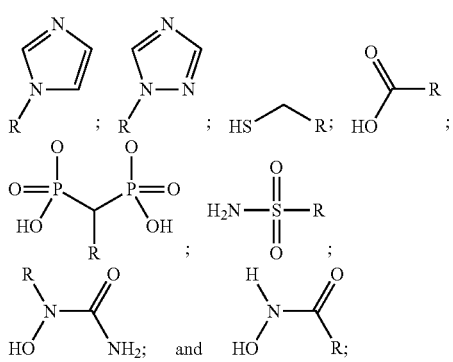

wherein: R is an attachment site through which the metal binding moiety can be attached to the targeting moiety, optionally through linker, $L_n$.

In some embodiments, the indoleamine 2,3-dioxygenase inhibitor is selected from the group of indoleamine 2,3-dioxygenase inhibitors presented in FIG. 27.

In addition to these targeting moieties, other known targeting moieties, identified by the screens outlined below or shown to bind to IDO can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

IDO activity can be measured using established methods. See Pereira et al., *J. Nat. Prod.* 2006, 69(10):1496; Malachowski et al., *Drugs Fut.* 2005, 30(9):897.

10. Lanosterol Demethylase

Lanosterol demethylases (EC 1.14.13.70, also known as sterol 14-demethylase, obtusufoliol 14-demethylase; lanosterol 14-demethylase; lanosterol 14α-demethylase; sterol 14α-demethylase, sterol 14α-demethylases, Erg11p, CYP51 or $P450_{14DM}$) are members of the cytochrome P450 superfamily (CYP), which includes a group of monooxygenases having a thiolate-ligated iron protoporphyrin as prosthetic group. Such heme proteins are widely distributed in many eukaryotes and some bacteria and participate in oxidative transformations of a large variety of lipophilic compounds including various xenobiotics. CYP51 catalyzes oxidative removal of the 14α-methyl group from postsqualene sterol precursors. Sixty-six lanosterol demethylase sequences are known from bacteria to human, their sequence homology ranging from ~25% between phyla to ~80% within a phylum. Even with only 22-33% amino acid identity across the biological kingdoms, the orthologous enzymes from bacteria to mammals preserve strict catalytic regio- and stereo specificity and have a very limited range of substrates. There are only four known CYP51 substrates: lanosterol, 24,25-dihydrolanosterol, 24-methylanedehidrolanosterol and obtusifoliol, with no other compounds being reported to be metabolized by this enzyme. See Lepesheva et al., *Journal of Biological Chemistry,* 281:3577-85 (2006), and Yoshida et al., *Journal of Biological Chemistry,* 259: 1655-1660 (1984).

Lanosterol demethylase, also known as sterol 14α-demethylase (14DM) or CYP51, is the main target of azole antifungal compounds such as fluconazole, econazole, clotrimazole and ketoconazole in fungi including *Saccharomyces cerevisiae* and *Candida albicans*. It is a member of the superfamily of heme-containing cytomchrome P450 enzymes (CYP) involved in metabolism of endogenous and xenobiotic substances. Lanosterol demethylase is a key enzyme in all sterol biosynthetic pathways, and is found in many species, including bacteria, fungi, and mammals. In all species, lanosterol demethylase catalyzes the removal of the C-14 methyl group in the sterol molecule. This is a key step in cholesterol, ergosterol, and phytosterol synthesis in animals, fungi, and plants. LD is a well-established target for the development of agents to treat cutaneous and systemic fungal disease. Akins, *Med Mycol.* 2005 June; 43(4):285-318.

In fungi, lanosterol demethylase reaction leads to an important precursor of ergosterol, an essential component in the membranes of fungi. However, mammalian and fungal lanosterol demethylase forms show difference in their ability to bind azole molecules known to inhibit cytochrome P450 activities. For example, fungal lanosterol demethylase binds fluconazole several orders of magnitude more tightly than mammalian isoforms, which is the basis for the design of azole inhibitors targeting fungal lanosterol demethylase versus the human form.

Azoles inhibit lanosterol demethylase activity by competitive, reversible binding to the heme cofactor located in the active site of lanosterol demethylase. Inhibition of lanosterol demethylaseactivity is lethal in fungi. However, treatment by fungistatic azole compound leads to the emergence of resistant clinical isolates over time. There are two important known mechanisms involved in such resistance. One is due to the mutations in lanosterol demethylase gene that results in reduced azole binding to lanosterol demethylase. The second is due to the increased expression of efflux pump genes, which leads to decreased intracellular drug accumulation. To combat azole resistance and to extend the spectrum of treatable pathogens, more potent azoles have been developed. One example is posaconazole, which unlike flucnazole and voriconazole, is not effluxed by the efflux pumps. Xiao et al., *Antimicrobial Agents and Chemotherapy,* 48:568-574, (2004).

Unlike the soluble bacterial P450s, all the fungal CYP51 proteins characterized to date are integral membrane proteins, making structural and biophysical characterization more challenging. Thus the X-ray crystal structure of CYP51 from *Mycobacterium tuberculosis* (MT-CYP51), which has more than 25% sequence identity to most fungal CYP51s was used to construct homology models for the CYP51 proteins from *Aspergillus fumigatus* (AF-CYP51A) and *Candida albicans* (CACYP51). Xiao et al., *Antimicrobial Agents and Chemotherapy,* 48:568-574, (2004).

Itraconazole, micafungin, and posaconazole have been studied as alternatives to fluconazole prophylaxis. Itraconazole showed no dramatic improvement over fluconazole as prophylaxis during liver and hematopoietic stem cell transplantation, primarily due to gastrointestinal side effects. In addition, detrimental changes to cyclophosphamide metabolism were noted for hematopoietic stem cell transplant recipients. Micafungin was superior to fluconazole during the pre-engraftment period of hematopoietic stem cell transplantation, because it was able to prevent mold infections, required less switches to empirical antifungal therapy, and functioned as well as fluconazole in preventing yeast infections. Van Burik and Jo-Anne, *Current Opinion in Infectious Diseases,* 18:479-483 (2005), all of these are incorporated herein by reference, particularly for the description and structures depicted therein.

R126638 is a novel triazole with in vitro activity similar to that of itraconazole against dermatophytes, and has been suggested to be an inhibitor of CYP51. Vanden Bossche et al.,

*Antimicrobial Agents and Chemotherapy*, 48:3272-8 (2004). Several non-azole lead molecules were obtained by coupling structure-based de novo design with chemical synthesis and biological evaluation, and all of the lead molecules exhibited a strong inhibitory effect on CYP51 of *Candida albicans*. Ji et al., *J. Med. Chem.*, 46:474-85 (2003), all of these are incorporated herein by reference, particularly for the description and structures depicted therein.

Other known CYP51 inhibitors include 15alpha-fluoro-24, 25-dihydrolanosterol, Morisaki et al., Chem Pharm Bull (Tokyo), 48:1474-9 (2000); SCH 56592, a triazole, Urbina et al., *Antimicrobial Agents and Chemotherapy*, 42:1771-7 (1998); Azalanstat (RS-21607), an imidazole-dioxolane compound was designed for the inhibition of mammalian lanosterol 14a-demethylase, Walker et al., *J. Med. Chem.*, 36:2235-2237 (1993); AFK-108 (1-[2-(2,4-dichlorophenyl)-2-((2E)-3,7-dimethylocta-2,6-dienyloxy)ethyl]-1H-imidazole), Ito et al., *Biochem Pharmacol.*, 48:1577-82 (1994), all of these are incorporated herein by reference, particularly for the description and structures depicted therein.

Also known as CYP51 inhibitors and suitable for use as targeting moieties are: metronidazole, clotrimazole, vibunazole, fenticonazole, croconazole, butoconazole, bifonazole, oxiconazole, fluconazole, terconazole, sulconazole, ketoconazole, micoazole nitrate, tioconazole, omoconazole, genaconazole, lanoconazole, flutrimazole, ebercona- zole, neticonazole, sertaconazole, voriconazole, posaconazole, lillconazole, isoconazole, econazole, fosflu- conazole, KP-103, albaconazole, terbiaminazole, embecona- zole, BAL-8557, R-136203, FX-0549, FX-0685, RBx-9050.

In some embodiments, inhibitors of lanosterol demethy- lase have metal binding moieties that are not unsubstituted imidazoles (5A2HA where the heteroatoms are both nitro- gen) and triazoles (5A3HA wherein the heteroatoms are all nitrogen). In addition, some embodiments do not utilize di- substituted imidazoles wherein one substituent group is a butyl group (in some cases of this embodiment, any alkyl is not preferred) and the other is chloride (in some cases of this embodiment, no halogen is preferred).

FIG. 16A-16S depicts a number of inhibitors of CYP51, which are suitable for use as targeting moieties in the pres- ently disclosed subject matter. FIG. 16A-16S shows the struc- tures of these known inhibitors along with possible sites of attachment of the linkers and metal binding moieties ("R"), as well as possible derivatives.

In some embodiments, the metallo-oxidoreductase inhibi- tor is a lanosterol demethylase inhibitor comprising a target- ing moiety, a metal binding moiety, and optionally a linker, and wherein the inhibitor has a formula selected from the group consisting of:

(I)

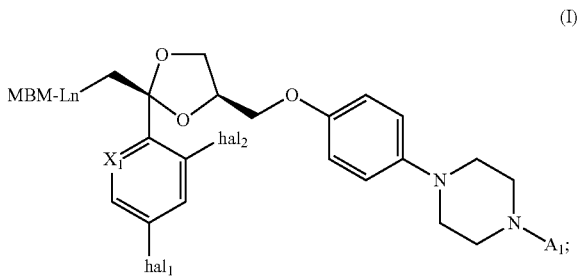

wherein:
$hal_1$ and $hal_2$ are each independently halogen;
$X_1$ is CH or N;

$A_1$ is selected from the group consisting of H, alkyl, branched alkyl, —C(=O)—CH$_3$, or a moiety having a structure selected from the group consisting of:

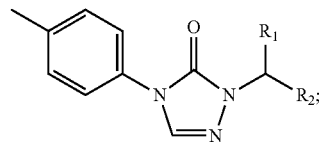

wherein:
$R_1$ is H or alkyl;
$R_2$ is alkyl or —CR$_3$R$_4$,
wherein $R_3$ is H or alkyl; and $R_4$ is selected from the group consisting of H, alkyl, —OH and —O—C(=O)—R$_5$;
wherein $R_5$ is selected from the group consisting of —CH$_2$NH$_2$; —CH(CH$_2$-phenyl)-NH$_2$; —CH$_2$N(CH$_2$CH$_3$)$_2$; —CH(CH$_2$(CH$_3$)$_2$)—NH$_2$; —CH(CH$_2$CH(CH$_3$)$_2$)—NH$_2$;

(b)

(II)

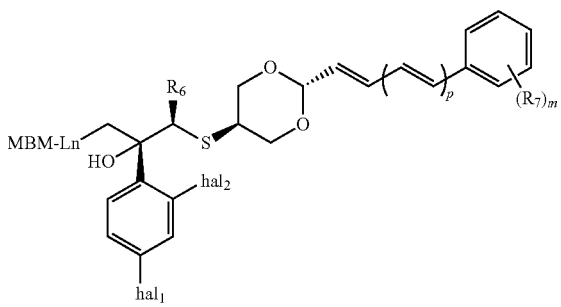

wherein:
m is an integer from 1 to 5;
p is an integer from 1 to 4;
$R_6$ is H or alkyl;
$R_7$ is selected from the group consisting of H, alkyl, halo- gen, —CN, —OCF$_3$; —S—CF$_3$; —CF$_3$; —S(=O)—CF$_3$; —CF$_3$; —C(=O)—NH$_2$; and combinations thereof;

(c)

(III)

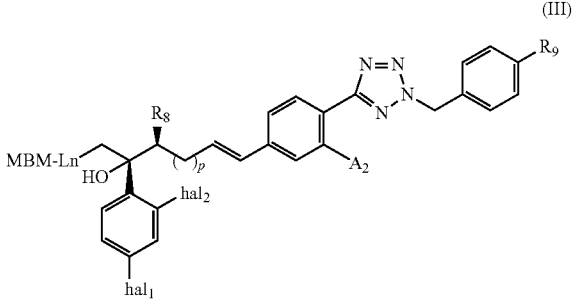

wherein:
p is an integer from 0 to 2;
$A_2$ is H or halogen;
$R_8$ is H or alkyl; and $R_9$ is selected from the group consisting of H, alkyl, —O—$CF_3$; and —$CF_3$;

(d)

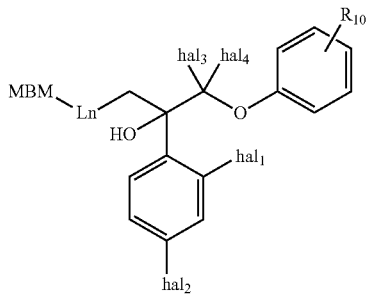

(IV)

$R_{10}$ is selected from the group consisting of: halogen, 4-fluorophenyl-piperazinyl, 3,4-methylenedioxy, 3-methoxypropylamino, 4-benzyloxycarbonylamino, 4-$NO_2$-phenyl-piperazinyl, and 4-methoxyimino;

(e)

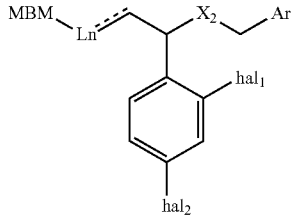

(V)

$X_2$ is O or S;

a dashed line indicates that a bond is present or absent; and

Ar is selected from the group consisting of -phenyl-S-phenyl; halo- or dihalophenyl; halothienyl; halophenoxymethyl; and halo-3-benzothienyl;

(f)

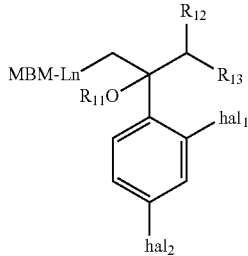

(VI)

wherein:

$R_{11}$ is H or P(=O)$O_2$;

$R_{12}$ is selected from the group consisting of H and alkyl;

$R_{13}$ is a nitrogen-containing heterocyclic ring or a nitrogen-containing fused heterocyclic ring selected from the group consisting of:

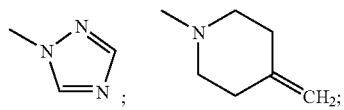

(g)

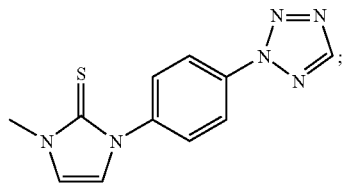

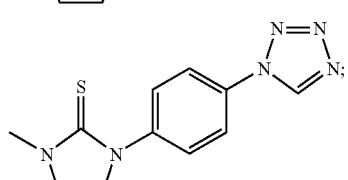

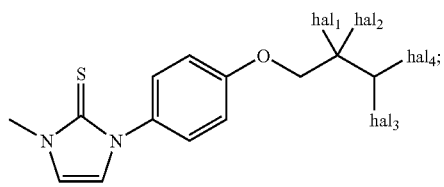

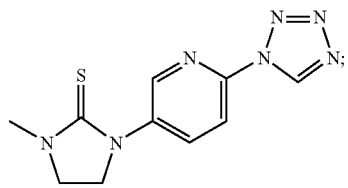

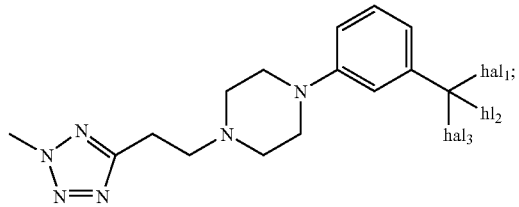

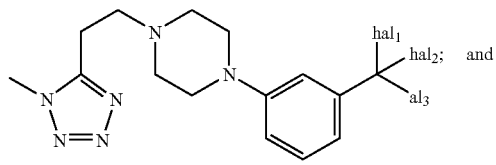

and

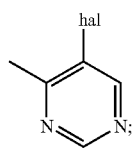

-continued

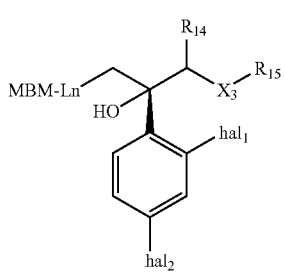
(VII)

wherein:
$R_{13}$ is H or alkyl;
$X_3$ is —S—$(CH_2)_q$— or —$NR_{16}$—C(=O)—, wherein q is an integer from 1 to 8 and $R_{16}$ is H or alkyl;
$R_{15}$ is selected from the group consisting of:

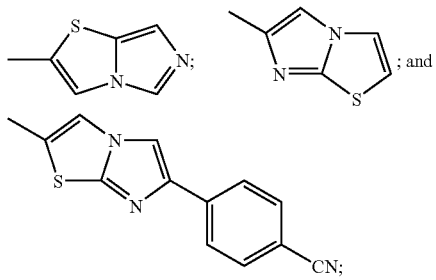

(VIII)

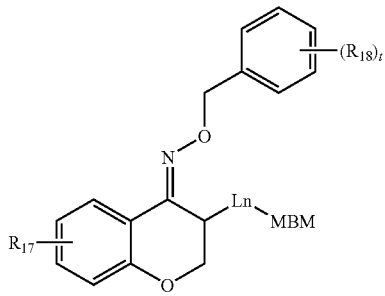

wherein:
t is an integer from 1 to 2; and
$R_{17}$ is H or halogen: and
each $R_{18}$ is halogen;

(i)

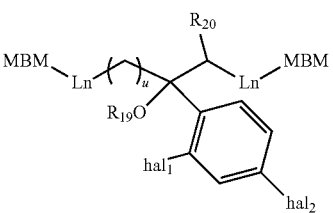
(IX)

wherein:
u is an integer from 1 to 3;
$R_{19}$ is H or P(=O)(OH)$_2$; and
$R_{20}$ is H or alkyl;

(j)

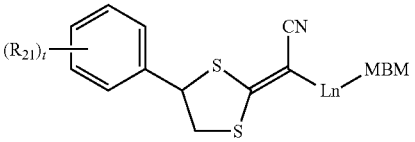
(X)

wherein:
t is an integer from 1 to 2;
each $R_{21}$ is halogen;

(k)

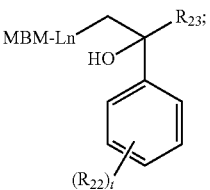
(XI)

wherein:
t is an integer from 1 to 2;
each $R_{22}$ is independently halogen; and
$R_{23}$ is selected from the group consisting of:

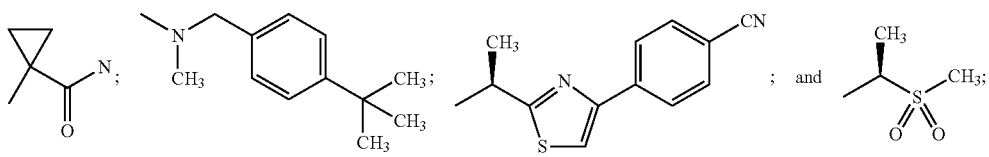

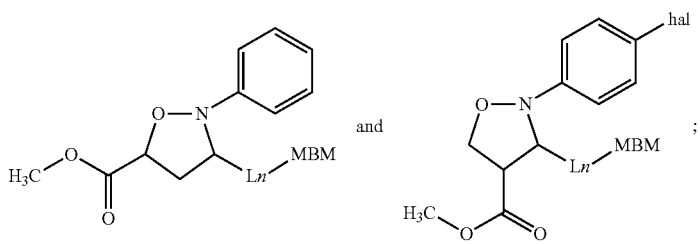

(l)

(m)
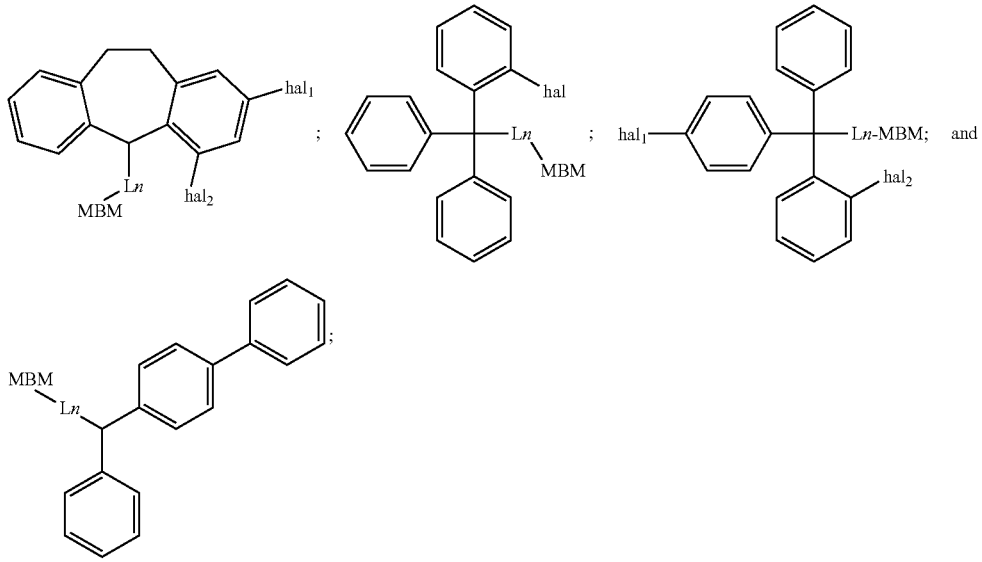
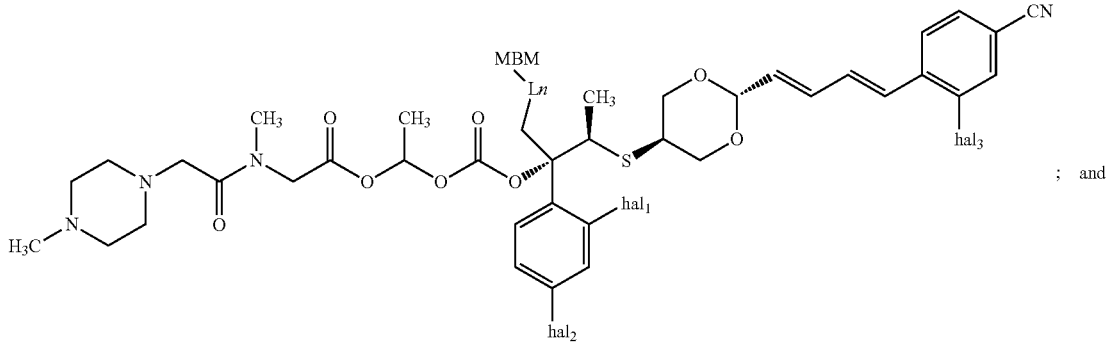
; and
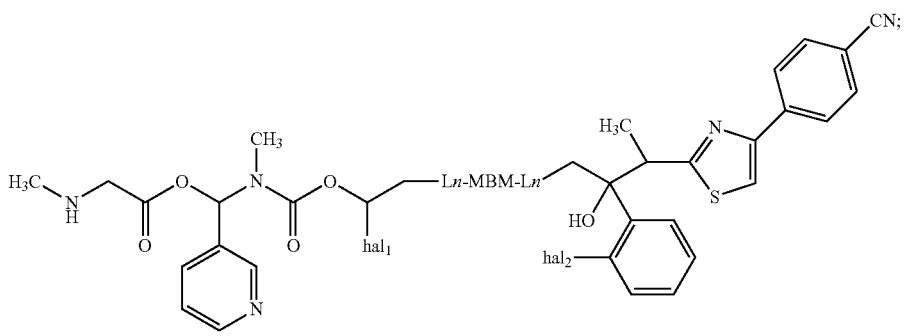
(o)
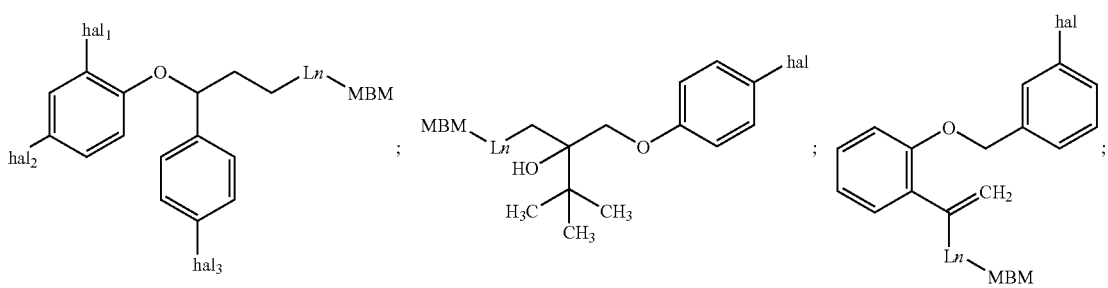

-continued

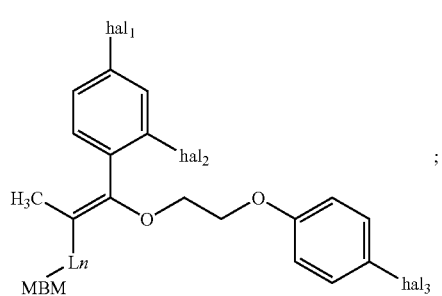 ; and 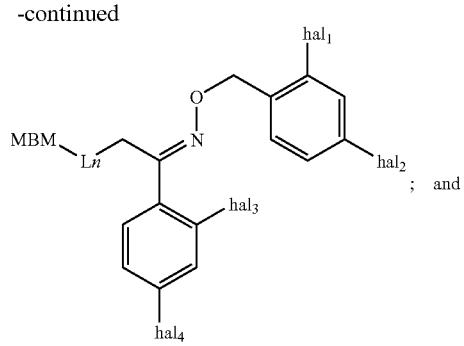 ; and

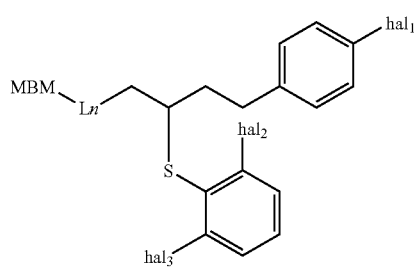 ; and 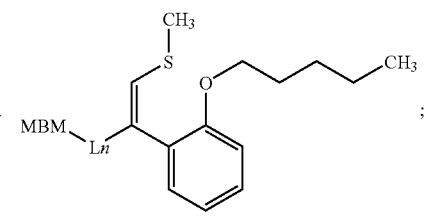 ;

(p)

wherein:

MBM is a metal binding moiety;

$L_n$ is a linker, wherein n is an integer from 0 to 1;

under the proviso that the metal binding moiety is not a metal binding moiety selected from the group consisting of:

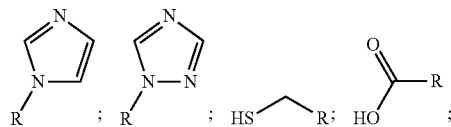

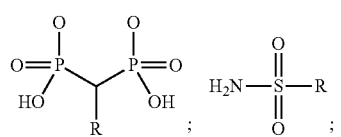

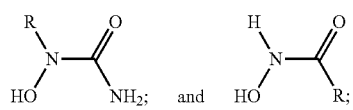

wherein: R is an attachment site through which the metal binding moiety can be attached to the targeting moiety, optionally through linker, $L_n$; and hal, $hal_1$, $hal_2$, $hal_3$, and $hal_4$ are each independently halogen; and pharmaceutically acceptable salts thereof.

In some embodiments, the lanosterol demethylase inhibitor is selected from the group of lanosterol demethylase inhibitors presented in FIG. 16A-16S. More particularly, in some embodiments, the lanosterol demethylase inhibitor is selected from the group consisting of:

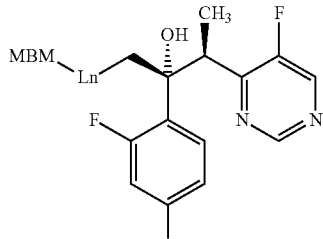

and

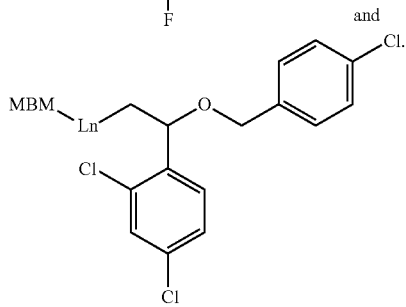

In some embodiments, the lanosterol demethylase inhibitor has the following formula:

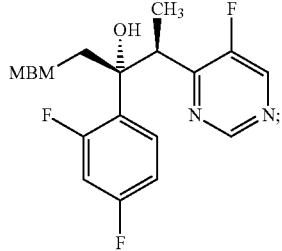

wherein MBM is selected from the group consisting of 3-thienyl, 4-imidazolyl, 4-(1,2,4-triazolyl), 1-(1,2,3-triazolyl), 1-tetrazolyl, 3-pyridyl, 4-pyridyl, 4-pyrimidinyl, 3-furanyl, 1-imidazolyl, 3-pyrrolyl, 5-thiazolyl, 5-oxazolyl, 4-thiazolyl, 4-isoxazolyl, 5-isothiazolyl, 3-pyrazolyl, 4-pyrazolyl, 2-tetrazolyl, 2-chloro-3-pyridyl, 2-pyrazinyl, 4-thiomorpholinyl, 3-cyano-4-pyrrolyl, 5-mercapto-1-(1,2,4-triazolyl), 6-pyrid-2-one-yl, 5-pyrimidinyl, 5-pyrazin-2-one-yl, 3-pyridazinyl, and 3-quinolinyl.

In some embodiments, the lanosterol demethylase inhibitor has the following formula:

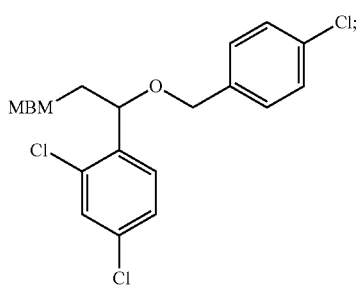

wherein MBM is selected from the group consisting of NHC(=S)NHCH$_3$, NHC(=S)NH CH$_3$, NHC(=O)SCH$_2$CH$_3$, NHSO$_2$CH$_3$, NHC(=O)CH$_2$SCH$_3$, N(OH)C(=O)H, 2-mercapto-1-imidazolyl, 4-thiomorpholinyl, 2-amino-5-thienyl, 2-amino-5-pyridyl, 4-amino-1-imidazolyl, and 2-amino-1-imidazolyl.

In one embodiment, the lanosterol demethylase inhibitor is:

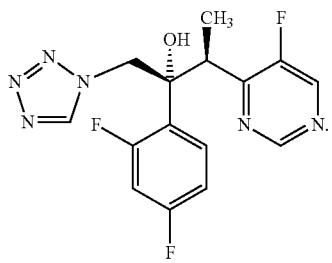

In addition to these targeting moieties, other known targeting moieties, identified by the screens outlined below or shown to bind to lanosterol demethylase can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

Lanosterol demethylase activity can be measured using established methods. See e.g., Yoshida et al., *Journal of Biological Chemistry*, 259:1655-1660 (1984); Lamb, et al., *Biochem. J.*, 364:555-562 (2002); Strömstedt et al., *Arch. Biochem. Biophys.*, 329:73-81(1996); Aoyama et al., *J Biol. Chem.* 259:1661-1666 (1984); Aoyama et al., *Biochem. Biophys. Res. Commun.*, 178:1064-1071 (1991); and Yamashita et al., *Journal of Biochemistry*, 128:93-99 (2000); herein incorporated by reference.

11. Nitric Oxide Synthase

Nitric oxide synthase (NOS) is a heme-containing metalloenzyme family which occurs in three isoforms named NOSI or neuronal NOS, NOSII or inducible NOS, and NOSIII or endothelial NOS. Nitric oxide synthases produces nitric oxide by catalysing a five-electron oxidation of a guanidino nitrogen of L-arginine (L-Arg). Oxidation of L-Arg to L-citrulline occurs via two successive monooxygenation reactions producing N$^\omega$-hydroxy-L-arginine (NOHLA) as an intermediate. NOS1 Produces NO in neuronal tissue in both the central and peripheral nervous system. Neuronal NOS also performs a role in cell communication and is associated with plasma membranes. NOS2 can be found in the immune system but is also found in the cardiovascular system. It uses the oxidative stress of NO (a free radical) to be used by macrophages in immune defense against pathogens. NOS3 Generates NO in blood vessels and is involved with regulating vascular function. The various NOS isoforms are well-established targets for the development of agents to treat septic shock, stroke and other cardiovascular diseases. Alderton et al., *Biochem. J.*, 357, 593-615.

Tirilazad mesylate, an inhibitor or NOS, is currently marketed for the treatment of acute stroke.

Targinine and tilarginine are two of a series of NG-monomethyl-L-arginine hydrochloride derivatives which have been demonstrated to inhibit NOS. Targinine and tilarginine are being investigated for use in the treatment of septic shock. See U.S. Pat. Nos. 5,028,627, 5,028,727 and 5,767,312, each of which is incorporated herein by reference in its entirety.

Aminotetrazole derivative have been described as potent and selective inhibitors of NOS. See U.S. Pat. No. 5,684,008, which is incorporated herein by reference in its entirety.

A series of condensed piperadine derivatives have been demonstrated to be inhibitors of NOS. See U.S. Pat. No.6, 228,866, which is incorporated herein by reference in its entirety.

A series of amidino derivatives have been claimed as inhibitors of NOS. See U.S. Pat. No. 6,369,272, which is incorporated herein by reference in its entirety.

FIG. 28 depicts a number of inhibitors of NOS, which are suitable for use as targeting moieties in the presently disclosed subject matter. FIG. 28 shows the structure of these known inhibitors along with possible sites of attachment of the linkers and metal binding moieties ("R"), as well as possible derivatives.

In some embodiments, the metallo-oxidoreductase inhibitor is a nitric oxide synthase inhibitor comprising a targeting moiety, a metal binding moiety, and optionally a linker, and wherein the inhibitor has a formula selected from the group consisting of:

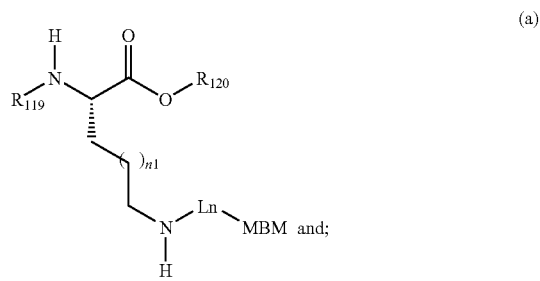

-continued

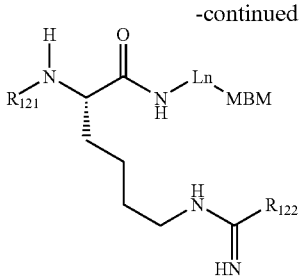

wherein:
n1 is an integer from 0 to 1;
$R_{119}$ and $R_{121}$ are each independently selected from the group consisting of H, acyl, and alkyl; and
$R_{120}$ and $R_{122}$ are each independently H or alkyl; and

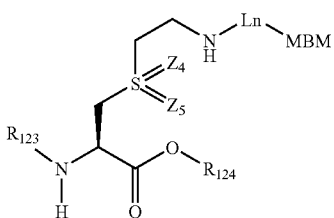
(b)

wherein:
$R_{123}$ is selected from the group consisting of H, acyl, and alkyl;
$R_{124}$ is H or alkyl; and
$Z_4$ and $Z_5$ are each independently O or null;
wherein:
MBM is a metal binding moiety;
$L_n$ is a linker, wherein n is an integer from 0 to 1;
under the proviso that the metal binding moiety is not a metal binding moiety selected from the group consisting of:

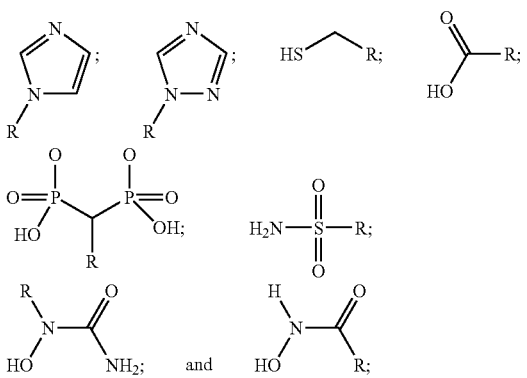

wherein: R is an attachment site through which the metal binding moiety can be attached to the targeting moiety, optionally through linker, $L_n$.

In some embodiments, the nitric oxide synthase inhibitor is selected from the group of nitric oxide synthase inhibitors presented in FIG. 28.

In addition to these targeting moieties, other known targeting moieties, identified by the screens outlined below or shown to bind to NOS can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

NOS activity can be measured using established methods. See Young et al., *Bioorg. Med. Chem. Lett.* 2000, 10(6): 597; Alderton et al., *Br. J. Pharmacol.* 2005, 145(3): 301; Naka et al., *Biochem. Biophys. Res. Commun.*, 2000, 270(2):663.

12. Retinoic Acid Hydroxylase

Retinoic acid hydroxylase (RAH) is a heme-containing member of the cytochrome P450 family and is also known as CYP26. RAH plays a key role in retinoic acid catabolism. RAH acts on retinoids, including all-trans-retinoic acid and its stereoisomer 9-cis-retinoic acid and is capable of both 4-hydroxylation and 18-hydroxylation. RAH is responsible for generation of several hydroxylated forms of retinoic acid, including 4-OH-retinoic acid, 4-oxo-retinoic acid and 18-OH-retinoic acid. Due to the importance of retinoic acid in various dermatologic diseases and cancer, RAH has been a target for the development of agents to treat psoriasis, acne and retinoic acid-related cancers. Mulvihill et al., *Bioorg. Med. Chem. Lett.* 2005, 15(6): 1669.

RAH inhibitors, also known as retinoic acid metabolism-blocking agents (RAMBAs), are known and include, for example, Liarozole (Liazal.™.) and R116010. Such RAH inhibitors have demonstrated therapeutic benefits in dermatological and cancerous conditions in vitro, in vivo, and in clinical settings. In several preclinical tumor models, Liarozole displayed antitumoral properties which correlated with decreased endogenous retinoic acid metabolism and therefore, an increase in RA accumulation within tumor cells. In cancer patients, Liarozole has been shown to increase the half-life of orally administered RA and 13-cis-RA. However, one of the limitations of Liarozole and many RAH inhibitors described in the literature is their lack of specificity. Liarozole as well as other RAH inhibitors inhibit other cytochrome P450-mediated reactions and are limited due to their lack of specificity towards other cytochrome P450 enzymes. Therefore, there is clearly a need within retinoid therapy for RAH inhibitors (RAMBA's) that are highly potent and selective that have greater selectivity to other cytochrome P450 enzymes, fewer side effects, and favorable drug-like properties including sufficient water solubility, bioavailability, sufficient pharmacokinetic properties, extraction ratios, and limited toxicity to balance the activity/toxicity ratio and for use in the treatment of various dermatological and cancerous conditions. See Njar et al., *Bioorganic & Medicinal Chemistry*, 14:4323-4340 (2006); and U.S. Patent Application Publication No. 20060009645, each of which is incorporated herein by reference in its entirety.

U.S. Pat. No. 6,303,785 describes inhibitors of cytochrome P450RAI. U.S. Pat. Nos. 6,291,677 and 6,124,330 and International Patent Publication No. WO 02/03912 A2 describe inhibitors of cytochrome P450RAI. Also have been described as inhibitors of the cytochrome P450RAI enzyme (RAH) are heteroaryl-naphthalenyl-alkylamines. U.S. Patent Application Publication No. 20060009645; [2-imidazol-1-yl-2-(6-alkoxy-naphthalen-2-yl)-1-methyl-ethyl]-dimethyl-amines, Mulyihill et al., *Bioorg. Med. Chem. Lett.*, 15:1669-73(2005); 3-[6-(2-Dimethylamino-1-imidazol-1-yl-butyl)-naphthalen-2-yloxy]-2,2-dimethyl-propionic acid and analogs, Mulvihill et al., *Bioorg. Med. Chem. Lett.*, 16:2729-33 (2006); 1-[benzofuran-2-yl-(4-alkyl/aryl-phenyl)-methyl]-1H-triazoles, Pautus et al., *Bioorg. Med. Chem.*, 14:3643-53 (2006); 2-benzyltetralone and 2-benzylidenetetralone derivatives, Yee et al., *J. Med. Chem.*, 48:7123-31 (2005); and ketoconazole, liarozole and R116010, U.S. Pat. No. 6,855,512, all of these patents and non-patent publications are incorporated herein by reference, particularly for the description and structures depicted therein.

FIG. 24A-24B depicts a number of inhibitors of RAH, which are suitable for use as targeting moieties in the presently disclosed subject matter. FIG. 24A-24B shows the structures of these known inhibitors along with possible sites of attachment of the linkers and metal binding moieties ("R"), as well as possible derivatives.

In some embodiments, the metallo-oxidoreductase inhibitor is a retinoic acid hydroxylase (CYP26) inhibitor comprising a targeting moiety, a metal binding moiety, and optionally a linker, and wherein the inhibitor has a formula selected from the group consisting of:

(a)
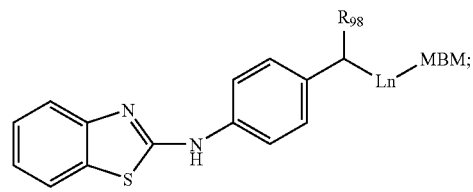

wherein $R_{98}$ is H or alkyl;

(b)
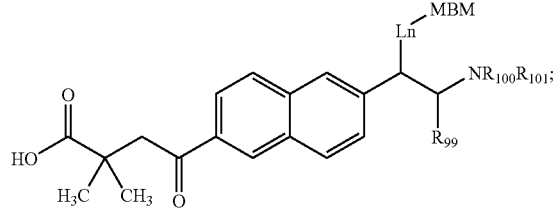

wherein:
$R_{99}$=H or alkyl; and
$R_{100}$ and $R_{101}$ are each selected from the group consisting of H, alkyl, and cycloalkyl;

(c)
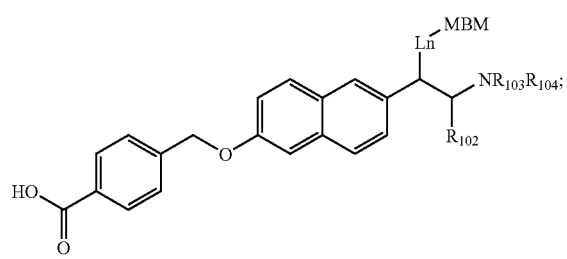

wherein:
$R_{102}$ is H or alkyl; and
$R_{103}$ and $R_{104}$ are each independently H, alkyl, cycloalkyl;

(d)
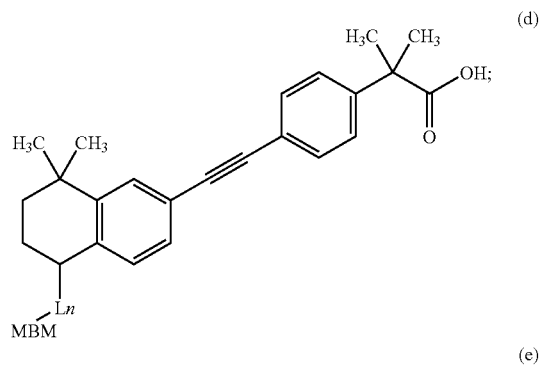

(e)
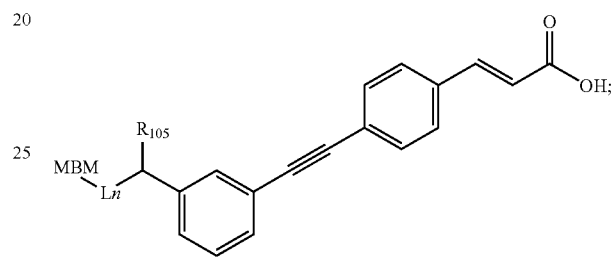

wherein $R_{105}$ is H or alkyl; and (f)
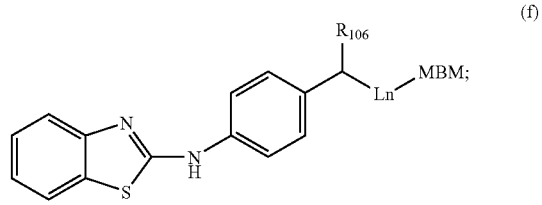

wherein $R_{106}$ is H or alkyl; and
wherein:
MBM is a metal binding moiety;
$L_n$ is a linker, wherein n is an integer from 0 to 1;
under the proviso that the metal binding moiety is not a metal binding moiety selected from the group consisting of:

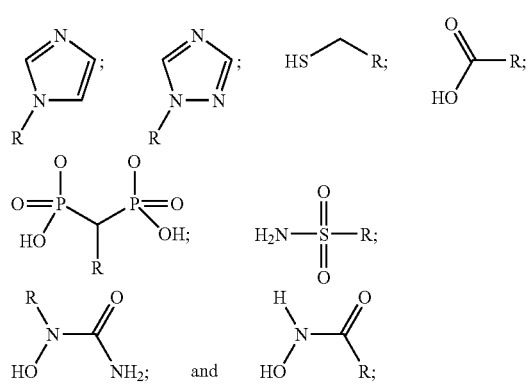

wherein: R is an attachment site through which the metal binding moiety can be attached to the targeting moiety, optionally through linker, $L_n$.

In some embodiments, the retinoic acid hydroxylase (CYP26) inhibitor is selected from the group of retinoic acid hydroxylase (CYP26) inhibitors presented in FIG. 24A-24B.

In addition to these targeting moieties, other known targeting moieties, identified by the screens outlined below or shown to bind to RAH can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

RAH activity can be measured using established methods. See e.g., Yee et al., *J. Med. Chem.*, 48:7123-31 (2005); Taimi et al., *J. Biol. Chem.*, 279:77-85 (2004); U.S. Pat. No. 6,855,512; and U.S. Patent Application Publication No. 20060009645, which is incorporated herein by reference in its entirety.

13. Vascular Adhesion Protein-1

Vascular adhesion protein-1 (VAP-1) is a copper-containing metalloenzyme also known as semicarbazide-sensitive amine oxidase or SSAO. VAP-1 is a protein present in the membrane of endothelial cells that possesses monoamine oxidase activity. It has been implicated as playing a role in lymphocyte transmigration and other pro-inflammatory processes. Due to the pro-inflammatory activity of VAP-1, it as become a well-established target for the development of agents to treat a variety of inflammatory illnesses such as rheumatoid arthritis, ulcerative colitis and psoriasis. Merinen et al., *Am. J. Pathol.* 2005 March; 166(3): 793-800.

A series of thiazole derivatives has been claimed as inhibitors of VAP-1. See US 2004259923.

A series of 1,3,4-oxadiazine derivatives have been demonstrated to be potent inhibitors of VAP-1. See WO 2002002541.

A series of hydrazine derivatives have been claimed as inhibitors of VAP-1. See U.S. Pat. No. 6,624,202.

A series of substituted thiazole derivatives have been demonstrated to be VAP-1 inhibitors. See US 2006011631 and WO 2006028269.

FIG. 29 depicts a number of inhibitors of VAP-1, which are suitable for use as targeting moieties in the presently disclosed subject matter. FIG. 29 shows the structure of these known inhibitors along with possible sites of attachment of the linkers and metal binding moieties ("R"), as well as possible derivatives.

In some embodiments, the metallo-oxidoreductase inhibitor is a vascular adhesion protein-1 inhibitor comprising a targeting moiety, a metal binding moiety, and optionally a linker, and wherein the inhibitor has a formula selected from the group consisting of:

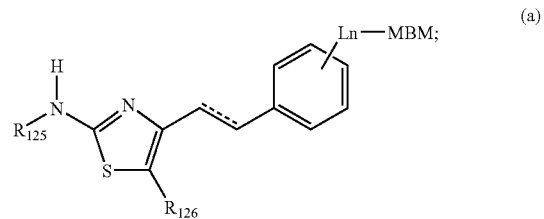

wherein:
$R_{125}$ is selected from the group consisting of H, acyl, and alkyl; and
$R_{126}$ is selected from the group consisting of H, alkyl, and aminoalkyl;

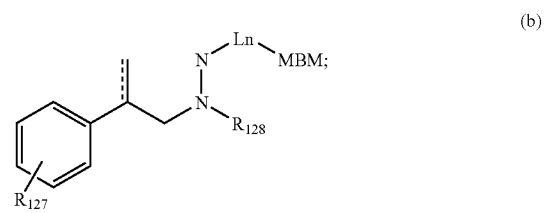

wherein:
$R_{127}$ is selected from the group consiting of H, halogen, and alkyl;
$R_{128}$ is selected from the group consisting of H, alkyl, acyl, and aralyl;

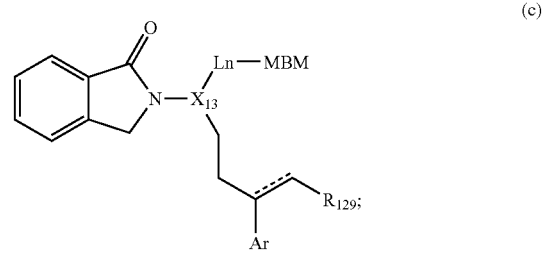

wherein:
$R_{129}$ is H or halogen;
$X_{13}$ is N or CH; and
Ar is substituted phenyl;

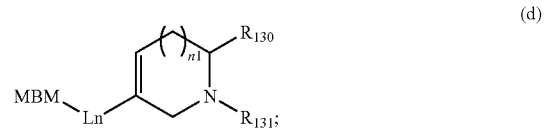

wherein:
n1 is an integer from 0 to 2;
$R_{130}$ is H or $CONHR_{132}$;
$R_{131}$ is selected from the group consisting of H, $CONHR_{133}COalkyl$, and $CO_2alkyl$; and
$R_{132}$ and $R_{133}$ are each independently selected from the group consisting of H, alkyl, and aralkyl;

wherein:
MBM is a metal binding moiety;
$L_n$ is a linker, wherein n is an integer from 0 to 1;
under the proviso that the metal binding moiety is not a metal binding moiety selected from the group consisting of:

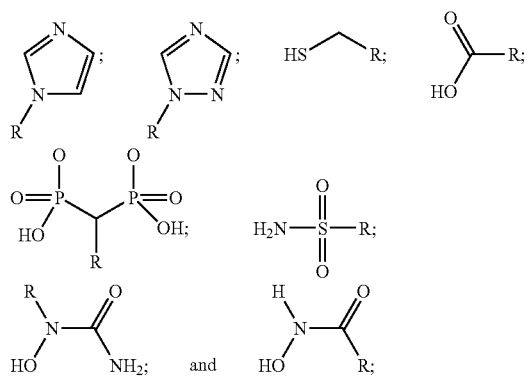

wherein: R is an attachment site through which the metal binding moiety can be attached to the targeting moiety, optionally through linker, $L_n$.

In some embodiments, the vascular adhesion protein-1 inhibitor is selected from the group of vascular adhesion protein-1 inhibitors presented in FIG. 29.

In addition to these targeting moieties, other known targeting moieties, identified by the screens outlined below or shown to bind to VAP-1 can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

VAP-1 activity can be measured using established methods, See Wang et al., J Med Chem 2006, 49(7): 2166; Yraola et al., J Med Chem 2006, 49(21): 6197.

14. Xanthine Oxidase

Xanthine oxidase (XO; EC 1.17.3.2, also known as hypoxanthine oxidase, hypoxanthine: oxygen oxidoreductase, Schardinger enzyme, hypoxanthine-xanthine oxidase, xanthine oxidoreductase, xanthine:$O_2$ oxidoreductase, or xanthine:xanthine oxidase) and xanthine dehydrogense (XD or XDH; EC 1.17.1.4, also known as NAD-xanthine dehydrogenase, xanthine-NAD oxidoreductase, xanthine/$NAD^+$ oxidoreductase, or xanthine oxidoreductase) are intercovertible forms of the same gene product known as xanthine oxidoreductase (XOR). XOR is a complex metalloflavoenzyme that catalyzes oxidation of hypoxanthine to xanthine and xanthine to uric acid with concomitant reduction of $NAD^+$ or molecular oxygen. The enzyme is a homodimeric protein of $M_r$ 300,000 and is composed of independent subunits; each subunit contains one molybdopterin, two non-identical iron sulfur centers ([2Fe-2S] clusters), and one FAD. The oxidative hydroxylation of xanthine to uric acid takes place at the molybdenum center, and reducing equivalents thus introduced are transferred rapidly via two iron sulfur centers to FAD, where physiological oxidation occurs. Nishino et al., J. Biol. Chem., 280:24888-24894 (2005).

Xanthine oxidase (XO) is a member of the molybdoenzyme family and is best known for its catalytic role in purine degradation, metabolizing hypoxanthine and xanthine to uric acid with concomitant generation of superoxide. Gene expression of XOR is regulated by oxygen tension, cytokines and glucocorticoids. Additionally, XOR can generate superoxide via NADH oxidase activity and can produce nitric oxide via nitrate and nitrite reductase activities. While a role for XOR beyond purine metabolism was first suggested in ischaemia-reperfusion injury, there is growing awareness that it also participates in endothelial dysfunction, hypertension and heart failure. Importantly, the XOR inhibitors allopurinol and oxypurinol attenuate dysfunction caused by XOR in these disease states. Attention to the broader range of XOR bioactivity in the cardiovascular system has prompted initiation of several randomized clinical outcome trials, particularly for congestive heart failure. Berry and Hare, J. Physiol., 555:589-606 (2004).

Both XD and XO catalyze the oxidation of purines to urate at the molybdenum center (the reductive half-reaction) and subsequent reduction of $O_2$ at the flavin center with generation of reactive oxygen species (ROS), either superoxide anion radical or hydrogen peroxide (the oxidative half-reaction). However, whereas XD requires NAD+ as an electron acceptor for these redox reactions, thereby generating the stable product NADH, XO is unable to use NAD+ as an electron acceptor, requiring instead the reduction of molecular oxygen for this purine oxidation and generating the highly reactive superoxide free radical. XO-generated reactive oxygen species (ROS) have been implicated in various clinicopathologic entities, including ischemia/reperfusion injury and multisystem organ failure. Inhibition of XO decreases the uric acid levels, and results in an antihyperuricemic effect. The concept of physiologic signal transduction mediated by ROS has been proposed, and the possibility of XD to XO conversion, with subsequent ROS generation, serving as the trigger of the microvascular inflammatory response in vivo has been hypothesized. Meneshian and Bulkley, Microcirculation, 9:161-75 (2002). Xanthine oxidase serum levels are significantly increased in various pathological states like hepatitis, inflammation, ischemia-reperfusion, carcinogenesis and aging and that ROS generated in the enzymatic process are involved in oxidative damage.

The mammalian enzymes exist in the $NAD^+$-dependent form (XDH) in freshly prepared samples from organs under normal conditions, i.e., they exhibit low xanthine/$O_2$ reductase activity but high xanthine/$NAD^+$ reductase activity, even in the presence of $O_2$. XDH can be converted reversibly to XO by oxidation of cysteine residues or irreversibly by limited proteolysis. XO has high reactivity toward $O_2$ but negligible reactivity toward $NAD^+$. As XO can reduce molecular oxygen to superoxide and hydrogen peroxide, XO is thought to be one of the key enzymes producing reactive oxygen species. Nishino et al., J. Biol. Chem., 280:24888-24894 (2005).

The crystal structures of bovine milk XDH and proteolytically produced XO have been solved and showed large conformational differences around the FAD. Although the transition seems to occur in a similar way, whether caused by cysteine modification or proteolysis, the identification of the responsible cysteine residues is still a matter of controversy. The crystal structure of bovine XOR shows that $Cys^{992}$ is situated on the surface of the molecule, but $Cys^{535}$ seems to be located in the long linker peptide between the FAD and the molybdopterin domains, although the residue is not visible in the crystal structure most probably due to its flexibility. The proteolytic cleavage site is also on the linker peptide. Based on detailed analyses of crystal structures of reversible XDH and proteolytic XO, as well as site-directed mutagenesis, it is concluded that the unique amino acid cluster of $Phe^{549}$, Arg[335] (corresponding to rat 334), Trp[336] (rat 335), and Arg[427] (rat 426) in the bovine enzyme sits at the center of a relay system that transmits modifications of the linker peptide caused by cysteine oxidation or proteolytic cleavage to the active site loop (Gln[423]-Lys[433]). The movement of the active site loop is considered to be the direct cause of the change in chemical behavior between XDH and XO. Nishino et al., *J. Biol. Chem.*, 280:24888-24894 (2005).

Allopurinol, first synthesized as a potential anticancer agent, is nowadays a clinically useful xanthine oxidase inhibitor used in the treatment of gout. Oxypurinol is the major metabolite of allopurinol. Chronic allopurinol administration for the inhibition of XO is clinically effective against the hyperuricemia associated with gout. However, its undesirable side effects have prompted efforts to isolate or synthesize other types of XO inhibitors. Moreover, both allopurinol and oxypurinol, owing to their purine-like structure, are known to undergo conversion to the corresponding nucleotides and can cause interactions with other enzymes involved in the purine metabolism. For this reason, new research programs had focused on the discovery and optimisation of new XO inhibitors having structures related to purine or of different type. Most of the compounds, obtained by synthesis or isolated from natural sources, as XO inhibitors are nitrogen and oxygen heterocyclics. These inhibitors include guanine based 9-(p-chlorophenyl)-guanine, 9-Phenylguanine, 9-phenyl-6-thioguanine, 9-(p-chlorophenyl)-8-azaguanine and 8-azaguanine; adenine based 8-azaadenine. Other inhibitors include phenyl-substituted 4(3H)-pteridones, 8-arylhypoxanthines, and 8-arylxanthines, 8-phenylhypoxanthine, 8-bromoxanthine, -nitropyrrolo[2,3-d]pyrimidin-4-one, 2-benzylthiohypoxanthine, 3-phenylpyrazolo[1,5-a]pyrimidin-7-one, and its m-toluyl derivative, 5-(p-chlorophenyl)pyrazolo[1,5-α]pyrimidin-7-one, 5-(p-nitrophenyl)pyrazolo[1,5-a]pyrimidin-7-one, 7-phenylpyrazolo[1,5-α]-s-triazine-4-one, 7-hydroxypyrazolo[1,5-α]pyrimidin-5-ones, 6-arylmethylidenehydrazino-7H-purines, triazolopurines, 3-substituted 7H-pyrazolo[4,3-e]-1,2,4-triazolo[4,3-c]-pyrimidin-5(6H)-ones, 2-amino-6-hydroxy-8-mercaptopurine, 2-amino-6-purine-thiol, 2-aminopurine, 2-(thioalkyl)purines, 4-amino-6-hydroxypyrazolo[3,4-d]pyrimidine, 4-amino-6-mercaptopyrazolo[3,4-d]pyrimidine, and 4-aminopyrazolo[3,4-d]pyrimidine, pyrimidine with thiopropylene or thioethylene binding group, 2-amino-4H-1,3-benzothiazin-4-one and 2-guanidino-4H-1,3-benzothiazin-4-one, 4-(Acylamino)-5-carbamoylimidazoles, 1H-1,2,3-triazole derivatives, 2-pyridylimidazoles, flavones and flavonols and flavonoid derivatives, flavanolignans, delphinidin, coumarins, norathyriol (1,3,6,7-tetrahydroxyxanthone), sulfuretin, ellagic acid, caffeic, chlorogenic and ferulic acids and their derivatives, purpurogallin, pentagalloylglucose, phenylethanoid isoacteoside, trans-p-coumaryl diacetate), trans-p-coniferyl diacetate, [1'S]-1'-acetoxychavicol acetate, [1'S]-1'-acetoxyeugenol acetate, 4-hydroxybenzaldehyde, anthragallol, anthraquinones, anthrarobin, benzophenones, phytosterols, steroidal glycosides, piceatannol, scirpusin A and scirpusin B, and folic acid. For review of XO inhibitors, see Borges et al., *Current Medicinal Chemistry*, 9:195-217 (2002), herein expressly incorporated by reference, particularly for the description and structures depicted therein.

Other inhibitors of xanthine oxidase include several pteridines, Oettl and and Reibnegger, *Biochim. Biophys. Acta*, 1430:387-395 (1999); thiazoles, Okamoto et al., *J. Biol. Chem.*, 278:1848-1855 (2003); phenyl pyrazoles, Ishibuchi et al., *Bioorg. Med. Chem. Lett.*, 11:879-882 (2001); aryl triazoles, Okamoto et al., *Proc. Natl. Acad. Sci. USA*, 101:7931-7936 (2004); and flavonoids, Lin et al., *Biochem. Biophys. Res. Commun.*, 294:167-172 (2002), Van Hoorn et al., *Eur. J. Pharmacol.*, 451:111-118 (2002), all of these are incorporated herein by reference, particularly for the description and structures depicted therein.

FIG. 21 depicts a number of inhibitors of xanthine oxidase, which are suitable for use as targeting moieties in the presently disclosed subject matter. FIG. 21 shows the structure of these known inhibitors along with possible sites of attachment of the linkers and metal binding moieties ("R"), as well as possible derivatives.

In some embodiments, the metallo-oxidoreductase inhibitor is a xanthine oxidase inhibitor comprising a targeting moiety, a metal binding moiety, and optionally a linker, and wherein the inhibitor has a formula selected from the group consisting of:

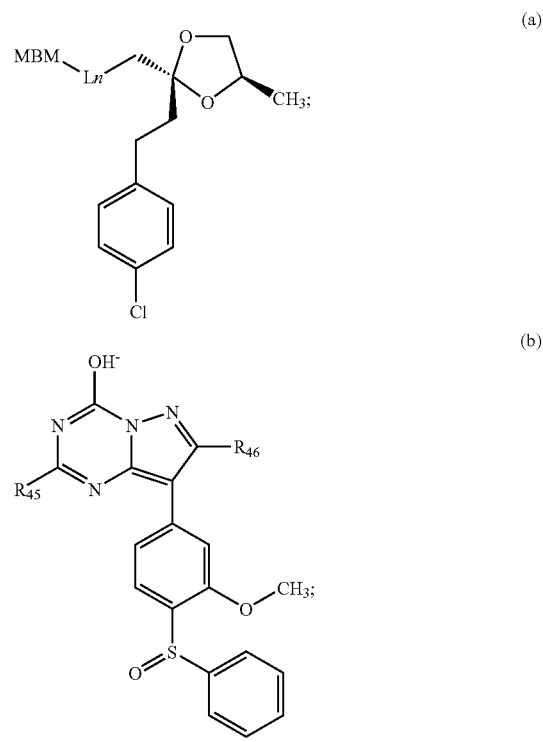

wherein at least one of $R_{45}$ and $R_{46}$ is $-L_n$-MBM;

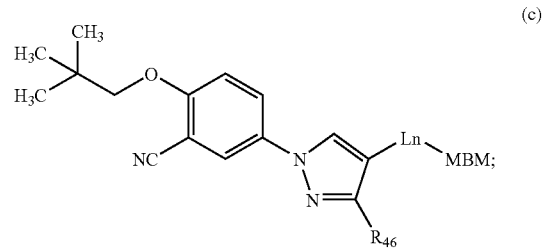

wherein $R_{46}$ is H or alkyl; and

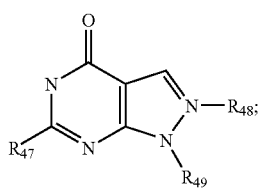

wherein at least one of $R_{47}$, $R_{48}$, and $R_{49}$ is -$L_n$-MBM;
wherein:
MBM is a metal binding moiety;
$L_n$ is a linker, wherein n is an integer from 0 to 1;
under the proviso that the metal binding moiety is not a metal binding moiety selected from the group consisting of:

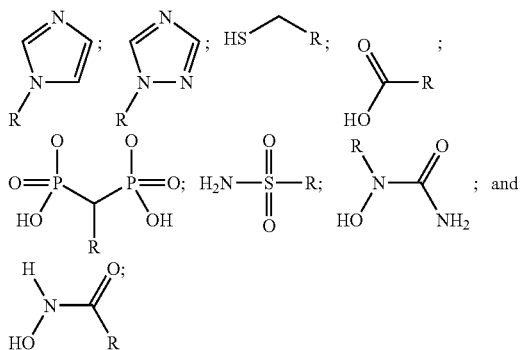

wherein: R is an attachment site through which the metal binding moiety can be attached to the targeting moiety, optionally through linker, $L_n$.

In some embodiments, the xanthine oxidase inhibitor is selected from the group of xanthine oxidase inhibitors presented in FIG. 21.

In addition to these targeting moieties, other known targeting moieties, identified by the screens outlined below or shown to bind to xanthine oxidase can be used. Thus, suitable targeting moieties include, but are not limited to, small organic molecules including known drugs and drug candidates, polysaccharides, fatty acids, vaccines, polypeptides, proteins (including peptides, as described herein), nucleic acids, carbohydrates, lipids, hormones including proteinaceous and steroid hormones, growth factors, receptor ligands, antigens, antibodies and enzymes, (as outlined below, collectively "candidate agents") and the like.

Xanthine oxidase activity can be measured using established methods. See e.g., Sasaoka, *J. Chromatogr.*, 424:392-7(1988); Sugiura et al., *Chem. Pharm. Bull.* (Tokyo), 29:430-2 (1981); and Nishino et al., *J. Biol. Chem.*, 280: 24888-24894 (2005), herein incorporated by reference.

C. Linkers

The inhibitors of the presently disclosed subject matter also optionally include a linker. That is, in some instances, the targeting moiety is linked directly to the metal binding moieties. Optionally, linkers comprising at least one atom can be used. By "linker" herein is meant at least one atom that provides a covalent linkage between the metal binding moiety and the targeting moiety. In some cases, there can be a single linker used, for example when the inhibitor has the general formula MBM-linker-TM or TM-linker-MBM. Alternatively, several linkers could be used; for example, in the case where more than one metal binding moieties or targeting moiety is used: MBM1-linker-MBM2-linker-TM, and the like.

Preferred linkers include, but are not limited to, alkyl or aryl groups, including substituted alkyl and heteroalkyl and aryl and heteroaryl groups, as outlined herein. Short straight alkyl chains are useful in many embodiments. The selection of the linker is generally done using well known molecular modeling techniques. In addition, the length of this linker can be important in order to achieve optimal results. In general, this can be modeled using the crystal structure of the oxidoreductase.

In some cases, the metal binding moieties and targeting moieties are covalently attached using well known chemistries. In many cases, both the metal binding moieties and the targeting moiety contains a chemical functional group that is used to add the components of the presently disclosed subject matter together, as is outlined herein. Thus, in general, the components of the presently disclosed subject matter are attached through the use of functional groups on each that can then be used for attachment. Preferred functional groups for attachment are amino groups, carboxy groups, oxo groups and thiol groups. These functional groups can then be attached, either directly or indirectly through the use of a linker. Linkers are well known in the art; for example, homo- or hetero-bifunctional linkers as are well known (see 1994 Pierce Chemical Company catalog, technical section on cross-linkers, pages 155-200, incorporated herein by reference). Alternatively, the whole molecule is synthesized in steps, rather than by joining two pieces.

D. Presently Disclosed Inhibitors

As described herein, the presently disclosed inhibitors comprise one or more targeting moieties and one or more metal binding moieties. As will be appreciated by those in the art, specific presently disclosed inhibitors comprise any of the targeting moieties outlined herein joined with an optional linker to any of the metal binding moieties outlined herein, such as those of the figures. Thus, FIG. 1A structures can be joined with FIG. 16 (1) structures, and the like. In addition, any of the targeting moieties can be joined with classes and/or subclasses of metal binding moieties, to form inhibitors to be tested for specific enzymatic properties such as Ki.

Thus, for example, any independently selected metal binding moiety, or class or subclass of metal binding moiety listed in Figures can be added to any independently selected targeting moiety. For example, 5-membered aromatic rings with heteroatoms can be added to any independently selected lanosterol demethylase inhibitor depicted in FIG. 26. Any and all combinations and subcombinations of any size are contemplated.

II. Production of Oxidoreductases

Oxidoreductase proteins of the presently disclosed subject matter can be shorter or longer than protein sequences described by the NCBI databases. Thus, in a preferred embodiment, included within the definition of oxidoreductase proteins are portions or fragments of the sequences described in NCBI databases, which are all herein expressly incorporated by reference. Portions or fragments of oxidoreductase proteins are considered oxidoreductase proteins if a) they share at least one antigenic epitope; or b) have at least the indicated homology; or c) preferably have oxidoreductase biological activity, e.g., if it is lanosteral demethylase, including, but not limited to the ability to catalyze oxidative removal of the 14α-methyl group from postsqualene sterol precursors; and d) if it is lanosteral demethylase, preferably hydrolyze lanoseroal selectively.

In general, the oxidoreductase enzymes used to test inhibitors are recombinant. A "recombinant protein" is a protein made using recombinant techniques, i.e., through the expression of a recombinant nucleic acid as depicted above. A recombinant protein is distinguished from naturally occurring protein by at least one or more characteristics. For example, the protein can be isolated or purified away from some or all of the proteins and compounds with which it is normally associated in its wild type host, and thus can be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an oxidoreductase protein from one organism in a different organism or host cell. Alternatively, the protein can be made at a significantly higher concentration than is normally seen, through the use of a inducible promoter or high expression promoter, such that the protein is made at increased concentration levels. Alternatively, the protein can be in a form not normally found in nature, as in the addition of an epitope tag or amino acid substitutions, insertions and deletions, as discussed below.

Also included within the definition of oxidoreductase proteins of the presently disclosed subject matter are amino acid sequence variants. These variants fall into one or more of three classes: substitutional, insertional or deletional variants. These variants ordinarily are prepared by site specific mutagenesis of nucleotides in the DNA encoding the oxidoreductase protein, using cassette or PCR mutagenesis or other techniques well known in the art, to produce DNA encoding the variant, and thereafter expressing the recombinant DNA in cell culture as outlined above. However, variant oxidoreductase protein fragments having up to about 100-150 residues can be prepared by in vitro synthesis using established techniques. Amino acid sequence variants are characterized by the predetermined nature of the variation, a feature that sets them apart from naturally occurring allelic or interspecies variation of the oxidoreductase protein amino acid sequence. The variants typically exhibit the same qualitative biological activity as the naturally occurring analogue, although variants also can be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis can be conducted at the target codon or region and the expressed oxidoreductase variants screened for the optimal combination of desired activity. Techniques for making substitution mutations at predetermined sites in DNA having a known sequence are well known, for example, M13 primer mutagenesis and PCR mutagenesis. Screening of the mutants is done using assays of oxidoreductase protein activities.

Amino acid substitutions are typically of single residues; insertions usually will be on the order of from about 1 to 20 amino acids, although considerably larger insertions can be tolerated. Deletions range from about 1 to about 20 residues, although in some cases deletions can be much larger.

Substitutions, deletions, insertions or any combination thereof can be used to arrive at a final derivative. Generally these changes are done on a few amino acids to minimize the alteration of the molecule. However, larger changes can be tolerated in certain circumstances. When small alterations in the characteristics of the oxidoreductase protein are desired, substitutions are generally made in accordance with Table 1:

TABLE 1

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table I. For example, substitutions can be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the oxidoreductase proteins as needed. Alternatively, the variant can be designed such that the biological activity of the oxidoreductase protein is altered. For example, glycosylation sites can be altered or removed, or the transmembrane domain can be removed for assay development.

Covalent modifications of oxidoreductase polypeptides are included within the scope of this presently disclosed subject matter. One type of covalent modification includes reacting targeted amino acid residues of an oxidoreductase polypeptide with an organic derivatizing agent that is capable of reacting with selected side chains or the N- or C-terminal residues of an oxidoreductase polypeptide. Derivatization with bifunctional agents is useful, for instance, for crosslinking oxidoreductase to a water-insoluble support matrix or surface for use in the method for purifying anti-oxidoreductase antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the oxidoreductase polypeptide included within the scope of this presently disclosed subject matter comprises altering the native glycosylation pattern of the polypeptide. "Altering the native glycosylation pattern" is intended for purposes herein to mean deleting one or more carbohydrate moieties found in native sequence oxidoreductase polypeptide, and/or adding one or more glycosylation sites that are not present in the native sequence oxidoreductase polypeptide.

Addition of glycosylation sites to oxidoreductase polypeptides can be accomplished by altering the amino acid sequence thereof. The alteration can be made, for example, by the addition of, or substitution by, one or more serine or threonine residues to the native sequence oxidoreductase polypeptide (for O-linked glycosylation sites). The oxidoreductase amino acid sequence can optionally be altered through changes at the DNA level, particularly by mutating the DNA encoding the oxidoreductase polypeptide at preselected bases such that codons are generated that will translate into the desired amino acids.

Another means of increasing the number of carbohydrate moieties on the oxidoreductase polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem., pp.* 259-306 (1981).

Removal of carbohydrate moieties present on the oxidoreductase polypeptide can be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo-and exo-glycosidases as described by Thotakura et al., *Meth. Enzymol.,* 138:350 (1987).

Another type of covalent modification of oxidoreductase comprises linking the oxidoreductase polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337, which is incorporated herein by reference in its entirety.

Oxidoreductase polypeptides of the presently disclosed subject matter also can be modified in a way to form chimeric molecules comprising an oxidoreductase polypeptide fused to another, heterologous polypeptide or amino acid sequence. In one embodiment, such a chimeric molecule comprises a fusion of an oxidoreductase polypeptide with a tag polypeptide which provides an epitope to which an anti-tag antibody can selectively bind. The epitope tag is generally placed at the amino-or carboxyl-terminus of the oxidoreductase polypeptide. The presence of such epitope-tagged forms of an oxidoreductase polypeptide can be detected using an antibody against the tag polypeptide. Also, provision of the epitope tag enables the oxidoreductase polypeptide to be readily purified by affinity purification using an anti-tag antibody or another type of affinity matrix that binds to the epitope tag. In an alternative embodiment, the chimeric molecule can comprise a fusion of an oxidoreductase polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; tubulin epitope peptide [Skinner et al., *J. Biol. Chem.,* 266: 15163-15166 (1991)]; and the T7 gene 10 protein peptide tag [Lutz-Freyermuth et al., *Proc. Natl. Acad. Sci. USA,* 87:6393-6397 (1990)].

Nucleic acids encoding the oxidoreductase proteins of the presently disclosed subject matter can be made as is known in the art. Similarly, using these nucleic acids a variety of expression vectors are made. The expression vectors can be either self-replicating extrachromosomal vectors or vectors which integrate into a host genome. Generally, these expression vectors include transcriptional and translational regulatory nucleic acid operably linked to the nucleic acid encoding the oxidoreductase proteins. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the oxidoreductase protein, as will be appreciated by those in the art; for example, transcriptional and translational regulatory nucleic acid sequences from *Bacillus* are preferably used to express the oxidoreductase protein in *Bacillus*. Numerous types of appropriate expression vectors, and suitable regulatory sequences are known in the art for a variety of host cells.

In general, the transcriptional and translational regulatory sequences can include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences include constitutive and inducible promoter sequences. The promoters can be either naturally occurring promoters, hybrid or synthetic promoters. Hybrid promoters, which combine elements of more than one promoter, are also known in the art, and are useful in the presently disclosed subject matter.

In addition, the expression vector can comprise additional elements. For example, the expression vector can have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector can be directed to a specific locus in the host cell by selecting the appropriate homologous sequence for inclusion in the vector. Constructs for integrating vectors and appropriate selection and screening protocols are well known in the art and are described in e.g., Mansour et al., *Cell*, 51:503 (1988) and Murray, *Gene Transfer and Expression Protocols, Methods in Molecular Biology, Vol. 7* (Clifton: Humana Press, 1991).

In addition, in a preferred embodiment, the expression vector contains a selection gene to allow the selection of transformed host cells containing the expression vector, and particularly in the case of mammalian cells, ensures the stability of the vector, since cells which do not contain the vector will generally die. Selection genes are well known in the art and will vary with the host cell used. By "selection gene" herein is meant any gene which encodes a gene product that confers resistance to a selection agent. Suitable selection agents include, but are not limited to, neomycin (or its analog G418), blasticidin S, histinidol D, bleomycin, puromycin, hygromycin B, and other drugs.

In a preferred embodiment, the expression vector contains a RNA splicing sequence upstream or downstream of the gene to be expressed in order to increase the level of gene expression. See Barret et al., *Nucleic Acids Res.* 1991; Groos et al., *Mol. Cell. Biol.* 1987; and Budiman et al., *Mol. Cell. Biol.* 1988.

A preferred expression vector system is a retroviral vector system such as is generally described in Mann et al., *Cell*, 33:153-9 (1993); Pear et al., *Proc. Natl. Acad. Sci. U.S.A.*, 90(18):8392-6 (1993); Kitamura et al., *Proc. Natl. Acad. Sci. U.S.A.*, 92:9146-50 (1995); Kinsella et al., *Human Gene Therapy*, 7:1405-13; Hofmann et al., *Proc. Natl. Acad. Sci. U.S.A.*, 93:5185-90; Choate et al., *Human Gene Therapy*, 7:2247 (1996); PCT/US97/01019 and PCT/US97/01048, and references cited therein, all of which are hereby expressly incorporated by reference.

The oxidoreductase proteins of the presently disclosed subject matter are produced by culturing a host cell transformed with nucleic acid, preferably an expression vector, containing nucleic acid encoding a oxidoreductase protein, under the appropriate conditions to induce or cause expression of the oxidoreductase protein. The conditions appropriate for oxidoreductase protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melanogaster* cells, *Saccharomyces cerevisiae* and other yeasts, *E. coli*, *Bacillus subtilis*, SF9 cells, C129 cells, 293 cells, *Neurospora*, BHK, CHO, COS, and HeLa cells, fibroblasts, Schwanoma cell lines, immortalized mammalian myeloid and lymphoid cell lines, Jurkat cells, mast cells and other endocrine and exocrine cells, and neuronal cells. See the ATCC cell line catalog, hereby expressly incorporated by reference.

In a preferred embodiment, the oxidoreductase proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for oxidoreductase protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, oxidoreductase proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of oxidoreductase protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage also can be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector also can include a signal peptide sequence that provides for secretion of the oxidoreductase protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector also can include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatargeting moietyent, electroporation, and others.

In one embodiment, oxidoreductase proteins are produced in insect cells. Expression vectors for the transformation of insect cells, and in particular, baculovirus-based expression vectors, are well known in the art and are described e.g., in O'Reilly et al., *Baculovirus Expression Vectors: A Laboratory Manual* (New York: Oxford University Press, 1994).

In a preferred embodiment, oxidoreductase protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The oxidoreductase protein also can be made as a fusion protein, using techniques well known in the art. Thus, for example, for the creation of monoclonal antibodies, if the desired epitope is small, the oxidoreductase protein can be fused to a carrier protein to form an immunogen. Alternatively, the oxidoreductase protein can be made as a fusion protein to increase expression, or for other reasons. For example, when the oxidoreductase protein is an oxidoreductase peptide, the nucleic acid encoding the peptide can be linked to other nucleic acid for expression purposes.

In one embodiment, the oxidoreductase nucleic acids, proteins and antibodies of the presently disclosed subject matter are labeled. By "labeled" herein is meant that nucleic acids, proteins and antibodies of the presently disclosed subject matter have at least one element, isotope or chemical compound attached to enable the detection of nucleic acids, proteins and antibodies of the presently disclosed subject matter. In general, labels fall into three classes: a) isotopic labels, which can be radioactive or heavy isotopes; b) immune labels, which can be antibodies or antigens; and c) colored or fluorescent dyes. The labels can be incorporated into the compound at any position.

In a preferred embodiment, the oxidoreductase protein is purified or isolated after expression. Oxidoreductase proteins can be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the oxidoreductase protein can be purified using a standard anti-oxidoreductase antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the oxidoreductase protein. In some instances no purification will be necessary.

Once expressed and purified if necessary, the oxidoreductase proteins and nucleic acids are useful in a number of applications.

III. Screening for Oxidoreductase Inhibitors

Screens can be designed to find targeting moieties that can bind to oxidoreductase proteins, and then these targeting moieties can be linked to the metal binding moieties to form oxidoreductase candidate inhibitors and then used in assays that evaluate the ability of the candidate inhibitors to modulate oxidoreductase bioactivity. Alternatively, targeting moieties can be linked with the metal binding moiety to first screen for binding activity to oxidoreductases and then screen inhibiting activity, or in opposite order. Thus, as will be appreciated by those in the art, there are a number of different assays which can be run; binding assays and activity assays.

A. Target Moiety Screening

In a preferred embodiment, the methods comprise combining oxidoreductase proteins and a candidate targeting moiety, and determining the binding of the targeting moiety to the oxidoreductase proteins. In general, as described herein, the assays are done by contacting a oxidoreductase protein with one or more targeting moieties to be tested.

Targeting moieties encompass numerous chemical classes. In one embodiment, the target moiety is an organic molecule, preferably small organic compounds having a molecular weight of more than 100 and less than about 2,500 daltons. Particularly preferred are small organic compounds having a molecular weight of more than 100 and less than about 2,000 daltons, more preferably less than about 1500 daltons, more preferably less than about 1000 daltons, more preferably less than 500 daltons. Targeting moieties comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Targeting moieties are also found among biomolecules including peptides, saccharides, fatty acids, steroids, purines, pyrimidines, derivatives, structural analogs or combinations thereof.

Targeting moieties are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In a preferred embodiment, the targeting moieties are organic chemical moieties, a wide variety of which are available in the literature.

In a preferred embodiment, the targeting moieties are obtained from combinatorial chemical libraries, a wide variety of which are available in the literature. By "combinatorial chemical library" herein is meant a collection of diverse chemical compounds generated in a defined or random manner, generally, but not always, by chemical synthesis. Millions of chemical compounds can be synthesized through combinatorial mixing.

In a preferred embodiment, the targeting moiety is a carbohydrate. By "carbohydrate" herein is meant a compound with the general formula $C_x(H_2O)_y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fructose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates. In particular, polysaccharides (including, but not limited to, arabinogalactan, gum arabic, mannan, and the like.) have been used to deliver MRI agents into cells; see U.S. Pat. No. 5,554,386, which is incorporated herein by reference in its entirety.

In a preferred embodiment, the targeting moiety is a lipid. "Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In a preferred embodiment, the targeting moieties are proteins. By "protein" herein is meant at least two covalently attached amino acids, which includes proteins, polypeptides, oligopeptides and peptides. The protein can be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the presently disclosed subject matter. "Amino acid" also includes imino acid residues such as proline and hydroxyproline. The side chains can be in either the (R) or the (S) configuration. In the preferred embodiment, the amino acids are in the (S) or L-configuration. If non-naturally occurring side chains are used, non-amino acid substituents can be used, for example to prevent or retard in vivo degradations. Peptide inhibitors of oxidoreductase enzymes find particular use.

In a preferred embodiment, the targeting moieties are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening in the systems described herein. Particularly preferred in this embodiment are libraries of bacterial, fungal, viral, and mammalian proteins, with the latter being preferred, and human proteins being especially preferred.

In some embodiments, the candidate agents are peptides. In this embodiment, it can be useful to use peptide constructs that include a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures. Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, and the like. See U.S. Pat. No. 6,153,380, which is incorporated herein by reference in its entirety.

Of particular use in screening assays are phage display libraries; see e.g., U.S. Pat. Nos. 5,223,409; 5,403,484; 5,571,698; and 5,837,500, all of which are expressly incorporated by reference in their entirety for phage display methods and constructs.

In a preferred embodiment, the targeting moieties are peptides of from about 5 to about 30 amino acids, with from about 5 to about 20 amino acids being preferred, and from about 7 to about 15 being particularly preferred. The peptides can be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they can incorporate any nucleotide or amino acid at any position. The synthetic process can be designed to generate randomized proteins or nucleic acids, to allow the formation of all or most of the possible combinations over the length of the sequence, thus forming a library of randomized targeting moieties.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, and the like, or to purines, and the like.

In a preferred embodiment, as is more fully outlined below, the candidate agents are either randomized proteins (including biased proteins or proteins with fusion partners) or expression products of cDNA libraries or libraries derived from cDNA libraries, such as fragmented (including randomly fragmented cDNA libraries). These are added to the cells as nucleic acids encoding these proteins. As will be appreciated by those in the art, these cDNA libraries can be full length or fragments, and can be in-frame, out-of-frame or read from the anti-sense strand.

In a preferred embodiment, the targeting moiety is an antibody. The term "antibody" includes antibody fragments, as are known in the art, including Fab Fab$_2$, single chain antibodies (Fv for example), chimeric antibodies, and the like, either produced by the modification of whole antibodies or those synthesized de novo using recombinant DNA technologies.

In a preferred embodiment, the antibody targeting moieties of the presently disclosed subject matter are humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies also can comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567, which is incorporated herein by reference in its entirety), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies also can be produced using various techniques known in the art, including phage display libraries [Hoogenboom and Winter, *J. Mol. Biol.,* 227:381 (1991); Marks et al., *J. Mol. Biol.,* 222:581 (1991)]. The techniques of Cole et al., and Boerner et al., are also available for the preparation of human monoclonal antibodies (Cole et al., *Monoclonal Antibodies and Cancer Therapy,* Alan R. Liss, p. 77 (1985) and Boerner et al., *J. Immunol.,* 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology,* 10:779-783 (1992); Lonberg et al., *Nature,* 368:856-859 (1994); Morrison, *Nature,* 368:812-13 (1994); Fishwild et al., *Nature Biotechnology,* 14:845-51 (1996); Neuberger, *Nature Biotechnology,* 14:826 (1996); Lonberg and Huszar, *Intern. Rev. Immunol.,* 13:65-93 (1995), each of which is incorporated herein by reference in its entirety.

Bispecific antibodies are monoclonal, preferably human or humanized, antibodies that have binding specificities for at least two different antigens. In the present case, one of the binding specificities is for a first target molecule and the other one is for a second target molecule.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537-539 (1983)]. Because of the random assor-targeting moietyent of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.* 10:3655-3659 (1991), each of which is incorporated herein by reference in its entirety.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the presently disclosed subject matter. Heteroconjugate antibodies are composed of two covalently joined antibodies. Such antibodies have, for example, been proposed to target immune system cells to unwanted cells [U.S. Pat. No. 4,676,980], and for treatargeting moietyent of HIV infection [WO 91/00360; WO 92/200373; EP 03089], each of which is incorporated herein by reference in its entirety. It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980, which is incorporated herein by reference in its entirety.

In a preferred embodiment, the candidate bioactive agents are nucleic acids. By "nucleic acid" or "oligonucleotide" or grammatical equivalents herein means at least two nucleotides covalently linked together. A nucleic acid of the presently disclosed subject matter will generally contain phosphodiester bonds, although in some cases, as outlined below, nucleic acid analogs are included that can have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, *Oligonucleotides and Analogues: A Practical Approach*, Oxford University Press), and peptide nucleic acid backbones and linkages (see Egholm, *J. Am. Chem. Soc.*, 114:1895 (1992); Meier, et al., *Chem. Int. Ed. Engl.*,31:1008 (1992); Nielsen, *Nature*, 365: 566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowski, et al., *Angew. Chem. Intl. Ed. English*, 30:423 (1991); Letsinger, et al., *J. Am. Chem. Soc.*, 110:4470 (1988); Letsinger, et al., *Nucleoside & Nucleotide*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook, and peptide nucleic acids. Nucleic acids containing one or more carbocyclic sugars are also included within the definition of nucleic acids (see Jenkins, et al., *Chem. Soc. Rev.*, (1995) pp. 169-176). Several nucleic acid analogs are described in Rawls, *C & E News*, Jun. 2, 1997, page 35. All of these references are hereby expressly incorporated by reference. These modifications of the ribose-phosphate backbone can be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs can be made. The nucleic acids can be single stranded or double stranded, as specified, or contain portions of both double stranded or single stranded sequence. The nucleic acid can be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine and the like.

In one embodiment, the nucleic acids are aptamers, see U.S. Pat. Nos. 5,270,163, 5,475,096, 5,567,588, 5,595,877, 5,637,459, 5,683,867,5,705,337, and related patents, each of which is incorporated herein by reference in its entirety.

It should be noted in the context of the presently disclosed subject matter that nucleosides (ribose plus base) and nucleotides (ribose, base and at least one phosphate) are used interchangeably herein unless otherwise noted.

As described above generally for proteins, nucleic acid targeting moieties can be naturally occurring nucleic acids, random and/or synthetic nucleic acids, or "biased" random nucleic acids. For example, digests of prokaryotic or eukaryotic genomes can be used as is outlined above for proteins.

In a preferred embodiment, a library of different targeting moieties is used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

Once expressed and purified, if necessary, the oxidoreductase proteins are used in screening assays for the identification of oxidoreductase candidate inhibitors comprising metal binding moieties and targeting moieties that bind to the oxidoreductase proteins and inhibit oxidoreductase activity.

In a preferred embodiment, the targeting moieties are screened first by using candidate agents as outlined herein for their desired properties and then linked to the metal binding moiety to form oxidoreductase candidate inhibitors for further screening using the method provided in the presently disclosed subject matter.

In another preferred embodiment, the targeting moiety is not pre-screened. The targeting moieties are linked to the metal binding moiety, then are used for screening using the method provided in the presently disclosed subject matter.

The targeting moieties are contacted with the oxidoreductase protein under reaction conditions that favor agent-target interactions. Generally, this will be physiological conditions. Incubations can be performed at any temperature which facilitates optimal activity, typically between 4° C. and 40° C. Incubation periods are selected for optimum activity, but also can be optimized to facilitate rapid high through put screening. Typically between 0.1 and 1 hour will be sufficient. Excess reagent is generally removed or washed away, in the case of solid phase assays. Assay formats are discussed below.

A variety of other reagents can be included in the assays. These include reagents like salts, neutral proteins, e.g., albumin, detergents, and the like which can be used to facilitate optimal oxidoreductase protein-targeting moiety binding and/or reduce non-specific or background interactions. Also reagents that otherwise improve the efficiency of the assay, such as protease inhibitors, nuclease inhibitors, anti-microbial agents, and the like, can be used. The mixture of components can be added in any order that provides for the requisite binding.

In one embodiment, solution phase binding assays are done. Generally in this embodiment, fluorescence resonance energy transfer (FRET) assays are done, by labeling both the targeting moieties and oxidoreductase proteins with different fluorophores with overlapping spectra. As energy transfer is distance dependent, in the absence of binding the excitation at one wavelength does not produce an emission spectra. Only if the two labels are close, e.g., when binding has occurred, will excitation at one wavelength result in the desired emission spectra of the second label.

In some embodiments, solid phase (heterogeneous) assays are done. In this case, binding assays are done wherein either the oxidoreductase protein or the targeting moiety is non-diffusably bound to an insoluble solid support, and detection is done by adding the other component which is labeled, as described below.

The insoluble supports can be made of any composition to which the compositions can be bound, is readily separated from soluble material, and is otherwise compatible with the overall method of screening. The surface of such supports can be solid or porous and of any convenient shape. Examples of suitable supports include microtiter plates, arrays, membranes and beads, and include, but are not limited to, glass and modified or functionalized glass, plastics (including acrylics, polystyrene and copolymers of styrene and other materials, polypropylene, polyethylene, polybutylene, polyurethanes, Teflon, and the like.), polysaccharides, nylon or nitrocellulose, resins, silica or silica based materials including silicon and modified silicon, carbon, metals, inorganic glasses, plastics, ceramics, and a variety of other polymers. In a some embodiments, the solid supports allow optical detection and do not themselves appreciably fluoresce. In addition, as is known the art, the solid support can be coated with any number of materials, including polymers, such as dextrans, acrylamides, gelatins, agarose, and the like. Exemplary solid supports include silicon, glass, polystyrene and other plastics and acrylics. Microtiter plates and arrays are especially convenient because a large number of assays can be carried out simultaneously, using small amounts of reagents and samples. The particular manner of binding of the composition is not crucial so long as it is compatible with the reagents and overall methods of the presently disclosed subject matter, maintains the activity of the composition and is nondiffusable.

In a preferred embodiment, the oxidoreductase protein is bound to the support, and a library of targeting moieties is added to the assay. Alternatively, the targeting moiety is bound to the support and the oxidoreductase protein is added. Attachment to the solid support is accomplished using well known methods, and will depend on the composition of the two materials to be attached. In general, for covalent attachment, attachment linkers are utilized through the use of functional groups on each component that can then be used for attachment. Preferred functional groups for attachment are amino groups, carboxy groups, oxo groups, hydroxyl groups and thiol groups. These functional groups can then be attached, either directly or indirectly through the use of a linker. Linkers are well known in the art; for example, homo- or hetero-bifunctional linkers are as well known (see 1994 Pierce Chemical Company catalog, technical section on cross-linkers, pages 155-200, incorporated herein by reference). In some embodiments, absorption or ionic interactions are utilized. In some cases, small molecule candidate agents are synthesized directly on microspheres, for example, which can then be used in the assays of the presently disclosed subject matter.

Following binding of the protein or targeting moiety, excess unbound material is removed by washing. The surface can then be blocked through incubation with bovine serum albumin (BSA), casein or other innocuous protein or other moiety.

In the binding assays, either the oxidoreductase protein, the targeting moiety (or, in some cases, the metal binding moiety, or substrate of oxidoreductase enzymes, described below) is labeled. By "labeled" herein is meant that the compound is either directly or indirectly labeled with a label which provides a detectable signal, e.g., radioisotope, fluorescers, enzyme, antibodies, particles such as magnetic particles, chemiluminescers, or specific binding molecules, and the like. Specific binding molecules include pairs, such as biotin and streptavidin, digoxin and antidigoxin and the like. For the specific binding members, the complementary member would normally be labeled with a molecule which provides for detection, in accordance with known procedures, as outlined above. The label can directly or indirectly provide a detectable signal.

Specific labels include optical dyes, including, but not limited to, chromophores, phosphors and fluorophores, with the latter being specific in many instances. Fluorophores can be either "small molecule" fluores, or proteinaceous fluores as described above. The labeled metal donor (e.g., the metal binding component) can be a chemical probe (such as Zinquin or Zinbo5) which undergoes a spectroscopic change when it releases the metal ion as described herein.

By "fluorescent label" is meant any molecule that can be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in *Molecular Probes Handbook* by Richard P. Haugland, hereby expressly incorporated by reference.

In one embodiment, the oxidoreductase protein is attached to the support, adding labeled targeting moiety, washing off excess reagent, and determining whether the label is present on the solid support. Various blocking and washing steps can be utilized as is known in the art.

In one embodiment, the targeting moieties are immobilized to the support, and a labeled oxidoreductase protein is added to determine binding.

Activity assays are done as are known in the art.

In one embodiment, any of the assays outlined herein can utilize robotic systems for high throughput screening. Many systems are generally directed to the use of 96 (or more) well microtiter plates, but as will be appreciated by those in the art, any number of different plates or configurations can be used. In addition, any or all of the steps outlined herein can be automated; thus, for example, the systems can be completely or partially automated.

As will be appreciated by those in the art, there are a wide variety of components which can be used, including, but not limited to, one or more robotic arms; plate handlers for the positioning of microplates; automated lid handlers to remove and replace lids for wells on non-cross contamination plates; tip assemblies for sample distribution with disposable tips; washable tip assemblies for sample distribution; 96 well loading blocks; cooled reagent racks; microtitler plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, tubes, magnetic particle, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this presently disclosed subject matter.

In a preferred embodiment, platforms for multi-well plates, multi-tubes, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, electroporator, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of the heat exchangers such as controlled blocks or platforms to provide accurate temperature control of incubating samples from 4° C. to 100° C.

In some preferred embodiments, the instrumentation will include a detector, which can be a wide variety of different detectors, depending on the labels and assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), SPR systems, luminescence, quenching, two-photon excitation, and intensity redistribution; CCD cameras to capture and transform data and images into quantifiable formats; and a computer workstation. These will enable the monitoring of the size, growth and phenotypic expression of specific markers on cells, tissues, and organisms; target validation; lead optimization; data analysis, mining, organization, and integration of the high-throughput screens with the public and proprietary databases.

These instruments can fit in a sterile laminar flow or fume hood, or are enclosed, self-contained systems as needed. Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic workstation includes one or more heating or cooling components. Depending on the reactions and reagents, either cooling or heating can be required, which can be done using any number of known heating and cooling systems, including Peltier systems.

In a preferred embodiment, the robotic apparatus includes a central processing unit that communicates with a memory and a set of input/output devices (e.g., keyboard, mouse, monitor, printer, and the like.) through a bus. The general interaction between a central processing unit, a memory, input/output devices, and a bus is known in the art. Thus, a variety of different procedures, depending on the experiments to be run, are stored in the CPU memory.

Accordingly, in some embodiments, the presently disclosed subject matter provides a method of screening for inhibitors of metallo-oxidoreductase, the method comprising: (a) providing a candidate inhibitor comprising: (i) a targeting moiety; (ii) a metal binding moiety; and (iii) optionally a linker; (b) contacting the inhibitor candidate with a metallo-oxidoreductase; and (c) determining the activity of the metallo-oxidoreductase.

As described in more detail herein below, in some embodiments, the targeting moiety comprises a lanosterol and the metallo-oxidoreductase is a lanosterol demethylase. In some embodiments, the lanosterol is a lanosterol derivative. In other embodiments, the targeting moiety comprises a protein. In some embodiments, the protein is a peptide.

In some embodiments, the metal binding moiety is a metal binding moiety of iron. In some embodiments, the metal binding moiety is selected from the group consisting of the metal binding moieties presented in FIGS. 1-15.

In some embodiments, the metallo-oxidoreductase is a lanosterol demethylase. In some embodiments, the lanosterol demethylase is a mammalian lanosterol demethylase. In some embodiments, the lanosterol demethylase is a human lanosterol demethylase, whereas in other embodiments, the lanosterol demethylase is a yeast lanosterol demethylase. The lanosterol demethylase can include a variant lanosterol demethylase.

In some embodiments, a plurality of different candidate inhibitors is contacted with the lanosterol demethylase. In some embodiments, the determining can be accomplished by measuring a substrate of lanosterol demethylase enzymes. In some embodiments, the substrate is lanosterol or a lanosterol derivative.

In some embodiments of the presently disclosed screening method, the determining is done by measuring a product resulted from the hydrolysis of the substrate by at least one step. In some embodiments, the product is a 14-demethylated metabolite or a derivative thereof.

In other embodiments, the determining is done by measuring a product resulting from the demethylation of the substrate by more than one step. In some embodiments, the product is a 14-demethylated metabolite derivative.

B. Screening for Lanosterol Demethylase Inhibitors

As provided immediately hereinabove, in one embodiment, the screening is done by directly assaying the ability of lanosterol demethylase candidate inhibitors to inhibit lanosterol demethylase enzymes activity. There are a variety of assays that can be used to assay the activity of lanosterol demethylase enzymes. See e.g., Yamashita et al., 128:93-99 (2000), hereby incorporated by reference.

In some embodiments, bioactivity assays are done to test whether the lanosterol demethylase candidate inhibitor inhibits lanosterol demethylase enzyme bioactivity. As for binding assays, activity assays can be either solution based, or rely on the use of components that are immobilized on solid supports. In this case, the bioactivity assay depends on the bioactivity of the lanosterol demethylase enzymes, and will be run accordingly. Thus, for example, lanosterol demethylase enzymes activity assays are well known, using a wide variety of generally commercially available substrates, including but not limited to, lanosterol or its derivatives. Generally a plurality of assay mixtures are run in parallel with different lanosterol demethylase inhibitor candidates concentrations to obtain a differential response to the various concentrations. Typically, one of these concentrations serves as a negative control, i.e., at zero concentration or below the level of detection.

In one embodiment, the methods comprise contacting the candidate inhibitor with a lanosterol demethylase enzyme. The candidate inhibitor and lanosterol demethylase enzymes can be added simultaneously or sequentially.

In one embodiment, the lanosterol demethylase enzymes are wild type, expressed by a cell line that expresses lanosterol demethylase enzyme. In another preferred embodiment, the lanosterol demethylase enzymes could also be expressed from a recombinant vector carrying the whole lanosterol demethylase genes or part of it, being transformed or transferred into host cells, integrated or not integrated in the chromosomes of the host cells. When lanosterol demethylase enzymes are produced as recombinant proteins from host cells, they could reside within the cell, or be secreted to the outside of the cells.

In one embodiment, the lanosterol demethylase enzyme is not purified.

In another embodiment, the lanosterol demethylase enzyme is purified, or partially purified.

In one embodiment, the assay is carried out using microsomes that contained lanosterol, from yeast or mammalian cells.

In one embodiment, the substrate is contained in micelles.

In other embodiment, the assay comprises NAPDH, which could be provided as NAPDH or by a source such as a NAPDH generating system.

In one embodiment, The assay is carried out aerobically. The assay comprises molecular oxygen. It could be free oxygen, or provided by a source, such as a molecular oxygen generating system.

In one embodiment, the assay for lanosterol demethylase activity is done by adding lanosterol demethylase candidate inhibitors to a cell culture expressing a lanosterol demethylase enzyme.

In another embodiment, the assay for lanosterol demethylase activity is done by mixing lanosterol demethylase candidate inhibitors with purified lanosterol demethylase enzyme in vitro.

A variety of other reagents can be included in the screening assays. These include reagents like salts, neutral proteins, e.g., albumin, detergents, and the like which can be used to facilitate optimal lanosterol demethylase enzyme activity and/or reduce non-specific or background actions. Also reagents that otherwise improve the efficiency of the assay, such as protease inhibitors, nuclease inhibitors, anti-microbial agents, and the like, can be used. The mixture of components can be added in any order that provides for the requisite assay.

Positive controls and negative controls can be used in the assays. Preferably all control and test samples are performed in at least triplicate to obtain statistically significant results. Incubation of all samples is for a time sufficient for lanosterol demethylase enzymes to act. Following incubation, all reactions are terminated by adding reaction termination agent, such as EDTA or other detergent to deactivate lanosterol demethylase enzymes. Other method such as heating could also be used to inactive lanosterol demethylase enzymes.

In one embodiment, a lanosterol demethylase enzymes substrate is in contact with the lanosterol demethylase enzymes and/or the lanosterol demethylase candidate inhibitors.

In another embodiment, for the test assay, lanosterol demethylase enzymes and lanosterol demethylase candidate inhibitors are in contact first, preferably after a period of pre-incubation, then are in contact with substrate; and for the control assay, lanosterol demethylase enzymes are in contact with substrate directly. In another preferred embodiment, lanosterol demethylase candidate inhibitors are in contact with substrate first, then are in contact with lanosterol demethylase enzymes; and for the control assay, substrate is in contact with lanosterol demethylase enzymes directly.

In a preferred embodiment, a "positive control" and/or a "negative control" could be used to control the reliability and quality of the assay. A positive control is an assay essentially same to an assay to test the effect of lanosterol demethylase candidate inhibitor except that the lanosterol demethylase candidate inhibitor is replaced by a known lanosterol demethylase inhibitor. One known lanosterol demethylase specific inhibitor is fluconazole. A negative control is an assay essentially same to an assay to test the effect of lanosterol demethylase candidate inhibitor except that the lanosterol demethylase candidate inhibitor is replaced by a known lanosterol demethylase non-inhibitor. In another preferred embodiment, a plurality of positive controls and/or negative controls is used.

The activity of lanosterol demethylase enzymes could be measured by their ability to catalyze a substrate. By "substrate" herein meant a molecule that lanosterol demethylase enzymes are capable of acting upon. When substrate are in contact lanosterol demethylase enzymes, lanosterol demethylase would catalyze a chemical reactions that involves the substrate that generally lead to some change to the substrate, or preferably, converts the substrate into a different molecule. Thus any molecule that lanosterol demethylase enzymes could act upon is a substrate, and preferably, selectively. One known lanosterol demethylase specific substrate is lanosterol. Though many derivatives of lanosterol through chemical or biological modification could also be specific substrate and be suited to the presently disclosed subject matter. A substrate could be lanosterol, a lanosterol derivative, or a lanoeterol analogue. In one preferred embodiment, the substrate is lanosterol.

In one embodiment, substrate, such as lanosterol or one of its derivatives, is directly or indirectly labeled to provide detectable signal as described above. For example, a radioisotope (such as $^3H$, $^{14}C$, $^{32}P$, $^{33}P$, $^{35}S$, or $^{125}I$), a fluorescent or chemiluminescent compound (such as fluorescein isothiocyanate, rhodamine, or luciferin), an enzyme (such as alkaline phosphatase, beta-galactosidase or horseradish peroxidase), antibodies, particles such as magnetic particles, or specific binding molecules, and the like. Specific binding molecules include pairs, such as biotin and streptavidin, digoxin and antidigoxin and the like. For the specific binding members, the complementary member would normally be labeled with a molecule which provides for detection, in accordance with known procedures, as outlined above. The label can directly or indirectly provide a detectable signal. A more complete list of flurophores is provided in the section of Targeting moiety.

In one preferred embodiment, the substrate is synthesized lanosterol.

In another embodiment, the substrate, such as lanosterol, is not labeled.

Demethylation of lanosterol by lanosterol demethylase enzymes can be measured by the decrease of lanosterol or the increase of the demethylation product(s), 14-demethylated metabolites. This could be done by comparing an assay wherein lanosterol demethylase enzymes are in contact with lanosterol demethylase candidate inhibitors ("test assay") and an assay wherein the lanosterol demethylase enzyme are not in contact with lanosterol demethylase inhibitors ("control assay"). The test assay and control assay are carried out under the same condition unless otherwise particularly described herein. Thus the lanosterol in the control assay will decrease comparing to the control assay, while there is increase of 14-demethylated metabolites or other molecules resulted due the activity of lanosterol demethylase enzymes. In contrast, in the test assay, due to the presence of the lanosterol demethylase candidate inhibitor, the lanosterol in the control assay will not decrease and there are no 14-demethylated metabolites or other molecules resulting from the hydrolysis by lanosterol demethylase enzymes after a period of time to allow the enzyme to act.

In a preferred embodiment, the activity of lanosterol demethylase enzymes is measured by the decrease of substrate. This could be done by comparing the amount of substrate in the assay sample before and after a period of time.

In a preferred embodiment, the activity of lanosterol demethylase enzymes is measured by the decrease of substrate such as lanosterol. This can be done by comparing the amount of substrate in the assay sample before after a period of time to allow the enzyme to act.

In a preferred embodiment, the activity of lanosterol demethylase enzymes is measured by the increase of lanosterol demethylase enzymes demethylation product. By "demethylation product" herein is meant the molecules resulted from the demethylation of the substrate by lanosterol demethylase enzyme, or molecules resulted from one or more down stream reaction following the hydrolysis of substrate by lanosterol demethylase enzyme. For example, when the substrate is lanosterol demethylase, the demthylation product is 14-demethylated metabolites, or trimethylsilylated derivatives of 14-demethylated metabolites, which is converted from the 14-demethylated metabolites by further down stream reaction, such as being trimethylsilylated with of N-trimethylsilylimidazole.

In one preferred embodiment, lanosterol demethylase enzyme activity is determined by the amount of adenosine after the reaction. In this embodiment, lanosterol demethylase enzymes are incubated with a substrate such as lanosterol, with or without lanosterol demethylase candidate inhibitor, in a buffer and at a temperature proper for lanosterol demethylase enzyme activity. After a desired period of time, the reaction is stopped by heating at a high temperature, such as 100 degrees for a period of time, preferably three minutes, to inactive the lanosterol demethylase enzymes. After cooling the sample to a lower temperature, a second agent that converts a 14-demethylated metabolite to a different form is added. In a preferred embodiment, the agent is N-trimethylsilylimidazole. The agent could also be an enzyme. After another incubation in a proper buffer, under proper temperature, and for a desired period of time, the reaction is stopped, such as by heating at high temperature for a period of time. Then the trimethylsilylated derivatives of 14-demethylated metabolites, if there are any, could be separated from lanosterol and 14-demethylated metabolite using standard method known in the art. In one embodiment, trimethylsilylated derivatives of 14-demethylated metabolites are separated from lanosterol and 14-demethylated metabolite using an affinity column. In another embodiment, they are separated by gas chromatography. After such separation, the amount of adenosine is then measured to determine the activity of lanosterol demethylase enzyme and the ability of lanosterol demethylase candidate inhibitor to inhibit lanosterol demethylase enzyme activity.

In another preferred embodiment, the screening is done by a competition assay. In such assay, a known lanosterol demethylase inhibitor, such as fluconazole, is used. Then in parallel assays, lanosterol demethylase candidate inhibitors are screened by replacing fluconazole in the otherwise same assay.

In one preferred embodiment, a plurality of lanosterol demethylase candidates could be used in combination according to a matrix to form mixtures, and the mixtures are used to test the ability to inhibit lanosterol demethylase enzyme activity. For example, a hundred of lanosterol demethylase candidate inhibitors could be assigned to a 10×10 matrix, and each column and row is mixed and tested for ability to inhibit lanosterol demethylase enzyme activities. There are thus total 20 samples to test. Then the test results are plotted against the matrix, and any double-positive in the matrix will be a positive result for lanosterol demethylase candidate inhibitors. This matrix thus could speed up the screening process. It could also be expended into more than two dimensions, such as three, four, or five dimensions.

In one embodiment, the candidate inhibitors are also tested against other enzymes, particularly other P450 enzymes, for specificity.

III. Pharmaceutical Compositions and Methods of Treatment

As previously discussed, the presently disclosed inhibitors inhibit the activity of oxidoreductase. As a consequence of these activities, the active compounds of the presently disclosed subject matter can be used in a variety of in vitro, in vivo and ex vivo contexts to inhibit activity, particularly in cases where oxidoreductase activity is implicated in disease states.

Accordingly, in some embodiments, the presently disclosed subject matter provides a method of inhibiting a metallo-oxidoreductase comprising contacting the metallo-oxidoreductase with a presently disclosed inhibitor. In some embodiments, the metallo-oxidoreductase is selected from the group consisting of 5-lipoxygenase, 17-alpha hydroxylase, alcohol dehydrogenase, aldosterone synthase, aromatase, cyclooxygenase, heme oxygenase, indoleamine 2,3-dioxygenase, lanosterol demethylase, nitric oxide synthase, retinoic acid hydroxylase, vascular adhesion protein-1, and xanthine oxidase.

Further, in some embodiments, the presently disclosed subject matter provides a method of treating a metallo-oxidoreductase related disorder comprising administering a composition of the presently disclosed inhibitors or a prodrug or salt thereof to a patient in need thereof. In some embodiments, the disorder is selected from disorders associated with 5-lipoxygenase, 17-alpha hydroxylase, alcohol dehydrogenase, aldosterone synthase, aromatase, cyclooxygenase, heme oxygenase, indoleamine 2,3-dioxygenase, lanosterol demethylase, nitric oxide synthase, retinoic acid hydroxylase, vascular adhesion protein-1, and xanthine oxidase.

When used to treat or prevent such diseases, the active compounds can be administered singly, as mixtures of one or more active compounds or in mixture or combination with other agents useful for treating such diseases and/or the symptoms associated with such diseases. The active compounds also can be administered in mixture or in combination with agents useful to treat other disorders. The active compounds can be administered per se in the form of prodrugs or as pharmaceutical compositions, comprising an active compound or prodrug.

Pharmaceutical compositions comprising the active compounds of the presently disclosed subject matter (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

The active compound or prodrug can be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases also can be formed.

Pharmaceutical compositions of the presently disclosed subject matter can take a form suitable for virtually any mode of administration, including, for example, topical, ocular, oral, baccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form, e.g., in ampules or in multidose containers, and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in conventional manner.

For rectal and vaginal routes of administration, the active compound(s) can be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed, although usually at the cost of greater toxicity.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) can not be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Assay of CYP51 Activity of Rat Liver and Testis

CYP51 activity is assayed principally as the following. The reaction mixture for determining hepatic CYP51 activity consists of lanosterol (47 nmol, dispersed with Tween 80), microsomes (5.0 mg protein), S-100 fraction (10 mg protein), KCN (1 mM), an NADPH-generating system, and 0.1 M potassium phosphate buffer, pH 7.5; and the final volume of the mixture is made up to 2.0 ml. The reaction mixture for determining testicular CYP51 activity is same as above except that the S-10 fraction (8.0 mg protein) is used as enzyme source instead of microsomes and S-100 fraction. The reaction is run aerobically at 37° C. for 10 min (liver) or 30 min (testis) under constant shaking. The reaction is terminated by saponification, and sterols are extracted with diethyl ether/petroleum ether (5/95). The extracted sterols are separated by TLC, and the fraction containing lanosterol and its 14-demethylated metabolites is extracted. The extracted sterols are trimethylsilylated and analyzed by GLC. The demethylase activity is calculated from the chromatographically determined conversion ratio of lanosterol to the two demethylated metabolites and the initial amount of lanosterol after correction of the endogenous metabolites by the gas-chromatogram of sterols extracted from the reaction mixture at the time zero of the incubation.

Example 2

Assay for Lanosterol 140-Demethylation by Reconstituted System

The standard reaction mixture (final volume, 2.0 ml) consists of 0.34 nmol of VYP51, 1.1 units of NADPH-cytochrome P-450 reductase, 13 nmol of lanosterol dispersed in 80 nmol of DLPC micelles, 0.2 mmol of potassium phosphate buffer (pH 7.5), 20 mmol of glucose 6-phosphate, 0.2 unit of glucose-6-phosphate dehydrogenase, and 0.3 pmol of NADPH. It is important to mix P-45014DM1 the reductase, and lanosterol-containing DLPC micelles before diluting with the buffer. This mixture contains a trace amount (about 0.001%) of Emulgen 913 and 0.025% sodium cholate derived from the CYP51 and reductase preparations, respectively. After preincubation of the mixture at 30° C. for 2 min, the reaction is started by the addition of NADPH, run at 30° C. for 10 min with constant shaking in air, and stopped by the addition of 5 ml of 10% KOH in methanol. After saponification of the mixture at 80° C. for 60 min, sterols are extracted with petroleum ether/diethyl ether (9:1, v/v) and the extract is evaporated. The residue is dissolved in and trimethylsilylated with 10 P I of N-trimethylsilylimidazole and analyzed in a Shimadzu GC-mini 2 gas chromatograph equipped with a hydrogen-flame ionization detector. Separation of derivatized sterols is performed in a glass capillary column coated with OV-17 (0 3 mm×50 m) at 255° C. using nitrogen as carrier gas. Trimethylsilylated derivatives of lanosterol and its demethylation product are clearly separated as two distinct peaks. The conversion ratio is calculated from the areas of the two peaks and the activity (nanomoles of product formed/min) is obtained from the amount of lanosterol added and the conversion ratio.

Example 3

Reconstituted CYP51 Catalytic Activity

Each reaction mixture contains 1 nmol/ml purified CYP51, 8 nmol of *E. coli* flavodoxin, 4 nmol of *E. coli* flavodoxin reductase and 23 nmol of lanosterol or 24-MDL. The reaction volume is adjusted to 950 µL, with 100 mM potassium phosphate buffer (pH 7.2). NADPH is added to a final concentration of 1 mM to start the reaction. All reactions are incubated at 37° C. for 20 min with gentle agitation. Reactions are stopped by the addition of 3 ml of methanol, and sterols are extracted by incubation with 90% (w/v) KOH in ethanol for 1 h at 80° C. in a preheated water bath. Following silylation for 1 h at 60° C. with 50 µL, of bis(trimethylsilyl) tri-fluoroacetamide (BSTFA) in 50 µL, of toluene, sterol substrates and metabolites are clearly separated and identified by GC-MS (VG 12-250; VG Biotech, Manchester, U.K.). The activity (nmol of demethylated product formed/min per nmol of CYP) is calculated using the amount of substrate added and the conversion ratio (calculated from the areas of the two peaks representing methylated and demethylated sterol).

Example 4

Tetrazole and Imidazole—Oxidoreductase PA

4.1 Procedure for the Synthesis of 2-(2,4-difluorophenyl)-3-(5-fluoropyrimidin-4-yl)-1-(1H-tetrazol-1-yl)butan-2-ol

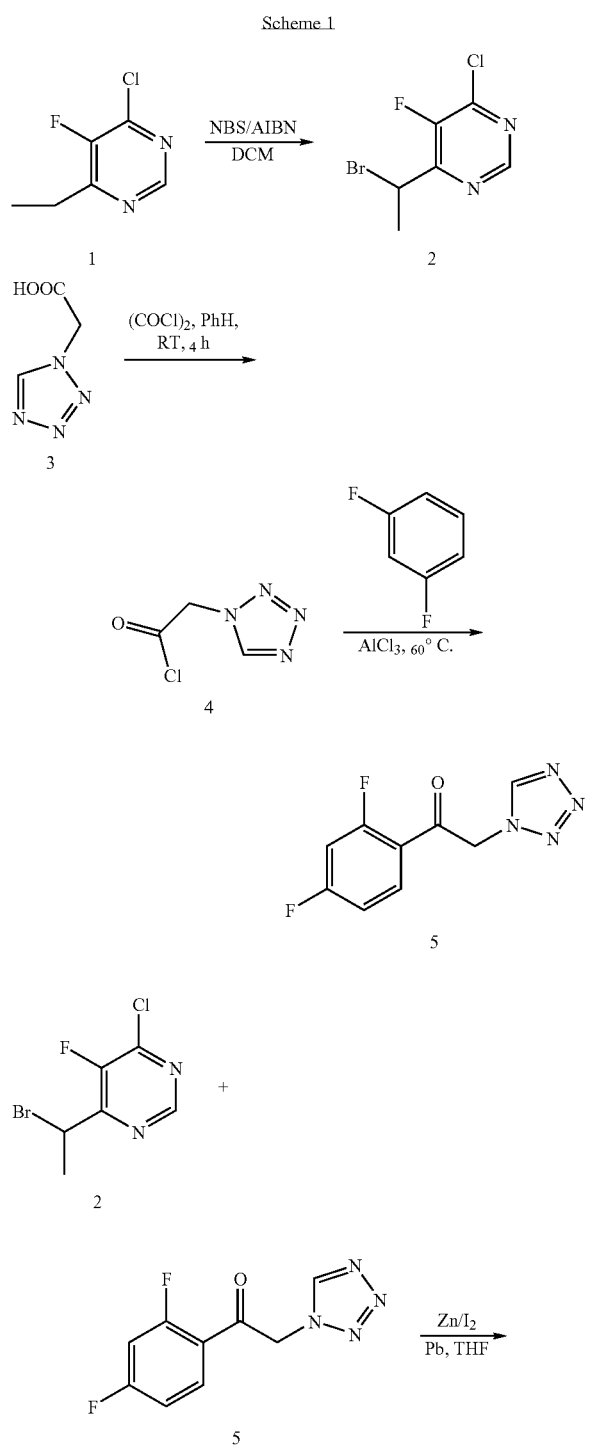

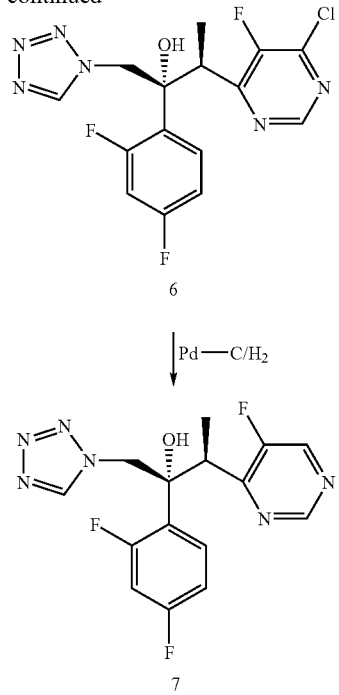

4.2 Procedure for the Synthesis of 4-(1-bromoethyl)-6-chloro-5-fluoropyrimidine To the stirred solution of 4-chloro-6-ethyl-5-fluoro pyrimidine 1 (10 gm, 62.50 mmol) in $CCl_4$ (150 mL) was added N-bromosuccinimide (12.7 gm, 71.35 mmol) and AIBN (511 mg, 3.12 mmol). The reaction mixture was refluxed for 4 hrs at 75° C. The progress of the reaction was monitored by TLC. The reaction mixture then diluted with DCM (500 mL) and washed successively with water, sodium meta bisulphite (100 mL) solution, water and brine solution. The organic layer was dried over anhydrous sodium sulfate and concentrated under reduced pressure to obtain the bromide 2 as yellowish oily syrup (14 gm, 58.58 mmol, 94%). $^1$H NMR ($CDCl_3$, 500 MHz): 2.10 (d, 3 H), 5.40 (q, 1 H), 8.80 (s, 1 H). Mass: 241($M^+$+2)

4.3 Procedure for the Synthesis of 2-(1H-tetrazol-1-yl)acetyl chloride

To a stirred solution of 2-(1H-tetrazol-1-yl)acetic acid 3 (1 gm, 7.81 mmol) in benzene (20 mL) was added oxalyl chloride (1.5 g, 11.81 mmol) and a catalytic amount of DMF. The reaction mixture was stirred at room temperature for 3 hrs. The reaction mixture was concentrated under vacuum and the crude acid chloride 4 obtained was used for the next step without any purification.

4.4 Procedure for the Synthesis 1-(2,4-difluorophenyl)-2-(1H-tetrazol-1-yl)ethanone 1,3-Difluorobenzene (0.86 mL, 7.54 mmol) and aluminium trichloride (1.25 gm, 9.36 mmol) was added to the crude acid chloride 4 obtained in the above reaction. The reaction mixture was stirred for 2 hrs. The progress of the reaction mixture was monitored by TLC. The reaction mixture was added to an ice cold water and conc. HCl mixture and stirred for 2 min. The aqueous layer was extracted with ethyl acetate (3×3 times). The combined ethyl acetate layers was washed with water, saturated brine solution and dried over anhydrous sodium sulfate. Evaporation of volatiles under reduced pressure gave crude product as viscous liquid. Purification of the crude material by column chromatography using ethyl acetate/hexane as the eluent afforded the desired product 5 (700 mg, 3.13 mmol, 40% for two steps). $^1$H NMR (CDCl$_3$, 500 MHz): 5.85 (d, 2 H), 6.98-7.21 (m, 2 H), 8.0-8.20 (m, 1 H), 8.80 (s,1 H). Mass: 225 (M$^-$+1).

4.5 Procedure for the Synthesis of 3-(6-chloro-5-fluoropyrimidin-4-yl)-2-(2,4-difluorophenyl)-1-(1H-tetrazol-1-yl)butan-2-ol In a two neck round bottom flask, zinc (freshly dried) (630 mg, 9.69 mmol) and catalytic amount of lead (12 mg) were taken in dry THF (3 mL). To this mixture was added a solution of iodine (300 mg, 1.19 mmol) in THF (2 mL) drop wise and stirred at room temperature for 10 min. Then a mixture of ketone 5 (600 mg, 2.68 mmol), bromide 2 (707 mg, 2.96 mmol) and iodine (377 mg, 1.49 mmol) in THF (5 mL) was introduced to the above solution under N$_2$ atmosphere at 0° C. The reaction mixture was stirred at 0° C. for 3 hrs. The progress of the reaction was monitored by TLC. The reaction mixture was quenched with aqueous acetic acid solution and filtered through a bed of celite. The filtrate obtained was distilled under vacuum to remove THF and then diluted with ethyl acetate. This solution was again distilled under vacuum and finally extracted with ethyl acetate (30 mL×3 times). The combined ethyl acetate layers was washed with saturated EDTA solution, water, saturated brine solution and the organic layer dried over anhydrous sodium sulfate. Evaporation under reduced pressure gave the alcohol 6 following chromatographic isolation of the indicated mixture of enantiomers (2R/3S and 2S/3R; 205 mg, 0.53 mmol, 20%). $^1$H NMR (CDCl$_3$, 500 MHz): 1.16 (d, 3 H), 4.19-4.24 (m, 1 H), 4.43 (d, 1 H), 5.08 (d, 1 H), 6.42 (s, 1H, OH), 6.80-6.92 (m, 2 H), 7.50-7.57 (m, 1 H), 8.58 (s, 1 H), 8.80 (s, 1 H). Mass: 385 (M$^+$+1).

4.6 General Procedure for the Synthesis of 2-(2,4-difluorophenyl)-3-(5-fluoropyrimidin-4-yl)-1-(1H-tetrazol-1-yl)butan-2-ol To a stirred solution of alcohol 6 (100 mg, 0.26 mmol) in ethanol (5 ml) was added sodium acetate (62 mg, 0.76 mmol) and a catalytic amount of 5% Pd/C (~10 mg) carefully under N$_2$ atmosphere. The reaction mixture was then stirred under H$_2$ atmosphere for 1-2 hrs. The progress of the reaction mixture was monitored by TLC. The reaction mixture then filtered through a bed of celite, the celite bed washed thoroughly with DCM (20 mL) and then the filtrate obtained was concentrated under vacuum to obtain the title compound 7 (74 mg, 81%) with HPLC purity of 98.07%. $^1$H NMR (CDCl$_3$, 500 MHz): 1.13 (d, 3 H), 4.17-4.23 (m, 1 H), 4.42 (d, 1H), 5.08 (d, 1H), 6.70 (s, 1 H, OH), 6.81-6.90 (m, 2 H), 7.50-7.58 (m, 1 H), 8.58 (s, 1 H), 8.72 (s, 1 H), 9.01 (s, 1 H). Mass: 350 (M$^+$+1).

Example 5

Imidazole Analogue

5.1 2-(2,4-difluorophenyl)-3-(5-fluoropyrimidin-4-yl)-1-(1H-imidazol-1-yl)butan-2-ol Following the above procedure starting from 1-N-imidazole-acetic acid, the title compound was isolated as a white solid (3 mg, 98% HPLC purity). $^1$H NMR (CDCl$_3$, 500 MHz): 1.13 (d, 3 H), 3.95 (d, 1 H), 4.10-4.14 (m, 1 H), 4.40 (d, 1 H), 6.40 (s, 1 H,), 6.70 (d, 2 H), 6.81-6.90 (m, 2 H), 7.23 (s, 1 H), 7.55-7.62 (m, 1 H), 8.58 (s, 1H), 9.01 (s, 1 H). Mass: 349 (M$^+$+1).

Example 6

In Vitro Antifungal Assays

The following testing protocols follow well-established CLSI guidelines. See NCCLS. *Reference Method for Broth Dilution Antifungal Susceptibility Testing of Yeasts; Approved Standard—Second Edition*. NCCLS document M27-A2, NCCLS, Wayne, Pa., 2002, which is incorporated by reference herein in its entirety.

Antifungal agents are prepared as stock concentrations in DMSO or water. Stock solutions may be stored frozen (<−70° C.) in aliquots. Once thawed for use, a stock preparation aliquot must be discarded at the end of the day. As a positive control, fluconazole stock is diluted in RPMI 1640 to a final concentration range of 64-0.12 μg/mL. Other positive controls, ketoconazole, voriconazole, and amphotericin B are diluted in RPMI 1640 to a final concentration of 16-0.03 μg/mL (and 1% DMSO). Panels may be prepared just prior to the evaluation, or prepared and stored frozen.

A suspension of *Candida albicans* is prepared in RPMI-1640 medium using colonies taken directly from a Sabouraud's agar plate culture. The suspension is adjusted to a turbidity equivalent to a 0.5 McFarland standard. The serially diluted concentrations of each test article are incubated for 24 hrs or 48 hrs at 35° C. with no CO$_2$ with the standardized suspension of *Candida albicans*. Negative control wells consist of medium only, and positive control wells will contain the test organism suspension. Following incubation, the plates are examined for inhibition of growth of the organism using a panel reader (Cooke Microtiter System). The test article is reported as having no antifungal activity if there is no inhibition of growth. If the test article has antifungal activity, the minimum inhibitory concentration (MIC) is determined. The MIC for amphotericin B is the lowest concentration of the test article that completely inhibits growth of *Candida albicans* in the microdilution wells (96-well plate). For fluconazole, voriconazole, ketoconazole and the test articles, the MIC is the lowest concentration that produces 50% or more growth inhibition.

The presently disclosed imidazole and 1-tetrazole analogues had an MIC of about 0.06 μg/mL to about 16.0 μg/mL.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. The lanosterol demethylase inhibitor, wherein the inhibitor is:

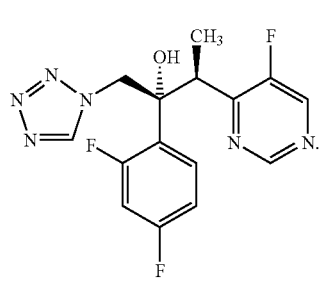

2. A pharmaceutical composition comprising a pharmaceutical carrier and the inhibitor of claim 1, or salt thereof.

3. A method of treating a fungal disorder comprising administering a composition of claim 2 or salt thereof to a patient in need thereof, wherein said disorder is caused by a *Candida* species.

4. The method of claim 3, wherein said *Candida* species is *Candida albicans*.

* * * * *